United States Patent
Barbosa et al.

(10) Patent No.: US 7,612,067 B2
(45) Date of Patent: Nov. 3, 2009

(54) IMIDAZOPYRIDAZINE COMPOUNDS

(75) Inventors: Heather Janelle Barbosa, Indianapolis, IN (US); Elizabeth Aaron Collins, Edinburgh, IN (US); Chafiq Hamdouchi, Carmel, IN (US); Erik James Hembre, Indianapolis, IN (US); Philip Arthur Hipskind, New Palestine, IN (US); Richard Duane Johnston, Greenfield, IN (US); Jianliang Lu, Fishers, IN (US); Michael John Rupp, Indianapolis, IN (US); Takako Takakuwa, Indianapolis, IN (US); Richard Craig Thompson, Frankfort, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/817,433

(22) PCT Filed: Mar. 20, 2006

(86) PCT No.: PCT/US2006/009942

§ 371 (c)(1),
(2), (4) Date: Aug. 30, 2007

(87) PCT Pub. No.: WO2006/102194

PCT Pub. Date: Sep. 28, 2006

(65) Prior Publication Data

US 2008/0113978 A1 May 15, 2008

Related U.S. Application Data

(60) Provisional application No. 60/663,816, filed on Mar. 21, 2005.

(51) Int. Cl.
| | |
|---|---|
| C07D 413/14 | (2006.01) |
| C07D 417/14 | (2006.01) |
| C07D 487/04 | (2006.01) |
| A61K 31/5355 | (2006.01) |
| A61K 31/5025 | (2006.01) |
| A61K 31/541 | (2006.01) |
| A61P 25/24 | (2006.01) |
| A61P 25/22 | (2006.01) |
| A61P 25/16 | (2006.01) |
| A61P 25/28 | (2006.01) |
| C07D 279/12 | (2006.01) |
| C07D 295/02 | (2006.01) |

(52) U.S. Cl. ............... 514/233.2; 514/228.2; 514/248; 544/58.2; 544/62; 544/117; 544/236

(58) Field of Classification Search ............ 514/222.2, 514/233.2, 248, 228.2; 544/61, 117, 236, 544/58.2
See application file for complete search history.

(56) References Cited

U.S. PATENT DOCUMENTS 7,105,550 B2 * 9/2006 Love et al. ............... 514/365

FOREIGN PATENT DOCUMENTS

| EP | 1 364 952 A | 11/2003 |
| EP | 1 466 527 A | 10/2004 |
| WO | WO 97/29109 A | 8/1997 |

OTHER PUBLICATIONS

Sabino, Psychopharmacology (2006) 189:175-186.*
Moreau, S., et al., Synthesis and anticonvulsant Properties of Triazolo- and Imidazopyridazinyl Carboxamides and Carboxylic Acids, Bioorganic & Medicinal Chemistry, Elsevier Science Ltd., GB, vol. 6, No. 7, 1988, pp. 983-991.

* cited by examiner

Primary Examiner—James O Wilson
Assistant Examiner—Cecilia M Jaisle
(74) Attorney, Agent, or Firm—R. Craig Tucker; Danica Hostettler

(57) ABSTRACT

The present invention relates to novel substituted imidazo[1,2-b]pyridazine compounds of Formula (I): pharmaceutical compositions thereof, and the use such compounds as corticotropin releasing factor 1 (CRF1) receptor antagonists in the treatment of psychiatric disorders and neurological diseases.

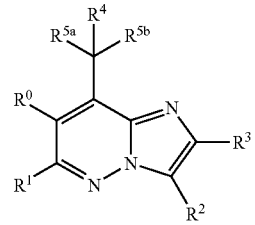

10 Claims, No Drawings

IMIDAZOPYRIDAZINE COMPOUNDS

This application is a 35 U.S.C. 371 National Stage Filing of PCT/US2006/009942 filed Mar. 20, 2006, which claims priority to U.S. Provisional Application No. 60/663,816, filed Mar. 21, 2005.

FIELD OF THE INVENTION

This invention relates to novel substituted imidazo[1,2-b] pyridazine compounds, pharmaceutical compositions thereof, and the use of such compounds as corticotropin releasing factor 1 (CRF1) receptor antagonists in the treatment of psychiatric disorders and neurological diseases.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., Proc. Natl. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response in the immune system to physiological, psychological, and immunological stressors [J. E. Blalock, Physiological Reviews 69:1 (1989); J. E. Morley, Life Sci. 41:527 (1987)].

There is evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [for a review, see: E. B. De Souze, Hosp. Practice 23:59 (1988)]. Furthermore, CRF is known to have a broad extrahypothalmic distribution in the CNS, contributing therein to a wide spectrum of autonomic behavioral and physiological effects [see, e.g., Vale et al., 1983; Koob, 1985; and E. B. De Souze et al., 1985]. For example, CRF concentrations are significantly increased in the cerebral spinal fluid of patients afflicted with affective disorder or major depression [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol. Psychiatry 25:355 (1989)]. Moreover, excessive levels of CRF are known to produce anxiogenic effects in animal models [see, e.g., Britton et al., 1982; Berridge and Dunn, 1986 and 1987]. The density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (intravenously administered) observed in depressed patients [P. W. Gold et al., Am. J. Psychiatry 141:619 (1984); F. Holsboer et al., Psychoneuroendocrinology 9:147 (1984); P. W. Gold et al., New Engl. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is also preliminary evidence that tricyclic antidepressants can alter CRF levels and thus modulate the numbers of receptors in the brain [Grigoriadis et al., Neuropsychopharmacology 2:53 (1989)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF both in the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist Ro 15-1788, which was without behavioral activity alone in the operant conflict test, reversed the effects of CRF in a dose-dependent manner while the benzodiazepine inverse agonist FG 7142 enhanced the actions of CRF [K. T. Britton et al., Psychopharmacology 94:396 (1988)]. Preliminary studies using the putative CRF receptor antagonist α-helical ovine CRF (9-41) in a variety of behavioral paradigms demonstrates that the antagonist produces "anxiolytic-like" effects that are qualitatively similar to the benzodiazepines [C. W. Berridge and A. J. Dunn, Horm. Behav. 21:393 (1987), Brain Research Reviews 15:71 (1990)].

CRF receptor subtypes, CRF1 and CRF2, have been identified and are distributed heterogeneously within the brain [D. T. Chalmers et al., TIPS 17:166-72 (1996)] thereby suggesting potential functional diversity [S. C. Heinrichs et al., Regul. Peptides 71:15 (1997)]. For example, widely distributed brain CRF1 receptors are strongly implicated in emotionality accompanying exposure to environmental stressors [G. Liebsch et al., Regul. Peptides 59: 229-39 (1995); D. W. Schulz, PNAS 93: 10477-82 (1996)]. Significantly, CRF1, not CRF2, receptors appear to mediate select anxiogenic like behaviors [Heinrichs et al., 1997]. A more discrete septal/hypothalmic distribution [D. T. Chalmers et al., J. Neurosci. 15(10): 6340-50 (1995)] and the availability of alternative endogenous ligands [J. Vaughan et al., Nature 378: 287-92 (1995)] suggest an altogether different functional role for the CRF2 receptor [Heinrichs et al., 1997]. For example, a novel CRF-family neuropeptide with preferential affinity for CRF2 relative to CRF1 receptors is reported to suppress appetite without producing the profile of behavioral activation observed with selective CRF1 agonism (H. Tezval et al., PNAS 101(25): 9468-9473 (2004)]. In many cases, CRF2 agonism produces similar effects to those reported for CRF1 antagonists or CRF1 gene deletion [S. C. Heinrichs, Trends in Pharmacological Sciences 20(8):311-5 (1999)]. While CRF2 agonists have been proposed as antiobesity agents, CRF1 antagonists may be an important treatment for obesity as well [C. Contoreggi et al., Neuroendocrinology 80(2): 111-23 (2004)].

In view of the above, efficacious and selective antagonists of CRF1 are desired as potentially valuable therapeutic agents for the treatment of psychiatric disorders and neurological diseases. It is thus desirable to discover new CRF1 antagonists.

SUMMARY OF THE INVENTION

The compounds of the present invention include CRF1 receptor antagonists. One embodiment of the present invention is a compound of Formula I:

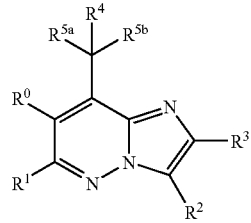

Formula I wherein:

R⁰ is hydrogen, halo, methyl or ethyl;

R¹ and R³ are independently methyl, methoxy, or trifluoromethyl;

R² is selected from the group consisting of:

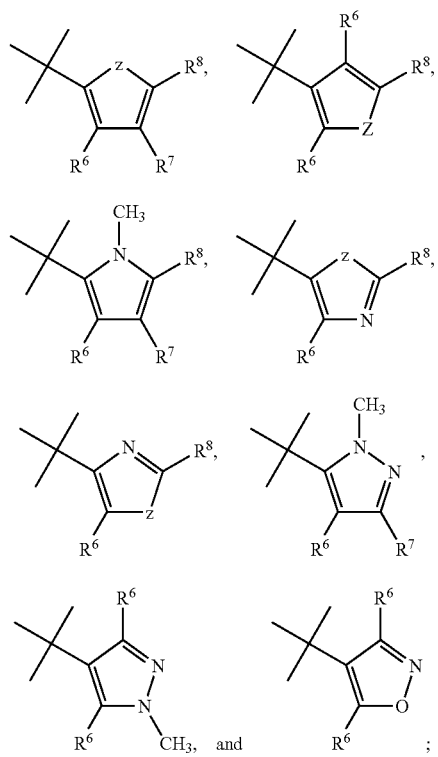

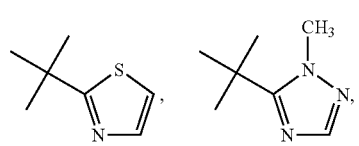

R⁴ is hydrogen, halo, or hydroxy;

R⁵ᵃ and R⁵ᵇ are independently ethyl or n-propyl;

R⁶ at each occurrence is independently hydrogen, halo, cyano, (C₁-C₄)alkyl, trifluoromethyl, methoxy, or phenyl;

R⁷ is hydrogen, halo, methyl, methoxy, dimethylamino,

R⁸ is selected from the group consisting of hydrogen, halo, cyano, (C₁-C₄)alkyl, RᵃRᵇN—, carbamyl, (C₁-C₂)alkoxy (C₁-C₂)alkyl, R¹¹—C(O)—,

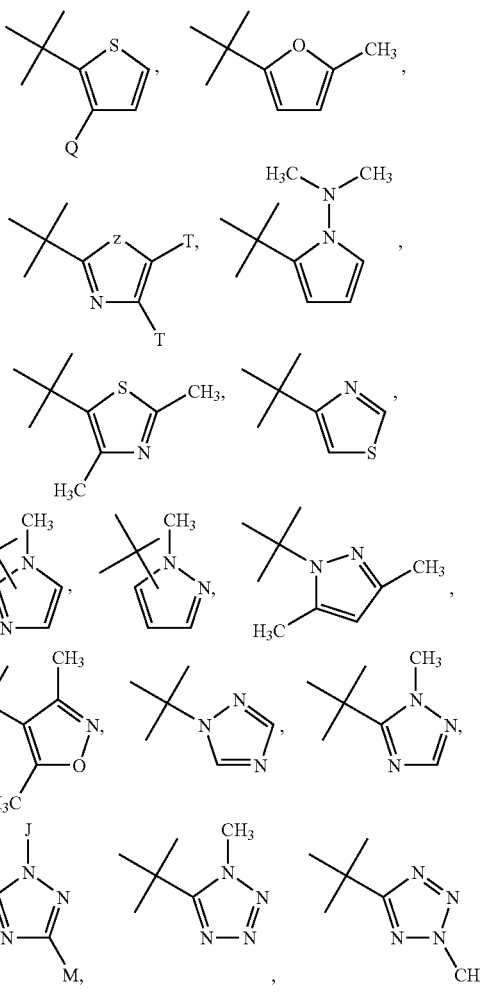

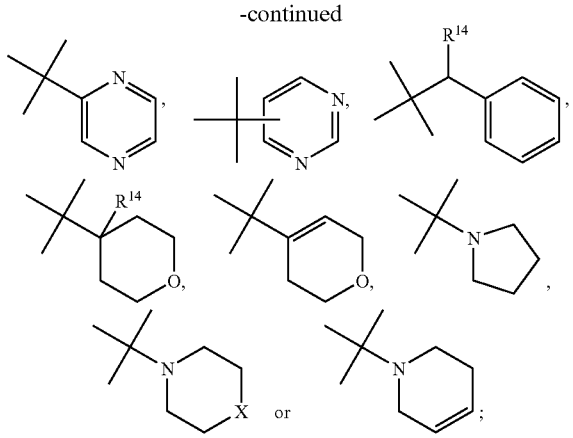

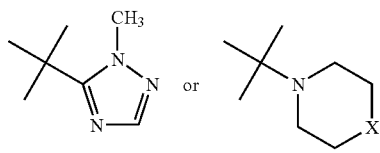

where X is O.

Another embodiment of the present invention is a pharmaceutical composition comprising a compound of Formula I, or a pharmaceutically acceptable salt thereof, and a pharmaceutically acceptable carrier, diluent or excipient.

Yet another embodiment of the present invention is a compound of Formula I, for use as a medicament.

A further embodiment of the present invention is use of a compound of Formula I for the manufacture of a medicament for treating anxiety, depression, major depressive disorder, alcohol withdrawal symptoms, or irritable bowel syndrome in a mammal. In another further embodiment, the mammal is a human.

$R^{11}$ is methoxy, methylamino, dimethylamino, or phenyl;
$R^{12}$ is hydrogen, halo, methyl, ethyl, trifluoromethyl, methoxy, trifluoromethoxy dimethylamino, acetyl, or methylsulfonyl;
$R^{13}$ is hydrogen, methyl or halo;
$R^{14}$ is hydrogen or hydroxy;
$R^{15}$ is methylthio, cyclopropyl, phenyl,

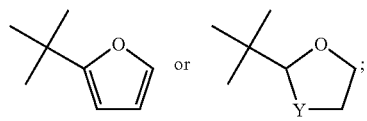

$R^a$ is hydrogen, $(C_1-C_5)$alkyl, $(C_3-C_5)$cycloalkyl, methoxy $(C_2-C_4)$alkyl, acetyl, $(C_1-C_2)$alkylsulfonyl, $(C_3)$alkenyl, $R^{15}$—$(CH_2)$n-, or $(C_1-C_2)$alkyl substituted with cyano, formyl, vinyl, or ethynyl;
$R^b$ is hydrogen or $(C_1-C_3)$alkyl;
X is —$CH_2$—, —CO—, —O—, —S— or —$SO_2$—;
Y is —$CH_2$— or —O—;
z is S or O;
n is 1 or 2;
Q is hydrogen or methyl;
T is hydrogen or methyl;
J is methyl, trifluoroethyl, or tert-butyl; and
M is methyl or halo;

and pharmaceutically acceptable salts thereof.

Another embodiment of the present invention is a compound of Formula I wherein $R^0$ and $R^4$ are hydrogen, $R^1$ and $R^3$ are methyl, and $R^{5a}$ and $R^{5b}$ are ethyl.

Yet another embodiment of the present invention is a compound of Formula I wherein $R^2$ is selected from the group consisting of

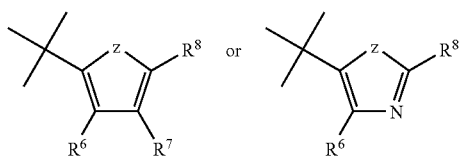

where z is S.

A further embodiment of the present invention is a compound of Formula I wherein $R^7$ is hydrogen.

Another another embodiment of the present invention is a compound of Formula I wherein $R^6$ is halo or methyl.

Yet another embodiment of the present invention is a compound of Formula I wherein $R^8$ is

DETAILED DESCRIPTION OF THE INVENTION

As used above, and throughout the description of the invention, the following terms, unless otherwise indicated, shall be understood to have the following meanings:

"Alkoxy" means an alkyl-O— group, wherein the alkyl group is as herein described. Exemplary alkoxy groups include methoxy, ethoxy, n-propoxy, i-propoxy, and n-butoxy.

"Alkyl" means a saturated aliphatic hydrocarbon group, which may be straight or branched, having 1 to 5 carbon atoms in the chain.

"Alkenyl" means an unsaturated aliphatic hydrocarbon group, which may be straight or branched, having 2 to 4 carbon atoms in the chain.

"Cycloalkyl" means a monocyclic group, having 3 to 5 carbon atoms.

"Halo" means fluoro, chloro, bromo, or iodo.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinateslaurylsulphonate salts, and the like. See, for example S. M. Berge, et al., "Pharmaceutical Salts," J. Pharm. Sci., 66, 1-19 (1977). Lists of suitable salts are found in Remington's Pharmaceutical Sciences, 17th ed., Mack Publishing. Company, Easton, Pa., 1985, p. 1418.

It will be understood that, as used herein, references to the compounds of Formula I are meant to also include the pharmaceutically acceptable salts thereof.

"Therapeutically effective amount" or "effective amount" means the amount of the compound of formula I of the present invention or pharmaceutical composition containing a compound of formula I of the present invention that will elicit the biological or medical response of or desired therapeutic effect on a tissue, system, animal or human that is being sought by the researcher, veterinarian, medical doctor or other clinician.

The terms "treatment," "treat," "treating," and the like, are meant to include both slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

The symbol "——"in a molecular structure indicates the position of attachment for that particular substituent.

When any variable occurs more than one time in any constituent or in formula I, its definition on each occurrence is independent of its definition at every other occurrence. Also, combinations of substituents and/or variables are permissible only if such combinations result in stable compounds. In choosing compounds of the present invention, one of ordinary skill in the art will recognize that the various substituents, i.e. $R^1$, $R^2$, etc., are to be chosen in conformity with well-known principles of chemical structure connectivity.

Under standard nomenclature used throughout this disclosure, the terminal portion of the designated side chain is described first, followed by the adjacent functionality toward the point of attachment. For example, an arylcarbonylaminoalkyl substituent is equivalent to aryl-C(O)—NH-alkyl-.

The present invention contemplates specific classes of compounds of Formula I. The following paragraphs describe such specific classes:
(a) $R^0$ is hydrogen;
(b) $R^1$ is methyl;
(c) $R^3$ is methyl;
(d) $R^1$ and $R^3$ are methyl;
(e) $R^2$ is

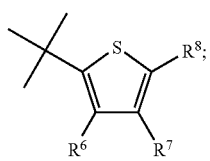

(f) $R^2$ is

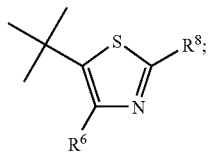

(g) $R^4$ is hydrogen;
(h) $R^{5a}$ is ethyl;
(i) $R^{5b}$ is ethyl;
(j) $R^{5a}$ and $R^{5b}$ are ethyl;
(k) $R^6$ is halo;
(l) $R^6$ is methyl;
(m) $R^7$ is hydrogen;
(n) $R^8$ is

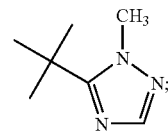

(o) $R^8$ is

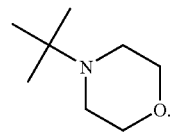

While all the compounds of Formula I are useful CRF1 receptor antagonists, the following paragraphs describe further specific classes:
(a) Each of $R^1$ and $R^3$ is methyl and each of $R^{5a}$ and $R^{5b}$ is ethyl;
(b) $R^1$ and $R^3$ are methyl, $R^{5a}$ and $R^{5b}$ are ethyl, and $R^0$ is hydrogen;
(c) $R^1$ and $R^3$ are methyl, $R^{5a}$ and $R^{5b}$ are ethyl, and $R^0$ and $R^4$ are hydrogen;
(d) $R^2$ is

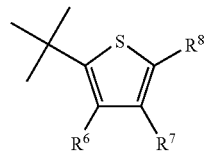

and $R^7$ is hydrogen;
(e) $R^2$ is

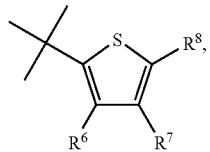

$R^7$ is hydrogen, and $R^6$ is halo;
(f) $R^2$ is

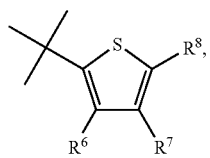

$R^7$ is hydrogen, and $R^6$ is methyl;

(g) $R^2$ is

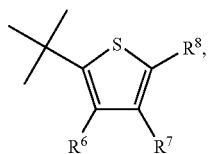

$R^7$ is hydrogen, and $R^6$ is halo or methyl, and $R^8$ is

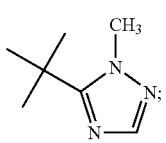

(h) $R^2$ is

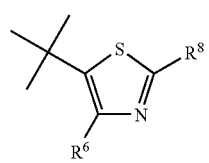

and $R^6$ is halo;

(i) $R^2$ is

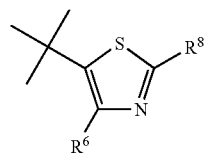

and $R^6$ is methyl;

(j) $R^2$ is

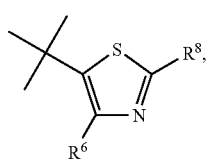

$R^6$ is halo or methyl, and $R^8$ is

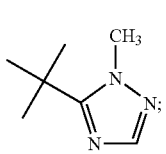

(k) $R^2$ is

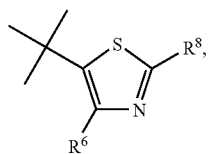

$R^6$ is halo or methyl, and $R^8$ is

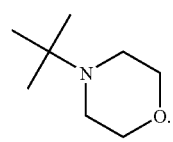

The following paragraphs describe even more specific classes of CRF1 receptor antagonists of the invention:

(a) $R^1$ and $R^3$ are methyl, $R^{5a}$ and $R^{5b}$ are ethyl, and $R^0$ and $R^4$ are hydrogen, $R^2$ is

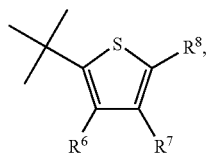

is $R^7$ is hydrogen, and $R^6$ is halo or methyl, and $R^8$ is

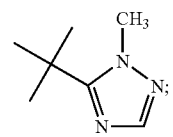

(b) $R^1$ and $R^3$ are methyl, $R^{5a}$ and $R^{5b}$ are ethyl, and $R^0$ and $R^4$ are hydrogen, $R^2$ is

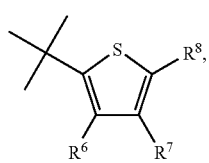

is $R^7$ is hydrogen, and $R^6$ is halo, and $R^8$ is

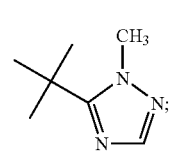

(c) $R^1$ and $R^3$ are methyl, $R^{5a}$ and $R^{5b}$ are ethyl, and $R^0$ and $R^4$ are hydrogen, $R^2$ is

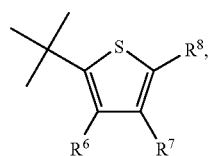

is $R^7$ is hydrogen, and $R^6$ is methyl, and $R^8$ is

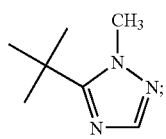

(d) $R^1$ and $R^3$ are methyl, $R^{5a}$ and $R^{5b}$ are ethyl, and $R^0$ and $R^4$ are hydrogen, $R^2$ is

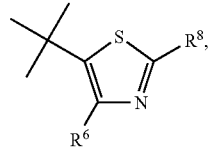

$R^6$ is halo or methyl, and $R^8$ is

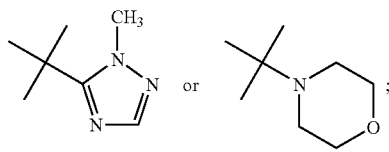

(e) $R^1$ and $R^3$ are methyl, $R^{5a}$ and $R^{5b}$ are ethyl, and $R^0$ and $R^4$ are hydrogen, $R^2$ is

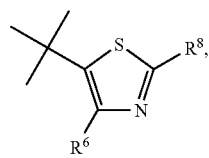

$R^6$ is halo, and $R^8$ is

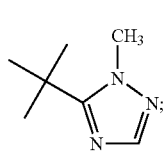

(f) $R^1$ and $R^3$ are methyl, $R^{5a}$ and $R^{5b}$ are ethyl, and $R^0$ and $R^4$ are hydrogen, $R^2$ is

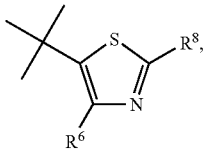

$R^6$ is halo, and $R^8$ is

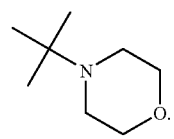

(g) $R^1$ and $R^3$ are methyl, $R^{5a}$ and $R^{5b}$ are ethyl, and $R^0$ and $R^4$ are hydrogen, $R^2$ is

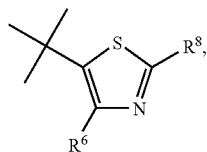

$R^6$ is methyl, and $R^8$ is

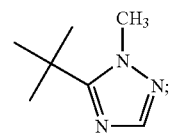

(h) $R^1$ and $R^3$ are methyl, $R^{5a}$ and $R^{5b}$ are ethyl, and $R^0$ and $R^4$ are hydrogen, $R^2$ is

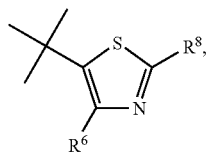

$R^6$ is methyl, and $R^8$ is

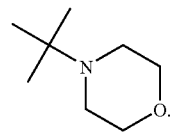

Preferably compounds of the invention exhibit a Ki value for CRF1 binding of 1 micromolar or less, more preferably of 500 nanomolar or less. Even more preferably, compounds of the invention exhibit a Ki value for CRF1 binding of 250 nanomolar or less, with 100 nanomolar or less being even further preferred. With even greater preference, compounds of the invention exhibit a Ki value for CRF1 binding of 30 nanomolar or less, while 15 nanomolar or less is even more greatly preferred. Compounds of the invention exhibiting a Ki value for CRF1 binding of 5 nanomolar or less are most preferred.

The present invention also provides a pharmaceutical composition comprising a compound of Formula I, or a pharmaceutically acceptable salt thereof and a pharmaceutically acceptable carrier, diluent, or excipient. A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa., 1985.

These compounds of formula I may be administered orally, topically, parenterally, by inhalation or spray or rectally in dosage unit formulations containing conventional non-toxic pharmaceutically acceptable carriers, adjuvants and vehicles.

The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Dosage forms suitable for administration generally contain from about 1 mg to about 300 mg of active ingredient per unit. In these pharmaceutical compositions, the active ingredient will ordinarily be present in an amount of about 0.5 to 95% by weight based on the total weight of the composition. Appropriate coatings may be applied to increase palatability or delayed adsorption.

The compounds of formula I are antagonists at the CRF1 receptor and are useful in the treatment of anxiety disorders, depression, major depressive disorder, and stress related disorders. Anxiety disorders are a group of diseases, recognized in the art, that includes phobic disorders, anxiety states, post-traumatic stress disorder and atypical anxiety disorders [The Merck Manual of Diagnosis and Therapy, 16th edition (1992)]. Emotional stress is often a precipitating factor in anxiety disorders, and such disorders generally respond to medications that lower response to stress. The compounds are also useful in smoking cessation programs. The method of treatment involves administration to a mammal (e.g. a human) an effective amount of a compound of the invention. In particular, therapeutically effective amounts of the compounds of this invention are amounts effective to antagonize, or lower, levels of corticotropin releasing factor (CRF) in a mammal (e.g. a human), thereby alleviating in the mammal's conditions characterized by abnormally high levels of CRF expression.

As such, the present invention provides a method for treating a condition which is treatable by reducing CRF1 receptor stimulation, comprising administering to the mammal (e.g. a human) in need thereof a compound of Formula I, or a pharmaceutically acceptable salt thereof, in an amount effective to antagonize CRF1 receptor stimulation.

The present invention also provides use of a compound of Formula I for the manufacture of a medicament for treating a condition which is treatable by reducing CRF1 receptor stimulation.

The present invention also provides a method of antagonizing CRF1 receptors in a warm-blooded animal, comprising administering to the animal a compound of the invention at amount effective to antagonize CRF1 receptors. The warm-blooded animal is preferably a mammal, and more preferably a human.

The present invention also provides a method of treating a disorder in a warm-blooded animal, which disorder manifests hypersecretion of CRF, or the treatment of which disorder can be effected or facilitated by antagonizing CRF1 receptors, comprising administering to the animal a therapeutically effective amount of a compound of the invention. The warm-blooded animal is preferably a mammal, and more preferably a human.

Compounds of Formula I, or a pharmaceutically acceptable salt thereof, are useful for treating various disorders and conditions in a mammal (e.g. human) including social anxiety disorder; panic disorder; obsessive-compulsive disorder; major depressive disorder; anxiety with co-morbid depressive illness; affective disorder; anxiety; depression; irritable bowel syndrome; post-traumatic stress disorder; supranuclear palsy; immune suppression; gastrointestinal disease; anorexia nervosa, bulimia, or other feeding disorder; drug or alcohol withdrawal symptoms; substance abuse disorder (e.g., nicotine, cocaine, ethanol, opiates, or other drugs); inflammatory disorder; fertility problems; disorders the treatment of which can be effected or facilitated by antagonizing CRF, including but not limited to disorders induced or facilitated by CRF; a disorder selected from inflammatory disorders such as rheumatoid arthritis and osteoarthritis, pain, asthma, psoriasis and allergies; generalized anxiety disorder; panic; phobias; obsessive-compulsive disorder; sleep disorders induced by stress; stress-related illnesses; pain perception such as fibromyalgia; mood disorders such as depression, including major depression, major depressive disorder, single episode depression, recurrent depression, child abuse induced depression, and postpartum depression; dysthemia; bipolar disorders; cyclothymia; fatigue syndrome; chronic fatigue syndrome; stress-induced headache; headache; cancer; human immunodeficiency virus (HIV) infections; neurodegenerative diseases such as Alzheimer's disease, Parkinson's disease, Huntington's disease, senile dementia of the Alzheimer's type, and multiinfarct dementia; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; obesity and the metabolic syndrome; infertility; premature birth; head traumas; spinal cord trauma; ischemic neuronal damage (e.g., cerebral ischemia such as cerebral hippocampal ischemia); excitotoxic neuronal damage; epilepsy; cardiovascular and heart related disorders including hypertension, tachycardia and congestive heart failure; stroke; immune dysfunctions including stress induced immune dysfunctions (e.g., stress induced fevers, stress induced infections in humans and animals, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependences on alcohol, cocaine, heroin, benzodiazepines, or other drugs); drug and alcohol withdrawal symptoms; osteoporosis; psychosocial dwarfism and hypoglycemia.

A compound of this invention can be administered to treat the above disorders or abnormalities by means that produce contact of the active agent with the agent's site of action in the body of a mammal (e.g. human), such as by oral or parenteral administration using appropriate dosage forms. The compounds can be administered by any conventional means available for use in conjunction with pharmaceuticals either as individual therapeutic agent or in combination of therapeutic agents. It can be administered alone, but will generally be administered with a pharmaceutical carrier selected on the basis of the chosen route of administration and standard pharmaceutical practice.

The therapeutically effective amounts of the compounds of the invention for treating the diseases or disorders described above in a warm-blooded animal can be determined in a variety of ways known to those of ordinary skill in the art, e.g., by administering various amounts of a particular agent to an animal afflicted with a particular condition and then determining the effect on the animal. Typically, therapeutically effective amounts of a compound of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular patient will depend upon a variety of factors including the activity of the specific compound employed, the age, body weight, general health, sex, diet, time of administration, route of administration, and rate of excretion, drug combination and the severity of the particular disease. Frequency of dosage may also vary depending on the compound used and the particular disease treated. However, for treatment of most CNS disorders, a dosage regimen of four-times daily or less is preferred. For the treatment of stress and depression, a dosage regimen of one or two-times daily is particularly preferred.

It will be appreciated that all combinations of specific and preferred embodiments discussed above and the examples discussed below are contemplated as being encompassed by the present invention, provided such combinations do not comprise inconsistent groupings. In addition, all examples described herein are for illustrative purposes, and are not intended to narrow the scope of the invention in any way.

Compounds of the invention can generally be prepared using the synthetic routes illustrated in the Schemes below. Starting materials can be prepared by procedures described in these schemes or by procedures that would be well known to one of ordinary skill in organic chemistry. The variables used in the schemes are as defined below or as in the claims.

The skilled artisan will appreciate that the introduction of certain substituents will create asymmetry in the compounds of Formula I. The present invention contemplates all enantiomers and mixtures of enantiomers and stereoisomers, that is, both the stereomerically pure form (e.g., geometrically pure, enantiomerically pure, or diastereomerically pure) and enantiomeric and stereoisomeric mixtures, including racemates. Enantiomeric and stereoisomeric mixtures can be resolved into their component enantiomers or stereoisomers by well known methods, such as chiral phase gas chromatography, chiral-phase high performance liquid chromatography, or crystallizing the compound as a chiral salt complex. Enantiomers and stereoisomers can also be obtained from stereomerically- or enantiomerically-pure intermediates, reagents, and catalysts by well known asymmetric synthetic methods.

Pharmaceutically acceptable salts are contemplated to be within the scope of the present invention. The compounds of the present invention are bases and salts of such compounds may be formed with acids, for example, a salt with inorganic acid such as hydrochloric acid or a salt with organic acid such as trifluoroacetic acid.

The compounds of this invention may be prepared by employing reactions as shown in the following schemes, in addition to other standard manipulations that are known in the literature or exemplified in the experimental procedures. These schemes, therefore, are not limited by the compounds listed nor by any particular substituents employed for illustrative purposes.

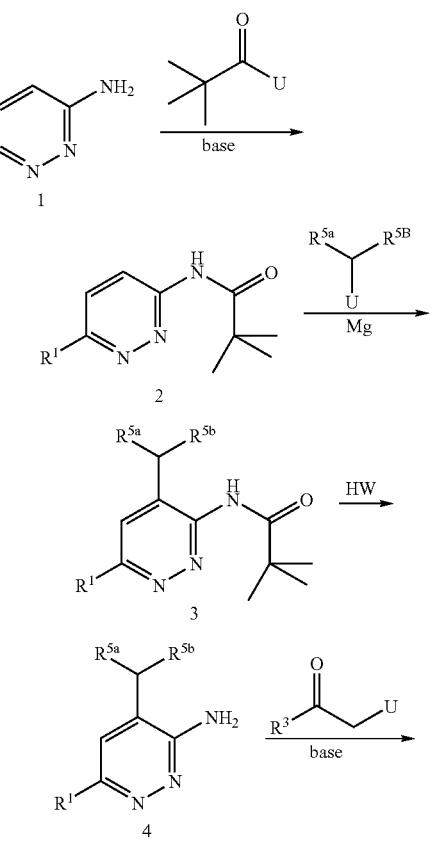

Scheme I
Synthesis of Imidazol[1,2-b]pyridazine fragment

-continued

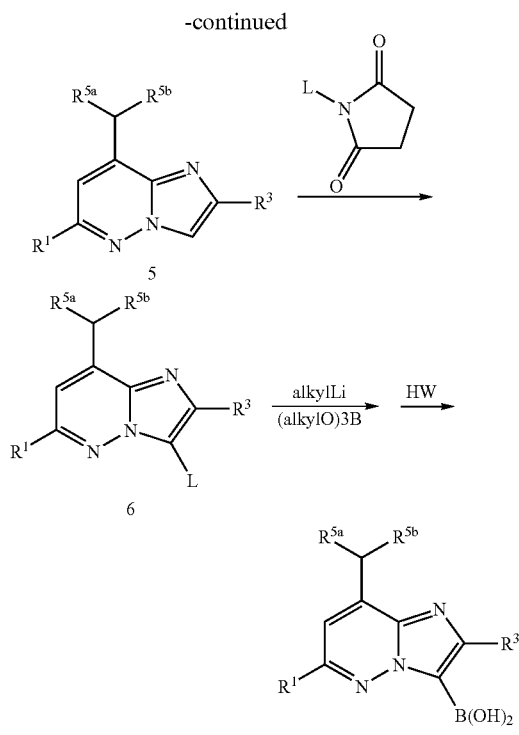

W = F, Cl, Br, I
L = Br, I
U = Cl, Br, I
$R^1$, $R^3$, $R^{5a}$, and $R^{5b}$ are defined supra.

In Scheme I, a substituted 3-amino-pyridazine 1 is acylated with pivaloyl halide and a base, e.g., triethylamine in a polar aprotic solvent, e.g., methylene chloride at from room temperature to the reflux to give amide 2. Amide 2 is treated with a Grignard reagent in diethylether or THF to give the 4-substituted amide 3. Amide 3 is hydrolyzed with aqueous HCl at from room temperature to 110° C. then neutralized to provide free amine 4. Amine 4 is treated with an alpha-halo ketone and base, e.g., sodium bicarbonate in 95% ethanol at from room temperature to 110° C. to give imidazopyridazine 5. Imidazopyridazine 5 is treated with a halogenating reagent e.g., N-iodo or N-bromosuccinimide in a polar aprotic solvent (e.g., acetonitrile) at from 0° C. to room temperature to give halide 6. Halide 6 undergoes halogen metal exchange with an alkyl lithium reagent, e.g., n-, sec-, or tert-butyllithium in diethylether or THF at from −78° C. to room temperature, followed by treatment with a trialkylborate, e.g., trimethylborate to give an intermediate boronic ester, which is hydrolyzed upon workup with aqueous HCl to provide boronic acid 7.

Scheme II
Synthesis of Compounds of Formula I by transition metal catalysis.

Equation 1.

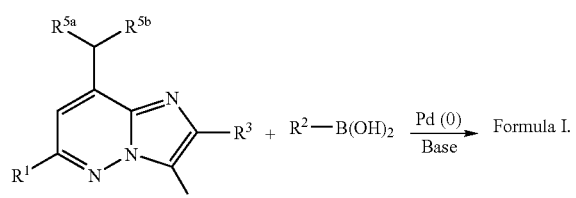

-continued
Equation 2.

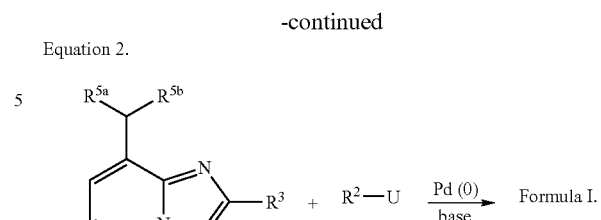

Where $R^2$-U is selected from the group consisting of:

[structures]

Equation 3.

$R^2—U$ $\xrightarrow{\text{1) alkyllithium} \atop \text{2) ZnCl2}}$
9

[structure]

$R^2—ZnU$ $\xrightarrow{\phantom{xx}6\phantom{xx}}$ Formula I.
10    Pd (0) base Equation 4.

$R^2—H$ $\xrightarrow{\text{1) alkyllithium or} \atop \text{LDA} \atop \text{2) ZnU}_2}$
11

[structure]

$R^2—ZnU$ $\xrightarrow{\phantom{xx}6\phantom{xx}}$ Formula I.
10    Pd (0) base Where R²—H is selected from the group consisting of:

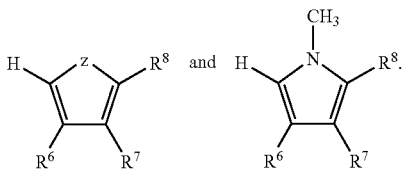

Equation 5.

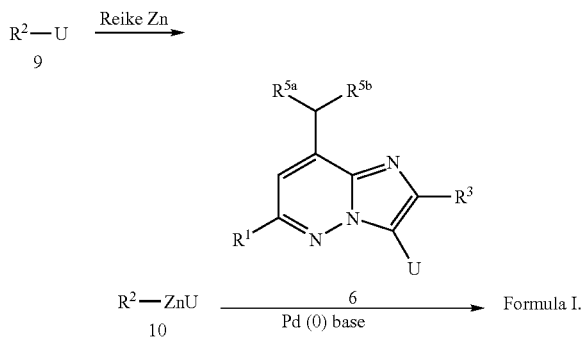

Equation 6.

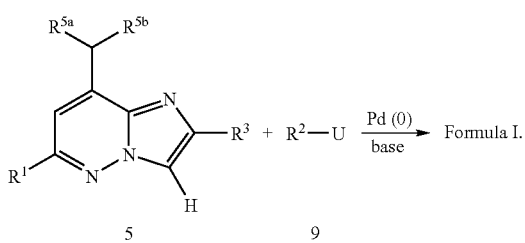

Equation 7.

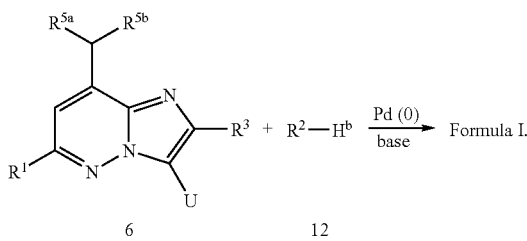

Where R²—H$^b$ is selected from:

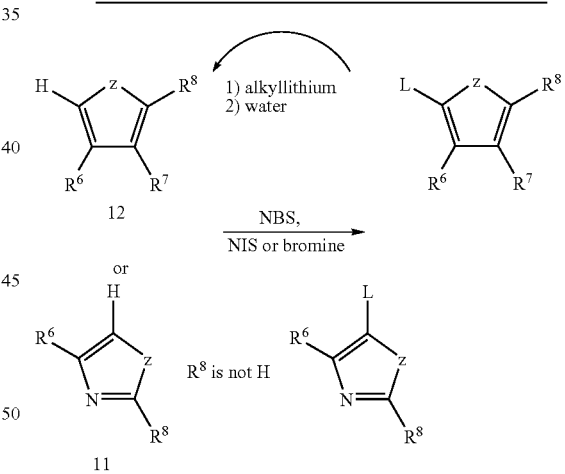

R¹, R², R³, R$^{5a}$, R$^{5b}$ R⁶, R⁷, R⁸, U, and z are defined supra.

In Scheme II equation 1, halide 6 can be used in a coupling reaction with a 5-membered ring heterocyclic boronic acid 8 in the presence of palladium catalysis, e.g., tetrakis-triphenylphosphine palladium (0) in a lower alkanol (methanol or n- or i-propanol)/DME mixture at from 70-120° C. to give compounds of formula I.

Alternately in equation 2, boronic acid 7 can be used in a coupling reaction with a 5 membered ring heterocyclic halide 9 and palladium catalysis, e.g., tetrakis-triphenylphosphine palladium (0) in a lower alkanol (methanol or n- or i-propanol)/DME mixture at from 70-120° C. to give a compound of formula I.

In equation 3, 5-membered ring heterocyclic halides 9 may undergo halogen-lithium exchange with, e.g., n-, sec- or tert-butyl lithium in THF or ether at −65° C., followed by lithium-zinc exchange with ZnCl₂ in either diethylether or THF at temperatures up to room temperature. The in situ organozinc reagent 10 may then undergo coupling with halide 6 in the presence of palladium, e.g., PdCl₂(dppf) in THF at from 70-120° C. to give a compound of formula I.

In equation 4, a 5-membered heterocyclic ring with a ring proton may be lithiated by either an alkyllithium, e.g., n-, sec- or tert-butyl lithium or lithium diisopropyl amide in THF or ether at −65° C. to room temperature followed by lithium-zinc exchange with anhydrous zinc halide in either diethylether or THF to give an organozinc reagent 10 that is used as in equation 3 above. One skilled in the art will also appreciate that commercially available organozinc reagents 10 can be used directly as an organozinc coupling partner.

Furthermore from equation 5, it may be advantageous or convenient to use Reike Zn in THF to directly convert a 5-membered ring heterocyclic halide 9 to an organozinc reagent 10 for coupling with a halide 6.

In equation 6, a 5 membered heterocyclic halide 9 can be directly coupled with the imidazo[1,2-b]pyridazine intermediate 5 in the presence of palladium, e.g., Pd₂(dba)₃, PdCl₂, Palladium acetate/TDBPP, or tetrakis-triphenylphosphine palladium (0) in DMF, THF, or NMP solvent from 70-120° C. to give a compound of formula I.

Alternately, from equation 7, the imidazo[1,2-b]pyridazine halide 6 may be directly coupled with a 5 membered heterocycle 11 in the presence of palladium, e.g., Pd₂(dba)₃, PdCl₂ or Palladium acetate/TDBPP in DMF, THF, or NMP solvent from 70-120° C. to give a compound of formula I.

Scheme III
Synthesis of Substituted 5 Membered Heterocyclic Halides

R⁶, R⁷, R⁸, L, and z are defined supra.

Several 5 membered heterocyclic rings and/or their bromides and/or iodides useful as starting materials for the synthesis of compounds of Formula I are commercially available or may be prepared by methods well know to the skilled artisan. From Scheme III, they may also be prepared by halogenation, e.g., with bromine, NBS or NIS. Furthermore, some of the intermediates 11 and 12 may be prepared by lithium halogen exchange followed by water quench.

Compounds of Formula I as intermediates in the preparation of other compounds of Formula I include the addition of aryllithium reagents (generated by the methods of equations 3 and 4 in Scheme II) to carbonyl compounds, e.g., aldehydes, ketones, esters, and Weinreb amides. The resulting carbinols or carbonyl compounds are further elaborated by halogenation under acidic conditions and by a second aryllithium addition, respectively.

Abbreviations

TBDMSCl or TBDMSiCl—tert-butyl-dimethylsilyl chloride
MS (ES)—Electrospray Mass spectrum
THF—tetrahydrofuran
DMSO—Dimethylsulfoxide
DMF—Dimethylformamide
DCM, CH2Cl2—dichloromethane
Dioxane—1,4-dioxane
N2—nitrogen gas
NIS—N-iodosuccinimide
NBS—N-bromosuccinimide
MeOH—methanol
EtOH—95% ethanol
RBF, RB—round bottom flask
RBSN—round bottom single neck flask
SiO2—silica gel
EtOAc, AcOEt—ethylacetate
GFF—glass microfiber filter
HPLC—high pressure liquid chromatography on silica gel
ISCO—ISCO brand low pressure liquid chromatography on silica gel
AcCl—acetyl chloride
LDA—lithium diisopropylamine
KOAc—Potassium Acetate
TBABr—Tetrabutyl ammonium bromide
NMP—N-Methylpyrrolidinone
TDBPP—Tris (2,4-di-t-butylphenyl) phosphite.
Pd$_2$ dba$_3$—Tris(dibenzylideneacetone)dipalladium
PdCl$_2$(dppf)—Dichloro(diphenylphosphinoferrocene)palladium
Tetrakis—tetrakis-(triphenylphosphine)-palladium
Dppf—1,1'-bis(diphenylphosphino)ferrocene)
r.t., RT—room temperature

EXAMPLES

Without further elaboration, it is believed that one skilled in the art can, using the preceding description, practice the present invention to its fullest extent. The following examples are provided to describe the invention in further detail. They are intended to illustrate and not to limit the invention in any way whatsoever. Examples 1-255 provide exemplary compounds and illustrate the preparation thereof. Examples A-D illustrate various biological assays that can be used for determining the biological properties of the compounds of the inventions. Those skilled in the art will promptly recognize appropriate variations from the procedures described in the examples.

Example 1

Preparation of 8-(1-ethyl-propyl)-3-(2,4-dimethyl-5-thiazolyl)-2,6-dimethyl-imidazo[1,2-b]pyridazine

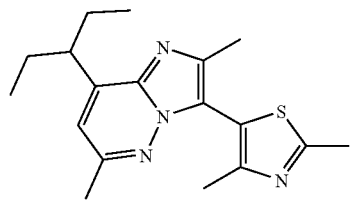

A. 6-Methyl-pyridizin-3-ylamine.

3-Chloro-6-methylpyridazine (25.0 g, 0.229 moles) is dissolve in 250 mL of NH$_4$OH and heated to 170° C. in a sealed container for 24 hours. The solvents are evaporated. The residue is triturated in methylene chloride, and a solid is filtered. This trituration procedure is repeated with the filtrate four times. The filtered solids are combined and dried in a vacuum oven overnight to obtain the title compound as an off-white solid 4.32 g (0.040 moles, 20%). $^1$H-NMR (dmso-d6): δ 7.1 (d, J=8.9 Hz, 1H); 6.67 (d, J=8.9 Hz, 1H); 6.04 (s, br, 2H); 2.33 (s, 3H) ppm. ES+=110 (100%, M+1).

B. 2,2-Dimethyl-N-(6-methyl-pyridazine-3-yl)-propionamide.

Method 1: To a dry flask is added 7.12 g (0.065 mole) of 6-methyl-pyridizin-3-ylamine in 170 ml dry methylene chloride. Next, 14.5 ml of triethylamine is added and the reaction is cooled to 0° C. Pivaloyl chloride (2.7 ml, 1.2 eq) is carefully added, and the reaction mixture is stir 10 minutes, removed from the bath, and stirred 4 hours more. Dichloromethane (200 mL) is added, and the reaction mixture is washed 3 times with saturated aqueous sodium bicarbonate, then brine. The organic layer is dried over sodium sulfate, filtered, and evaporated to an oil. The crude product is purified via silica gel chromatography using a hexane:ethyl acetate gradient giving the title compound as a white solid weighing 1.51 g (7.8 mmoles, 42.7%). $^1$H-NMR (DMSO-d$_6$), δ 10.39 (s, 1H); 8.11 (d, J=9.30 Hz, 1H); 7.51 (d, J=9.29 Hz, 1H); 2.54 (s, 3H); 1.23 (s, 9H) ppm. ES$^+$=194 (M+1).

Method 2: To a dry pressure tube is added 200 mg (1.56 mol) of 3-chloro-5-methylpyridazine, 190 mg (1.87 mmol) of trimethylacetamide, 14.6 mg (0.023 mmol) of rac-2,2'-bis (diphenylphosphine)-1,1'-binaphthyl, tris(dibenzylideneacetone)-dipalladium (0), 762.4 mg (2.34 mmol) of cesium carbonate and 1.5 ml dry tetrahydrofuran. The pressure tube is purged with nitrogen and sealed. The reaction is heated to 100° C. overnight. The reaction is then cooled, diluted with dichloromethane, and filtered through celite. Solvents are evaporated and the crude product is purified via silica gel chromatography using a ethyl acetate:hexane gradient to obtain 91 mg (0.47 mmol, 30%) as a white solid.

C. N-[4-(1-Ethyl-propyl)-6-methyl-pyridazin-3-yl]-2,2-dimethyl-propionamide.

Activated magnesium powder (19.2 g, 0.792 moles) is added to a dry 3 L flask fitted with a condenser and a drop funnel. The entire apparatus is heated with a gun dry under vacuum and allowed to cool. Enough ether is added to cover the magnesium. 3-Bromopentane (100 g, 0.662 mmol) is added to the addition funnel in 175 ml of diethyl ether. A ⅓ of the bromopentane solution is added to the magnesium and the reaction mixture is stirred under nitrogen until bubbling occurs. Then, the rest is dripped in at such a rate that the bubbling continues gently. The reaction is stirred for 30 minutes after bubbling ceases. Next, 2,2-dimethyl-N-(6-methyl-pyridazine-3-yl)-propionamide (21.3 g, 0.110 mmol) dissolved in 225 ml of dry THF is added dropwise. The reaction mixture is stirred for 1 hour. Saturated sodium tartrate (1 L) is carefully added, and the reaction is stirred for 30 minutes. The reaction mixture is transferred to a larger flask, 2 L of ethyl acetate is added, and the reaction is stirred 1 hour more. The layers are separate and the aqueous layer is extracted several times with ethyl acetate. The organic extracts are combined, and the solvents are evaporated. The residue is taken up in 600 mL of dichloromethane, and iodine (28 g, 0.110 mol) is added. The reaction is stirred for 2 hours. The organic layer is washed once with aqueous solution of sodium sulfite and then with water. The organic layer is dried over sodium sulfate, filtered, and evaporated to red oil. The crude product is purified via silica gel chromatography using a hexanes:ethyl acetate gradient. The product fractions are combined and evaporated. The residue is triturated in ethyl acetate and a light tan solid is filtered to obtain 12.0 g (45.6 mmol, 41%) of the title compound. $^1$H-NMR (DMSO-d$_6$), δ 9.88 (s, 1H); 7.59 (s, 1H); 2.60 (s, 3H); 2.39-2.42 (m, 1H); 1.21-1.37 (m, 2H); 1.38-1.43 (m, 2H); 1.23 (s, 9H); 0.71 (t, J=7.49 Hz, 6H) ppm. MS/ES$^+$=264.

D. 4-(1-Ethyl-propyl)-6-methyl-pyridazin-3-ylamine.

N-[4-(1-Ethyl-propyl)-6-methyl-pyridazin-3-yl]-2,2-dimethyl-propionamide (12.0 g, 45 mmol) is dissolved in 60 mL of concentrated hydrochloric acid. The reaction mixture is heated to 95° C. in a sealed flask for 2 hours. The reaction is worked up by pouring over ice and extracting with ethyl acetate three times. The organic layer is discarded, and the pH of the aqueous layer is adjusted using 2 N sodium hydroxide. The basic solution is extracted with ethyl acetate five times. The organic extracts are combined, dried over magnesium sulfate, filtered, and evaporated to obtain 6.68 g (37 mmol, 81%) of the title compound as a brownish oil. $^1$H-NMR (DMSO-d$_6$), δ 6.95 (s, 1H); 5.89 (s, br, 2H); 2.52-2.56 (m, 1H); 2.34 (s, 3H); 1.44-1.58 (m, 4H); 0.72 (t, J=7.04 Hz, 6H) ppm. MS/ES$^+$=180 (100%, M+1).

E. 8-(1-Ethyl-propyl)-2,6-dimethyl-imidazo[1,2-b]pyridazine.

4-(1-Ethyl-propyl)-6-methyl-pyridazin-3-ylamine (850 mg, 4.74 mmol), chloroacetone (0.415 ml, 5.22 mL) and 20 mL of ethanol are heated in the microwave at 110° C. for 35 minutes. Sodium bicarbonate (1.2 g, 14.2 mmol) is added, and the reaction mixture is heated in an oil bath at 100° C. overnight. The solvent is evaporate and the residue is taken up in ethyl acetate and washed three times with brine. The organic layer is dried over sodium sulfate, filtered, and evaporated to a brown oil. The crude product is purified via silica gel chromatography using a hexane:ethyl acetate gradient. The title compound is an oil weighing 3.69 g (17.0 mmol, 84%). $^1$H-NMR (DMSO-d$_6$), δ 7.34 (s, 1H); 6.84 (s, 1H); 2.85-3.10 (m, 1H); 2.43 (s, 3H); 2.32 (s, 3H); 1.70-1.80 (m, 4H); 0.712 (t, J=7.49 Hz, 6H) ppm. MS/ES$^+$=219 (100%, M+2).

F. 8-(1-Ethyl-propyl)-3-iodo-2,6-dimethyl-imidazo[1,2-b]pyridazine.

8-(1-Ethyl-propyl)-2,6-dimethyl-imidazo[1,2-b]pyridazine (5.1 g, 0.023 moles) and 50 mL of dry acetonitrile are added to a nitrogen purged flask and are cooled to 0° C. NIS (5.54 g, 0.025 moles) in 90 mL of dry acetonitrile is added. The bath is allowed to come to room temperature, and the reaction to stir overnight. The solvents are evaporated. The residue is taken up in ethyl acetate, washed two times with 50% aqueous solution of sodium thiosulfate and with brine. The organic layer is dried over sodium sulfate, filtered, and evaporated to a residue again. The crude product is triturated in a small amount of acetonitrile, and a solid is filter off. The trituration is repeated several times to obtain the title compound as a light tan solid weighing 7.29 g (0.021 moles, 91%). $^1$H-NMR (DMSO-d$_6$), δ 6.96 (s, 1H); 3.0-3.3 (m, 1H); 2.51 (s, 3H); 2.35 (s, 3H); 1.71-1.80 (m, 4H); 0.71 (t, J=7.48 hz, 6H) ppm. MS/ES$^+$=344 (100%, M+1).

G. 8-(1-Ethyl-propyl)-2,6-dimethyl-imidazo[1,2-b]pyridazine-3-yl boronic acid.

In an oven dried nitrogen purged 3 neck 50 mL round bottom flask, 1.00 g (2.91 mmol) of 8-(1-ethyl-propyl)-3-iodo-2,6-dimethyl-imidazo[1,2-b]pyridazine in 60 mL of dry THF is cooled to −78° C. 4.12 mL (7.00 mmol) of 1.7 M tert-butyllithium in hexanes is added and reaction is stirred at −78° C. for 1 hour. 0.818 mL (7.30 mmol) of trimethyl borate is added and reaction is followed by MS and TLC (1:1 Hexane:EA) Indication of product is observed by mass spectrum. The reaction is allowed to stir for an additional hour, quenched with 1 N hydrochloric acid, and diluted with ethyl acetate. The organic layer is separated, and the aqueous layer is extracted three times with 100 mL of ethyl acetate. The extracts are combined, dried over MgSO$_4$, filtered, and concentrated. The reaction residue is triturated in hexanes and a solid is filter off. MS, ES$^+$=262.2 (M+1).

H. 8-(1-Ethyl-propyl)-3-(2,4-dimethyl-5-thiazolyl)-2,6-dimethyl-imidazo[1,2-b]pyridazine.

To a microwave pressure tube is added 0.340 g (1.30 mmol) of 8-(1-ethyl-propyl)-2,6-dimethyl-imidazo[1,2-b]pyridazine-3-yl boronic acid, 0.100 g (0.521 mmol) of 5-bromo-2,4-dimethylthiazole, 0.361 g (0.313 mmol) of Pd(PPh$_3$)$_4$, 0.650 mL (1.30 mmol) of 2 M aqueous Na2CO3, and 2 mL 7:3:2 DME:H2O:EtOH, and the mixture is heated at 160° C. for 40 min. Reaction is checked by MS which indicates product present. The reaction mixture is partitioned between 75 mL of ethyl acetate and 75 mL of water. The layers are separated and the aqueous is extracted 3×50 mL of ethyl acetate, dried (MgSO4), and concentrated under vacuum. The crude mixture is purified by chromatography using hexanes/ethyl acetate as a solvent system. The product containing fractions are combined to obtain 0.100 g of the product, 58% yield. MS, ES+=329.2 (M+1); $^1$H-NMR (DMSO-d6)=6.974 (s, 1H); 3.085-3.052 (m, 1H); 2.665 (s, 3H); 2.438 (s, 3H); 2.290 (s, 3H); 2.147 (s, 3H); 1.849-1.727 (m, 4H); 0.776-0.738 (m, 6H) ppm.

Example 2

Preparation of 8-(1-ethyl-propyl)-3-(2-ethyl-4-methyl-5-yl)-2,6-dimethyl-imidazo[1,2-b]pyridazine

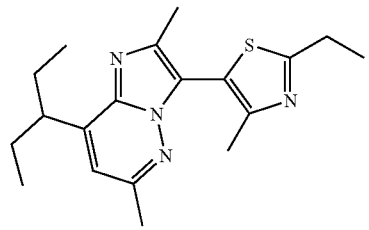

A. 5-Bromo-2-ethyl-4-methylthiazole.

In an oven dried, N$_2$ purged, 50 mL round bottom flask, 1.00 g (7.86 mmol) of 2-ethyl-4-methylthiazole is reacted with 0.487 mL (9.43 mmol) of bromine in 7 mL of acetic acid at room temperature. Reaction is checked by MS after 2 hours. The reaction mixture is partitioned between 50 mL H$_2$O and 25 mL of CH$_2$Cl$_2$. The layers are separated and the aqueous is extracted 3×25 mL of CH$_2$Cl$_2$. The organics are combined and washed 1×25 mL 1N Na$_2$S$_2$O$_3$, dried (MgSO$_4$), and concentrated under vacuum to give 1.38 g of the title compound, 85% yield. MS, ES+=206.0 (M+1); $^1$H-NMR (DMSO-d6)=2.940-2.810 (m, 2H); 2.253-2.251 (m, 3H); 1.225-1.222 (m, 3H) ppm.

B. 8-(1-Ethyl-propyl)-3-(2-ethyl-4-methyl-5-thiazolyl)-2,6-dimethyl-imidazo[1,2-b]pyridazine.

Using a procedure similar to Example 1H, 5-bromo-2-ethyl-4-methylthiazole produces the title product in 27% yield. MS, ES+=343.2 (M+1); $^1$H-NMR (DMSO-d6)=6.975 (s, 1H); 3.090-3.056 (m, 1H); 3.025-2.968 (m, 2H); 2.439 (s, 3H); 2.291 (s, 3H); 2.155 (s, 3H); 1.835-1.744 (m, 4H); 1.338-1.300 (m, 3H); 0.776-0.740 (m, 6H) ppm.

Example 3

Preparation of 8-(1-ethyl-propyl)-3-(2-isopropyl-4-methyl-5-thiazolyl)-2,6-dimethyl-imidazo[1,2-b]pyridazine

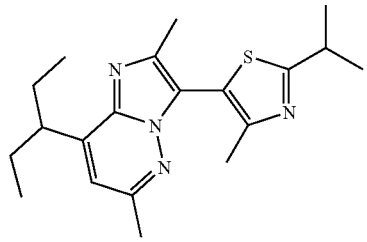

A. 5-Bromo-2-isopropyl-4-methylthiazole.

Using a procedure similar to Example 2A, 2-isopropyl-4-methylthiazole produces the title product in 90% yield. MS, ES+=220.0 (M+1); $^1$H-NMR (DMSO-d6)=3.210-3.175 (m, 1H); 2.257 (s, 3H); 1.264-1.248 (d, 6H) ppm.

B. 8-(1-Ethyl-propyl)-3-(2-isopropyl-4-methyl-5-thiazolyl)-2,6-dimethyl-imidazo[1,2-b]pyridazine.

Using a procedure similar to Example 1H, 5-bromo-2-isopropyl-4-methylthiazole produces the title product in 29% yield. MS, ES+=357.2 (M+1); $^1$H-NMR (DMSO-d6)=6.990 (s, 1H); 3.120-3.050 (m, 1H); 2.442 (s, 3H); 2.294 (s, 3H); 2.158 (s, 3H); 1.810-1.750 (m, 4H); 1.362-1.344 (d, 6H); 0.777-0.741 (m, 6H) ppm.

Example 4

Preparation of 8-(1-ethyl-propyl)-3-(4-methyl-2-phenyl-5-thiazolyl)-2,6-dimethyl-imidazo[1,2-b]pyridazine

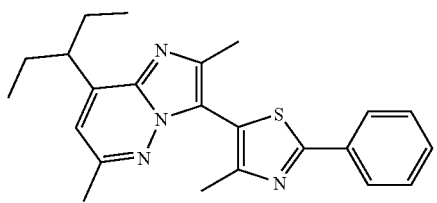

A. 5-Bromo-4-methyl-2-phenylthiazole.

Using a procedure similar to Example 2A, 4-methyl-2-phenylthiazole produces the title product in 90% yield. MS, ES+=256.0 (M+1); $^1$H-NMR (DMSO-d6)=7.900-7.867 (m, 2H); 7.538-7.512 (m, 3H); 2.407 (s, 3H) ppm.

B. 8-(1-Ethyl-propyl)-3-(4-methyl-2-phenyl-5-thiazolyl)-2,6-dimethyl-imidazo[1,2-b]pyridazine.

Using a procedure similar to Example 1H, 5-bromo-4-methyl-2-phenylthiazole produces the title product in 24% yield. MS, ES+=391.3 (M+1); $^1$H-NMR (DMSO-d6)=8.005-7.995 (m, 2H); 7.538-7.534 (m, 3H); 7.010 (s, 1H); 3.185-3.095 (m, 1H); 2.496 (s, 3H); 2.394 (s, 3H); 2.316 (s, 3H); 1.895-1.785 (m, 4H); 0.826-0.788 (m, 6H) ppm.

Example 5

Preparation of 8-(1-ethyl-propyl)-3-[4-methyl-2-(2-methyl)propyl-5-thiazolyl]-2,6-dimethyl-imidazo[1,2-b]pyridazine

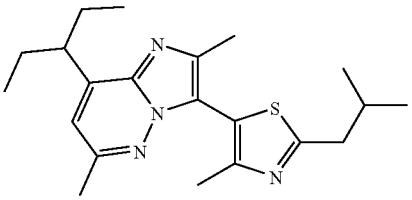

A. 5-Bromo-4-methyl-2-(2-methyl)propylthiazole.

Using a procedure similar to Example 2A, 4-methyl-2-(2-methyl)propylthiazole produces the title product in 96% yield. MS, ES+=234.1 (M+1); $^1$H-NMR (DMSO-d6)=2.744 (m, 2H); 2.259 (s, 3H); 1.895-2.000 (m, 1H); 0.905-0.888 (m, 6H) ppm.

B. 8-(1-Ethyl-propyl)-3-(4-methyl-2-(2-methyl)propyl-5-thiazolyl)-2,6-dimethyl-imidazo[1,2-b]pyridazine.

Using a procedure similar to Example 1H, 5-bromo-4-methyl-2-(2-methyl)propylthiazole produces the title product in 7% yield. MS, ES+=371.3 (M+1); $^1$H-NMR (DMSO-d6)=7.013 (s, 1H); 3.109 (m, 1H); 2.892-2.875 (d, 2H); 2.517 (s, 3H); 2.513 (s, 3H); 2.476 (s, 3H); 2.107-2.073 (m, 1H); 1.868-1.780 (m, 4H); 1.018-1.002 (d, 6H); 0.813-0.775 (m, 6H) ppm.

Example 6

Preparation of 8-(1-Ethyl-propyl)-3-[4-methyl-5-thiazolyl]-2,6-dimethyl-imidazo[1,2-b]pyridazine

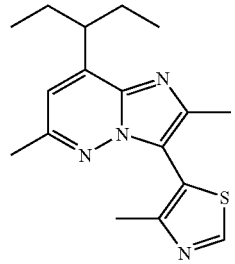

3.00 g of 8-(1-Ethyl-propyl)-3-iodo-2,6-dimethyl-imidazo[1,2-b]pyridazine (8.74 mmol), 4.32 g of 4-methyl-2H-thiazole (43.6 mmol), 453 mg of triphenylphosphine (1.73 mmol) and 5.85 g of cesium carbonate (18.0 mmol) are placed into the sealed tube with 20 ml of DMF and N2 gas is bubbled in for 40 min. 39 mg of Pd2 dba3 (0.43 mmol) is added and the tube is sealed and heated at 130° C. overnight. The cooled reaction mixture is filtered and applied onto silica-gel column (Hexane→Hexane:AcOEt=3:1) to give 2.12 g of the title compound (77%). $^1$H-NMR (DMSO-d6) δ 9.215 (s, 1H); 6.993 (s, 1H); 3.079 (m, 1H); 2.480 (s, 3H); 2.439 (s, 3H); 2.302 (s, 3H); 1.824-1.751 (m, 4H); 0.780-0.743 (m, 6H) ppm. MS, ES+=315.2.

Example 7

Preparation of 8-(1-ethyl-propyl)-2,6-dimethyl-3-(4-methyl-2-pyridin-2-yl-thiazol-5-yl)-imidazo[1,2-b]pyridazine

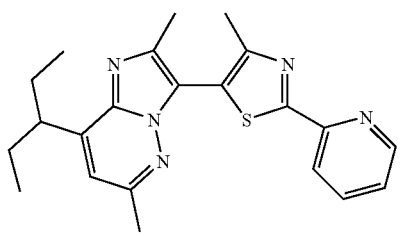

A. 8-(1-ethyl-propyl)-3-[2-bromo-4-methyl-5-thiazolyl]-2,6-dimethyl-imidazo[1,2-b]pyridazine.

In an oven dried, N2 purged, 15 mL round bottom flask, 0.028 g (0.089 mmol) of 8-(1-ethyl-propyl)-3-[4-methyl-5-thiazolyl]-2,6-dimethyl-imidazo[1,2-b]pyridazine. in 1.5 mL of dry $CH_2Cl_2$ is cooled to 0 C. 0.019 g (0.107 mmol) of NBS is added and reaction is stirred overnight allowing bath to come to room temperature. Reaction mixture is directly purified by chromatography using hexane/ethyl acetate as solvent system. The product containing fractions are combined to obtain 0.012 g, 34% yield. MS, ES+=395.1 (M+1); $^1$H-NMR (DMSO-d6)=7.070 (s, 1H); 3.10 (m, 1H); 2.49 (s, 3H); 2.36 (s, 3H); 2.25 (s, 3H); 1.85-1.78 (m, 4H); 0.81-0.77 (m, 6H) ppm.

B. 8-(1-Ethyl-propyl)-2,6-dimethyl-3-(4-methyl-2-pyridin-2-yl-thiazol-5-yl)-imidazo[1,2-b]pyridazine.

A mixture of 3-(2-bromo-4-methyl-thiazol-5-yl)-8-(1-ethyl-propyl)-2,6-dimethyl-imidazo[1,2-b]pyridazine (380 mg, 0.96 mmol), 2-pyridinezinc bromide (0.5 M in THF, 2.1 mL, 4 mmol), Pd(PPh$_3$)$_4$ (30 mg, 0.026 mmol) and THF (3 mL) is heated at 80° C. for 18 hours. Ethyl acetate (20 mL) is added. The organic layer is separated, dried over magnesium sulfate, filtered, and the solvent removed in vacuo. Purification is performed via silica gel chromatography using a 3:1 mixture of hexanes and ethyl acetate as eluent to produce the title compound 325 mg (86%). $^1$H-NMR (CDCl$_3$), δ 9.55 (m, 1H); 8.10 (m, 1H); 7.73 (m, 1H); 7.26 (m, 1H); 6.58 (s, 1H); 3.24 (m, 1H); 2.43 (s, 3H); 2.40 (s, 3H); 2.33 (s, 3H); 1.76 (m, 4H); 0.80 (t, 6H) ppm. MS/ES+=391 (100%, M+1).

Example 8

Preparation of 8-(1-ethyl-propyl)-3-[4-methyl-2-(3-pyridyl)-5-thiazolyl]-2,6-dimethyl-imidazo[1,2-b]pyridazine

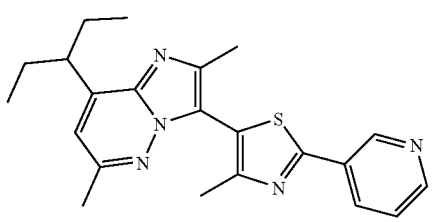

To a microwave pressure tube is added 0.070 g (0.178 mmol) of 8-(1-ethyl-propyl)-3-[2-bromo-4-methyl-5-thiazolyl]-2,6-dimethyl-imidazo[1,2-b]pyridazine, 0.066 g (0.534 mmol) of pyridine-3-boronic acid, 0.103 g (0.089 mmol) of Pd(PPh3)4, 0.267 mL (0.534 mmol) of 2 M aqueous Na2CO3, and 1 mL 7:3:2 DME:H2O:EtOH, and the mixture is heated at 160° C. for 60 min. The reaction mixture is partitioned between 25 mL of ethyl acetate and 25 mL of water. The layers are separated and the aqueous is extracted 3×25 mL of ethyl acetate, dried (MgSO4), and concentrated under vacuum. The crude mixture is purified by chromatography using hexanes/Ethyl acetate as a solvent system. The product containing fractions are combined to obtain 0.045 g of the product, 64% yield. MS, ES+=392.2 (M+1); $^1$HNMR (DMSO-d6) δ 9.18 (s, 1H); 8.65 (m, 1H); 8.34 (d, 1H); 7.60 (m, 1H); 7.06 (s, 1H); 3.06 (m, 1H); 2.50 (s, 3H); 2.40 (s, 3H); 2.34 (s, 3H); 1.87-1.82 (m, 4H); 0.83-0.79 (m, 6H) ppm.

Example 9

Preparation of 8-(1-ethyl-propyl)-3-[4-methyl-2-(4-pyridyl)-5-thiazolyl]-2,6-dimethyl-imidazo[1,2-b]pyridazine

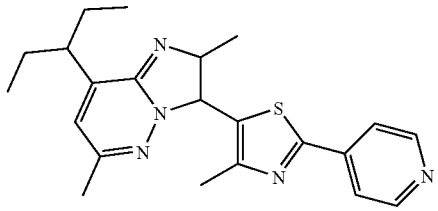

Using a procedure similar to Example 8, pyridine-4-boronic acid produces the title compound in 10% yield. MS, ES+=392.3 (M+1); $^1$HNMR (DMSO-d6)=8.79 (s, 2H); 7.80 (m, 2H); 7.07 (s, 1H); 3.12 (m, 1H); 2.50 (s, 3H); 2.40 (s, 3H); 2.36 (s, 3H); 1.90-1.80 (m, 4H); 0.83-0.79 (m, 6H) ppm.

Example 10

Preparation of 8-(1-ethyl-propyl)-3-[4-methyl-2-(thiophene-2-yl)-5-thiazolyl]-2,6-dimethyl-imidazo[1,2-b]pyridazine

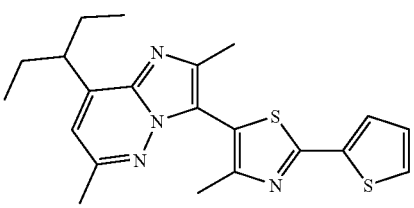

Using a procedure similar to Example 8, thiophene-2-boronic acid produces the title compound in 89% yield. MS, ES+=397.1 (M+1); $^1$H-NMR (DMSO-d6)=7.81-7.79 (d, 1H); 7.78-7.77 (d, 1H); 7.21-7.20 (m, 1H); 7.05 (s, 1H); 3.19-3.15 (m, 1H); 2.50 (s, 3H); 2.39 (s, 3H); 2.27 (s, 3H); 1.85-1.83 (m, 4H); 0.82-0.79 (m, 6H) ppm.

Example 11

Preparation of 8-(1-ethyl-propyl)-3-[4-methyl-2-(2-fluorophenyl)-5-thiazolyl]-2,6-dimethyl-imidazo[1,2-b]pyridazine

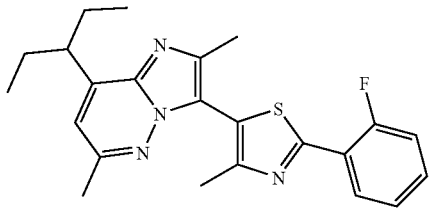

Using a procedure similar to Example 8, 2-fluorophenyl boronic acid produces the title compound in 82% yield. MS, ES+=409.2 (M+1); $^1$H-NMR (DMSO-d6)=8.32-8.28 (m, 1H); 7.60-7.58 (m, 1H); 7.57-7.41 (m, 2H); 7.05 (s, 1H); 3.13-3.12 (m, 1H); 2.49 (s, 3H); 2.40 (s, 3H); 2.35 (s, 3H); 1.91-1.780 (m, 4H); 0.87-0.79 (m, 6H) ppm.

Example 12

Preparation of 8-(1-ethyl-propyl)-3-[4-methyl-2-(4-fluorophenyl)-5-thiazolyl]-2,6-dimethyl-imidazo[1,2-b]pyridazine

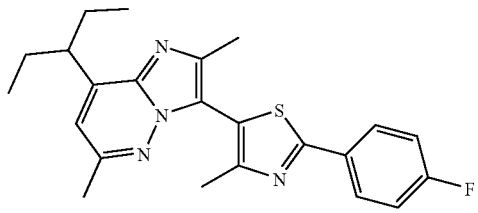

Using a procedure similar to Example 8, 4-fluorophenyl boronic acid produces the title compound in 63% yield where the crude mixture is purified by chromatography using 2% methanol in dichloromethane as a solvent system. MS, ES+=409.2 (M+1); $^1$H-NMR (DMSO-d6)=8.06-8.03 (m, 2H); 7.408-7.36 (m, 2H); 7.05 (s, 1H); 3.14-3.11 (m, 1H); 2.50 (s, 3H); 2.39 (s, 3H); 2.31 (s, 3H); 1.90-1.78 (m, 4H); 0.83-0.79 (m, 6H) ppm.

Example 13

Preparation of 8-(1-ethyl-propyl)-3-[4-methyl-2-(3-fluorophenyl)-5-thiazolyl]-2,6-dimethyl-imidazo[1,2-b]pyridazine

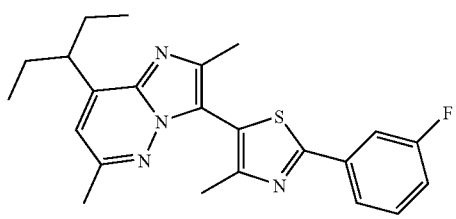

Using a procedure similar to Example 8, 3-fluorophenyl boronic acid produces the title compound in 77% yield where the crude mixture is purified by chromatography using 2% methanol in dichloromethane as a solvent system. MS, ES+=409.2 (M+1); $^1$H-NMR (DMSO-d6)=7.84-7.78 (m, 2H); 7.64-7.57 (m, 2H); 7.41-7.36 (m, 1H); 7.06 (s, 1H); 3.15-3.111 (m, 1H); 2.45 (s, 3H); 2.40 (s, 3H); 2.32 (s, 3H); 1.91-1.78 (m, 4H); 0.83-0.79 (m, 6H) ppm.

Example 14

Preparation of 8-(1-ethyl-propyl)-3-[4-methyl-2-(2,4-difluorophenyl)-5-thiazolyl]-2,6-dimethyl-imidazo[1,2-b]pyridazine

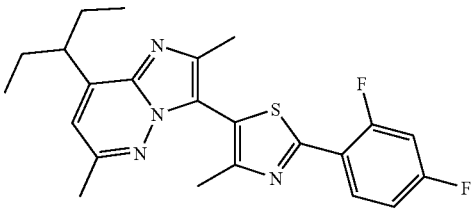

Using a procedure similar to Example 8, 2,4-difluorophenyl boronic acid produces the title compound in 76% yield. MS, ES+=427.2 (M+1); $^1$H-NMR (DMSO-d6)=8.370-8.310 (m, 1H); 7.586-7.540 (m, 1H); 7.36-7.32 (m, 1H); 7.054 (s, 1H); 3.14-3.13 (m, 1H); 2.492 (s, 3H); 2.391 (s, 3H); 2.345 (s, 3H); 1.906-1.797 (m, 4H); 0.826-0.788 (m, 6H) ppm.

Example 15

Preparation of 8-(1-ethyl-propyl)-3-[4-methyl-2-(o-tolyl)-5-thiazolyl]-2,6-dimethyl-imidazo[1,2-b]pyridazine

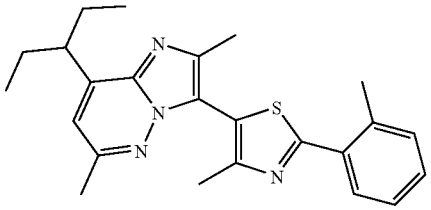

Using a procedure similar to Example 8, o-tolyl boronic acid produces the title compound in 87% yield where the crude mixture is purified by silica gel chromatography using 2% methanol in dichloromethane as a solvent system. MS, ES+=405.2 (M+1); $^1$H-NMR (DMSO-d6)=7.857-7.838 (d, 1H); 7.429-7.419 (d, 2H); 7.393-7.352 (m, 1H); 7.049 (s, 1H); 3.145-3.114 (m, 1H); 2.647 (s, 3H); 2.502 (s, 3H); 2.406 (s, 3H); 2.337 (s, 3H); 1.907-1.782 (m, 4H); 0.827-0.791 (m, 6H) ppm.

Example 16

Preparation of 8-(1-ethyl-propyl)-3-[4-methyl-2-(3,4-difluorophenyl)-5-thiazolyl]-2,6-dimethyl-imidazo[1,2-b]pyridazine

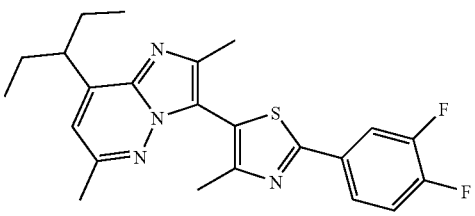

Using a procedure similar to Example 8, 3,4-difluorophenyl boronic acid produces the title compound in 74% yield where the crude mixture is purified by chromatography using 2% methanol in dichloromethane as a solvent system. MS, ES+=427.2 (M+1); $^1$H-NMR (DMSO-d6)=8.07-8.02 (m, 1H); 7.849 (s, 1H); 7.66-7.59 (m, 1H); 7.062 (s, 1H); 3.12-

3.11 (m, 1H); 2.498 (s, 3H); 2.392 (s, 3H); 2.319 (s, 3H) 1.905-1.779 (m, 4H); 0.826-0.790 (m, 6H) ppm.

Example 17

Preparation of 8-(1-ethyl-propyl)-3-[4-methyl-2-(4-fluoro-2-methylphenyl)-5-thiazolyl]-2,6-dimethyl-imidazo[1,2-b]pyridazine

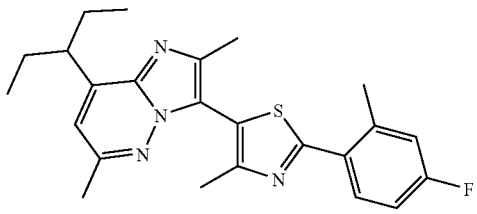

Using a procedure similar to Example 8, 4-fluoro-2-methylphenyl boronic acid produces the title compound 0.040 g (37% yield). MS, ES+=423.2 (M+1); $^1$H-NMR (DMSO-d6) =7.918-7.882 (m, 1H); 7.323-7.241 (d, 1H); 7.234-7.192 (m, 1H); 7.049 (s, 1H); 3.142-3.111 (m, 1H); 2.650 (s, 3H); 2.499 (s, 3H); 2.401 (s, 3H); 2.330 (s, 3H); 1.905-1.779 (m, 4H); 0.969-0.788 (m, 6H) ppm.

Example 18

Preparation of 8-(1-ethyl-propyl)-3-[4-methyl-2-(4-trifluoromethoxyphenyl)-5-thiazolyl]-2,6-dimethyl-imidazo[1,2-b]pyridazine

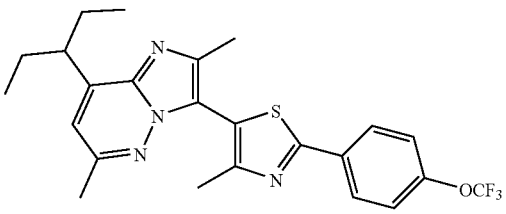

To a microwave pressure tube is added 0.100 g (0.254 mmol) of 8-(1-ethyl-propyl)-3-[2-bromo-4-methyl-5-thiazolyl]-2,6-dimethyl-imidazo[1,2-b]pyridazine, 0.157 g (0.762 mmol) of 4-(trifluoromethoxy)benzene boronic acid, 0.147 g (0.127 mmol) of Pd(PPh3)4, 0.381 mL (0.762 mmol) of 2 M aqueous sodium carbonate, and 2 mL Ethanol. The reaction mixture is heated in the microwave at 160° C. for up to 1 hour. The reaction mixture is partitioned between 50 mL of ethyl acetate and 50 mL of water. The layers are separated and the aqueous is extracted 3×50 mL of ethyl acetate, dried (MgSO4), and concentrated under vacuum. The crude mixture is purified by chromatography using 2% methanol in dichloromethane as a solvent system. The product containing fractions are combined to obtain 0.085 g of the product, 70% yield. MS, ES+=475.2 (M+1); $^1$H-NMR (DMSO-d6)=8.134-8.112 (d, 2H); 7.553-7.532 (d, 2H); 7.059 (s, 1H); 3.142-3.113 (m, 1H); 2.500 (s, 3H); 2.399 (s, 3H); 2.330 (s, 3H); 1.907-1.782 (m, 4H); 0.827-0.791 (m, 6H) ppm.

Example 19

Preparation of 8-(1-ethyl-propyl)-2,6-dimethyl-3-(4-methyl-thiophen-3-yl)-imidazo[1,2-b]pyridazine

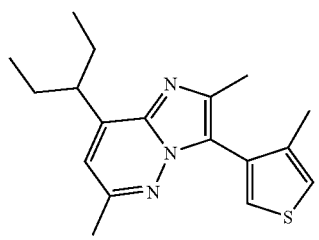

A. 4,4,5,5-Tetramethyl-2-(4-methyl-thiophen-3-yl)-[1,3,2]dioxaborolane.

To a 250 mL round bottom flask is added 3-bromo-4-methyl-thiophene (5.00 g, 28.24 mmol), bis(pinacolato)diboron (7.89 g, 31.06 mmol) and KOAc (8.32 g, 84.72 mmol) in DMSO (85 mL). The mixture is degassed by bubbling $N_2$ for 5 min, PdCl$_2$(dppf)$_2$.CH$_2$Cl$_2$ (1.15 g, 1.42 mmol) is added and the reaction mixture is heated to and stirred at 85° C. overnight. The reaction is cooled to rt, and diluted with EtOAc (400 mL), washed with H$_2$O (3×300 mL); dried with MgSO$_4$, filtered and concentrated. Purification of the crude material by chromatography to give the title compound (3.69 g, 16.5 mmol, 58%). ES-MS (m/z): calcd for $C_{11}H_{17}BO_2S$ (M$^+$): 224.1; found: 224.9.

B. 4-Methyl 3-thiophene boronic acid.

A solution of 4,4,5,5-tetramethyl-2-(4-methyl-thiophen-3-yl)-[1,3,2]dioxaborolane (3.69 g, 16.47 mmol) in acetone (30 mL) is treated with H$_2$O (30 mL), followed by NaIO$_4$ (7.05 g, 32.95 mmol). The resulting mixture is stirred at rt overnight. The organic solvent is removed in vacuo. The residue is diluted with H$_2$O (50 mL), extracted with EtOAc ((2×100 mL). The organic extracts are combined, dried with Na$_2$SO$_4$, filtered and concentrated. Purification of the crude material by chromatography gives the title compound (0.82 g, 5.78 mmol, 35%). $^1$H NMR (CDCl$_3$): δ 1.33 (s, 3H), 2.64-2.66 (m, 2H), 7.00-7.02 (m, 1H), 8.27 (d, J=3.0 Hz, 1H). ES-MS (m/z): calcd for $C_5H_7BO_2S$ (M−H)$^−$: 141.0; found: 141.1.

C. 8-(1-Ethyl-propyl)-2,6-dimethyl-3-(4-methyl-thiophen-3-yl)-imidazo[1,2-b]pyridazine.

To a 100 mL round bottom flask containing 4-methyl 3-thiophene boronic acid (0.27 g, 1.91 mmol), and 8-(1-ethyl-propyl)-3-iodo-2,6-dimethyl-imidazo[1,2-b]pyridazine (0.65 g, 1.91 mmol) in 20 mL of a stock solution (DME:H$_2$O: EtOH=7:3:2) is added 2 M Na$_2$CO$_3$ (1.9 mL). The resulting mixture is degassed by bubbling N$_2$ for 5 min. Then Pd(PPh$_3$)$_4$ (0.11 g, 0.096 mmol) is added. The reaction mixture is refluxed overnight. The reaction is diluted with H$_2$O (20 mL); extracted with EtOAc (3×30 mL); dried (Na$_2$SO$_4$), filtered and purification of the crude material by chromatography gives the title compound (0.52 g, 1.66 mmol, 87%). $^1$H NMR (CDCl$_3$): δ 0.89 (t, J=7.5 Hz, 6H), 1.75-1.90 (m, 4H), 2.13 (d, J=0.8 Hz, 3H), 2.44 (s, 3H), 2.49 (s, 3H), 3.30-3.39 (m, 1H), 6.64 (s, 1H), 7.08-7.11 (m, 1H), 7.34 (d, J=3.1 Hz, 1H). ES-MS (m/z): calcd for $C_{18}H_{23}N_3S$ (M+H)$^+$: 314.5; found: 314.2.

Example 20

Preparation of 8-(1-ethyl-propyl)-2,6-dimethyl-3-(3-methyl-thiophen-2-yl)-imidazo[1,2-b]pyridazine

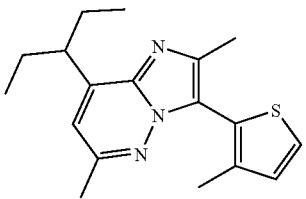

To mixture of 8-(1-ethyl-propyl)-3-iodo-2,6-dimethyl-imidazo[1,2-b]pyridazine (12.0 g, 34.96 mmol) and PdCl$_2$(dppf) (1.28 g, 1.75 mmol) is added a 0.5 M solution of 3-methyl-2-thienylzinc bromide in THF (100 mL, 50.0 mmol). The mixture is stirred at 65° C. overnight, diluted with EtOAc (500 mL), washed with 10% citric acid (500 mL), water (400 mL), brine (400 mL), dried over MgSO$_4$, filtered and concentrated. The residue is purified by ISCO (10%-20% EtOAc/hexane gradient) furnish the title compound (8.83 g, 28.17 mmol, 81%). $^1$H NMR (CDCl$_3$), δ 0.92 (t, J=7.4 Hz, 6H), 1.78-1.95 (m, 4H), 2.18 (s, 3H), 2.50 (s, 3H), 2.54 (s, 3H), 3.33-3.43 (m, 1H), 6.69 (s, 1H), 7.06 (d, J=4.9 Hz, 1H), 7.46 (d, J=4.9 Hz, 1H). LC/MS (m/z): calcd. for C$_{18}$H$_{23}$N$_3$S (M+H)$^+$: 314.6; found: 314.2.

Example 21

Preparation of 3-(5-bromo-3-methyl-thiophen-2-yl)-8-(1-ethyl-propyl)-2,6-dimethyl-imidazo[1,2-b]pyridazine

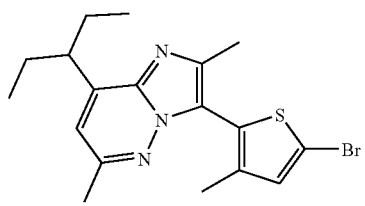

To a solution of 8-(1-Ethyl-propyl)-2,6-dimethyl-3-(3-methyl-thiophen-2-yl)-imidazo[1,2-b]pyridazine (8.83 g, 28.17 mmol) and CH$_2$Cl$_2$ (90 mL) is added NBS (5.26 g, 29.58 mmol). The solution is stirred at ambient temperature for 2 hours. The solution is washed with water (3×75 mL), dried over MgSO4, filtered and concentrated to furnish the title compound (10.5 g, 26.76 mmol, 95%). $^1$H NMR (CDCl$_3$), δ 0.87 (t, J=7.3 Hz, 6H), 1.73-1.93 (m, 4H), 2.09 (s, 3H), 2.44 (s, 3H), 2.51 (s, 3H), 3.26-3.36 (m, 1H), 6.68 (s, 1H), 6.98 (d, J=4.9 Hz, 1H) ppm. LC/MS (m/z): calcd. for C$_{18}$H$_{22}$BrN$_3$S (M+H)$^+$: 392.6; found: 392.1, 394.1.

Example 22

Preparation of 5-[8-(1-ethyl-propyl)-2,6-dimethyl-imidazo[1,2-b]pyridazin-3-yl]-4-methyl-thiophene-2-carboxylic acid methyl ester

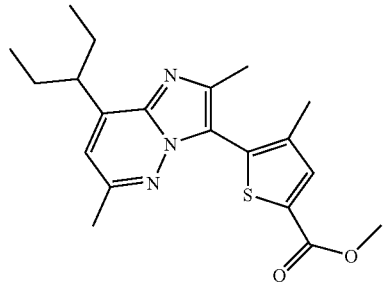

A solution of 3-(5-bromo-3-methyl-thiophen-2-yl)-8-(1-ethyl-propyl)-2,6-dimethyl-imidazo[1,2-b]pyridazine (1.00 g, 2.66 mmol) in CH$_3$OH (12 mL), DMSO (18 mL), Et$_3$N (2.0 mL) with Pd(OAc)$_2$ (0.12 g, 0.538 mmol), dppf (0.937 g, 1.69 mmol) is reacted at CO atmosphere (100 psi) at 80° C. for 24 h. The reaction mixture is diluted with EtOAc (200 mL), washed with 0.1 M HCl (2×50 mL), brine (50 mL); dried with Na$_2$SO$_4$; filtered through silica gel and eluted with excess EtOAc. Purification of the crude material by chromatography gives the title compound (0.79 g, 2.12 mmol, 80%). $^1$H NMR (CDCl$_3$): δ 0.89 (t, J=7.7 Hz, 6H), 1.75-1.93 (m, 4H), 2.15 (s, 3H), 2.50 (s, 3H), 2.53 (s, 3H), 3.32-3.42 (m, 1H), 3.91 (s, 3H), 6.72 (s, 1H), 7.73 (s, 1H). ES-MS (m/z): calcd for C$_{20}$H$_{25}$N$_3$O$_2$S (M+H)$^+$: 372.5; found: 372.2.

Example 23

Preparation of 5-[8-(1-ethyl-propyl)-2,6-dimethyl-imidazo[1,2-b]pyridazin-3-yl]-4-methyl-thiophene-2-carboxylic acid methylamide

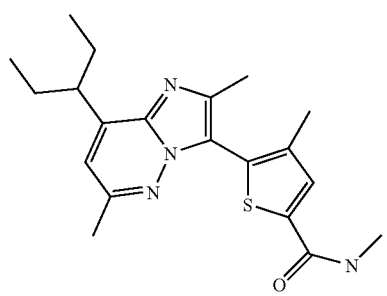

A. 5-[8-(1-Ethyl-propyl)-2,6-dimethyl-imidazo[1,2-b]pyridazin-3-yl]-4-methyl-thiophene-2-carboxylic acid.

A solution of (1-ethyl-propyl)-2,6-dimethyl-imidazo[1,2-b]pyridazin-3-yl]-4-methyl-thiophene-2-carboxylic acid methyl ester (0.78 g, 2.10 mmol) in CH$_3$OH (10 mL) is treated with 5.0 M NaOH (2.1 mL, 10.5 mmol). The resulting reaction mixture is refluxed for 4 h. Organic solvent is removed in vacuo; the aqueous residue is acidified by the addition of 2.0 M HCl to pH 5~6; it is then extracted with EtOAc (3×50 mL); dried (Na$_2$SO$_4$); filtered and concentration to give the title compound (0.74 g, 2.07 mmol, 98%). $^1$H NMR (DMSO-d6): δ 0.79 (t, J=7.6 Hz, 6H), 1.75-1.86 (m, 4H), 2.06 (s, 3H), 2.36 (s, 3H), 2.47 (s, 3H), 3.06-3.14 (m, 1H), 7.01 (s, 1H), 7.68 (s, 1H), 13.1 (bs, 1H). ES-MS (m/z): calcd for C$_{19}$H$_{23}$N$_3$O$_2$S (M+H)$^+$: 358.5; found: 358.2.

B. 5-[8-(1-Ethyl-propyl)-2,6-dimethyl-imidazo[1,2-b]pyridazin-3-yl]-4-methyl-thiophene-2-carboxylic acid methylamide.

5-[8-(1-Ethyl-propyl)-2,6-dimethyl-imidazo[1,2-b]pyridazin-3-yl]-4-methyl-thiophene-2-carboxylic acid (0.17 g, 0.47 mmol) is reacted with 2.0 M oxalyl chloride in $CH_2Cl_2$ (3.0 mL) at rt for 1 h. The excess reagent and solvent are removed in vacuo. The residue is dissolved in $CH_2Cl_2$ (3 mL), cooled to 0° C. and treated with 2.0 M methyl amine in THF (3 mL). The reaction is stirred at 0° C. for 10 min and rt for 30 min. It is diluted with EtOAc (50 mL), washed with $H_2O$ (15 mL0, 0.1 M NaOH (2×30 mL); dried ($Na_2SO_4$); filtered and concentrated. Purification of the crude material by chromatography to give the title compound (0.91 g, 0.25 mmol, 53%). $^1H$ NMR ($CDCl_3$): δ 0.89 (t, J=7.2 Hz, 6H), 1.75-1.91 (m, 4H), 2.14 (s, 3H), 2.47 (s, 3H), 2.52 (s, 3H), 3.02 (d, J=4.8 Hz, 3H), 3.28-3.36 (m, 1H), 5.90-6.01 (m, 1H), 6.69 (s, 1H), 7.43 (s, 1H). ES-MS (m/z): calcd for $C_{20}H_{26}N_4OS$ $(M+H)^+$: 371.5; found: 371.2.

Example 24

Preparation of 8-(1-ethyl-propyl)-2,6-dimethyl-3-[3-methyl-5-(1-methyl-1H-imidazol-2-yl)-thiophen-2-yl]-imidazo[1,2-b]pyridazine

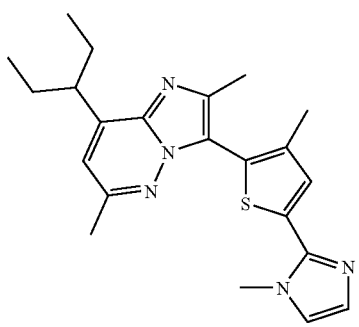

3-(5-Bromo-3-methyl-thiophen-2-yl)-8-(1-ethyl-propyl)-2,6-dimethyl-imidazo-[1,2-b]pyridazine (0.98 g, 2.51 mmol) and 1-methyl-1H-imidazole (0.2 mL), Pd(OAc)$_2$ (34 mg, 0.15 mmol), PPh$_3$ (79 mg, 0.299 mmol), Cs$_2$CO$_3$ (1.95 g, 6.0 mmol) in DMF (50 mL) is stirred under $N_2$ at 130-140° C. overnight. The reaction mixture is cooled, diluted with EtOAc (300 mL), washed with $H_2O$ (3×100 mL); dried ($Na_2SO_4$); filtered and concentrated. Purification of the resulting crude material by chromatography yields the title compound (0.51 g, 1.29 mmol, 51%). $^1H$ NMR ($CDCl_3$): δ 0.89 (t, J=7.5 Hz, 6H), 1.77-1.92 (m, 4H), 2.17 (s, 3H), 2.51 (s, 3H), 2.54 (s, 3H), 3.30-3.40 (m, 1H), 3.81 (s, 3H), 6.69 (s, 1H), 7.02 (s, 1H), 7.24 (s, 1H), 7.52 (s, 1H). ES-MS (m/z): calcd for $C_{22}H_{27}N_5S$ $(M+H)^+$: 394.6; found: 394.3.

Example 25

Preparation of 8-(1-ethyl-propyl)-2,6-dimethyl-3-[3-methyl-5-(2-methyl-2H-[1,2,4]triazol-3-yl)-thiophen-2-yl]-imidazo[1,2-b]pyridazine

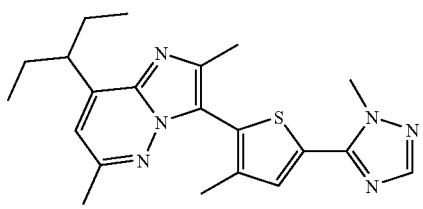

To a –78° C. solution of 1-methyl-1,2,4-triazole (0.15 mL, 2.04 mmol) and THF (3 mL) is added a 1.34 M solution of n-Bu-Li in hexanes (1.60 mL, 2.14 mmol) over 20 minutes, then stirred at –78° C. for 1.5 hours. A 0.5 M solution of ZnCl$_2$ in THF (4.28 mL, 2.14 mmol) is added and the solution warmed to ambient temperature. 3-(5-Bromo-3-methyl-thiophen-2-yl)-8-(1-ethyl-propyl)-2,6-dimethyl-imidazo[1,2-b]pyridazine (0.40 g, 1.019 mmol) and PdCl$_2$(dppf) (0.037 g, 0.051 mmol) is added and the solution heated at 65° C. overnight diluted with $CH_2Cl_2$ (30 mL). The organic layer is washed with 10% citric acid (20 mL), water (20 mL), brine (20 mL), dried over $MgSO_4$, filtered and concentrated. The residue is purified by ISCO (20%-60% EtOAc/hexane gradient). The residue is dissolved in $Et_2O$, treated with Darco®-60 for 15 minutes, dried with $Na_2SO_4$, and filtered to furnish the title compound (0.24 g, 0.61 mmol, 60%). $^1H$ NMR ($CDCl_3$), δ 0.88 (t, J=7.4 Hz, 6H), 1.75-1.93 (m, 4H), 2.20 (s, 3H), 2.50 (s, 3H), 2.51 (s, 3H), 3.28-3.37 (m, 1H), 4.14 (s, 3H), 6.69 (s, 1H), 7.45 (s, 1H), 7.87 (s, 1H). LC/MS (m/z): calcd. for $C_{21}H_{26}N_6S$ $(M+H)^+$: 395.6; found: 395.2.

Example 26

Preparation of 5-[8-(1-ethyl-propyl)-2,6-dimethyl-imidazo[1,2-b]pyridazin-3-yl]-4-methyl-thiophene-2-carbonitrile

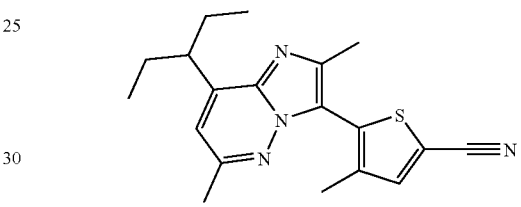

A solution of 3-(5-bromo-3-methyl-thiophen-2-yl)-8-(1-ethyl-propyl)-2,6-dimethyl-imidazo[1,2-b]pyridazine (0.50 g, 1.28 mmol), DMF (5 mL), and Zn(CN)$_2$ (0.090 g, 0.76 mmol) is degassed with nitrogen for 15 minutes. Pd(PPh$_3$)$_4$ (0.74 g, 0.064 mmol) and the solution heated at 100° C. overnight. The solution is diluted with EtOAc (50 mL), washed with 2 M NH$_4$OH (2×30 mL), brine (30 mL), dried over MgSO$_4$, filtered and concentrated. Purified by ISCO column chromatography (15%-20% EtOAc/hexane gradient) furnish the title compound (0.39 g, 1.15 mmol, 91%). $^1H$ NMR (CDCl$_3$), δ 0.87 (t, J=7.5 Hz, 6H), 1.74-1.91 (m, 4H), 2.15 (s, 3H), 2.46 (s, 3H), 2.51 (s, 3H), 3.26-3.34 (m, 1H), 6.72 (s, 1H), 7.53 (s, 1H). LC/MS (m/z): calcd. for $C_{19}H_{22}N_4S$ $(M+H)^+$: 339.6; found: 339.2.

Example 27

Preparation of (2-{5-[8-(1-ethyl-propyl)-2,6-dimethyl-imidazo[1,2-b]pyridazin-3-yl]-4-methyl-thiophen-2-yl}-pyrrol-1-yl)-dimethyl-amine

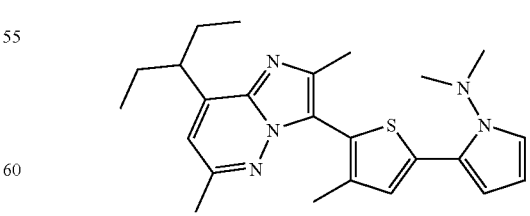

To a 0° C. solution 1-(dimethylamino)-pyrrole (0.24 mL, 2.04 mmol) and THF (4 mL) is added 1.24 M n-BuLi (1.73 mL, 2.14 mmol). The solution is warmed to ambient temperature and stirred for two hours. 0.5 M ZnCl$_2$ (4.28 mL, 2.14 mmol) is added and the solution is stirred for one hour. 3-(5-

Bromo-3-methyl-thiophen-2-yl)-8-(1-ethyl-propyl)-2,6-dimethyl-imidazo[1,2-b]pyridazine (0.40 g, 1.02 mmol) and PdCl₂(dppf) (0.037 g, 0.051 mmol) is added and the solution is heated at 65° C. overnight. The solution is diluted with EtOAc (30 mL), washed with sat. NH₄Cl (30 mL), dried over MgSO₄, filtered and concentrated. The residue is purified by ISCO flash chromatography (15%-20% EtOAc gradient) furnish the title compound (0.41 g, 0.97 mmol, 95%). ¹H NMR (CDCl₃) δ 0.87 (t, J=7.5 Hz, 6H), 1.73-1.91 (m, 4H), 2.11 (s, 3H), 2.51 (s, 6H), 2.83 (s, 6H), 3.29-3.39 (m, 1H), 6.18-6.21 (m, 1H), 6.35 (dd, J=4.0, 1.8 Hz, 1H), 6.65 (s, 1H), 6.98 (dd, J=4.0, 1.8 Hz, 1H), 7.25 (s, 1H). LC/MS (m/z): calcd. for C₂₄H₃₁N₅S (M+H)⁺: 422.2; found: 422.4.

Example 28 and 29

Preparation of 8-(1-ethyl-propyl)-2,6-dimethyl-3-[3-methyl-5-(2-methyl-2,5-dihydro-1H-tetrazol-5-yl)-thiophen-2-yl]-imidazo[1,2-b]pyridazine and 8-(1-ethyl-propyl)-2,6-dimethyl-3-[3-methyl-5-(1-methyl-1H-tetrazol-5-yl)-thiophen-2-yl]-imidazo[1,2 b]pyridazine Ex 28
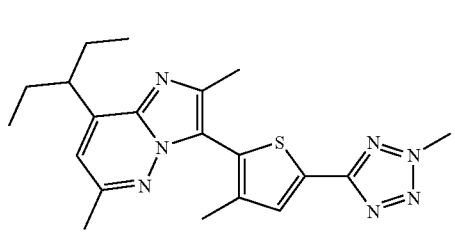

Ex. 29
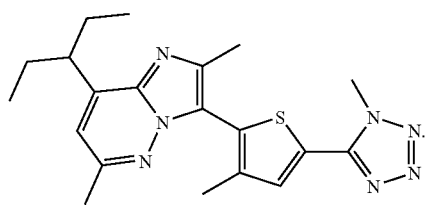

A. 8-(1-ethyl-propyl)-2,6-dimethyl-3-[3-methyl-5-(1H-tetrazol-5-yl)-thiophen-2-yl]-imidazo[1,2-b]pyridazine.

To a solution of 5-[8-(1-ethyl-propyl)-2,6-dimethyl-imidazo[1,2-b]pyridazin-3-yl]-4-methyl-thiophene-2-carbonitrile (0.25 g, 0.74 mmol) and DMF (2.5 mL) is added Et₃N·HCl (0.31 g, 2.22 mmol) and NaN₃ (0.14 g, 2.20 mmol). The solution is heated at 100° C. overnight. The solution is diluted with water (20 mL) and extracted with EtOAc (3×15 mL), the combined organic layers are washed with 0.1 M HCl (20 mL), water (20 mL), brine (20 mL), dried over MgSO₄, filtered and concentrated. The residue is recrystallized from acetonitrile furnish the title compound (0.14 g, 0.37 mmol, 50%). ¹H NMR (CDCl₃), δ 0.81 (t, J=7.5 Hz, 6H), 1.66-1.87 (m, 4H), 2.17 (s, 3H), 2.50 (s, 3H), 2.53 (s, 3H), 3.26-3.35 (m, 1H), 6.83 (s, 1H), 7.84 (s, 1H). LC/MS (m/z): calcd. for C₁₉H₂₃N₇S (M+H)⁺: 382.6; found: 382.2.

B. 8-(1-ethyl-propyl)-2,6-dimethyl-3-[3-methyl-5-(2-methyl-2,5-dihydro-1H-tetrazol-5-yl)-thiophen-2-yl]-imidazo[1,2-b]pyridazine and 8-(1-ethyl-propyl)-2,6-dimethyl-3-[3-methyl-5-(1-methyl-1H-tetrazol-5-yl)-thiophen-2-yl]-imidazo[1,2 b]pyridazine.

To a solution of 8-(1-ethyl-propyl)-2,6-dimethyl-3-[3-methyl-5-(1H-tetrazol-5-yl)-thiophen-2-yl]-imidazo[1,2-b]pyridazine (0.14 g, 0.35 mmol) and THF (3 mL) is added Et₃N (0.1 mL, 0.71 mmol) and MeI (0.024 mL, 0.39 mmol). The solution is stirred overnight, diluted with EtOAc (20 mL), washed with water (15 mL), 0.1 M HCl (15 mL), brine (15 mL), dried over MgSO₄, filtered and concentrated. The residue is purified by ISCO column chromatography (20%-40% EtOAc/hexane gradient) furnish Ex. 28 (0.71 g, 0.18 mmol, 51%), and Ex. 29 (0.031 g, 0.078 mmol, 22%).

Ex. 28: ¹H NMR (CDCl₃), δ 0.88 (t, J=7.4 Hz, 6H), 1.75-1.92 (m, 4H), 2.18 (s, 3H), 2.50 (s, 3H), 2.51 (s, 3H), 3.28-3.38 (m, 1H), 4.38 (s, 3H), 6.68 (s, 1H), 7.71 (s, 1H). LC/MS (m/z): calcd. for C₂₀H₂₅N₇S (M+H)⁺: 396.6; found: 396.3.

Ex. 29: ¹H NMR (CDCl₃), δ 0.89 (t, J=7.4 Hz, 6H), 1.73-1.94 (m, 4H), 2.23 (s, 3H), 2.50 (s, 3H), 2.52 (s, 3H), 3.28-3.37 (m, 1H), 4.30 (s, 3H), 6.62 (s, 1H), 7.63 (s, 1H). LC/MS (m/z): calcd. for C₂₀H₂₅N₇S (M+H)⁺: 396.6; found: 396.3.

Example 30

Preparation of 8-(1-ethyl-propyl)-2,6-dimethyl-3-(3-methyl-5-pyridin-4-yl-thiophen-2-yl)-imidazo[1,2-b]pyridazine

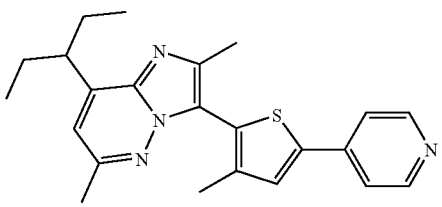

A. 3-(5-Boronic acid-3-methyl-thiophen-2-yl)-8-(1-ethyl-propyl)-2,6-dimethyl-imidazo[1,2-b]pyridazine.

To a –78° C. solution of 3-(5-bromo-3-methyl-thiophen-2-yl)-8-(1-ethyl-propyl)-2,6-dimethyl-imidazo[1,2-b]pyridazine (1.20 g, 3.06 mmol) and THF (10 mL) is added 1.30 M n-Bu-Li (2.47 mL, 3.21 mmol) drop wise. The solution is stirred at –78° C. for one hour. B(OMe)₃ (0.38 mL, 3.65 mmol) is added and the solution is warmed to ambient temperature and stirred for 2 hours. 1 M HCl is added and the solution stirred for 10 minutes extracted with CH₂Cl₂ (2×30 mL), dried over MgSO₄, filtered and concentrated to furnish the title compound (0.47 g, 1.32 mmol, 43%). ¹H NMR (CDCl₃), δ 0.92 (t, J=7.5 Hz, 6H), 1.71-1.98 (m, 4H), 2.02 (s, 3H), 2.64 (s, 3H), 2.69 (s, 3H), 3.64-3.83 (m, 1H), 7.06 (d, J=5.3 Hz, 1H), 7.54 (d, J=5.3 Hz, 1H), 7.20 (s, 1H). LC/MS (m/z): calcd. for C₁₈H₂₄BN₃O₂S (M+H)⁺: 358.4; found: 358.2.

B. 8-(1-Ethyl-propyl)-2,6-dimethyl-3-(3-methyl-5-pyridin-4-yl-thiophen-2-yl)-imidazo[1,2-b]pyridazine.

A solution of 3-(5-boronic acid-3-methyl-thiophen-2-yl)-8-(1-ethyl-propyl)-2,6-dimethyl-imidazo[1,2-b]pyridazine (0.25 g, 0.70 mmol), 4-bromopyridine hydrochloride (0.16 g, 0.84 mmol), and 2 M Na₂CO₃ (0.87 mL, 1.75 mmol) and n-PrOH (2.5 mL) is degassed with nitrogen for 10 minutes. Pd(PPh₃)₄ (0.040 g, 0.035 mmol) is added and the solution heated at 85° C. overnight. The solution is diluted with CH₂Cl₂ (40 mL), washed with 10% Na₂CO₃ (30 mL), water (30 mL), brine (30 mL), dried over MgSO₄, filtered and concentrated. The residue is purified by ISCO column chromatography (20%-40% EtOAc/hexane gradient) furnish the title compound (0.16 g, 0.41 mmol, 59%). ¹H NMR (CDCl₃), δ 0.88 (t, J=7.5 Hz, 6H), 1.74-1.93 (m, 4H), 2.17 (s, 3H), 2.49

(s, 3H), 2.52 (s, 3H), 3.28-3.38 (m, 1H), 6.68 (s, 1H), 7.43 (s, 1H), 7.52 (d, J=5.5 Hz, 2H), 8.62 (d, J=5.5 Hz, 2H). LC/MS (m/z): calcd. for $C_{23}H_{26}N_4S$ (M+H)$^+$: 391.2 found: 391.2.

Example 31

Preparation of 8-(1-ethyl-propyl)-2,6-dimethyl-3-(3-methyl-5-pyridin-3-yl-thiophen-2-yl)-imidazo[1,2-b]pyridazine

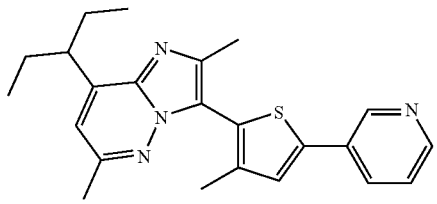

To a −78° C. solution of 3-(5-bromo-3-methyl-thiophen-2-yl)-8-(1-ethyl-propyl)-2,6-dimethyl-imidazo[1,2-b]pyridazine (0.50 g, 1.27 mmol), and THF (5 mL) is added 1.34 M n-Bu-Li (1.0 mL, 1.34 mmol). The solution is stirred for at −78° C. for 30 minutes and 0.5 M $ZnCl_2$ in THF (2.7 mL, 1.34 mmol) is added and the solution warmed to ambient temperature. After 30 minutes 3-bromopyridine (0.15 mL, 1.53 mmol) and $PdCl_2$(dppf) (0.047 g, 0.064 mmol) is added and the solution heated at 65° C. overnight. The solution is diluted with $CH_2Cl_2$ (40 mL), washed with 10% citric acid (20 mL), water (20 mL), brine (20 mL) dried over $MgSO_4$, filtered and concentrated. The residue is purified by ISCO column chromatography (20%-40% EtOAc/hexane gradient) concentrated and re-dissolved in $Et_2O$. The solution is treated with Darco®-60 for 15 minutes, dried over $Na_2SO_4$, and filtered thru Celite® furnish the title compound (0.26 g, 0.67 mmol, 52%). $^1$H NMR (CDCl$_3$), δ 0.88 (t, J=7.5 Hz, 6H), 1.74-1.92 (m, 4H), 2.17 (s, 3H), 2.50 (s, 3H), 2.52 (s, 3H), 3.28-3.38 (m, 1H), 6.68 (s, 1H), 7.26-7.32 (m, 2H), 7.86 (dt, J=7.9, 1.8 Hz, 1H), 850 (d, J=3.2 Hz, 1H), 8.89 (s, 1H). LC/MS (m/z): calcd. for $C_{23}H_{26}N_4S$ (M+H)$^+$: 391.6; found: 391.2.

Example 32

Preparation of 8-(1-ethyl-propyl)-2,6-dimethyl-3-(3-methyl-5-pyridin-2-yl-thiophen-2-yl)-imidazo[1,2-b]pyridazine

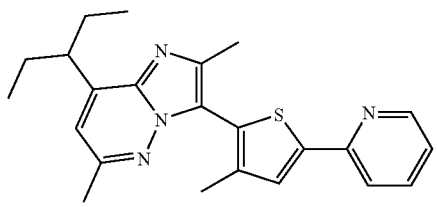

To a mixture of 3-(5-bromo-3-methyl-thiophen-2-yl)-8-(1-ethyl-propyl)-2,6-dimethyl-imidazo[1,2-b]pyridazine (0.50 g, 1.27 mmol) and $PdCl_2$(dppf) (0.047 g, 0.064 mmol) is added a 0.5 M solution of 2-pyridylzinc bromide in THF (5.1 mL, 2.55 mmol). The mixture is stirred at 65° C. overnight, diluted with EtOAc (50 mL), washed with 10% citric acid (50 mL), water (40 mL), brine (40 mL), dried over $MgSO_4$, filtered and concentrated. The residue is purified by ISCO column chromatography (20%-40% EtOAc/hexane gradient) furnish the title compound (0.45 g, 1.15 mmol, 89%). $^1$H NMR (CDCl$_3$), δ 0.88 (t, J=7.5 Hz, 6H), 1.75-1.93 (m, 4H), 2.17 (s, 3H), 2.52 (s, 6H), 3.30-3.39 (m, 1H), 6.67 (s, 1H), 7.12-7.16 (m, 1H), 7.53 (s, 1H), 7.63-7.71 (m, 2H), 8.57 (dt, J=1.3, 4.8 Hz, 1H). LC/MS (m/z): calcd. for $C_{23}H_{26}N_4S$ (M+H)$^+$: 391.6; found: 391.2.

Example 33

Preparation of 8-(1-ethyl-propyl)-2,6-dimethyl-3-(3-methyl-5-pyridin-2-yl-thiophen-2-yl)-imidazo[1,2-b]pyridazine hydrochloride

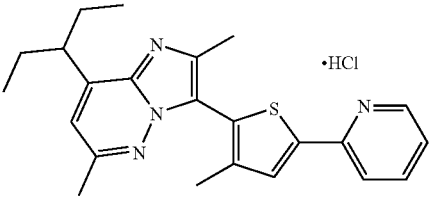

To a solution of 8-(1-ethyl-propyl)-2,6-dimethyl-3-(3-methyl-5-pyridin-2-yl-thiophen-2-yl)-imidazo[1,2-b]pyridazine (0.15 g, 38 mmol) and MeOH (2 mL) is added AcCl (0.028 mL, 0.39 mmol). After one hour the solution is concentrated and the residue recrystallized from EtOAc/hexane furnish the title compound (0.11 g, 0.26 mmol, 69%). $^1$H NMR (CDCl$_3$), δ 0.97 (t, J=7.4 Hz, 6H), 1.75-2.03 (m, 4H), 2.17 (s, 3H), 2.66 (s, 3H), 2.77 (s, 3H), 3.86-3.98 (m, 1H), 7.17 (s, 1H), 7.21-7.30 (m, 2H), 7.62 (bs, 1H), 7.67-7.7.82 (m, 2H), 8.60 (d, J=4.8 Hz, 1H). LC/MS (m/z): calcd. for $C_{23}H_{26}ClN_5S$ (M+H)$^+$: 428.1; found: 391.2.

Example 34

Preparation of 8-(1-ethyl-propyl)-2,6-dimethyl-3-[3-methyl-5-(2-methyl-2H-pyrazol-3-yl)-thiophen-2-yl]-imidazo[1,2-b]pyridazine

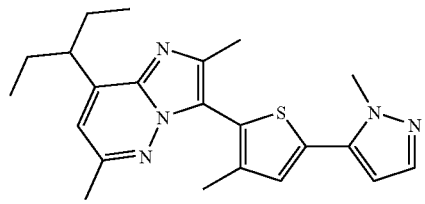

Using a procedure similar to Example 25, 1-methylpyrazole (0.17 g, 2.04 mmol), 1.56 M n-Bu-Li (1.34 mL, 2.09 mmol), $ZnCl_2$ (4.3 mL, 2.14 mmol), 3-(5-bromo-3-methyl-thiophen-2-yl)-8-(1-ethyl-propyl)-2,6-dimethyl-imidazo[1,2-b]pyridazine (0.40 g, 1.02 mmol) and $PdCl_2$(dppf) (0.037 g, 0.051 mmol) furnish the title compound (0.35 g, 0.89 mmol, 88%). $^1$H NMR (CDCl$_3$), δ 0.88 (t, J=7.5 Hz, 6H), 1.74-1.92 (m, 4H), 2.17 (s, 3H), 2.50 (s, 3H), 2.52 (s, 3H), 3.28-3.38 (m, 1H), 4.05 (s, 3H), 6.42 (d, J=1.8 Hz, 1H), 6.68 (s, 1H), 7.08 (s, 1H), 7.46 (d, J=1.8 Hz, 1H). LC/MS (m/z): calcd. for $C_{22}H_{27}N_5S$ (M+H)$^+$: 394.7; found: 394.2.

Example 35

Preparation of 8-(1-ethyl-propyl)-2,6-dimethyl-3-(3-methyl-5-thiazol-4-yl-thiophen-2-yl)-imidazo[1,2-b]pyridazine

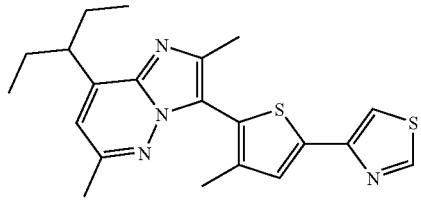

Using a procedure similar to Example 31, from 3-(5-bromo-3-methyl-thiophen-2-yl)-8-(1-ethyl-propyl)-2,6-dimethyl-imidazo[1,2-b]pyridazine (0.40 g, 1.02 mmol), 1.34 M n-Bu-Li (0.8 mL, 1.07 mmol), 0.5 M $ZnCl_2$ in THF (2.14 mL, 1.07 mmol), 4-bromo-thiazole (0.20 mL, 1.22 mmol) and $PdCl_2$(dppf) (0.037 g, 0.051 mmol) furnish the title compound (0.16 g, 0.40 mmol, 40%). $^1$H NMR (CDCl$_3$), δ 0.92 (t, J=7.4 Hz, 6H), 1.70-1.96 (m, 4H), 2.17 (s, 3H), 2.64 (s, 3H), 2.66 (s, 3H), 3.38-3.48 (m, 1H), 7.16 (d, J=1.8 Hz, 1H), 7.44 (s, 1H), 7.51 (d, J=1.8 Hz, 1H), 7.86 (d, J=1.8 Hz, 1H). LC/MS (m/z): calcd. for $C_{21}H_{24}N_4S_2$ (M+H)$^+$: 397.7; found: 397.2.

Example 36

Preparation of 8-(1-ethyl-propyl)-2,6-dimethyl-3-[3-methyl-5-(6-methyl-pyridin-2-yl)-thiophen-2-yl]-imidazo[1,2-b]pyridazine

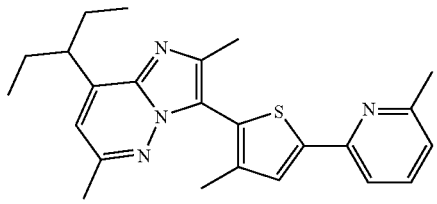

Using a procedure similar to Example 32, 3-(5-bromo-3-methyl-thiophen-2-yl)-8-(1-ethyl-propyl)-2,6-dimethyl-imidazo[1,2-b]pyridazine (0.60 g, 1.53 mmol) and $PdCl_2$(dppf) (0.056 g, 0.076 mmol) and 0.5 M solution of 6-methyl-2-pyridylzinc bromide in THF (6.0 mL, 3.06 mmol) furnish the title compound (0.29 g, 0.72 mmol, 47%). $^1$H NMR (CDCl$_3$), δ 0.89 (t, J=7.5 Hz, 6H), 1.73-1.93 (m, 4H), 2.16 (s, 3H), 2.50 (s, 3H), 2.52 (s, 3H), 2.58 (s, 3H), 3.31-3.40 (m, 1H), 6.67 (s, 1H), 7.00 (d, J=7.9 Hz, 1H), 7.45 (d, J=7.9 Hz, 1H), 7.52 (s, 1H), 8.56 (t, J=7.7 Hz, 1H). LC/MS (m/z): calcd. for $C_{24}H_{28}N_4$ (M+H)$^+$: 405.7; found: 405.2.

Example 37

Preparation of 8-(1-ethyl-propyl)-2,6-dimethyl-3-(3-methyl-5-phenyl-thiophen-2-yl)-imidazo[1,2-b]pyridazine

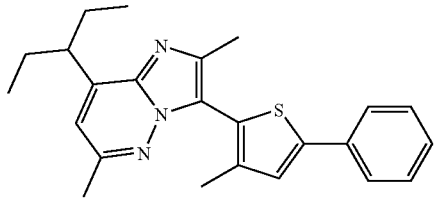

Using a procedure similar to Example 32, 3-(5-bromo-3-methyl-thiophen-2-yl)-8-(1-ethyl-propyl)-2,6-dimethyl-imidazo[1,2-b]pyridazine (0.50 g, 1.27 mmol) and $PdCl_2$(dppf) (0.05 g, 0.069 mmol) and 0.5 M solution of phenylzinc iodide in THF (5.5 mL, 2.76 mmol) furnish the title compound (0.25 g, 0.64 mmol, 50%). $^1$H NMR (CDCl$_3$), δ 0.90 (t, J=7.5 Hz, 6H), 1.76-1.94 (m, 4H), 2.17 (s, 3H), 2.52 (s, 3H), 2.53 (s, 3H), 3.31-3.41 (m, 1H), 6.68 (s, 1H), 7.26 (s, 1H), 7.27-30 (m, 1H), 7.35-7.41 (m, 2H), 7.61-7.66 (m, 2H). LC/MS (m/z): calcd. for $C_{24}H_{27}N_3S$ (M+H)$^+$: 390.3; found: 390.3.

Example 38

Preparation of 8-(1-ethyl-propyl)-3-[5-(3-fluoro-phenyl)-3-methyl-thiophen-2-yl]-2,6-dimethyl-imidazo[1,2-b]pyridazine

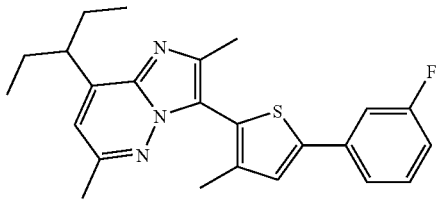

Using a procedure similar to Example 32, 3-(5-bromo-3-methyl-thiophen-2-yl)-8-(1-ethyl-propyl)-2,6-dimethyl-imidazo[1,2-b]pyridazine (0.50 g, 1.27 mmol) and $PdCl_2$(dppf) (0.047 g, 0.063 mmol) and 0.5 M solution of 3-fluorophenylzinc iodide in THF (5.1 mL, 2.55 mmol) furnish the title compound (0.24 g, 0.59 mmol, 46%). $^1$H NMR (CDCl$_3$), δ 0.90 (t, J=7.5 Hz, 6H), 1.76-1.94 (m, 4H), 2.17 (s, 3H), 2.51 (s, 3H), 2.53 (s, 3H), 3.31-3.39 (m, 1H), 6.69 (s, 1H), 6.94-7.01 (m, 1H), 7.26 (s, 1H), 7.30-7.42 (m, 3H). LC/MS (m/z): calcd. for $C_{24}H_{26}FN_3S$ (M+H)$^+$: 408.7; found: 408.2.

Example 39

Preparation of 8-(1-ethyl-propyl)-3-[5-(4-fluoro-phenyl)-3-methyl-thiophen-2-yl]-2,6-dimethyl-imidazo[1,2-b]pyridazine

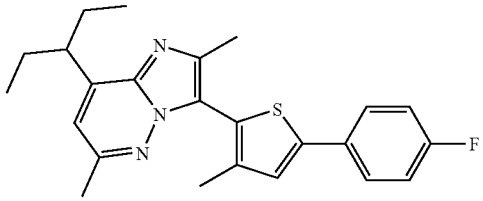

A slurry of 0.05 g/mL of Reike® Zn in THF (0.26 g, 4.01 mmol) and 1-bromo-4-fluoro-benzene (0.29 mL, 2.68 mmol) is heated at a reflux overnight. The solution is filtered under nitrogen. 3-(5-bromo-3-methyl-thiophen-2-yl)-8-(1-ethyl-propyl)-2,6-dimethyl-imidazo[1,2-b]pyridazine (0.35 g, 0.89 mmol) and $PdCl_2$(dppf) (0.033 g, 0.045 mmol) are added, and the solution is heated at a reflux overnight diluted with EtOAc (30 mL), washed with 10% citric acid (20 mL), water (20 mL), brine (20 mL), dried over $MgSO_4$, filtered and concentrated. The residue is purified by ISCO column chromatography (10%-15% EtOAc/hexane gradient) furnish the title compound (0.091 g, 0.22 mmol, 25%). $^1$H NMR (CDCl$_3$), δ 0.88 (t, J=7.5 Hz, 6H), 1.74-1.92 (m, 4H), 2.15 (s, 3H), 2.50 (s, 3H), 2.52 (s, 3H), 3.30-3.38 (m, 1H), 6.68 (s, 1H), 7.08 (d, J=8.8 Hz, 1H), 7.18 (s, 1H), 7.59 (dd, J=8.5, 5.3 Hz, 2H). LC/MS (m/z): calcd. for $C_{24}H_{26}FN_3S$ (M+H)$^+$: 408.7; found: 408.3.

Example 40

Preparation of 8-(1-ethyl-propyl)-2,6-dimethyl-3-[3-ethyl-5-(6-methyl-pyridin-2-yl)-thiophen-2-yl]-imidazo[1,2-b]pyridazine

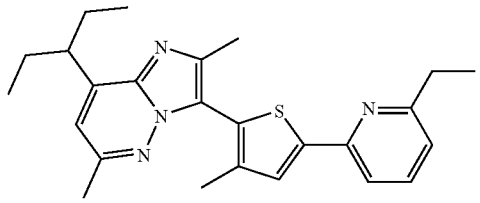

Using a procedure similar to Example 31, 2-bromo-6-ethyl pyridine (0.26 g, 1.41 mmol), 1.56 M n-Bu-Li (0.94 mL, 1.47 mmol), 0.5 M ZnCl$_2$ in THF (3.0 mL, 1.53 mmol), 3-(5-bromo-3-methyl-thiophen-2-yl)-8-(1-ethyl-propyl)-2,6-dimethyl-imidazo[1,2-b]pyridazine (0.50 g, 1.27 mmol) and PdCl$_2$(dppf) (0.047 g, 0.064 mmol) produce the title compound (0.15 g, 0.36 mmol, 28%). $^1$H NMR (CDCl$_3$), δ 0.90 (t, J=7.5 Hz, 6H), 1.34 (t, J=7.5 Hz, 3H), 1.75-1.94 (m, 4H), 2.16 (s, 3H), 2.51 (s, 3H), 2.52 (s, 3H), 2.85 (q, J=16.2, 7.5 Hz, 2H), 3.31-3.41 (m, 1H), 6.67 (s, 1H), 7.01 (d, J=7.8 Hz, 1H), 7.46 (d, J=7.9 Hz, 1H), 7.53 (s, 1H), 8.59 (t, J=7.8 Hz, 1H). LC/MS (m/z): calcd. for C$_{25}$H$_{30}$N$_4$S (M+H)$^+$: 419.3; found: 419.3.

Example 41

Preparation of 8-(1-ethyl-propyl)-2,6-dimethyl-3-[3-methyl-5-(6-methyl-pyridin-2-yl)-thiophen-2-yl]-imidazo[1,2-b]pyridazine hydrochloride

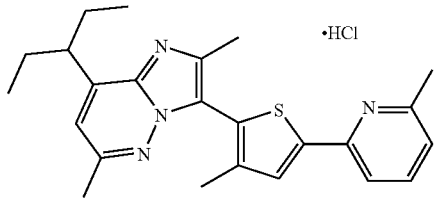

Using a procedure similar to Example 33, 8-(1-ethyl-propyl)-2,6-dimethyl-3-[3-methyl-5-(6-methyl-pyridin-2-yl)-thiophen-2-yl]-imidazo[1,2-b]pyridazine (0.55 g, 1.36 mmol), MeOH (6 mL) and AcCl (0.098 mL, 1.36 mmol) furnish the title compound (0.11 g, 0.25 mmol, 42%). $^1$H NMR (CDCl$_3$), δ 0.96 (t, J=7.2 Hz, 6H), 1.74-1.89 (m, 2H), 1.89-2.02 (m, 2H), 2.22 (s, 3H), 2.68 (s, 3H), 2.78 (s, 3H), 3.08 (s, 3H), 3.88-3.98 (m, 1H), 7.23 (s, 1H), 7.40 (d, J=6.9 Hz, 1H), 7.71 (d, J=4.8 Hz, 1H), 8.06 (s, 1H), 8.82 (s, 1H). LC/MS (m/z): calcd. for C$_{24}$H$_{29}$ClN$_4$S (M+H)$^+$: 441.3; found: 405.2.

Example 42

Preparation of 8-(1-ethyl-propyl)-2,6-dimethyl-3-(3-methyl-5-thiazol-2-yl-thiophen-2-yl)-imidazo[1,2-b]pyridazine

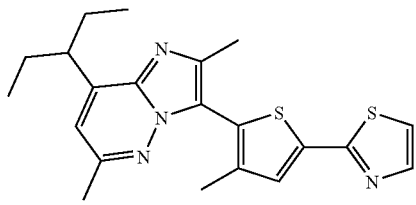

Using a procedure similar to Example 32, 3-(5-bromo-3-methyl-thiophen-2-yl)-8-(1-ethyl-propyl)-2,6-dimethyl-imidazo[1,2-b]pyridazine (0.46 g, 1.17 mmol), 0.5 M 2-thiazolylzinc bromide in THF (4.7 mL, 2.35 mmol) and PdCl$_2$(dppf) (0.043 g, 0.059 mmol) furnish the title compound (0.32 g, 0.81 mmol, 70%). $^1$H NMR (CDCl$_3$), δ 0.90 (t, J=7.5 Hz, 6H), 1.76-1.94 (m, 4H), 2.18 (s, 3H), 2.52 (s, 3H), 2.53 (s, 3H), 3.31-3.40 (m, 1H), 7.70 (s, 1H), 7.27 (d, J=3.6 Hz, 1H), 7.47 (s, 1H), 7.78 (d, J=3.6 Hz, 1H). LC/MS (m/z): calcd. for C$_{21}$H$_{24}$N$_4$S$_2$ (M+H)$^+$: 397.7; found: 397.1.

Example 43

Preparation of 8-(1-ethyl-propyl)-2,6-dimethyl-3-(3-methyl-5-pyrazin-2-yl-thiophen-2-yl)-imidazo[1,2-b]pyridazine

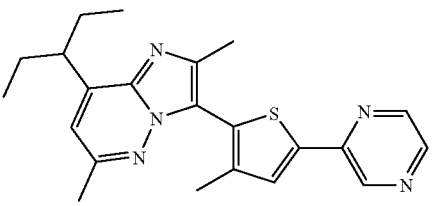

Using a procedure similar to Example 31, 3-(5-bromo-3-methyl-thiophen-2-yl)-8-(1-ethyl-propyl)-2,6-dimethyl-imidazo[1,2-b]pyridazine (0.40 g, 1.02 mmol) (example Rupp-2), 2-chloropyrazine (0.11 mL, 1.22 mmol), 1.42 M n-Bu-Li (1.52 mL, 1.07 mmol), 0.5 M ZnCl$_2$ in THF (2.14 mL, 1.07 mmol), and PdCl$_2$(dppf) (0.037 g, 0.051 mmol) furnish the title compound (0.19 g, 0.49 mmol, 48%). $^1$H NMR (CDCl$_3$), δ 0.90 (t, J=7.5 Hz, 6H), 1.75-1.94 (m, 4H), 2.20 (s, 3H), 2.52 (s, 3H), 2.53 (s, 3H), 3.31-3.40 (m, 1H), 6.69 (s, 1H), 7.63 (s, 1H), 8.40 (d, J=2.6 Hz, 1H), 8.51 (t, J=1.9 Hz, 1H), 8.96 (d, J=0.9 Hz, 1H). LC/MS (m/z): calcd. for C$_{22}$H$_{25}$N$_5$S (M+H)$^+$: 392.3; found: 392.2.

Example 44

Preparation of 8-(1-ethyl-propyl)-2,6-dimethyl-3-(4-methyl-[2,2']bithiophenyl-5-yl)-imidazo[1,2-b]pyridazine

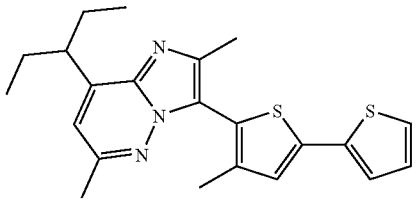

Using a procedure similar to Example 32, from 3-(5-bromo-3-methyl-thiophen-2-yl)-8-(1-ethyl-propyl)-2,6-dimethyl-imidazo[1,2-b]pyridazine (0.30 g, 0.76 mmol), 0.5 M 2-thiophenlyzinc bromide in THF (3.0 mL, 1.53 mmol) and PdCl$_2$(dppf) (0.028 g, 0.038 mmol) furnish the title compound (0.25 g, 0.63 mmol, 83%). $^1$H NMR (CDCl$_3$), δ 0.89 (t, J=7.5 Hz, 6H), 1.75-1.93 (m, 4H), 2.14 (s, 3H), 2.50 (s, 3H), 2.53 (s, 3H), 3.30-3.39 (m, 1H), 6.68 (s, 1H), 7.02 (dd, J=5.0, 3.6 Hz, 1H), 7.11 (s, 1H), 7.19 (d, J=3.6 Hz, 1H), 7.19 (dd, J=5.0, 1.0 Hz, 1H). LC/MS (m/z): calcd. for C$_{22}$H$_{25}$N$_3$S$_2$ (M+H)$^+$: 396.7; found: 396.2.

Example 45

Preparation of 3-(5-butyl-3-methyl-thiophen-2-yl)-8-(1-ethyl-propyl)-2,6-dimethyl-imidazo[1,2-b]pyridazine

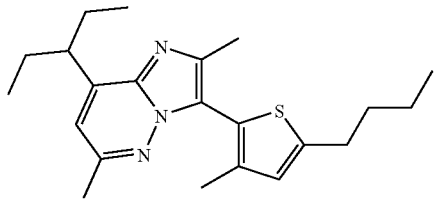

Using a procedure similar to Example 25 from 3-(5-bromo-3-methyl-thiophen-2-yl)-8-(1-ethyl-propyl)-2,6-dimethyl-imidazo[1,2-b]pyridazine (0.40 g, 0.1.02 mmol), 1.34 M n-Bu-Li (1.60 mL, 2.14 mmol), 0.5 M ZnCl$_2$ (4.3 mL, 2.14 mmol) and PdCl$_2$(dppf) (0.037 g, 0.051 mmol) furnishes the title compound (0.25 g, 0.69 mmol, 68%). $^1$H NMR (CDCl$_3$), δ 0.88 (t, J=7.5 Hz, 6H), 0.97 (t, J=7.5 Hz, 3H), 1.40-1.51 (m, 2H), 1.67-1.92 (m, 6H), 2.07 (s, 3H), 2.46 (s, 3H), 2.51 (s, 3H), 2.83 (t, J=8.0 Hz, 2H), 3.30-3.38 (m, 1H), 6.64 (s, 1H), 6.70 (s, 1H) LC/MS (m/z): calcd. for C$_{22}$H$_{31}$N$_3$S (M+H)$^+$: 370.3; found: 370.2.

Example 46

Preparation of 8-(1-ethyl-propyl)-2,6-dimethyl-3-[3-methyl-5-(1-methyl-1H-pyrazol-3-yl)-thiophen-2-yl]-imidazo[1,2-b]pyridazine

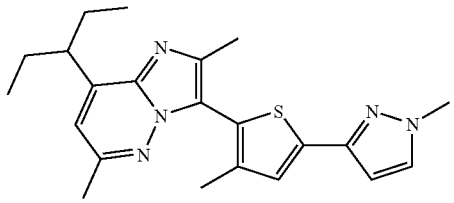

Using a procedure analogous to Example 31, 3-(5-bromo-3-methyl-thiophen-2-yl)-8-(1-ethyl-propyl)-2,6-dimethyl-imidazo[1,2-b]pyridazine (0.40 g, 1.02 mmol), 1.42 M n-Bu-Li (0.75 mL, 1.07 mmol), 0.5 M ZnCl$_2$ in THF (2.14 mL, 1.07 mmol), 3-bromo-1-methyl-1H-pyrazole (Pavlik, J.; Kurzweil, E.; *J. Org. Chem.*, 1991, 56, 22, 6313) (0.20 g, 1.22 mmol) and PdCl$_2$(dppf) (0.037 g, 0.051 mmol) furnish the title compound (0.041 g, 0.10 mmol, 10%). $^1$H NMR (CDCl$_3$) δ 0.90 (t, J=7.5 Hz, 6H), 1.75-1.94 (m, 4H), 2.15 (s, 3H), 2.51 (s, 3H), 2.52 (s, 3H), 3.31-3.41 (m, 1H), 3.95 (s, 3H), 6.47 (d, J=2.2 Hz, 1H), 6.67 (s, 1H), 7.25 (s, 1H), 7.36 (d, J=2.2 Hz, 1H). LC/MS (m/z): calcd. for C$_{22}$H$_{27}$N$_5$S (M+H)$^+$: 394.3; found: 394.2.

Example 47

Preparation of 8-(1-ethyl-propyl)-2,6-dimethyl-3-[4-methyl-2-(2-methyl-2H-[1,2,4]triazol-3-yl)-thiazol-5-yl]-imidazo[1,2-b]pyridazine

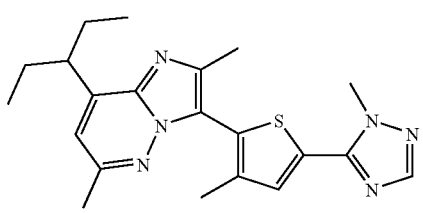

82 mg of 1-Methyl-1,2,4-triazole (0.99 mmol) is dissolved in 2 ml of dry THF and cooled to −78° C. and 0.4 ml of n-butyllithium 2.5 M in hexane (0.99 mmol) is added. The reaction mixture is stirred at −78 C to room temperature for 10 min and cooled to −78° C. again. 1.98 ml of 0.5 M zinc chloride 0.5 M solution in THF (0.99 mmol) is added and stirred at −78 C to room temperature for 15 min. 265 mg of 3-(2-bromo-4-methyl-thiazol-5-yl)-8-(1-ethyl-propyl)-2,6-dimethyl-imidazo[1,2-b]pyridazine (0.66 mmol) and 27 mg of PdCl2(dppf) (0.033 mmol) are added and the vial is capped with a Teflon cap and heated at 80° C. for 2 days. The reaction is cooled to room temperature and quenched with sat. NH4Cl and extracted with CH2Cl2. The separated CH2Cl2 layer is dried over Na2SO4 and evaporated. The crude product is applied onto a silica-gel chromatography column (Hexane:AcOEt:2 M NH3 in MeOH=10:2:1) to give 57 mg of the title product. Yield 22%. mass spectrum (m/e): 396 (M+1). $^1$H-NMR (CDCl$_3$): δ 7.96 (s, 1H), 6.77 (s, 1H), 4.45 (s, 3H), 3.36 (m, 1H), 2.55 (s, 3H), 2.52 (s, 3H), 2.47 (s, 3H), 1.88 (m, 4H), 0.92 (t, J=7.3 Hz, 6H).

Example 48

Preparation of 3-[4-bromo-2-(2-methyl-2H-[1,2,4]triazol-3-yl)-thiazol-5-yl]-8-(1-ethyl-propyl)-2,6-dimethyl-imidazo[1,2-b]pyridazine

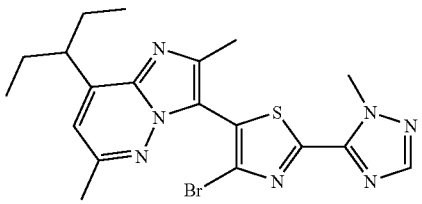

82 mg of 1-methyl-1,2,4-triazole (0.99 mmol) is dissolved in 2 ml of dry THF and cooled to −78° C. and 0.4 ml of n-butyllithium 2.5 M in hexane (0.99 mmol) is added. The reaction mixture is stirred at −78° C. to room temperature for 10 min and cooled to −78° C. again. 1.98 ml of 0.5 M zinc chloride 0.5 M solution in THF (0.99 mmol) is added and stirred at −78° C. to room temperature for 15 min. 152 mg of 3-(2,4-dibromo-thiazol-5-yl)-8-(1-ethyl-propyl)-2,6-dimethyl-imidazo[1,2-b]pyridazine (0.33 mmol) and 27 mg of PdCl2(dppf) (0.033 mmol) are added and the vial is capped with a Teflon cap and heated at 80° C. for 2 days. The reaction is cooled to room temperature and quenched with sat. NH4Cl1 and extracted with CH2Cl2. The separated CH2Cl2 layer is dried over Na2SO4 and evaporated. The crude product is applied onto a silica-gel chromatography column (Hexane:AcOEt:2M NH3 in MeOH=10:2:1) to give 88 mg of the title product. Yield 54%. mass spectrum (m/e): 461 (M+1). $^1$H-NMR (CDCl$_3$): 7.98 (s, 1H), 6.77 (s, 1H), 4.44 (s, 3H), 3.35 (m, 1H), 2.59 (s, 3H), 2.55 (s, 3H), 1.88 (m, 4H), 0.92 (t, J=7.5 Hz, 6H).

Example 49

Preparation of 3-[4-chloro-2-(2-methyl-2H-[1,2,4]triazol-3-yl)-thiazol-5-yl]-8-(1-ethyl-propyl)-2,6-dimethyl-imidazo[1,2-b]pyridazine

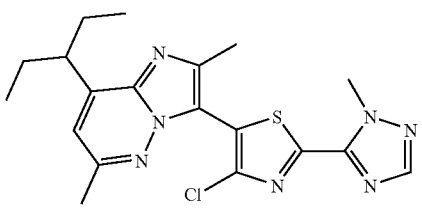

175 mg of 3-[4-Bromo-2-(2-methyl-2H-[1,2,4]triazol-3-yl)-thiazol-5-yl]-8-(1-ethyl-propyl)-2,6-dimethyl-imidazo

[1,2-b]pyridazine (0.38 mmol) and 56 mg of copper chloride (0.57 mmol) are placed into 4 ml vial with 3.0 ml of dry DMF and the vial is capped with a Teflon cap. The vial is heated at 130° C. overnight. The reaction mixture is applied onto a silica-gel chromatography column (Hexane:AcOEt=3:1 and hexane:AcOEt=8:1) to give 91 mg of crude product. The pure product is recrystallized from Et2O/Hexane. 73 mg (46%). mass spectrum (m/e): 416 (M+1). $^1$H-NMR (CDCl$_3$): 7.98 (s, 1H), 6.80 (s, 1H), 4.44 (s, 3H), 3.35 (m, 1H), 2.59 (s, 3H), 1.88 (m, 4H), 0.92 (t, J=7.5 Hz, 6H).

Example 50

Preparation of 8-(1-ethyl-propyl)-2,6-dimethyl-3-(4-methyl-oxazol-5-yl)-imidazo[1,2-b]pyridazine

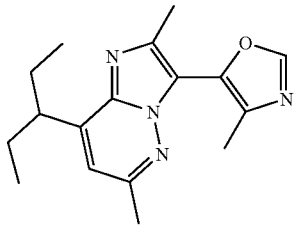

686 mg of 8-(1-Ethyl-propyl)-3-iodo-2,6-dimethyl-imidazo[1,2-b]pyridazine (2.0 mmol), 830 mg of 4-methyl-oxazole. (10 mmol), 105 mg of triphenylphosphine (0.4 mmol) and 1.30 g of cesium carbonate (4.0 mmol) are placed into tube with 10 ml of dry DMF. N2 gas is bubbled in for 20 min and 92 mg of Pd2 dba3 (0.1 mmol) is added. The tube is sealed and heated at 130° C. overnight. After being cooled to room temperature, water and CHCl2 are added to the mixture. The CHCl2 layer is separated, washed with sat. NaCl, dried over Na2SO4 and evaporated. The crude product is applied onto a silica-gel chromatography column (Hexane:AcOEt=5:1) to give 234 mg of the title product. Yield 39%. mass spectrum (m/e): 299 (M+1). $^1$H-NMR (CDCl3): 8.06 (s, 1H), 6.75 (s, 1H), 3.34 (m, 1H), 2.56 (s, 3H), 2.50 (s, 3H), 2.29 (s, 3H), 1.86 (m, 4H), 0.90 (t, J=7.4 Hz, 6H).

Example 51

Preparation of N-{5-[8-(1-Ethyl-propyl)-2,6-dimethyl-imidazo[1,2-b]pyridazin-3-yl]-4-methyl-oxazol-2-yl}-dimethylamine

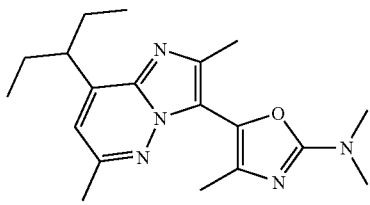

A. 3-(2-Bromo-4-methyl-oxazol-5-yl)-8-(1-ethyl-propyl)-2,6-dimethyl-imidazo[1,2-b]pyridazine.

230 mg of 8-(1-Ethyl-propyl)-2,6-dimethyl-3-(4-methyl-oxazol-5-yl)-imidazo[1,2-b]pyridazine (0.77 mmol) is dissolved in 20 ml of CH2Cl2 and 178 mg of NBS (1.0 mmol) is added. The reaction mixture is stirred at room temperature overnight. The reaction mixture is washed with sat. Na2S2O3, sat. NaCl, dried over Na2SO4 and evaporated. The crude product is applied onto a silica-gel chromatography column (Hexane:AcOEt=3:1) to give 36 mg of the title compound. Yield 12%. mass spectrum (m/e): 378 (M+1). $^1$H-NMR (CDCl3): 6.82 (s, 1H), 3.39 (m, 1H), 2.58 (s, 3H), 2.53 (s, 3H), 2.26 (s, 3H), 1.85 (m, 1H), 0.89 (t, J=7.4 Hz, 6H).

B. N-{5-[8-(1-Ethyl-propyl)-2,6-dimethyl-imidazo[1,2-b]pyridazin-3-yl]-4-methyl-oxazol-2-yl}-dimethylamine.

32 mg of 3-(2-Bromo-4-methyl-oxazol-5-yl)-8-(1-ethyl-propyl)-2,6-dimethyl-imidazo[1,2-b]pyridazine (0.08 mmol) and 78 mg of cesium carbonate (0.24 mmol) are placed into vial with 3 ml of dimethylamine 2.0 M in THF. The vial is capped with a Teflon cap and heated at 110° C. for 3 days. The reaction mixture is cooled to room temperature, concentrated, and applied onto a silica-gel chromatography column (Hexane:AcOEt:2M NH3 in MeOH=10:2:1) to give 24 mg of the title product. Yield 89%. mass spectrum (m/e): 342 (M+1). $^1$H-NMR (CDCl3): 6.71 (s, 1H), 3.34 (m, 1H), 3.13 (s, 6H), 2.56 (s, 3H), 2.49 (s, 3H), 2.14 (s, 3H), 1.84 (m, 4H), 0.89 (t, J=7.5 Hz, 6H).

Example 52

Preparation of 8-(1-ethyl-propyl)-2,6-dimethyl-3-[(4-methyl-2-ethylamino)-thiazol-5-yl]-imidazo[1,2-b]pyridazine

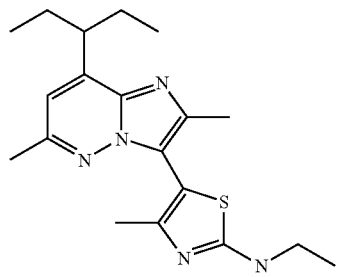

The title compound is prepared essentially as described in Example 51B. employing 2.0 ml of ethylamine 2.0 M in THF and 182 g of cesium carbonate (0.56 mmol), 78%. mass spectrum (m/e): 358 (M+1); $^1$H-NMR (CDCl3): 6.69 (s, 1H), 5.23 (br, 1H), 3.38 (m, 3H), 2.56 (s, 3H), 2.46 (s, 3H), 2.17 (s, 3H), 1.85 (m, 4H), 1.35 (t, 3H, J=7.2 Hz), 0.90 (t, 6H, J=7.2 Hz).

Example 53

Preparation of 3-[5-(2,4-dimethyl-thiazol-5-yl)-3-methyl-thiophen-2-yl]-8-(1-ethyl-propyl)-2,6-dimethyl-imidazo[1,2-b]pyridazine

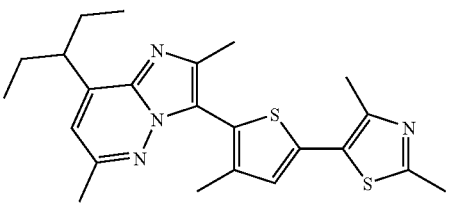

To a –78° C. mixture of 2,4-dimethylthiazole (0.23 g, 2.04 mmol) and THF (3 mL) is added 1.6 M t-Bu-Li in hexane (1.30 mL, 2.09 mmol). The mixture is stirred at –78° C. for 15 minutes. 0.5 M ZnCl$_2$ in THF (4.3 mL, 2.14 mmol) is added and the solution warmed to ambient temperature. 3-(5-bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) is added and mixture is stirred at 65° C. overnight, diluted with EtOAc (20 mL), washed with 10% citric acid (15 mL), water (15 mL), brine (15 mL), dried over MgSO$_4$, filtered and concentrated. The residue is purified by silica gel chromatography (0%-15% EtOAc/hexane gradient) furnish the title compound (0.21 g, 0.49 mmol, 49%). $^1$H NMR (CDCl$_3$), δ 0.87 (t, J=7.5 Hz, 6H), 1.73-1.91 (m, 4H), 2.14 (s, 3H), 2.49 (s, 3H), 2.52 (s, 3H), 2.57 (s, 3H), 2.66 (s, 3H), 3.28-3.38 (m, 1H), 6.68 (s, 1H), 7.00 (s, 1H). LC/MS (m/z): calcd. for C$_{23}$H$_{28}$N$_4$S$_2$ (M+H)$^+$: 425.3; found: 425.2.

Example 54

Preparation of 3-[5-(4,5-dimethyl-thiazol-2-yl)-3-methyl-thiophen-2-yl]-8-(1-ethyl-propyl)-2,6-dimethyl-imidazo[1,2-b]pyridazine

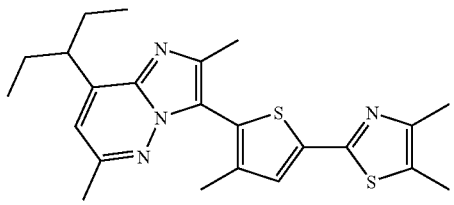

Using a procedure similar to Example 25, from 4,5-dimethylthiazole (0.22 mL, 2.04 mmol), 1.56 M n-Bu-Li (1.34 mL, 2.09 mmol), ZnCl$_2$ (4.3 mL, 2.14 mmol), 3-(5-bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) furnish the title compound (0.27 g, 0.64 mmol, 63%). $^1$H NMR (CDCl$_3$), δ 0.89 (t, J=7.5 Hz, 6H), 1.74-1.91 (m, 4H), 2.13 (s, 3H), 2.36 (s, 3H), 2.38 (s, 3H), 2.49 (s, 3H), 2.51 (s, 3H), 3.29-3.38 (m, 1H), 6.67 (s, 1H), 7.32 (s, 1H). LC/MS (m/z): calcd. for C$_{23}$H$_{28}$N$_4$S$_2$ (M+H)$^+$: 425.3; found: 425.2.

Example 55

Preparation of 8-(1-ethyl-propyl)-2,6-dimethyl-3-[3-methyl-5-(2-methyl-pyridin-4-yl)-thiophen-2-yl]-imidazo[1,2-b]pyridazine

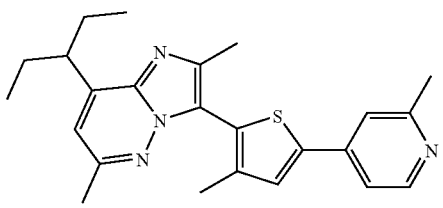

Using a procedure similar to Example 31, from 4-bromo-2-methylpyridine (Fukaya et. el. Chem. Pharm. Bull., 1990, 38, 2446) (0.21 g, 1.22 mmol), 1.56 M n-Bu-Li (0.69 mL, 1.07 mmol), 0.5 M ZnCl$_2$ in THF (2.2 mL, 1.12 mmol), 3-(5-bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) furnish the title compound (0.058 g, 0.14 mmol, 14%). $^1$H NMR (CDCl$_3$), δ 0.87 (t, J=7.5 Hz, 6H), 1.73-1.91 (m, 4H), 2.16 (s, 3H), 2.48 (s, 3H), 2.51 (s, 3H), 2.58 (s, 3H), 3.27-3.37 (m, 1H), 6.68 (s, 1H), 7.29 (d, J=5.3 Hz, 1H), 7.35 (s, 1H), 7.41 (s, 1H), 8.46 (t, J=5.3 Hz, 1H). LC/MS (m/z): calcd. for C$_{24}$H$_{28}$N$_4$S (M+H)$^+$: 405.3; found: 405.2.

Example 56

Preparation of 8-(1-ethyl-propyl)-2,6-dimethyl-3-[3-methyl-5-(1-methyl-1H-pyrazol-4-yl)-thiophen-2-yl]-imidazo[1,2-b]pyridazine

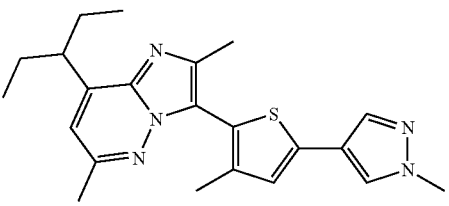

Using a procedure analogous to Example 31, from 3-(5-bromo-3-methyl-thiophen-2-yl)-8-(1-ethyl-propyl)-2,6-dimethyl-imidazo[1,2-b]pyridazine (0.40 g, 1.02 mmol), 1.42 M n-Bu-Li (0.75 mL, 1.07 mmol), 0.5 M ZnCl$_2$ in THF (2.14 mL, 1.07 mmol), 4-bromo-1-methyl-1H-pyrazole (0.25 g, 1.53 mmol) and PdCl$_2$(dppf) (0.037 g, 0.051 mmol) furnishes the title compound (0.092 g, 0.23 mmol, 23%). $^1$H NMR (CDCl$_3$) δ 0.88 (t, J=7.4 Hz, 6H), 1.73-1.92 (m, 4H), 2.12 (s, 3H), 2.48 (s, 3H), 2.52 (s, 3H), 3.29-3.38 (m, 1H), 3.92 (s, 3H), 6.66 (s, 1H), 6.98 (s, 1H), 7.54 (s, 1H), 7.68 (s, 1H). LC/MS (m/z): calcd. for C$_{22}$H$_{27}$N$_5$S (M+H)$^+$: 394.3; found: 394.2.

Example 57

Preparation of 4-{5-[8-(1-ethyl-propyl)-2,6-dimethyl-imidazo[1,2-b]pyridazin-3-yl]-4-methyl-thiophen-2-yl}-tetrahydro-pyran-4-ol

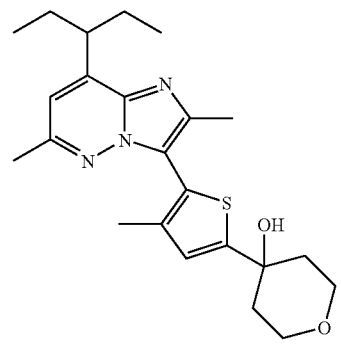

To a −78° C. solution of 3-(5-bromo-3-methyl-thiophen-2-yl)-8-(1-ethyl-propyl)-2,6-dimethyl-imidazo[1,2-b]pyridazine (0.60 g, 1.53 mmol) and THF (10 mL) is added 1.56 M n-Bu-Li (1.03 mL, 1.61 mmol). After 30 minutes tetrahydro-pyran-4-one (0.21 mL, 2.29 mmol) is added over 5 minutes. The solution is stirred at −78° C. for 2 hours, warmed to ambient temperature, diluted with EtOAc (50 mL), washed with sat. NH$_4$Cl (50 mL), dried over MgSO$_4$, filtered and concentrated. The residue is purified by ISCO column chromatography (20%-100% EtOAc/hexane gradient) furnish the title compound (0.38 g, 0.92 mmol, 60%). $^1$H NMR (CDCl$_3$), δ 0.88 (t, J=7.5 Hz, 6H), 1.74-1.91 (m, 4H), 1.91-2.00 (m, 2H), 2.11 (s, 3H), 2.20-2.30 (m, 2H), 2.46 (s, 3H), 2.51 (s, 3H), 3.30-3.39 (m, 1H), 3.83-3.98 (m, 5H), 6.66 (s, 1H), 6.93 (s, 1H). LC/MS (m/z): calcd. for C$_{23}$H$_{31}$N$_3$O$_2$S (M+H)$^+$: 414.3; found: 414.2.

Example 58

Preparation of 8-(1-ethyl-propyl)-2,6-dimethyl-3-[3-methyl-5-(tetrahydro-pyran-4-yl)-thiophen-2-yl]-imidazo[1,2-b]pyridazine

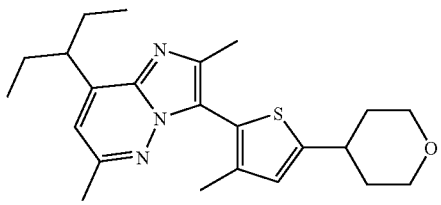

Method A.

To a solution of 4-{5-[8-(1-ethyl-propyl)-2,6-dimethyl-imidazo[1,2-b]pyridazin-3-yl]-4-methyl-thiophen-2-yl}-tetrahydro-pyran-4-ol (0.25 g, 0.604 mmol) and CH$_2$Cl$_2$ (10 mL) is added TFA (0.79 mL, 10.28 mmol) and Et$_3$SiH (0.25 mL, 1.57 mmol). The solution is concentrated, dissolved in EtOAc (30 mL), washed with sat. NaHCO$_3$ (30 mL), dried over MgSO$_4$, filtered and concentrated. The residue is purified by ISCO column chromatography (10%-15% EtOAc/hexane gradient), is dissolved in EtOH (25 mL), 10% Pd/C (0.07 g, 0.066 mmol) is added and the solution stirred under an atmosphere of H$_2$. After 2 hours the solution is filtered thru Celite® and concentrated. The residue is purified by ISCO column chromatography (30% EtOAc in hexane) furnish the title compound (0.033 g, 0.083 mmol, 14%). $^1$H NMR (CDCl$_3$), δ 0.88 (t, J=7.5 Hz, 6H), 1.74-1.95 (m, 4H), 1.97-2.04 (m, 2H), 2.09 (s, 3H), 2.20-2.30 (m, 2H), 2.46 (s, 3H), 2.52 (s, 3H), 3.00-3.11 (m, 1H), 3.30-3.40 (m, 1H), 3.54 (dt, J=11.8, 2.2 Hz, 2H), 4.08 (dd, J=11.8, 2.2 Hz, 2H), 6.65 (s, 1H), 6.75 (s, 1H). LC/MS (m/z): calcd. for C$_{23}$H$_{31}$N$_3$OS (M+H)$^+$: 398.7; found: 398.2.

Method B.

A. 4-(5-Bromo-4-methyl-thiophen-2-yl)-tetrahydro-pyran-4-ol.

To a −78° C. solution of 2-bromo-3-methyl-thiophene (2.0 g, 17.75 mmol) and THF (30 mL) is added 2.0 M LDA (9.32 mL, 18.63 mmol). After 30 minutes at −78° C. tetrahydro-pyran-4-one (2.3 mL, 23.07 mmol) is added and the solution is warmed to ambient temperature. The solution is washed with sat. NH$_4$Cl (30 mL). The aqueous phases is extracted with EtOAc. The combined organic layers are dried over MgSO$_4$, filtered and concentrated. The residue is purified by ISCO column chromatography (30%-100% EtOAc/hexane gradient) furnish the title compound (2.3 g, 8.30 mmol, 47%). $^1$H NMR (CDCl$_3$), δ 1.82 (m, 2H), 2.00 (s, 3H), 2.06-2.15 (m, 3H), 2.16 (s, 3H), 3.77-3.84 (m, 2H), 3.87 dt, J=11.3, 2.2 Hz, 2H), 6.67 (s, 1H). LC/MS (m/z): calcd. for C$_{10}$H$_{13}$BrO$_2$S (M+H)$^+$: 277.0; found: 260.9.

B. 4-(5-Bromo-4-methyl-thiophen-2-yl)-tetrahydro-pyran.

To a solution of 4-(5-bromo-4-methyl-thiophen-2-yl)-tetrahydro-pyran-4-ol (2.3 g, 8.30 mmol) and 1,2-dichloroethane (50 mL) is added ZnI$_2$ (3.97 g, 12.45 mmol) and sodium cyanoborohydride (3.91, 62.23 mmol). The solution is stirred for 1 hour, filtered thru celite and concentrated. The residue is purified by ISCO column chromatography (5%-10% EtOAc/hexane gradient) furnish the title compound (1.53 g, 5.86 mmol, 71%). $^1$H NMR (CDCl$_3$), δ 1.69-1.82 (m, 2H), 1.84-1.92 (m, 2H), 2.14 (s, 3H), 2.84-2.98 (m, 1H), 3.49 (dt, J=11.8, 2.2 Hz, 2H), 4.00-4.07 (m, 2H), 6.51 (s, 1H).

C. 8-(1-Ethyl-propyl)-2,6-dimethyl-3-[3-methyl-5-(tetrahydro-pyran-4-yl)-thiophen-2-yl]-imidazo[1,2-b]pyridazine.

Using a procedure similar to Example 25, 4-(5-bromo-4-methyl-thiophen-2-yl)-tetrahydropyran (0.83 g, 3.19 mmol), 1.56 M n-Bu-Li (2.04 mL, 3.19 mmol), ZnCl$_2$ (6.4 mL, 3.19 mmol), 8-(1-ethyl-propyl)-3-iodo-2,6-dimethyl-imidazo[1,2-b]pyridazine (0.50 g, 1.56 mmol) and Pd(PPh$_3$)$_4$ (0.092 g, 0.008 mmol) furnish the title compound (0.072 g, 0.18 mmol, 11%). Spectrum identical to that from Method A.

Example 59

Preparation of 3-[5-(3,4-difluoro-phenyl)-3-methyl-thiophen-2-yl]-8-(1-ethyl-propyl)-2,6-dimethyl-imidazo[1,2-b]pyridazine

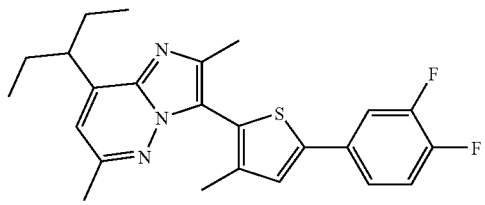

Using a procedure similar to Example 32, 3-(5-bromo-3-methyl-thiophen-2-yl)-8-(1-ethyl-propyl)-2,6-dimethyl-imidazo[1,2-b]pyridazine (0.50 g, 1.27 mmol) and PdCl$_2$(dppf) (0.047 g, 0.064 mmol) and 0.5 M solution of 3,4-difluorophenylzinc bromide in THF (5.1 mL, 2.55 mmol) are reacted. The residue is purified by ISCO column chromatography (15%-20% EtOAc/hexane gradient) and is chromatographed (50× 250 C18 Symmetry column, 30-80% water: 0.1% TPA/ACN: 0.1% TFA gradient) furnish the title compound (0.18 g, 0.42 mmol, 33%). $^1$H NMR (CDCl$_3$), δ 0.90 (t, J=7.5 Hz, 6H), 1.76-1.94 (m, 4H), 2.16 (s, 3H), 2.50 (s, 3H), 2.54 (s, 3H), 3.31-3.40 (m, 1H), 6.69 (s, 1H), 7.13-7.21 (m, 1H), 7.18 (s, 1H), 7.31-7.36 (m, 1H), 7.39-7.46 (m, 1H). LC/MS (m/z): calcd. for C$_{24}$H$_{25}$F$_2$N$_3$S (M+H)$^+$: 426.3; found: 426.2.

Example 60

Preparation of 3-(5-benzyl-3-methyl-thiophen-2-yl)-8-(1-ethyl-propyl)-2,6-dimethyl-imidazo[1,2-b]pyridazine

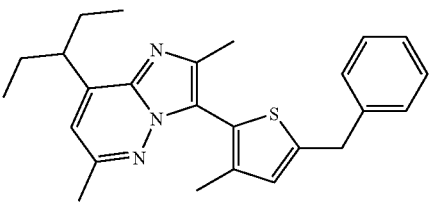

Using a procedure similar to Example 32, 3-(5-bromo-3-methyl-thiophen-2-yl)-8-(1-ethyl-propyl)-2,6-dimethyl-imidazo[1,2-b]pyridazine (0.30 g, 0.765 mmol) and PdCl$_2$(dppf) (0.028 g, 0.038 mmol) and 0.5 M solution of benzylzinc bromide in THF (4.6 mL, 2.29 mmol) are reacted. The residue is purified by ISCO column chromatography (15%-20% EtOAc/hexane gradient) and is chromatographed (50×250 C18 Symmetry column, 40-65% water: 0.1% TFA/ACN: 0.1% TFA gradient) furnish the title compound (0.062 g, 0.15 mmol, 20%). $^1$H NMR (CDCl$_3$), δ 0.88 (t, J=7.5 Hz, 6H), 1.73-1.92 (m, 4H), 2.06 (s, 3H), 2.45 (s, 3H), 2.51 (s, 3H), 3.29-3.39 (m, 1H), 4.16 (s, 2H), 6.65 (s, 1H), 6.68 (s, 1H), 7.22-7.29 (m, 1H), 7.31-7.36 (m, 4H). LC/MS (m/z): calcd. for C$_{25}$H$_{29}$N$_3$S (M+H)$^+$: 404.3; found: 404.2.

Example 61

Preparation of 8-(1-ethyl-propyl)-2,6-dimethyl-3-(3-methyl-4-pyridin-3-yl-thiophen-2-yl)-imidazo[1,2-b]pyridazine

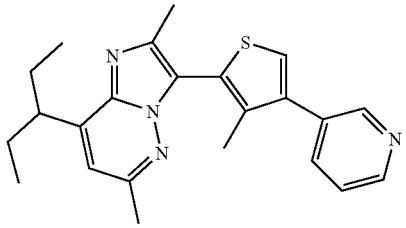

A solution of 3-(4-bromo-3-methyl-thiophen-2-yl)-8-(1-ethyl-propyl)-2,6-dimethyl-imidazo[1,2-b]pyridazine (0.25 g, 0.64 mmol), pyridine-3-boronic acid (0.086 g, 0.70 mmol), 2 M $Na_2CO_3$ (0.48 mL, 0.96 mmol) and, n-PrOH (3 mL), is degassed with nitrogen for 10 minutes. Pd(OAc)$_2$ (2.7 mg, 0.0013 mmol) and PPh$_3$ (0.010 g, 0.038 mmol) are added and the solution is heated at 90° C. overnight. The solution is diluted with EtOAc (30 mL), washed with 10% $Na_2CO_3$ (30 mL), water (30 mL), brine (30 mL), dried over $MgSO_4$, filtered, and concentrated. The residue is purified by ISCO (20-40% EtOAc gradient) furnish the title compound (0.051 g, 0.13 mmol, 20%). $^1$H NMR (CDCl$_3$) δ 0.88 (t, J=7.5 Hz, 6H), 1.74-1.92 (m, 4H), 2.09 (s, 3H), 2.50 (s, 3H), 2.52 (s, 3H), 3.29-3.40 (m, 1H), 6.69 (s, 1H), 7.33-7.43 (m, 1H), 7.47 (s, 1H), 7.80 (d, J=7.9 Hz, 1H), 8.61 (bs, 1H), 8.78 (bs, 1H). LC/MS (m/z): calcd. for $C_{23}H_{26}N_4S$ (M+H)$^+$: 391.2; found: 391.4.

Example 62

Preparation of 8-(1-ethyl-propyl)-3-[5-(6-methoxy-pyridin-2-yl)-3-methyl-thiophen-2-yl]-2,6-dimethyl-imidazo[1,2-b]pyridazine

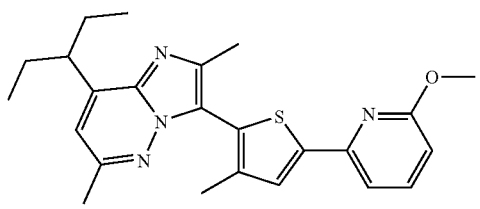

Using a procedure similar to Example 32, from 3-(5-bromo-3-methyl-thiophen-2-yl)-8-(1-ethyl-propyl)-2,6-dimethyl-imidazo[1,2-b]pyridazine (0.30 g, 0.765 mmol) and PdCl$_2$(dppf) (0.028 g, 0.038 mmol) and 0.5 M solution of 6-methoxy-2-pyridylzinc bromide in THF (3.0 mL, 1.53 mmol) furnish the title compound (0.12 g, 0.29 mmol, 38%). $^1$H NMR (CDCl$_3$), δ 0.88 (t, J=7.5 Hz, 6H), 1.73-1.92 (m, 4H), 2.15 (s, 3H), 2.50 (s, 3H), 2.51 (s, 3H), 3.29-3.38 (m, 1H), 3.98 (s, 3H), 6.61 (d, J=7.5 Hz, 1H), 6.70 (s, 1H), 7.23 (d, J=7.5 Hz, 1H), 7.52 (s, 1H), 7.56 (d, J=7.7 Hz, 1H). LC/MS (m/z): calcd. for $C_{24}H_{28}N_4OS$ (M+H)$^+$: 421.3; found: 421.3.

Example 63

Preparation of 8-(1-ethyl-propyl)-2,6-dimethyl-3-[3-methyl-5-(4-methyl-pyridin-2-yl)-thiophen-2-yl]-imidazo[1,2-b]pyridazine

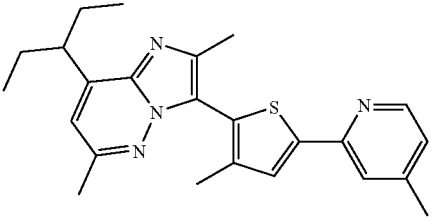

Using a procedure similar to Example 32, from 3-(5-bromo-3-methyl-thiophen-2-yl)-8-(1-ethyl-propyl)-2,6-dimethyl-imidazo[1,2-b]pyridazine (0.30 g, 0.765 mmol) and PdCl$_2$(dppf) (0.028 g, 0.038 mmol) and 0.5 M solution of 4-methyl-2-pyridylzinc bromide in THF (3.0 mL, 1.53 mmol) furnish the title compound (0.21 g, 0.52 mmol, 68%). $^1$H NMR (CDCl$_3$), δ 0.90 (t, J=7.5 Hz, 6H), 1.75-1.93 (m, 4H), 2.17 (s, 3H), 2.40 (s, 3H), 2.52 (s, 6H), 3.30-3.40 (m, 1H), 6.67 (s, 1H), 6.97 (d, J=4.8 Hz, 1H), 7.49 (s, 1H), 7.52 (s, 1H), 8.42 (d, J=4.8 Hz, 1H). LC/MS (m/z): calcd. for $C_{24}H_{28}N_4S$ (M+H)$^+$: 405.3; found: 405.3.

Example 64

Preparation of 8-(1-ethyl-propyl)-2,6-dimethyl-3-[3-methyl-5-(3-methyl-pyridin-2-yl)-thiophen-2-yl]-imidazo[1,2-b]pyridazine

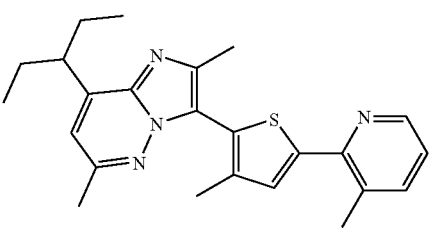

Using a procedure similar to Example 32, from 3-(5-bromo-3-methyl-thiophen-2-yl)-8-(1-ethyl-propyl)-2,6-dimethyl-imidazo[1,2-b]pyridazine) (0.30 g, 0.765 mmol) and PdCl$_2$(dppf) (0.028 g, 0.038 mmol) and 0.5 M solution of 3-methyl-2-pyridylzinc bromide in THF (5.0 mL, 2.50 mmol) furnish the title compound (0.22 g, 0.54 mmol, 71%). $^1$H NMR (CDCl$_3$), δ 0.88 (t, J=7.5 Hz, 6H), 1.74-1.92 (m, 4H), 2.17 (s, 3H), 2.50 (s, 3H), 2.51 (s, 3H), 2.63 (s, 3H), 3.29-3.39 (m, 1H), 6.67 (s, 1H), 7.06-7.14 (m, 1H), 7.44 (s, 1H), 7.74 (dd, J=7.5, 0.9 Hz, 1H), 8.47 (dd, J=4.9, 0.9 Hz, 1H). LC/MS (m/z): calcd. for $C_{24}H_{28}N_4S$ (M+H)$^+$: 405.3; found: 405.3.

Example 65

Preparation of (6-{5-[8-(1-ethyl-propyl)-2,6-dimethyl-imidazo[1,2-b]pyridazin-3-yl]-4-methyl-thiophen-2-yl}-pyridin-2-yl)-dimethyl-amine

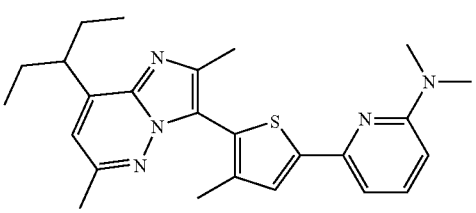

Using a procedure similar to Example 39, from Rieke® Zn in THF (0.20 g, 3.06 mmol), (6-bromo-pyridin-2-yl)-dimethyl-amine (Newkomw et. el. *J. Org. Chem.*, 1988, 3, 786) (0.41 mL, 2.04 mmol), 3-(5-bromo-3-methyl-thiophen-2-yl)-8-(1-ethyl-propyl)-2,6-dimethyl-imidazo[1,2-b]pyridazine (0.35 g, 0.89 mmol), and PdCl$_2$(dppf) (0.037 g, 0.051 mmol) furnish the title compound (0.16 g, 0.37 mmol, 36%). $^1$H NMR (CDCl$_3$), δ 0.89 (t, J=7.5 Hz, 6H), 1.75-1.93 (m, 4H), 2.15 (s, 3H), 2.51 (s, 3H), 2.52 (s, 3H), 3.21 (s, 6H), 3.30-3.40 (m, 1H), 6.40 (d, J=8.4 Hz, 1H), 6.66 (s, 1H), 6.95 (d, J=7.4 Hz, 1H), 7.45 (dd, J=8.4, 7.4 Hz, 1H), 7.46 (s, 1H). LC/MS (m/z): calcd. for C$_{25}$H$_{31}$N$_5$S (M+H)$^+$: 434.3; found: 434.3.

Example 66

Preparation of 8-(1-ethyl-propyl)-2,6-dimethyl-3-[3-methyl-5-(5-methyl-pyridin-2-yl)-thiophen-2-yl]-imidazo[1,2-b]pyridazine

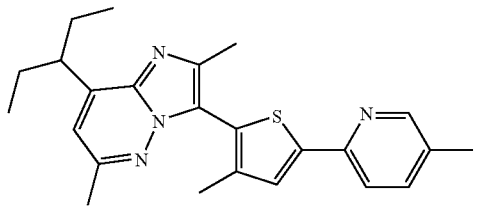

Using a procedure similar to Example 32, from 3-(5-bromo-3-methyl-thiophen-2-yl)-8-(1-ethyl-propyl)-2,6-dimethyl-imidazo[1,2-b]pyridazine (0.30 g, 0.765 mmol) and PdCl$_2$(dppf) (0.028 g, 0.038 mmol) and 0.5 M solution of 4-methyl-2-pyridylzinc bromide in THF (3.0 mL, 1.53 mmol) furnish the title compound (0.23 g, 0.57 mmol, 74%). $^1$H NMR (CDCl$_3$), δ 0.90 (t, J=7.5 Hz, 6H), 1.75-1.93 (m, 4H), 2.16 (s, 3H), 2.35 (s, 3H), 2.51 (s, 3H), 2.52 (s, 3H), 3.31-3.41 (m, 1H), 6.67 (s, 1H), 7.48 (s, 1H), 7.50 (d, J=2.2 Hz, 1H), 7.56 (d, J=7.9 Hz, 1H), 8.39-8.40 (m, 1H). LC/MS (m/z): calcd. for C$_{24}$H$_{28}$N$_4$S (M+H)$^+$: 405.3; found: 405.3.

Example 67

Preparation of 8-(1-ethyl-propyl)-3-[5-(6-methanesulfonyl-pyridin-2-yl)-3-methyl-thiophen-2-yl]-2,6-dimethyl-imidazo[1,2-b]pyridazine

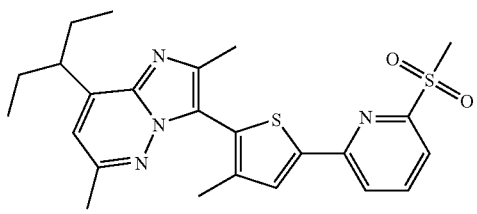

A. 2-Bromo-6-methanesulfonyl-pyridine.

To a solution of 2-bromo-6-methylsulfanyl-pyridine (Testaferri et. el *Tetrahedron*, 1985, 41, 1373) (2.15 g, 10.53 mmol) and CH$_2$Cl$_2$ (30 mL) is added 56-87% mCPBA (12 g, 42.15 mmol). The solution is cooled with ice to ambient temperature and the solution is stirred for 2 hour, washed with sat. Na$_2$S$_2$O$_3$ (15 mL), sat. NaHCO$_3$ (2×15 mL) dried over MgSO$_4$, filtered and concentrated. The residue is purified by recrystallization from EtOAc/hexane furnish the title compound (1.71 g, 7.24 mmol, 69%). $^1$H NMR (CDCl$_3$), δ 3.26 (s, 3H), 7.73 (dd, J=8.0, 0.9 Hz, 1H), 7.82 (dd, J=8.0, 7.5 Hz, 1H), 8.05 (dd, J=7.5, 0.9 Hz, 1H). LC/MS (m/z): calcd. for C$_6$H$_6$BrNO$_2$S (M+H)$^+$: 235.9; found: 235.9.

B. 8-(1-ethyl-propyl)-3-[5-(6-methanesulfonyl-pyridin-2-yl)-3-methyl-thiophen-2-yl]-2,6-dimethyl-imidazo[1,2-b]pyridazine.

Using a procedure similar to Example 25, 2-bromo-6-methanesulfonyl-pyridine (0.29 mL, 1.22 mmol), 1.3 M n-Bu-Li (0.82 mL, 1.07 mmol), ZnCl$_2$ (2.14 mL, 1.07 mmol), 3-(5-bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) furnish the title compound (0.13 g, 0.28 mmol, 27%). $^1$H NMR (CDCl$_3$), δ0.88 (t, J=7.5 Hz, 6H), 1.75-1.93 (m, 4H), 2.18 (s, 3H), 2.50 (s, 3H), 2.52 (s, 3H), 3.30 (s, 3H), 3.30-3.38 (m, 1H), 6.70 (s, 1H), 7.64 (s, 1H), 7.83 (dd, J=7.6, 0.8 Hz, 1H), 7.89 (dd, J=7.9, 0.8 Hz, 1H), 7.93 (dd, J=7.9, 7.6 Hz, 1H). LC/MS (m/z): calcd. for C$_{24}$H$_{28}$N$_4$O$_2$S$_2$ (M+H)$^+$: 469.3; found: 469.2.

Example 68

Preparation of 8-(1-ethyl-propyl)-2,6-dimethyl-3-[3-methyl-5-(6-trifluoromethyl-pyridin-2-yl)-thiophen-2-yl]-imidazo[1,2-b]pyridazine

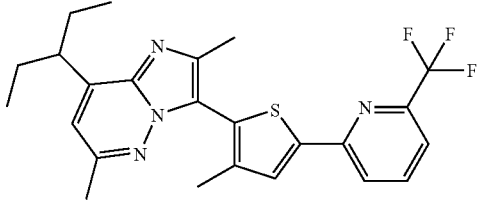

Using a procedure similar to Example 25, 2-chloro-6-trifluoromethyl-pyridine (0.29 mL, 1.22 mmol), 1.34 M n-Bu-Li (0.80 mL, 1.07 mmol), ZnCl$_2$ (2.14 mL, 1.07 mmol), 3-(5-bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) furnish the title compound (0.20 g, 0.44 mmol, 43%). $^1$H NMR (CDCl$_3$), δ 0.90 (t, J=7.5 Hz, 6H), 1.76-1.94 (m, 4H), 2.18 (s, 3H), 2.51 (s, 3H), 2.53 (s, 3H), 3.30-3.40 (m, 1H), 6.69 (s, 1H), 7.50 (dd, J=7.5, 0.9 Hz, 1H), 7.65 (s, 1H), 7.78 (d, J=7.9 Hz, 1H), 7.84 (dd, J=7.9, 7.5 Hz, 1H). LC/MS (m/z): calcd. for C$_{24}$H$_{25}$F$_3$N$_4$S (M+H)$^+$: 459.3. found: 459.2.

Example 69

Preparation of 8-(1-ethyl-propyl)-2,6-dimethyl-3-[3-methyl-4-(2-methyl-2H-[1,2,4]triazol-3-yl)-thiophen-2-yl]-imidazo[1,2-b]pyridazine

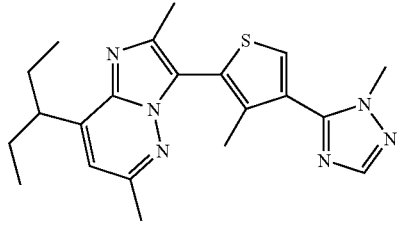

To a slurry of 0.05 g/mL of Reike® Zn in THF (3.0 mL, 2.29 mmol) is added a solution of 5-bromo-1-methyl-1H-[1,2,4]triazole and THF (2 mL). The solution was heated at 65° C. for 1 hour, cooled to ambient temperature and the excess Zn allowed to settle for 1 hour. The solution was transferred to a flask containing 3-(4-bromo-3-methyl-thiophen-2-yl)-8-(1-ethyl-propyl)-2,6-dimethyl-imidazo[1,2-b]pyridazine (example Rupp-152) (0.32 g, 0.70 mmol) and PdCl$_2$(dppf) (0.028 g, 0.038 mmol). The solution is heated at 65° C. overnight, diluted with EtOAc (30 mL), washed with sat. NH$_4$Cl (30 mL), dried over MgSO$_4$, filtered and concentrated. The residue is purified by ISCO (50%-100% Et$_2$O) to furnish the title compound (0.058 g, 0.15 mmol, 19%). $^1$H NMR (CDCl$_3$) δ 0.86 (t, J=7.5 Hz, 6H), 1.73-1.92 (m, 4H), 2.11 (s, 3H), 2.47 (s, 3H), 2.49 (s, 3H), 3.27-3.37 (m, 1H), 3.97 (s, 3H), 6.68 (s, 1H), 7.64 (s, 1H), 7.99 (s, 1H). LC/MS (m/z): calcd. for C$_{21}$H$_{26}$N$_6$S (M+H)$^+$: 395.2; found: 395.4.

Example 70

Preparation of 1-(6-{5-[8-(1-ethyl-propyl)-2,6-dimethyl-imidazo[1,2-b]pyridazin-3-yl]-4-methyl-thiophen-2-yl}-pyridin-2-yl)-ethanone

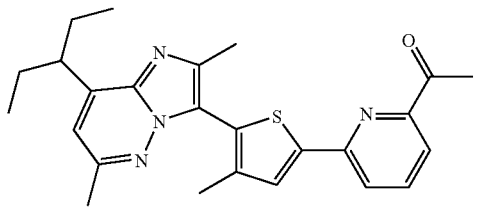

A. 3-[5-(6-Bromo-pyridin-2-yl)-3-methyl-thiophen-2-yl]-8-(1-ethyl-propyl)-2,6-dimethyl-imidazo[1,2-b]pyridazine.

Using a procedure similar to Example 25, 2,6-dibromopyridine (0.91 g, 3.82 mmol), 1.34 M n-Bu-Li (1.50 mL, 2.00 mmol), ZnCl$_2$ (4.0 mL, 2.00 mmol), 3-(5-bromo-3-methyl-thiophen-2-yl)-8-(1-ethyl-propyl)-2,6-dimethyl-imidazo[1,2-b]pyridazine (0.75 g, 1.92 mmol) and PdCl$_2$(dppf) (0.070 g, 0.096 mmol) furnish the title compound (0.26 g, 0.55 mmol, 29%). $^1$H NMR (CDCl$_3$), δ 0.89 (t, J=7.4 Hz, 6H), 1.74-1.93 (m, 4H), 2.16 (s, 3H), 2.50 (s, 3H), 2.52 (s, 3H), 3.30-3.39 (m, 1H), 6.68 (s, 1H), 7.31 (dd, J=7.5, 1.3 Hz, 1H), 7.49-7.57 (m, 2H), 7.58 (s, 1H).

B. 1-(6-{5-[8-(1-Ethyl-propyl)-2,6-dimethyl-imidazo[1,2-b]pyridazin-3-yl]-4-methyl-thiophen-2-yl}-pyridin-2-yl)-ethanone.

To a −78° C. solution of 3-[5-(6-bromo-pyridin-2-yl)-3-methyl-thiophen-2-yl]-8-(1-ethyl-propyl)-2,6-dimethyl-imidazo[1,2-b]pyridazine) (0.26 g, 0.55 mmol), and THF (5 mL), is added 1.34 M n-Bu-Li (0.43 mL, 0.58 mmol). After 30 minutes N-methoxy-N-methyl-acetamide (0.065 mL, 0.61 mmol) is added and the solution warmed to ambient temperature. The solution is diluted with EtOAc (30 mL), washed with sat. NH$_4$Cl (25 mL), dried over MgSO$_4$, filtered and concentrated. The residue is purified by ISCO column chromatography (15-20% EtOAc/hexane gradient) furnish the title compound (0.030 g, 0.069 mmol, 13%). $^1$H NMR (CDCl$_3$), δ 0.89 (t, J=7.5 Hz, 6H), 1.75-1.93 (m, 4H), 2.19 (s, 3H), 2.52 (s, 3H), 2.53 (s, 3H), 2.77 (s, 3H), 3.30-3.40 (m, 1H), 6.69 (s, 1H), 7.59 (s, 1H), 7.77-7.85 (m, 2H), 7.87 (dd, J=6.8, 2.2 Hz, 1H). LC/MS (m/z): calcd. for C$_{25}$H$_{28}$N$_4$OS (M+H)$^+$: 433.3; found: 433.2.

Example 71

Preparation of 8-(1-ethyl-propyl)-2,6-dimethyl-3-[3-methyl-5-(5-trifluoromethyl-pyridin-2-yl)-thiophen-2-yl]-imidazo[1,2-b]pyridazine

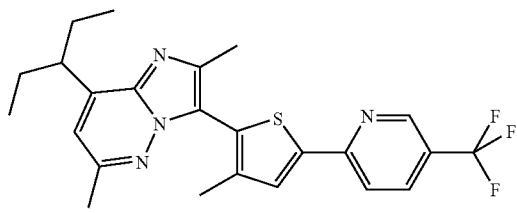

Using a procedure similar to Example 32, from 2-bromo-5-trifluoromethyl-pyridine (2.14 mL, 1.07 mmol), 1.34 M n-Bu-Li (0.80 mL, 1.07 mmol), ZnCl$_2$ (2.14 mL, 1.07 mmol), 3-(5-bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) furnish the title compound (0.17 g, 0.37 mmol, 36%). $^1$H NMR (CDCl$_3$), δ 0.90 (t, J=7.3 Hz, 6H), 1.76-1.94 (m, 4H), 2.18 (s, 3H), 2.19 (s, 3H), 2.53 (s, 3H), 3.31-3.40 (m, 1H), 6.70 (s, 1H), 7.63 (s, 1H), 7.74 (d, J=8.4 Hz, 1H), 7.78 (dd, J=8.4, 2.2 Hz, 1H), 7.79-7.82 (m, 1H). LC/MS (m/z): calcd. for C$_{24}$H$_{25}$F$_3$N$_4$S (M+H)$^+$: 459.3; found: 459.2.

Example 72

Preparation of 8-(1-ethyl-propyl)-3-(5-methoxymethyl-3-methyl-thiophen-2-yl)-2,6-dimethyl-imidazo[1,2-b]pyridazine

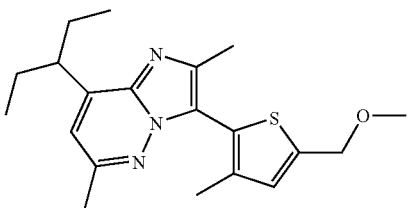

To a −78° C. solution of 3-(5-bromo-3-methyl-thiophen-2-yl)-8-(1-ethyl-propyl)-2,6-dimethyl-imidazo[1,2-b]pyridazine (0.30 g, 0.76 mmol) and THF (3 mL) is added 1.34 M n-Bu-Li (0.50 mL, 0.80 mmol). After 30 minutes iodo-methoxy-methane (0.097 mL, 1.15 mmol) is added and the solution warmed to ambient temperature. After 1 hour the solution is diluted with EtOAc (40 mL) washed with water (30 mL), brine (30 mL), dried over MgSO$_4$, filtered and concentrated. The residue is purified by ISCO column chromatography (15%-20% EtOAc/hexane gradient) furnish the title compound (0.12 g, 0.34 mmol, 44%). $^1$H NMR (CDCl$_3$), δ 0.87 (t, J=7.5 Hz, 6H), 1.72-1.90 (m, 4H), 2.09 (s, 3H), 2.45 (s, 3H), 2.49 (s, 3H), 3.28-3.37 (m, 1H), 3.44 (s, 3H), 4.61 (s, 2H), 6.65 (s, 1H), 6.93 (s, 1H). LC/MS (m/z): calcd. for C$_{20}$H$_{27}$N$_3$OS (M+H)$^+$: 358.3; found: 358.3.

Example 73

Preparation of 3-[5-(2-ethoxy-ethyl)-3-methyl-thiophen-2-yl]-8-(1-ethyl-propyl)-2,6-dimethyl-imidazo[1,2-b]pyridazine

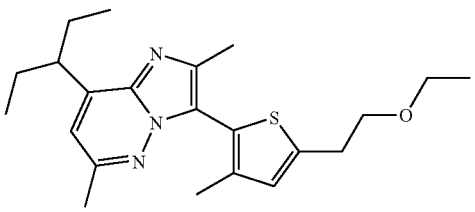

Using a procedure similar to Example 72, from of 3-(5-bromo-3-methyl-thiophen-2-yl)-8-(1-ethyl-propyl)-2,6-dimethyl-imidazo[1,2-b]pyridazine (0.30 g, 0.76 mmol), 1.34 M n-Bu-Li (0.53 mL, 0.84 mmol), 1-bromo-2-ethoxy-ethane (0.13 mL, 1.15 mmol) and KI (0.013 g, 0.076 mmol) furnish the title compound (0.11 g, 0.29 mmol, 38%). $^1$H NMR (CDCl$_3$), δ 0.86 (t, J=7.5 Hz, 6H), 1.23 (t, J=7.0 Hz, 3H), 1.72-1.90 (m, 4H), 2.06 (s, 3H), 2.45 (s, 3H), 2.49 (s, 3H), 3.09 (t, J=7.0 Hz, 2H), 3.28-3.37 (m, 1H), 3.55 (q, J=7.0

Hz, 2H), 3.71 (t, J=7.0 Hz, 2H), 6.64 (s, 1H), 6.77 (s, 1H). LC/MS (m/z): calcd. for $C_{22}H_{31}N_3OS$ (M+H)+: 386.3 found: 386.3.

Example 74

Preparation of {5-[8-(1-ethyl-propyl)-2,6-dimethyl-imidazo[1,2-b]pyridazin-3-yl]-4-methyl-thiophen-2-yl}-phenyl-methanol

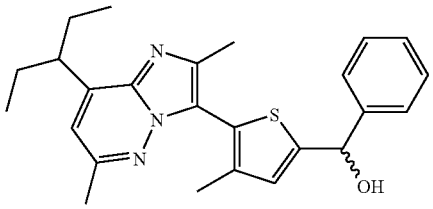

A. (5-Bromo-4-methyl-thiophen-2-yl)-phenyl-methanol.

To a −78° C. solution of 2-bromo-3-methyl-thiophene (4.7 g, 26.54 mmol) and Et$_2$O (100 mL) is added 2.0 M LDA (14.6 mL, 29.2 mmol). After 1 hour benzaldehyde (3.0 mL, 29.2 mmol) is added and the solution warmed to ambient temperature and stirred for 2 hour. The solution is washed with sat. NH$_4$Cl (75 mL), dried over MgSO$_4$, filtered and concentrated. The residue is purified by ISCO column chromatography (20%-30% EtOAc/hexane gradient) furnish the title compound (3.29 g, 11.62 mmol, 44%). $^1$H NMR (CDCl$_3$), δ 2.11 (s, 3H), 3.38-3.46 (m, 1H), 5.90 (s, 1H), 6.54 (s, 1H), 7.30-7.45 (m, 5H). LC/MS (m/z): calcd. for $C_{12}H_{11}BrOS$ (M+H)+: 281.0, 283.0; found: 264.9, 266.9.

B. {5-[8-(1-Ethyl-propyl)-2,6-dimethyl-imidazo[1,2-b]pyridazin-3-yl]-4-methyl-thiophen-2-yl}-phenyl-methanol.

Using a procedure analogous to Example 30C, from 3-(5-boronic acid-3-methyl-thiophen-2-yl)-8-(1-ethyl-propyl)-2,6-dimethyl-imidazo[1,2-b]pyridazine (0.30 g, 0.1.15 mmol), (5-bromo-4-methyl-thiophen-2-yl)-phenyl-methanol (0.33 g, 1.15 mmol), 2 M Na$_2$CO$_3$ (0.86 mL, 1.72 mmol) n-PrOH (1 mL), Pd(OAc)$_2$ (0.0052 g, 0.023 mmol), and PPh$_3$ (0.018, 0.069 mmol). The residue is purified by ISCO column chromatography (20%-30% EtOAc/hexane gradient) and is chromatographed (50×250 C18 Symmetry column, 25-70% water: 0.1% TFA/ACN: 0.1% TFA gradient) furnish the title compound (0.017 g, 0.041 mmol, 3.5%). $^1$H NMR (CDCl$_3$), δ 0.86 (t, J=7.5 Hz, 6H), 1.72-1.90 (m, 4H), 2.04 (s, 3H), 2.43 (s, 3H), 2.49 (s, 3H), 2.75 (bs, 1H), 3.26-3.38 (m, 1H), 6.05 (s, 1H), 6.65 (s, 1H), 6.76 (s, 1H), 7.30-7.45 (m, 3H), 7.50-7.56 (m, 1H). LC/MS (m/z): calcd. for $C_{25}H_{29}N_3OS$ (M+H)+: 420.3; found: 420.3.

Example 75

Preparation of 3-(4,5-dibromo-3-methyl-thiophen-2-yl)-8-(1-ethyl-propyl)-2,6-dimethyl-imidazo[1,2-b]pyridazine

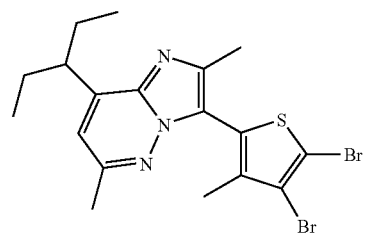

To a solution of 3-(5-bromo-3-methyl-thiophen-2-yl)-8-(1-ethyl-propyl)-2,6-dimethyl-imidazo[1,2-b]pyridazine (4.00 g, 10.20 mmol) and AcOH (40 mL) is added Br$_2$ (0.57 mL, 11.21 mmol) and the solution heated at 110° C. overnight. Br$_2$ (0.57 mL, 11.21 mmol) is added and the solution heated at 110° C. for 2 hours. The solution is poured into 5 M NaOH (200 mL) and ice (200 mL). The slurry is extracted with EtOAc (2×150 mL). The combined organic layers are washed with water (200 mL), 20% NaHSO$_3$ (200 mL), sat. NaHCO$_3$ (200 mL) dried over MgSO$_4$, filtered and concentrated. The residue is purified by ISCO (5%-15% EtOAc gradient) furnish the title compound (2.66 g, 5.64 mmol, 55%). $^1$H NMR (CDCl$_3$) δ 0.86 (t, J=7.5 Hz, 6H), 1.72-1.91 (m, 4H), 2.12 (s, 3H), 2.43 (s, 3H), 2.50 (s, 3H), 3.25-3.35 (m, 1H), 6.69 (s, 1H). LC/MS (m/z): calcd. for $C_{18}H_{21}Br_2N_3S$ (M+H)+: 470.0; found: 470.3.

Example 76

Preparation of 3-(4-bromo-3-methyl-thiophen-2-yl)-8-(1-ethyl-propyl)-2,6-dimethyl-imidazo[1,2-b]pyridazine

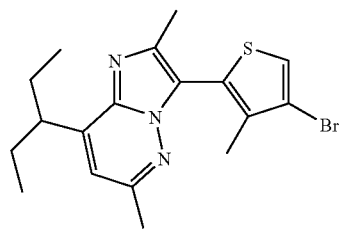

To a −78° C. solution of 3-(4,5-dibromo-3-methyl-thiophen-2-yl)-8-(1-ethyl-propyl)-2,6-dimethyl-imidazo[1,2-b]pyridazine (0.22 g, 0.47 mmol) and THF (3 mL) is added 1.6 M n-BuLi (0.31 mL, 0.49 mmol). After 20 minutes the solution is quenched with water (1 mL), warmed to ambient temperature, diluted with EtOAc (30 mL), washed with brine (30 mL), dried over MgSO$_4$, filtered and concentrated. The residue is purified by ISCO (5%-10% EtOAc gradient) furnish the title compound (0.056 g, 0.14 mmol, 31%). $^1$H NMR (CDCl$_3$) δ 0.87 (t, J=7.5 Hz, 6H), 1.73-1.93 (m, 4H), 2.09 (s, 3H), 2.44 (s, 3H), 2.49 (s, 3H), 3.27-3.36 (m, 1H), 6.68 (s, 1H), 7.44 (s, 1H). LC/MS (m/z): calcd. for $C_{18}H_{22}BrN_3S$ (M+H)+: 392.2; found: 392.3.

Example 77

Preparation of 3-{2,6-Dimethyl-3-[3-methyl-5-(6-methyl-pyridin-2-yl)-thiophen-2-yl]-imidazo[1,2-b]pyridazin-8-yl}-pentan-3-ol

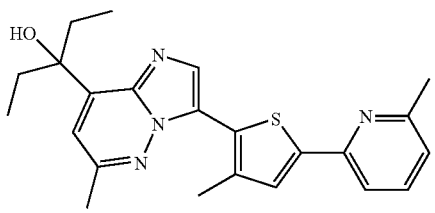

A. 2-(5-Bromo-4-methyl-thiophen-2-yl)-6-methyl-pyridine.

To a −78° C. solution of 2-bromo-3-methyl-thiophene (2.0 mL, 17.75 mmol) and THF (30 mL) is added 2.0 M LDA (9.76 mL, 19.52 mmol). After 45 minutes 0.5 M ZnCl$_2$ (39.0 mL, 19.50 mmol) is added and the solution stirred for 30 minutes. 2-Bromo-6-methyl-pyridine (2.4 mL, 21.29 mmol) and Pd(PPh$_3$)$_4$ (0.50 g, 0.44 mmol) is added and the solution is warmed to ambient temperature and stirred for 2 hour. The solution is washed with sat. NH$_4$Cl (20 mL). The aqueous layer is extracted with CH₂Cl₂ (30 mL). The combined organic layers are washed with sat. NH₄Cl (20 mL), dried over Na₂SO₄, filtered and concentrated. The residue is purified by ISCO column chromatography (10%-20% EtOAc/hexane gradient) furnish the title compound (2.34 g, 8.73 mmol, 49%). ¹H NMR (CDCl₃), δ 2.21 (s, 3H), 2.54 (s, 3H), 6.99 (d, J=7.9 Hz, 1H), 7.23 (s, 1H), 7.33 (d, J=7.9 Hz, 1H), 7.53 (dd, J=7.9, 7.9 Hz, 1H). LC/MS (m/z): calcd. for C₁₁H₁₀BrNS (M+H)⁺: 267.0, 269.0; found: 267.7, 269.5.

B. 2,6-Dimethyl-3-[3-methyl-5-(6-methyl-pyridin-2-yl)-thiophen-2-yl]-imidazo[1,2-b]pyridazine.

A solution of 2,6-dimethyl-imidazo[1,2-b]pyridazine (below) (0.50 g, 3.39 mmol), 2-(5-bromo-4-methyl-thiophen-2-yl)-6-methyl-pyridine (1.00 g, 3.73 mmol), Cs₂CO₃ (2.32 g, 7.13 mmol) and DMF (5 mL) is de-gassed for 15 minutes with N₂. Pd₂(dba)₃ (0.15 g, 0.16 mmol) and PPh₃ (0.17 g, 0.65 mmol) is added and the solution is heated at 130° C. overnight. The solution is diluted with CH₂Cl₂ (30 mL) washed with water (2×25 mL), brine (25 mL) dried over MgSO₄, filtered and concentrated. The residue is purified by ISCO column chromatography (100% EtOAc), followed by recrystallization from acetonitrile/water furnish the title compound (0.45 g, 1.35 mmol, 39%). ¹H NMR (CDCl₃), δ 2.13 (s, 3H), 2.50 (s, 3H), 2.53 (s, 3H), 2.57 (s, 3H), 6.90 (d, J=9.2 Hz, 1H), 7.01 (d, J=7.5 Hz, 1H), 7.46 (d, J=8.0 Hz, 1H), 7.52 (s, 1H), 7.56 (dd, J=8.0, 7.5 Hz, 1H), 7.77 (d, J=9.2 Hz, 1H). LC/MS (m/z): calcd. for C₁₉H₁₈N₄S (M+H)⁺: 335.1; found: 335.1.

C. 1-{2,6-Dimethyl-3-[3-methyl-5-(6-methyl-pyridin-2-yl)-thiophen-2-yl]-imidazo[1,2-b]pyridazin-8-yl}-propan-1-one.

To a −78° C. solution of 2,6-dimethyl-3-[3-methyl-5-(6-methyl-pyridin-2-yl)-thiophen-2-yl]-imidazo[1,2-b]pyridazine (0.34 g, 1.02 mmol) and THF (9 mL) is added 2.0 M LDA (0.61 mL, 1.22 mmol). After 3 minutes, N-methoxy-N-methyl-propionamide (Wolberg et. el. *Chem. Eur. J.*, 2001, 7, 4562) (1.17 g, 1.42 mmol) is added and the solution stirred for 20 minutes, warmed to ambient temperature and stirred for 30 minutes. The solution is diluted with EtOAc (50 mL) washed with sat. NH₄Cl (30 mL), dried over MgSO₄, filtered and concentrated. The residue is purified by ISCO column chromatography (20%-30% EtOAc/hexane gradient) furnish the title compound (0.10 g, 0.26 mmol, 25%). ¹H NMR (CDCl₃), δ 1.28 (t, J=7.0 Hz, 3H), 2.13 (s, 3H), 2.54 (s, 3H), 2.58 (s, 6H), 3.59 (q, J=7.0 Hz, 2H), 7.03 (d, J=7.5 Hz, 1H), 7.33 (s, 1H), 7.47 (d, J=7.9 Hz, 1H), 7.55 (bs, 1H), 7.58 (dd, J=7.9, 7.5 Hz, 1H). LC/MS (m/z): calcd. for C₂₂H₂₂N₄OS (M+H)⁺: 391.2; found: 391.2.

D. 3-{2,6-Dimethyl-3-[3-methyl-5-(6-methyl-pyridin-2-yl)-thiophen-2-yl]-imidazo[1,2-b]pyridazin-8-yl}-pentan-3-ol.

To a −0° C. solution of 1-{2,6-dimethyl-3-[3-methyl-5-(6-methyl-pyridin-2-yl)-thiophen-2-yl]-imidazo[1,2-b]pyridazin-8-yl}-propan-1-one (0.040 g, 0.10 mmol) and Et₂O (5 mL) is added 3.0 M ethyl magnesium bromide (0.68 mL, 2.05 mmol). The solution is warmed to ambient temperature, diluted with EtOAc (30 mL) washed with sat. NH₄Cl (20 mL), dried over MgSO₄, filtered and concentrated. The residue is purified by ISCO column chromatography (20%-30% EtOAc/hexane gradient) furnish the title compound (0.016 g, 0.038 mmol, 37%). ¹H NMR (CDCl₃), δ 0.89 (t, J=7.4 Hz, 6H), 1.92-2.01 (m, 4H), 2.14 (s, 3H), 2.46 (s, 3H), 2.53 (s, 3H), 3.57 (s, 3H), 6.39 (s, 1H), 6.66 (s, 1H), 7.01 (d, J=7.5 Hz, 1H), 7.46 (d, J=7.9 Hz, 1H), 7.52 (s, 1H), 7.57 (dd, J=7.9, 7.5 Hz, 1H). LC/MS (m/z): calcd. for C₂₄H₂₈N₄OS (M+H)⁺: 421.3; found: 421.3.

Example 78

Preparation of 8-(1-ethyl-propyl)-2,6-dimethyl-3-(3-methyl-4-thiazol-2-yl-thiophen-2-yl)-imidazo[1,2-b]pyridazine

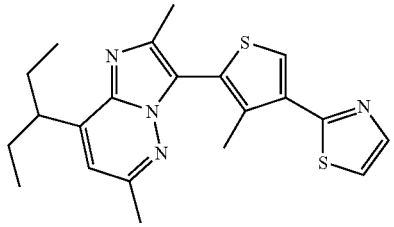

To a flask containing 3-(4-bromo-3-methyl-thiophen-2-yl)-8-(1-ethyl-propyl)-2,6-dimethyl-imidazo[1,2-b]pyridazine (0.25 g, 0.64 mmol) and PdCl₂(dppf) (0.023 g, 0.032 mmol) is added a 0.5 M solution of 2-thiazolylzinc bromide (3.82 mL, 1.91 mmol). The solution is heated at 65° C. overnight, diluted with EtOAc (30 mL), washed with sat. NH₄Cl (25 mL), dried over MgSO₄, filtered and concentrated. The residue is purified by ISCO (15%-20% EtOAc gradient) furnish the title compound (0.19 g, 0.48 mmol, 76%). ¹H NMR (CDCl₃) δ 0.88 (t, J=7.5 Hz, 6H), 1.75-1.92 (m, 4H), 2.36 (s, 3H), 2.47 (s, 3H), 2.50 (, 3H), 3.29-3.39 (m, 1H), 6.69 (s, 1H), 7.33 (d, J=3.3 Hz, 1H), 7.89 (d, J=3.3 Hz, 1H), 7.99 (s, 1H). LC/MS (m/z): calcd. for C₂₁H₂₄N₄S₂ (M+H)⁺: 397.2; found: 397.3.

Example 79

Preparation of 8-(1-Ethyl-propyl)-2,6-dimethyl-3-(3-methyl-5-o-tolyl-thiophen-2-yl)-imidazo[1,2-b]pyridazine

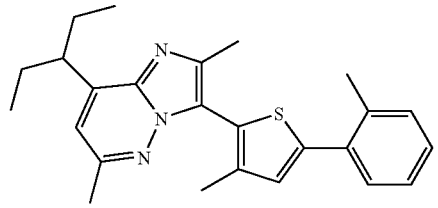

Using the procedure analogous to Example 32, 3-(5-bromo-3-methyl-thiophen-2-yl)-8-(1-ethyl-propyl)-2,6-dimethyl-imidazo[1,2-b]pyridazine (0.15 g, 0.38 mmol) and PdCl₂(dppf) (0.014 g, 0.019 mmol) and 0.5M solution of 2-methylphenylzinc iodide in THF (3 mL, 1.53 mmol) furnish the title compound (0.069 g, 0.17 mmol, 46%). ¹H NMR (CDCl₃) δ 0.90 (t, J=7.5 Hz, 6H), 1.76-1.94 (m, 4H), 2.19 (s, 3H), 2.53 (s, 3H), 2.54 (s, 3H), 2.55 (s, 3H), 3.32-3.40 (m, 1H), 6.68 (s, 1H), 7.02 (s, 1H), 7.22-7.30 (m, 3H), 7.48-7.53 (m, 1H). LC/MS (m/z): calcd. for C₂₅H₂₉N₃S (M+H)⁺: 404.3; found: 404.3.

Example 80

Preparation of {5-[8-(1-ethyl-propyl)-2,6-dimethyl-imidazo[1,2-b]pyridazin-3-yl]-4-methyl-thiophen-2-yl}-phenyl-methanone

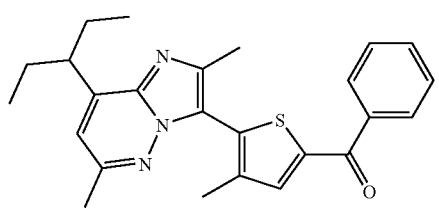

To a −78° C. solution of 3-(5-bromo-3-methyl-thiophen-2-yl)-8-(1-ethyl-propyl)-2,6-dimethyl-imidazo[1,2-b]pyridazine (0.30 g, 0.76 mmol) and THF (5 mL) is added 1.30 M n-Bu-Li (0.50 mL, 0.80 mmol). After 30 minutes N-methoxy-N-methyl-benzamide (0.13 mL, 0.84 mmol) is added, the solution is warmed to ambient temperature, and stirred overnight. The solution is diluted with EtOAc (20 mL), washed with sat. NH$_4$Cl (15 mL), water (15 mL), brine (15 mL), dried over MgSO$_4$, filtered and concentrated. The residue is purified by ISCO column chromatography (15%-20% EtOAc/hexane gradient) furnish the title compound (0.066 g, 0.16 mmol, 21%). $^1$H NMR (CDCl$_3$), δ 0.89 (t, J=7.4 Hz, 6H), 1.74-1.93 (m, 4H), 2.18 (s, 3H), 2.52 (s, 3H), 2.54 (s, 3H), 3.29-3.38 (m, 1H), 6.71 (s, 1H), 7.49-7.54 (m, 2H), 7.56 (s, 1H), 7.57-7.62 (m, 1H), 7.89-7.94 (m, 2H). LC/MS (m/z): calcd. for C$_{25}$H$_{27}$N$_3$OS (M+H)$^+$: 418.2; found: 418.2.

Example 81

Preparation of 8-(1-ethyl-propyl)-2,6-dimethyl-3-(3-methyl-5-oxazol-2-yl-thiophen-2-yl)-imidazo[1,2-b]pyridazine

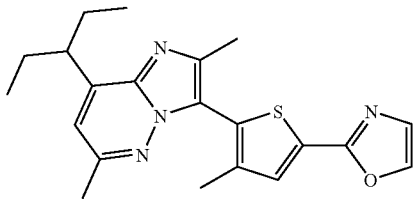

To a −78° C. solution of oxazole (0.14 g, 2.04 mmol) and THF (3 mL) is added 1.6 M t-Bu-Li in hexane (1.32 mL, 2.14 mmol). The mixture is stirred at −78° C. for 15 minutes. 0.5 M ZnCl$_2$ in THF (4.3 mL, 2.14 mmol) is added and the solution warmed to ambient temperature. 3-(5-Bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) is added and mixture is stirred at 65° C. overnight, diluted with EtOAc (30 mL), washed with 10% citric acid (20 mL), water (20 mL), brine (20 mL), dried over MgSO$_4$, filtered and concentrated. The residue is purified by ISCO column chromatography (20% EtOAc/hexane gradient) and is chromatographed (50×250 C18 Symmetry column, 20-70% water: 0.1% TFA/ACN: 0.1% TFA gradient) to furnish the title compound (0.020 g, 0.053 mmol, 5%). $^1$H NMR (CDCl$_3$), δ 0.89 (t, J=7.5 Hz, 6H), 1.75-1.93 (m, 4H), 2.17 (s, 3H), 2.49 (s, 3H), 2.51 (s, 3H), 3.29-3.38 (m, 1H), 6.69 (s, 1H), 7.19 (s, 1H), 7.59 (s, 1H), 7.65 (s, 1H). LC/MS (m/z): calcd. for C$_{21}$H$_{24}$N$_4$OS (M+H)$^+$: 381.3; found: 381.1.

Example 82

Preparation of 8-(1-ethyl-propyl)-2,6-dimethyl-3-[3-methyl-5-(5-methyl-furan-2-yl)-thiophen-2-yl]-imidazo[1,2-b]pyridazine

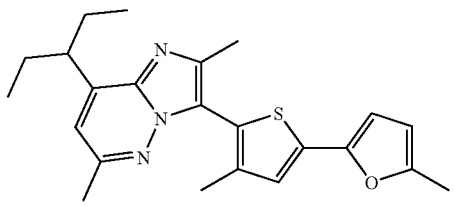

To a 0° C. mixture of 2-methylfuran (0.18 mL, 2.04 mmol) and Et$_2$O (2 mL) is added 1.6 M t-Bu-Li in hexane (1.30 mL, 2.14 mmol). The mixture is heated at a reflux for 30 minutes, cooled to 0° C., and 0.5 M ZnCl$_2$ in THF (4.3 mL, 2.14 mmol) is added and the solution warmed to ambient temperature. 3-(5-bromo-3-methyl-thiophen-2-yl)-8-(1-ethyl-propyl)-2,6-dimethyl-imidazo[1,2-b]pyridazine (0.40 g, 1.02 mmol) and PdCl$_2$(dppf) (0.037 g, 0.051 mmol) is added and mixture is stirred at 65° C. overnight, diluted with EtOAc (30 mL), washed with 10% citric acid (15 mL), water (15 mL), brine (15 mL), dried over MgSO$_4$, filtered and concentrated. The residue is purified by ISCO column chromatography (20% EtOAc/hexane gradient) furnish the title compound (0.20 g, 0.51 mmol, 50%). $^1$H NMR (CDCl$_3$), δ 0.89 (t, J=7.5 Hz, 6H), 1.74-1.92 (m, 4H), 2.12 (s, 3H), 2.35 (s, 3H), 2.48 (s, 3H), 2.51 (s, 3H), 3.29-3.38 (m, 1H), 6.62 (dd, J=3.1, 0.9 Hz, 1H), 6.40 (d, J=3.1 Hz, 1H), 6.66 (s, 1H), 7.12 (s, 1H). LC/MS (m/z): calcd. for C$_{23}$H$_{27}$N$_3$OS (M+H)$^+$: 394.3; found: 394.2.

Example 83

Preparation of 3-(3-chloro-thiophen-2-yl)-8-(1-ethyl-propyl)-2,6-dimethyl-imidazo[1,2-b]pyridazine

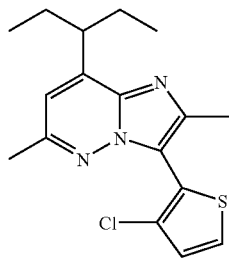

To a flask of 2-bromo-3-chloro-thiophene (Lemaire et. el., Synth. Commun., 1994, 24, 95) (2.53 g, 12.82 mmol) is added 0.05 g/mL Reike® zinc in THF (25 mL, 19.24 mmol). The solution is heated at a reflux for 2 hours. The excess zinc is allowed to settle and the solution transferred to a flask containing 8-(1-ethyl-propyl)-3-iodo-2,6-dimethyl-imidazo[1,2-b]pyridazine (example KW1-A03735-193) (2.01 g, 6.41 mmol) and PdCl$_2$(dppf) (0.23 g, 0.32 mmol). The solution is heated at a reflux overnight, quenched with sat. NH$_4$Cl (25 mL) and extracted with EtOAc (2×25 mL). The combined organic layers are dried over MgSO$_4$, filtered and concentrated. The residue is purified by ISCO column chromatography (2%-15% EtOAc/hexane gradient) furnish the title compound (1.32 g, 6.68 mmol, 62%). $^1$H NMR (CDCl$_3$), δ 0.87 (t, J=7.5 Hz, 6H), 1.74-1.91 (m, 4H), 2.48 (s, 3H), 2.49 (s, 3H), 3.37-3.36 (m, 1H), 6.67 (s, 1H), 7.07 (d, J=5.4 Hz, 1H), 7.48 (d, J=5.4 Hz, 1H). LC/MS (m/z): calcd. for C$_{17}$H$_{20}$ClN$_3$S (M+H)$^+$: 334.1; found: 334.1.

Example 84

Preparation of 3-(5-bromo-3-chloro-thiophen-2-yl)-8-(1-ethyl-propyl)-2,6-dimethyl-imidazo[1,2-b]pyridazine

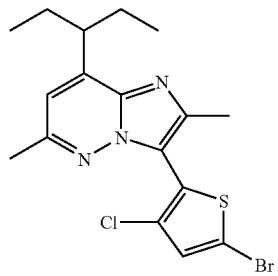

To a solution of 3-(3-chloro-thiophen-2-yl)-8-(1-ethyl-propyl)-2,6-dimethyl-imidazo[1,2-b]pyridazine. (1.15 g, 3.44 mmol) and CH$_2$Cl$_2$ (12 mL) is added NBS (0.64 g, 3.62 mmol). The solution is stirred at ambient temperature overnight, washed with water (2×75 mL), brine (75 mL), dried over Na$_2$SO$_4$, filtered and concentrated to furnish the title compound (1.36 g, 3.29 mmol, 96%). $^1$H NMR (CDCl$_3$), δ 0.88 (t, J=7.5 Hz, 6H), 1.74-1.92 (m, 4H), 2.49 (s, 3H), 2.53 (s, 3H), 3.26-3.36 (m, 1H), 6.70 (s, 1H), 7.07 (s, 1H). LC/MS (m/z): calcd. for C$_{17}$H$_{19}$BrClN$_3$S (M+H)$^+$: 412.1; found: 412.0.

Example 85

Preparation of 3-[3-chloro-5-(6-methyl-pyridin-2-yl)-thiophen-2-yl]-8-(1-ethyl-propyl)-2,6-dimethyl-imidazo[1,2-b]pyridazine

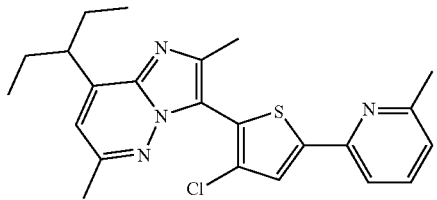

Method A.

To a flask of 3-(5-bromo-3-chloro-thiophen-2-yl)-8-(1-ethyl-propyl)-2,6-dimethyl-imidazo[1,2-b]pyridazine (0.30 g, 0.73 mmol) and PdCl$_2$(dppf) (0.027 g, 0.036 mmol) is added 0.5 M solution of 6-methyl-2-pyridylzinc bromide in THF (2.9 mL, 1.45 mmol). The mixture is stirred at 65° C. overnight, diluted with EtOAc (50 mL), washed with sat. NH$_4$CL (40 mL), water (40 mL), brine (40 mL), dried over MgSO$_4$, filtered and concentrated. The residue is purified by ISCO column chromatography (20%-40% EtOAc/hexane gradient) furnish the title compound (0.072 g, 0.17 mmol, 23%). $^1$H NMR (CDCl$_3$), δ 0.89 (t, J=7.5 Hz, 6H), 1.75-1.93 (m, 4H), 2.52 (s, 3H), 2.53 (s, 3H), 3.58 (s, 3H), 3.30-3.39 (m, 1H), 6.70 (s, 1H), 7.06 (d, J=7.5 Hz, 1H), 7.46 (d, J=7.7 Hz, 1H), 7.54 (s, 1H), 7.60 (dd, J=7.7, 7.5 Hz, 1H). LC/MS (m/z): calcd. for C$_{23}$H$_{25}$ClN$_4$S (M+H)$^+$: 425.2; found: 425.2.

Method B.

A. 2-(4-Chloro-thiophen-2-yl)-6-methyl-pyridine.

To a solution of 2-bromo-4-chloro-thiophene (Gronowitz, Rosén *Chemica Scripta,* 1971, 1, 33) (1.50 g, 7.60 mmol) and 0.5 M solution of 6-methyl-2-pyridylzinc bromide in THF (23.00 mL, 11.39 mmol) is added Pd(PPh$_3$)$_4$ (0.18 g, 0.15 mmol). The solution is heated at 40° C. overnight, diluted with Et$_2$O (50 mL), washed with sat. NH$_4$Cl (40 mL), dried over MgSO$_4$, filtered on concentrated. The residue is purified by ISCO column chromatography (5%-20% EtOAc/hexane gradient) furnish the title compound (0.45 g, 2.15 mmol, 28%). $^1$H NMR (CDCl$_3$), δ 2.56 (s, 3H), 7.02 (d, 7.7 Hz, 1H), 7.13 (d, J=0.9 Hz, 1H), 7.36 (d, J=7.9 Hz, 1H), 7.39 (d, J=0.9 Hz, 1H), 7.54 (dd, J=7.9, 7.7, 1H).

B. 2-(5-bromo-4-chloro-thiophen-2-yl)-6-methyl-pyridine.

To a 0° C. solution of 2-(4-chloro-thiophen-2-yl)-6-methyl-pyridine (example Rupp-96) (0.45 g, 1.45 mmol) and CH$_2$Cl$_2$ (10 mL) is added Br$_2$ (0.15 mL, 2.91 mmol). The solution is warmed to ambient temperature and stirred for 1 hour. The solution is washed with sat. NaHCO$_3$ (10 mL), sat. Na$_2$S$_2$O$_3$ (10 mL), dried over MgSO$_4$, filtered and concentrated to furnish the title compound (0.59 g, 2.04, 95%). $^1$H NMR (CDCl$_3$), δ 2.55 (s, 3H), 7.05 (d, 7.9 Hz, 1H), 7.29 (s, 1H), 7.34 (d, J=7.9 Hz, 1H), 7.58 (dd, J=7.9, 7.9, 1H). LC/MS (m/z): calcd. for C$_{10}$H$_7$BrClNS (M+H)$^+$: 288.0; found: 287.9.

C. 3-[3-Chloro-5-(6-methyl-pyridin-2-yl)-thiophen-2-yl]-8-(1-ethyl-propyl)-2,6-dimethyl-imidazo[1,2-b]pyridazine.

A solution of 8-(1-ethyl-propyl)-2,6-dimethyl-imidazo[1,2-b]pyridazine (0.39 g, 1.78 mmol), 2-(5-bromo-4-chloro-thiophen-2-yl)-6-methyl-pyridine (0.59 g, 2.04 mmol), Cs$_2$CO$_3$ (1.23 g, 3.77 mmol), and DMF (5 mL), is de-gassed with N$_2$ for 15 minutes. PPh$_3$ (0.089 g, 0.34 mmol) and Pd$_2$(dba)$_3$ (0.079 g, 0.86 mmol) is added and the solution heated at 110° C. for 48 hours. The solution is diluted with EtOAc (30 mL), washed with sat. NH$_4$Cl (25 mL), dried over MgSO$_4$, filtered and concentrated. The residue is purified by ISCO column chromatography (20%-30% EtOAc/hexane gradient) and is chromatographed (19×300 C18 Symmetry column, 20-45% water: 0.1% TFA/ACN: 0.1% TFA gradient) furnish the title compound (0.078 g, 0.18 mmol, 10%). Spectrum identical to Method A.

Example 86

Preparation of 3-(3-chloro-5-pyridin-3-yl-thiophen-2-yl)-8-(1-ethyl-propyl)-2,6-dimethyl-imidazo[1,2-b]pyridazine

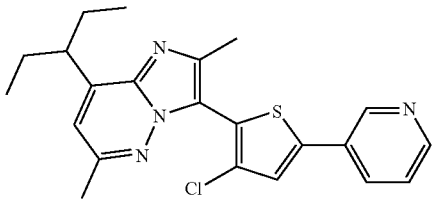

Method A.

A solution of 3-(5-bromo-3-chloro-thiophen-2-yl)-8-(1-ethyl-propyl)-2,6-dimethyl-imidazo[1,2-b]pyridazine (0.25 g, 0.61 mmol), pyridine-3-boronic acid (0.082 g, 0.67 mmol), 2 M Na$_2$CO$_3$ (0.45 mL, 0.91 mmol) and, n-PrOH (1 mL), is degassed with nitrogen for 10 minutes. Pd(OAc)$_2$ (0.0027 g, 0.0012 mmol) and PPh$_3$ (0.0095 g, 0.036 mmol) are added and the solution is heated at 88° C. overnight. The solution is diluted with EtOAc (15 mL), washed with water (10 mL), sat. NaHCO$_3$ (10 mL), dried over MgSO$_4$, filtered and concentrated. Purified by ISCO column chromatography (15-40% EtOAc/hexane gradient) furnish the title compound (0.095 g, 0.23 mmol, 38%). $^1$H NMR (CDCl$_3$), δ 0.89 (t, J=7.5 Hz, 6H), 1.75-1.93 (m, 4H), 2.53 (s, 3H), 2.54 (s, 3H), 3.29-3.38 (m, 1H), 6.71 (s, 1H), 7.32-7.37 (m, 2H), 7.85-7.90 (m, 1H), 8.57 (d, J=4.0 Hz, 1H), 8.89 (s, 1H). LC/MS (m/z): calcd. for C$_{22}$H$_{23}$ClN$_4$S (M+H)$^+$: 411.2; found: 411.2.

Method B.

A. 3-(4-Chloro-thiophen-2-yl)-pyridine.

A solution of 2-bromo-4-chloro-thiophene (Gronowitz, Rosén *Chemica Scripta,* 1971, 1, 33) (1.45 g, 7.34 mmol), pyridine-3-boronic acid (0.95 g, 7.71 mmol), 2 M Na$_2$CO$_3$ (5.50 mL, 11.01 mmol) and, n-PrOH (3 mL), is degassed with N$_2$ for 10 minutes. Pd(OAc)$_2$ (0.033 g, 0.15 mmol) and PPh$_3$ (0.12 g, 0.44 mmol) are added and the solution is heated at 85° C. for 48 hours, diluted with CH$_2$Cl$_2$ (50 mL), washed with 10% Na$_2$CO$_3$ (2×30 mL), dried over MgSO$_4$, filtered and concentrated. The residue is purified by ISCO column chromatography (20%-30% EtOAc/hexane gradient) furnish the title compound (0.74 g, 3.78 mmol, 51%). $^1$H NMR (CDCl$_3$), δ 7.12-7.13 (m, 1H), 7.20 (d, J=1.4 Hz, 1H), 7.31 (dd, J=8.0, 4.9 Hz, 1H), 7.78-7.82 (m, 1H), 8.55 (d, J=4.9 Hz, 1H), 8.82 (d, J=2.2 Hz, 1H).

B. 3-(5-Bromo-4-chloro-thiophen-2-yl)-pyridine.

Using a procedure similar to Example 85 Method B. step B, 3-(4-chloro-thiophen-2-yl)-pyridine (0.74 g, 3.78 mmol), and Br$_2$ (0.39 mL, 7.56 mmol) furnish the title compound (0.99 g, 3.61 mmol, 95%). $^1$H NMR (CDCl$_3$), δ 7.13 (s, 1H), 7.34 (dd, J=8.1, 4.4 Hz, 1H), 7.74-7.78 (m, 1H), 8.58 (d, J=4.4 Hz, 1H), 8.78 (s, 1H).

C. 3-(3-Chloro-5-pyridin-3-yl-thiophen-2-yl)-8-(1-ethyl-propyl)-2,6-dimethyl-imidazo[1,2-b]pyridazine.

Using a procedure similar to Example 85 Method B Step C, from 8-(1-ethyl-propyl)-2,6-dimethyl-imidazo[1,2-b]pyridazine (0.50 g, 2.30 mmol), 3-(5-bromo-4-chloro-thiophen-2-yl)-pyridine) (0.76 g, 2.76 mmol), Cs$_2$CO$_3$ (1.57 g, 4.83 mmol), PPh$_3$ (0.11 g, 0.44 mmol) and Pd$_2$(dba)$_3$ (0.10 g, 0.11 mmol). The residue is purified by ISCO column chromatography (15%-30% EtOAc/hexane gradient) furnish the title compound (0.35 g, 0.85 mmol, 37%). Spectrum identical to Method A.

Example 87

Preparation of 3-[3-chloro-5-(4-fluoro-phenyl)-thiophen-2-yl]-8-(1-ethyl-propyl)-2,6-dimethyl-imidazo[1,2-b]pyridazine

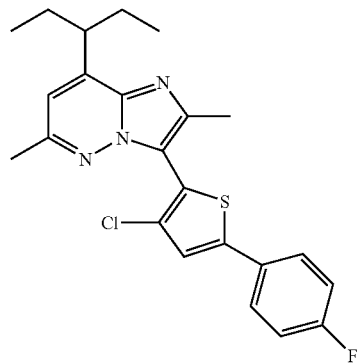

Using a procedure similar to Example 25, 3-(5-bromo-3-chloro-thiophen-2-yl)-8-(1-ethyl-propyl)-2,6-dimethyl-imidazo[1,2-b]pyridazine (0.25 g, 0.61 mmol), 4-fluorophenylboronic acid (0.093 g, 0.67 mmol), 2 M Na$_2$CO$_3$ (0.45 mL, 0.91 mmol), n-PrOH (2 mL), Pd(OAc)$_2$ (0.0068 g, 0.030 mmol) and PPh$_3$ (0.016 g, 0.061 mmol) furnish the title compound (0.041 g, 0.096 mmol, 16%). $^1$H NMR (CDCl$_3$), δ 0.89 (t, J=7.5 Hz, 6H), 1.76-1.94 (m, 4H), 2.53 (s, 3H), 2.54 (s, 3H), 3.29-3.38 (m, 1H), 6.70 (s, 1H), 7.07-7.13 (m, 2H), 7.22 (s, 1H), 7.54-7.60 (m, 2H). LC/MS (m/z): calcd. for C$_{23}$H$_{23}$ClFN$_3$S (M+H)$^+$: 428.2; found: 428.1.

Example 88

Preparation of 3-[3-chloro-5-(2-methyl-2H-[1,2,4]triazol-3-yl)-thiophen-2-yl]-8-(1-ethyl-propyl)-2,6-dimethyl-imidazo[1,2-b]pyridazine

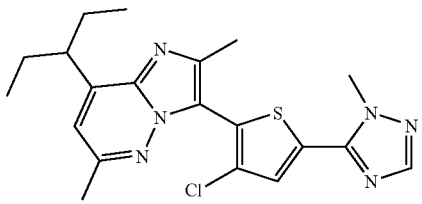

Method A.

To a −78° C. solution of 1-methyl-1,2,4-triazole (0.18 mL, 2.33 mmol) and THF (3 mL) is added a 1.56 M solution of n-Bu-Li in hexanes (1.49 mL, 2.33 mmol). The solution is stirred at −78° C. for 30 minutes, 0.5 M solution of ZnCl$_2$ in THF (4.70 mL, 2.33 mmol) is added and the solution warmed to ambient temperature. 3-(5-bromo-3-chloro-thiophen-2-yl)-8-(1-ethyl-propyl)-2,6-dimethyl-imidazo[1,2-b]pyridazine (0.32 g, 0.78 mmol) and PdCl$_2$(dppf) (0.028 g, 0.039 mmol) is added and the solution heated at 60° C. for 2 days, diluted with EtOAc (50 mL), washed with sat. NH$_4$Cl (30 mL), water (30 mL), brine (30 mL), dried over MgSO$_4$, filtered and concentrated. The residue is purified by ISCO column chromatography (20%-10% EtOAc/hexane gradient) furnish the title compound (0.19 g, 0.46 mmol, 59%). $^1$H NMR (CDCl$_3$), δ 0.89 (t, J=7.5 Hz, 6H), 1.76-1.94 (m, 4H), 2.53 (s, 3H), 2.54 (s, 3H), 3.29-3.37 (m, 1H), 4.16 (s, 3H), 6.73 (s, 1H), 7.48 (s, 1H), 7.90 (s, 1H). LC/MS (m/z): calcd. for C$_{20}$H$_{23}$ClN$_6$S (M+H)$^+$: 415.2; found: 415.1.

Method B.

A 5-L reaction flask equipped with a cooling bath, air stirrer, gas dispersion tube and thermometer probe is charged with 5-(5-bromo-4-chloro-thiophen-2-yl)-1-methyl-1H-[1,2,4]triazole (162.0 g, 0.745 moles), 8-(1-ethyl-propyl)-2,6-dimethyl-imidazo[1,2-b]pyridazine (250.1 g, 0.898 moles), NMP (800 mL), KOAc (366.0 g), TBABr (50.5 g), and additional NMP (700 mL) to form a mixture. While stirring, N$_2$ is bubbled through the mixture for 1 hour. A mixture of Pd(OAc)$_2$ (8.37 g) and TDBPP (24.56 g) are added in one portion, then heated to 120° C. for 3 hours. The reaction is cooled to 50° C. and transferred to a 12 L flask. The mixture is cooled to 20-25° C., then added de-ionized H$_2$O (3.5 L) is added dropwise to precipitate out a sticky solid that gradually solidifies with stirring overnight. The solids are filtered, washed with de-ionized H$_2$O (2×2 L), and fried on the filter plate for 30-60 minutes. The crude solids (595 g) are warmed in EtOAc (6.0 L) to 30° C., then filtered through GFF paper to remove insolubles. The filtrate is dried over Na$_2$SO$_4$, treated with Darco (30.0 g), heated to 35° C., filtered, and concentrated to give brown solids (432 g). The crude solids are eluted through a silica plug (1.0 kg) with CH$_2$Cl$_2$ (4.0 L), followed by EtOAc (16.0 L). Similar fractions are combined and concentrated under vacuum to approximately 6.0 L, then treated with Darco overnight with stirring. After filtering off the Darco through GFF paper, the filtrate is concentrated to solids (336 g). The solids are crystallized from EtOAc:heptane (1:2) to afford the title compound as a pale yellow solid (187 g, 60.5%, >98% area-% by reverse phase: Zorbax SB-C8, 4.6 mm×250 mm, 5 microns, UV=218 nm, flow rate 1.0 mL/min., oven temp. 25° C., isocratic=30% water (0.1% TFA) & 70% AcCN.

Example 89

Preparation of 8-(1-Ethyl-propyl)-2,6-dimethyl-3-[3-methyl-5-(3-methyl-3H-imidazol-4-yl)-thiophen-2-yl]-imidazo[1,2-b]pyridazine

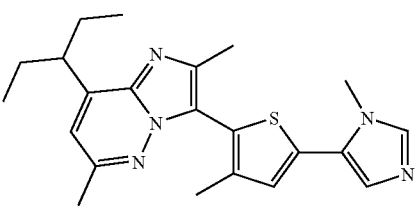

Using the procedure analogous to Example 31, 3-(5-bromo-3-methyl-thiophen-2-yl)-8-(1-ethyl-propyl)-2,6- dimethyl-imidazo[1,2-b]pyridazine (0.40 g, 1.02 mmol), 1.34M n-Bu-Li (0.80 mL, 1.07 mmol), 0.5M ZnCl₂ in THF (2.14 mL, 1.07 mmol), 5-iodo-1-methyl-1H-imidazole (0.24 g, 1.22 mmol) and PdCl₂(dppf) (0.037 g, 0.051 mmol) furnish the title compound (0.061 g, 0.15 mmol, 15%). ¹H NMR (CDCl₃) δ 0.89 (t, J=7.4 Hz, 6H), 1.75-1.93 (m, 4H), 2.17 (s, 3H), 2.50 (s, 3H), 2.53 (s, 3H), 3.24-3.38 (m, 1H), 3.61 (s, 3H), 6.68 (s, 1H), 7.02 (s, 1H), 7.23 (s, 1H), 7.55 (s, 1H). LC/MS (m/z): calcd. for $C_{22}H_{27}N_5S$ (M+H)⁺: 394.3; found: 394.2.

Example 90

Preparation of 8-(1-ethyl-propyl)-2,6-dimethyl-3-(2-methyl-thiophen-3-yl)-imidazo[1,2-b]pyridazine

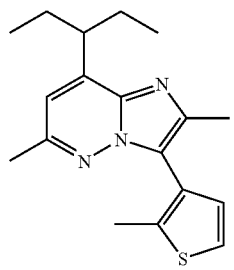

A. 4,4,5,5-Tetramethyl-2-(2-methyl-thiophen-3-yl)-[1,3,2]dioxaborolane.

A mixture of 3-bromo-2-methyl-thiophene (Saika et. el. *Chem. Soc. Chem. Communication,* 18, 1994, 2133; Steinkopf et. el.; *Justus Liebigs Ann. Chem.,* 513, 1934, 281; 3.1 g, 17.51 mmol), DMSO (50 mL), 4,4,5,5,4',4',5',5'-Octamethyl-[2,2']bi[[1,3,2]dioxaborolanyl] (4.90 g, 19.26 mmol), and KOAc (5.20 g, 52.58 mmol) is de-gassed with N₂ for 15 minutes. PdCl₂(dppf) (0.70 g, 0.88 mmol) is added and the solution stirred at ambient temperature overnight, then warmed to 85° C. for 3 hours. The solution is diluted with water (200 mL), extracted with EtOAc (2×100 mL). The combined organic layers washed with water (2×200 mL), brine (200 mL) dried over MgSO₄, filtered and concentrated. The residue is purified by ISCO column chromatography (5%-20% EtOAc/hexane gradient) furnish the title compound (1.52 g, 6.78 mmol, 39%). ¹H NMR (CDCl₃), δ 1.34 (s, 12H), 2.72 (s, 3H), 7.04 (d, J=5.0 Hz, 1H), 7.22 (d, 5.0 Hz, 1H).

B. 2-Methyl-thiophene-3-boronic acid.

To a solution of 4,4,5,5-tetramethyl-2-(2-methyl-thiophen-3-yl)-[1,3,2]dioxaborolane (1.52 g, 6.78 mmol), acetone (15 mL) and water (15 mL) is added NaIO₄ (2.90 g, 13.56 mmol). The solution is stirred at ambient temperature for 24 hours, then heated to a reflux for 24 hours. The solution is concentrated dissolved in EtOAc (1450 mL), washed with water (100 mL), dried over MgSO₄, filtered and concentrated to furnish the title compound (0.75 g, 5.49 mmol, 78%). ¹H NMR (CDCl₃), δ 2.93 (s, 3H), 7.10 (d, J=5.3 Hz, 1H), 7.51 (d, 5.3 Hz, 1H).

C. 8-(1-Ethyl-propyl)-2,6-dimethyl-3-(2-methyl-thiophen-3-yl)-imidazo[1,2-b]pyridazine.

(1.65 g, 4.80 mmol), 2-methyl-thiophene-3-boronic acid (0.75 g, 5.28 mmol), 2 M Na₂CO₃ (3.60 mL, 7.20 mmol) and n-PrOH (20 mL) is degassed with N₂ for 10 minutes. Pd(OAc)₂ (0.022 g, 0.096 mmol) PPh₃ (0.076 g, 0.29 mmol) is added and the solution heated at 60° C. for 24 hours, then heated at 90° C. for 24 hours. The solution is concentrated, diluted in EtOAc (50 mL) washed with 10% Na₂CO₃ (40 mL), water (40 mL), brine (40 mL) dried over MgSO₄, filtered and concentrated. The residue is purified by ISCO column chromatography (10%-15% EtOAc/hexane gradient) furnish the title compound (0.78 g, 2.49 mmol, 52%). ¹H NMR (CDCl₃), δ 0.89 (t, J=7.5 Hz, 6H), 1.74-1.94 (m, 4H), 2.38 (s, 3H), 2.44 (s, 3H), 2.50 (s, 3H), 3.30-3.40 (m, 1H), 6.64 (s, 1H), 7.11 (d, J=5.3 Hz, 1H), 7.20 (d, J=5.3 Hz, 1H). LC/MS (m/z): calcd. for $C_{18}H_{23}N_3S$ (M+H)⁺: 314.2; found: 314.2.

Example 91

Preparation of 3-(5-bromo-2-methyl-thiophen-3-yl)-8-(1-ethyl-propyl)-2,6-dimethyl-imidazo[1,2-b]pyridazine

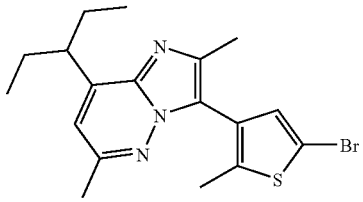

To a solution of 8-(1-ethyl-propyl)-2,6-dimethyl-3-(2-methyl-thiophen-3-yl)-imidazo[1,2-b]pyridazine. (0.76 g, 2.42 mmol) and CH₂Cl₂ (10 mL) is added NBS (0.60 g, 3.37 mmol). The solution is stirred at ambient temperature for 2 hours and concentrated. The solution is dissolved in Et₂O (30 mL) washed with water (3×30 mL), brine (30 mL) dried over MgSO₄, filtered and concentrated to furnish the title compound (0.95 g, 2.42 mmol, >99%). ¹H NMR (CDCl₃), δ 0.88 (t, J=7.5 Hz, 6H), 1.74-1.93 (m, 4H), 2.31 (s, 3H), 2.42 (s, 3H), 2.51 (s, 3H), 3.29-3.38 (m, 1H), 6.66 (s, 1H), 7.04 (s, 1H). LC/MS (m/z): calcd. for $C_{18}H_{22}BrN_3S$ (M+H)⁺: 392.2; found: 392.1.

Example 92

Preparation of 8-(1-ethyl-propyl)-2,6-dimethyl-3-(2-methyl-5-phenyl-thiophen-3-yl)-imidazo[1,2-b]pyridazine

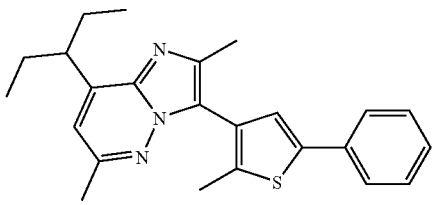

Using a procedure similar to Example 32, from 3-(5-bromo-2-methyl-thiophen-3-yl)-8-(1-ethyl-propyl)-2,6-dimethyl-imidazo[1,2-b]pyridazine (0.20 g, 0.51 mmol) and PdCl₂(dppf) (0.019 g, 0.025 mmol) and 0.5 M solution of phenylzinc iodide in THF (2.0 mL, 1.02 mmol). The residue is purified by column chromatography (0-10% EtOAc/hexane gradient) and is chromatographed (50×250 C18 Symmetry column, 30-70% water: 0.1% TFA/ACN: 0.1% TFA gradient) furnish the title compound (0.081 g, 0.21 mmol, 41%). ¹H NMR (CDCl₃), δ 0.90 (t, J=7.5 Hz, 6H), 1.75-1.94 (m, 4H), 2.40 (s, 3H), 2.48 (s, 3H), 2.52 (s, 3H), 3.32-3.41 (m, 1H), 6.66 (s, 1H), 7.23-7.30 (m, 1H), 7.32 (s, 1H), 7.34-7.41 (m, 2H), 7.57-7.63 (m, 2H). LC/MS (m/z): calcd. for $C_{24}H_{27}N_3S$ (M+H)⁺: 390.2; found: 390.2.

Example 93

Preparation of 8-(1-ethyl-propyl)-2,6-dimethyl-3-(2-methyl-5-thiazol-2-yl-thiophen-3-yl)-imidazo[1,2-b]pyridazine

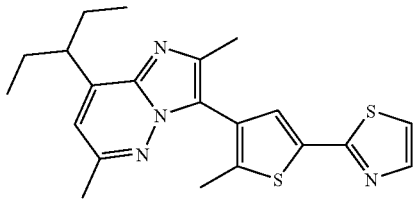

Using a procedure similar to Example 32, from 3-(5-bromo-2-methyl-thiophen-3-yl)-8-(1-ethyl-propyl)-2,6-dimethyl-imidazo[1,2-b]pyridazine (0.20 g, 0.51 mmol), 0.5 M 2-thiazolylzinc bromide in THF (8.1 mL, 4.05 mmol) and PdCl$_2$(dppf) (0.019 g, 0.025 mmol) furnish the title compound (0.20 g, 0.50 mmol, >99%). $^1$H NMR (CDCl$_3$), δ 0.87 (t, J=7.5 Hz, 6H), 1.74-1.91 (m, 4H), 2.40 (s, 3H), 2.45 (s, 3H), 2.50 (s, 3H), 3.29-3.38 (m, 1H), 6.60 (s, 1H), 7.22 (d, J=3.2 Hz, 1H), 7.52 (s, 1H), 7.75 (d, J=3.2 Hz, 1H). LC/MS (m/z): calcd. for C$_{21}$H$_{24}$N$_4$S$_2$ (M+H)$^+$: 397.1; found: 397.2.

Example 94

Preparation of 8-(1-ethyl-propyl)-2,6-dimethyl-3-[2-methyl-5-(6-methyl-pyridin-2-yl)-thiophen-3-yl]-imidazo[1,2-b]pyridazine

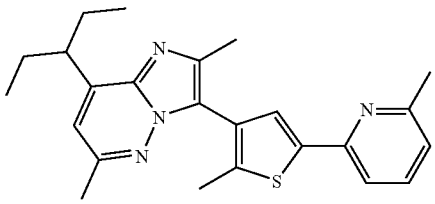

Using a procedure similar to Example 32, from 3-(5-bromo-2-methyl-thiophen-3-yl)-8-(1-ethyl-propyl)-2,6-dimethyl-imidazo[1,2-b]pyridazine (0.24 g, 0.61 mmol) and PdCl$_2$(dppf) (0.022 g, 0.031 mmol) and 0.5 M solution of 6-methyl-2-pyridylzinc bromide in THF (3.7 mL, 1.84 mmol) furnish the title compound (0.086 g, 0.21 mmol, 34%). $^1$H NMR (CDCl$_3$), δ 0.89 (t, J=7.5 Hz, 6H), 1.75-1.93 (m, 4H), 2.39 (s, 3H), 2.46 (s, 3H), 2.51 (s, 3H), 2.57 (s, 3H), 3.31-3.40 (m, 1H), 6.65 (s, 1H), 6.97 (d, J=7.8 Hz, 1H), 7.41 (d, J=7.8 Hz, 1H), 7.50-7.56 (m, 2H). LC/MS (m/z): calcd. for C$_{24}$H$_{28}$N$_4$ (M+H)$^+$: 405.2; found: 405.2.

Example 95

Preparation of 8-(1-Ethyl-propyl)-2,6-dimethyl-3-(3-methyl-5-pyrimidin-5-yl-thiophen-2-yl)-imidazo[1,2-b]pyridazine

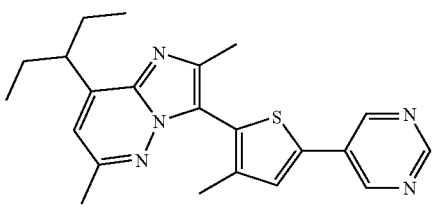

Using a procedure similar to Example 74B, from of 3-(5-bromo-3-methyl-thiophen-2-yl)-8-(1-ethyl-propyl)-2,6-dimethyl-imidazo[1,2-b]pyridazine (0.20 g, 0.51 mmol), 5-pyrimidine boronic acid (0.076 g, 0.61 mmol), 2 M Na$_2$CO$_3$ (0.38 mL, 0.76 mmol), Pd(OAc)$_2$ (0.0023 g, 0.011 mmol), PPh$_3$ (0.0080 g, 0.0031 mmol), and n-PrOH (2 mL) is furnished the title compound (0.084 g, 0.21 mmol, 42%). $^1$H NMR (CDCl$_3$), δ 0.86 (t, J=7.5 Hz, 6H), 1.72-1.91 (m, 4H), 2.17 (s, 3H), 2.48 (s, 3H), 2.51 (s, 3H), 3.26-3.36 (m, 1H), 6.69 (s, 1H), 7.74 (s, 1H), 8.95 (s, 2H), 9.10 (s, 1H). LC/MS (m/z): calcd. for C$_{22}$H$_{25}$N$_5$S (M+H)$^+$: 392.3; found: 392.2.

Example 96

Preparation of 3-[5-(3,5-Dimethyl-isoxazol-4-yl)-3-methyl-thiophen-2-yl]-8-(1-ethyl-propyl)-2,6-dimethyl-imidazo[1,2-b]pyridazine

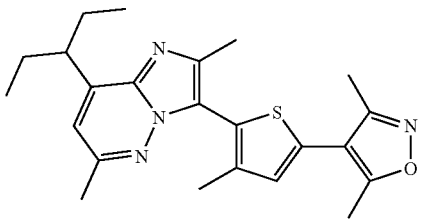

To a flask of 4-iodo-3,5-dimethyl-isoxazole (0.34 g, 1.53 mmol) is added a solution of Rieke® zinc 5 g/100 mL in THF (3 mL, 2.29 mmol). The slurry is heated at a reflux for 4 hours, the zinc is allowed to settle and the solution transferred to a flask of 3-(5-bromo-3-methyl-thiophen-2-yl)-8-(1-ethyl-propyl)-2,6-dimethyl-imidazo[1,2-b]pyridazine (0.30 g, 0.76 mmol) and PdCl$_2$(dppf) (0.028 g, 0.038 mmol). The solution is heated at 50° C. overnight, diluted with EtOAc (20 mL), washed with 0.1 M HCl (15 mL), water (15 mL), brine (15 mL) dried over MgSO$_4$, filtered and concentrated. The residue is purified by ISCO column chromatography (15%-30% EtOAc/hexane gradient) furnish the title compound (0.22 g, 0.54 mmol, 71%). $^1$H NMR (CDCl$_3$), δ 0.92 (t, J=7.5 Hz, 6H), 1.78-1.96 (m, 4H), 2.21 (s, 3H), 2.47 (s, 3H), 2.53 (s, 3H), 2.56 (s, 3H), 2.61 (s, 3H), 3.33-3.42 (m, 1H), 6.72 (s, 1H), 6.98 (s, 1H). LC/MS (m/z): calcd. for C$_{23}$H$_{28}$N$_4$OS (M+H)$^+$: 409.3; found: 409.2.

Example 97

Preparation of 8-(1-ethyl-propyl)-2,6-dimethyl-3-(3-methyl-5-pyrimidin-2-yl-thiophen-2-yl)-imidazo[1,2-b]pyridazine

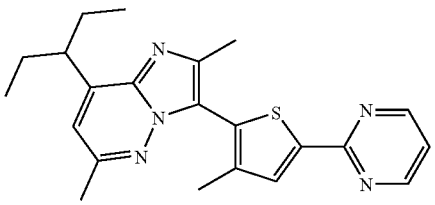

A solution of 3-(5-bromo-3-methyl-thiophen-2-yl)-8-(1-ethyl-propyl)-2,6-dimethyl-imidazo[1,2-b]pyridazine (0.30 g, 0.76 mmol), 2-tributylstannanyl-pyrimidine (0.34 g, 0.92 mmol) and THF (5 mL) is de-gassed with N$_2$ for 10 minutes Triphenylarsine (0.047 g, 0.15 mmol) and Pd$_2$(dba)$_3$ (0.035 g, 0.038 mmol) is added and the solution heated at 55° C. for 48 hours and concentrated. The residue is purified by ISCO column chromatography (15%-30% EtOAc/hexane gradient), dissolved in acetonitrile (20 mL), washed with hexane (3×20 mL) and concentrated to furnished the title compound (0.097 g, 0.25 mmol, 32%). $^1$H NMR (CDCl$_3$), δ 0.88 (t, J=7.4 Hz, 6H), 1.74-1.92 (m, 4H), 2.18 (s, 3H), 2.51 (s, 3H), 2.52 (s, 3H), 3.29-3.38 (m, 1H), 6.67 (s, 1H), 7.08 (t, J=4.8, 1H), 7.93 (s, 1H), 8.69 (s, 2H). LC/MS (m/z): calcd. for C$_{22}$H$_{25}$N$_5$S (M+H)$^+$: 392.3; found: 392.2.

Example 98

Preparation of 8-(1-ethyl-propyl)-2,6-dimethyl-3-(1,3,5-trimethyl-1H-pyrazol-4-yl)-imidazo[1,2-b]pyridazine

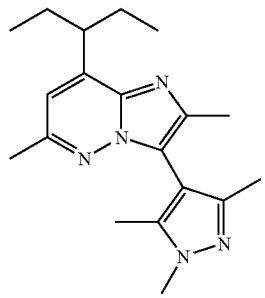

A. 1,3,5-Trimethylpyrazole-4-boronic acid.

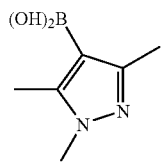

To a dry flask is added 300 mg (1.59 mmol) of 4-bromo-1,3,5-trimethylpyrazole to 4.0 ml THF. The mixture is cooled to −78° C. and 1 eq of n-BuLi (1.6 M) is added via syringe. The mixture is stirred 1.5 hrs, and 0.19 ml of trimethylborate (1.08 eq) is added. The reaction mixture is stirred 2 hrs, allowing bath to reach −10° C., then 1.5 ml of 5N HCl is added and stirred 30 minutes longer. The aqueous layer is extracted 3 times with ethyl acetate. The combined organics are dried over MgSO4, filtered, and evaporated to an oil. The oil is dissolved in methanol/methylene chloride and re-evaporated. The residue is triturated with acetone/ethyl acetate then filtered to obtain title compound as a white solid 92.1 mg (37.6%). $^1$H-NMR (DMSO-d$_6$): δ5.92 (s); 3.72 (s, 3H); 2.34 (s, 3H); 2.26 (s, 3H) ppm.

B. 8-(1-Ethyl-propyl)-2,6-dimethyl-3-(1,3,5-trimethyl-1H-pyrazol-4-yl)-imidazo[1,2-b]pyridazine.

3-Iodo-2,6-dimethyl-8-(1-ethyl-propyl)-imidazo[1,2-b]pyridazine (200 mg, 0.582 mmol), 1,3,5-trimethylpyrazole-4-boronic acid (233 mg, 1.53 mmol), Pd(PPh3)4 (13.4 mg, 0.01 mmol) are combined in a microwave pressure tube. Then 0.58 ml of 2N Na2CO3 and 3.0 ml of dimethoxyethane/H20/ethanol (7:3:2) solution is added. The mixture is microwaved at 155° C. for 20 minutes. Water is added and the mixture is extracted four times with ethyl acetate. The combined organics are dried over MgSO4, filtered, then evaporated to a residue which is chromatographed using hexanes, then 1:1 hexanes:ethyl acetate, then 100% ethyl acetate to give the title compound (6.4%) as a yellow oil. 1H-NMR (DMSO-d$_6$): δ6.86 (s, 1H); 3.73 (s, 3H); 3.06-3.10 (m, 1H); 2.41 (s, 3H); 2.22 (s, 3H); 2.03 (s, 3H); 1.93 (s, 3H); 1.74-1.83 (m, 4H); 0.77 (t, J=7.26 Hz, 6H) ppm. MS/ES+=327 (100%, M+2).

Example 99

Preparation of 2,6-Dimethyl-8-(1-propyl-butyl)-3-(1,3,5-trimethyl-1H-pyrazol-4-yl)-imidazo[1,2-b]pyridazine

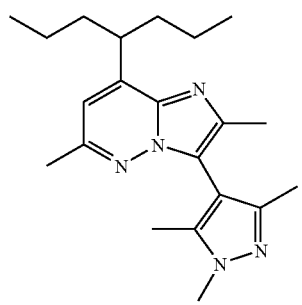

3-Iodo-2,6-dimethyl-8-(1-propyl-butyl)-imidazo[1,2-b]pyridazine (75 mg, 0.20 mmol), 1,3,5-trimethylpyrazole-4-boronic acid (80 mg, 0.52 mmol), 2N Na2CO3 solution (0.22 ml), and 5.0 mg (0.0004 mmol) of Pd(PPh3)4 are combined in microwave pressure vessel with 1.5 ml of dimethylether/H2O/ethanol (7:3:2) solution. The mixture is microwaved at 140° C. for 25 minutes. The mixture is evaporated and chromatographed on silica gel column using hexanes then 3:1 hexane:ethyl acetate, then 1:1 hexane:ethyl acetate to give the title compound (22.8%) as a clear oil. $^1$H-NMR (DMSO-d$_6$): δ6.88 (s, 1H); 3.72 (s, 3H); 3.06-3.10 (m, 1H); 2.40 (s, 3H); 2.21 (s, 3H); 2.02 (s, 3H); 1.92 (s, 3H); 1.60-1.76 (m, 4H); 1.08-1.21 (m, 4H); 0.82 (t, J=7.49 Hz, 6H) ppm. MS/ES+354 (100%, M+1).

Example 100

Preparation of 5-[8-(1-Ethyl-propyl)-2,6-dimethyl-imidazo[1,2-b]pyridazin-3-yl]-4-methyl-thiophene-2-carboxylic acid dimethylamide

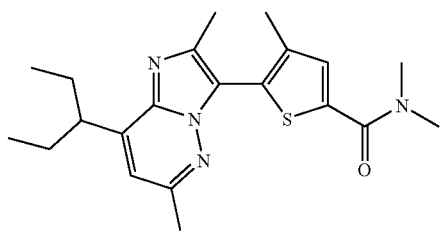

Using a procedure analogous to Example 23B, 5-[8-(1-ethyl-propyl)-2,6-dimethyl-imidazo[1,2-b]pyridazin-3-yl]-4-methyl-thiophene-2-carboxylic acid (151 mg, 0.42 mmol) and 2.0 M dimethylamine (2.0 mL, 4 mmol) give the title compound (161 mg, 0.42 mmol, 100%). $^1$H NMR (CDCl$_3$): δ 0.89 (t, J=7.4 Hz, 6H), 1.75-1.94 (m, 4H), 2.14 (s, 3H), 2.51 (s, 3H), 2.53 (s, 3H), 3.15-3.50 (m, 7H), 6.72 (s, 1H), 7.30 (s, 1H). ES-MS (m/z): calcd for C21H28N4OS (M+H)$^+$: 385.6 found: 385.3.

Example 101

Preparation of 8-(1-ethyl-propyl)-2,6-dimethyl-3-[3-methyl-5-(1-methyl-1H-Imidazol-3-yl)-thiophen-2-yl]-imidazo[1,2-b]pyridazine

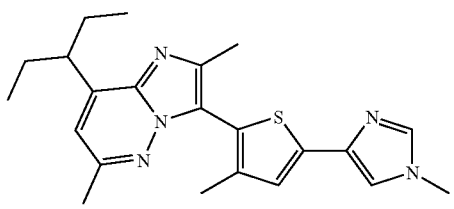

Using a procedure similar to Example 31. from 3-(5-bromo-3-methyl-thiophen-2-yl)-8-(1-ethyl-propyl)-2,6-dimethyl-imidazo[1,2-b]pyridazine (0.40 g, 1.02 mmol), 1.34 M n-BuLi (0.80 mL, 1.07 mmol), 0.5 M ZnCl$_2$ in THF (2.14 mL, 1.07 mmol), 3-iodo-1-methyl-1H-imidazole (0.24 mL, 1.22 mmol) and PdCl$_2$(dppf) (0.037 g, 0.051 mmol) furnish the title compound (0.030 g, 0.076 mmol, 8%). $^1$H NMR (CDCl$_3$), δ 0.89 (t, J=7.5 Hz, 6H), 1.74-1.93 (m, 4H), 2.13 (s, 3H), 2.50 (s, 3H), 2.51 (s, 3H), 3.31-3.40 (m, 1H), 3.72 (s, 3H), 6.66 (s, 1H), 7.09 (d, J=1.3 Hz, 1H), 7.19 (s, 1H), 7.86 (d, J=1.3 Hz, 1H). LC/MS (m/z): calcd. for C$_{22}$H$_{27}$N$_5$S (M+H)$^+$: 394.2; found: 394.2.

Example 102

Preparation of N-{4-chloro-5-[8-(1-ethyl-propyl)-2,6-dimethyl-imidazo[1,2-b]pyridazin-3-yl]-thiazol-2-yl}-morpholine, hydrochloride salt

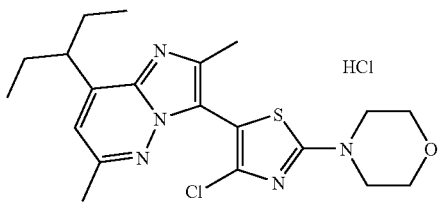

IPA (225.0 mL) is added to compound N-{4-chloro-5-[8-(1-ethyl-propyl)-2,6-dimethyl-imidazo[1,2-b]pyridazin-3-yl]-thiazol-2-yl}-morpholine (18.8 g, 0.0448 mmol, below) in a 1 L 1-neck round-bottomed flask The starting material slurry is heated to 50° C. on a Buchi bath, at which time a hazy solution resulted. Concentrated (12 M) aqueous HCl (3.73 mL, 0.0448 mmole, 1.0 eq) is added all at once, and the hazy solution is stirred at 50° C. on the Buchi for 10 minutes, then evaporated to a yellow solid under vacuum. After 20 minutes at room temperature under vacuum (weight of 20.9 g), acetone (100 mL) is added and the resulting yellow slurry is stirred at room temperature for 1 hour, then cooled with an ice bath and stirred for an additional 1 hour. The slurry is filtered, rinsed with acetone, and dried overnight under vacuum at 40° C. to provide pale yellow-white crystalline solid 19.18 g (94%). $^1$H NMR (DMSO): δ 7.52 (s, 1H), 3.73 (t, J=4.6, 4H), 3.49 (t, J=5.2 Hz, 4H), 3.39 (m, 1H), 2.57 (s, 3H), 2.49 (s, 3H), 1.77 (m, 4H), 0.80 (t, J=7.4 Hz, 6H).

Example 103

Preparation of 8-(1-ethyl-propyl)-3-[5-(2-fluoro-phenyl)-3-methyl-thiophen-2-yl]-2,6-dimethyl-imidazo[1,2-b]pyridazine

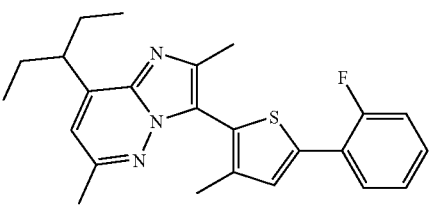

Using a procedure analogous to Example 30B, 3-(5-boronic acid-3-methyl-thiophen-2-yl)-8-(1-ethyl-propyl)-2,6-dimethyl-imidazo[1,2-b]pyridazine (0.18 g, 0.50 mmol), 1-bromo-2-fluoro-benzene (0.072 g, 0.65 mmol), and 2 M Na$_2$CO$_3$ (0.38 mL, 0.76 mmol), n-PrOH (2 mL), and Pd(PPh$_3$)$_4$ (0.029 g, 0.025 mmol) furnish the title compound (0.022 g, 0.054 mmol, 11%). $^1$H NMR (CDCl$_3$), δ 0.93 (t, J=7.4 Hz, 6H), 1.71-1.96 (m, 4H), 2.19 (s, 3H), 2.66 (s, 3H), 2.67 (s, 3H), 3.41-3.50 (m, 1H), 7.15 (s, 1H), 7.15-7.23 (m, 2H), 7.28-7.35 (m, 1H), 7.45 (d, J=1.4 Hz, 1H), 7.66 (dt, J=7.8, 1.6 Hz, 1H). LC/MS (m/z): calcd. for C$_{24}$H$_{26}$FN$_3$S (M+H)$^+$: 408.2; found: 408.2.

Example 104

Preparation of 3-(3-chloro-5-pyrimidin-2-yl-thiophen-2-yl)-8-(1-ethyl-propyl)-2,6-dimethyl-imidazo[1,2-b]pyridazine

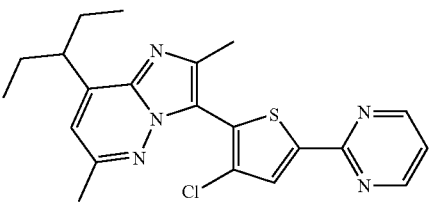

A. 3-(3-Chloro-thiophen-2-yl-5-boronic acid)-8-(1-ethyl-propyl)-2,6-dimethyl-imidazo[1,2-b]pyridazine.

To a −78° C. solution of 3-(3-chloro-thiophen-2-yl)-8-(1-ethyl-propyl)-2,6-dimethyl-imidazo[1,2-b]pyridazine (2.0 g, 5.97 mmol) and THF (30 mL) is added 1.6 M n-BuLi (4.1 mL). After 30 minutes B(OMe)$_3$ (0.74 mL, 6.59 mmol) is added, the solution is warmed to ambient temperature and stirred overnight. 1 M HCl (30 mL) is added and the solution stirred for 20 minutes. The solution is made basic with 5 M NaOH. The organic layer is extracted with 1 M NaOH (30 mL). The combined aqueous layers are made acidic with 5 M HCl, K$_3$PO$_4$.3H$_2$O is added and the PH adjusted to 5.5 using 1 M NaOH. The combined aqueous layers are extracted with EtOAc (200 mL), washed with brine (150 mL), dried over MgSO$_4$, filtered and concentrated to furnish the title compound (2.20 g, 5.82 mmol, 97%). LC/MS (m/z): calcd. for C$_{17}$H$_{21}$BClN$_3$O$_2$S (M+H)$^+$: 378.7; found: 378.0.

B. 3-(3-Chloro-5-pyrimidin-2-yl-thiophen-2-yl)-8-(1-ethyl-propyl)-2,6-dimethyl-imidazo[1,2-b]pyridazine.

A solution of 3-(3-chloro-thiophen-2-yl-5-boronic acid)-8-(1-ethyl-propyl)-2,6-dimethyl-imidazo[1,2-b]pyridazine (0.25 g, 0.66 mmol), 2-bromo-pyrimidine (0.21 g, 1.32 mmol), 2 M $Na_2CO_3$ (0.66 mL, 1.32 mmol) and i-PrOH (3 mL) are degassed with $N_2$ for 15 minutes. $Pd(OAc)_2$ (7.4 mg, 0.033 mmol) and $PPh_3$ (0.026 g, 0.099 mmol) are added and the solution is heated at 90° C. overnight. The solution is diluted with EtOAc (35 mL), washed with 10% $Na_2CO_3$ (35 mL), brine (35 mL), dried over $Na_2SO_4$, filtered and concentrated. The residue is purified by ISCO column chromatography (20%-30% EtOAc/hexane gradient) furnish the title compound (0.077 g, 0.19 mmol, 29%). $^1$H NMR ($CDCl_3$) δ 0.88 (d, J=7.4 Hz, 6H), 1.75-1.93 (m, 4H), 2.53 (s, 3H), 2.54 (s, 3H), 3.27-3.40 (m, 1H), 6.71 (s, 1H), 7.16 (t, J=5.0 Hz, 1H), 8.00 (s, 1H), 8.74 (d, J=5.0 Hz, 2H). LC/MS (m/z): calcd. for $C_{21}H_{22}ClN_5S$ (M+H)$^+$: 412.1; found: 412.2.

Example 105

Preparation of 3-(3-chloro-5-thiazol-2-yl-thiophen-2-yl)-8-(1-ethyl-propyl)-2,6-dimethyl-imidazo[1,2-b]pyridazine

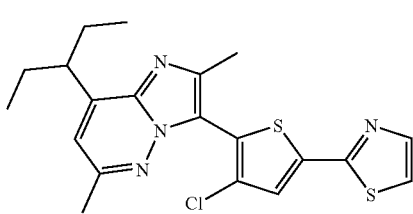

Using a procedure similar to Example 104, 3-(3-chloro-thiophen-2-yl-5-boronic acid)-8-(1-ethyl-propyl)-2,6-dimethyl-imidazo[1,2-b]pyridazine (0.25 g, 0.66 mmol), 2-bromo-pyrimidine (0.21 g, 1.32 mmol), 2 M $Na_2CO_3$ (0.66 mL, 1.32 mmol) and i-PrOH (3 mL), $Pd(OAc)_2$ (7.4 mg, 0.033 mmol), and $PPh_3$ (0.026 g, 0.099 mmol) furnish the title compound (0.099 g, 0.24 mmol, 35%). $^1$H NMR ($CDCl_3$) δ 0.88 (d, J=7.5 Hz, 6H), 1.74-1.92 (m, 4H), 2.52 (s, 3H), 2.53 (s, 3H), 3.28-3.38 (m, 1H), 6.71 (s, 1H), 7.33 (t, J=3.3 Hz, 1H), 7.49 (s, 1H), 7.81 (d, J=3.3 Hz, 2H). LC/MS (m/z): calcd. for $C_{21}H_{22}ClN_5S$ (M+H)$^+$: 417.1; found: 417.1.

Example 106

Preparation of 3-[3-chloro-5-(2-methyl-2H-pyrazol-3-yl)-thiophen-2-yl]-8-(1-ethyl-propyl)-2,6-dimethyl-imidazo[1,2-b]pyridazine

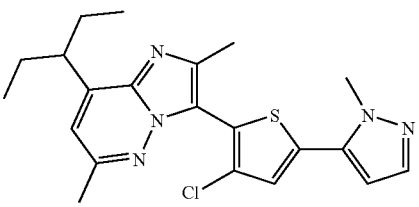

To a −78° C. solution of 1-methyl-1H-pyrazole (0.12 g, 1.45 mmol) and THF (4 mL) is added 1.6 M n-BuLi (0.91 mL, 1.45 mmol). After 45 minutes 0.5 M $ZnCl_2$ (2.9 mL, 1.45 mmol) is added and the solution is warmed to ambient temperature. After 30 minutes 3-(5-bromo-3-chloro-thiophen-2-yl)-8-(1-ethyl-propyl)-2,6-dimethyl-imidazo[1,2-b]pyridazine (example Rupp-88) (0.30 g, 0.73 mmol) and $PdCl_2$(dppf) (0.027 g, 0.036 mmol) are added and the solution heated at 65° C. overnight, diluted with EtOAc (30 mL), washed with sat. $NH_4Cl$ (2×30 mL), dried over $MgSO_4$, filtered and concentrated. The residue is purified by ISCO column chromatography (15%-30% EtOAc/hexane gradient) furnish the title compound (0.15 g, 0.36 mmol, 50%). $^1$H NMR ($CDCl_3$) δ 0.88 (d, J=7.5 Hz, 6H), 1.74-1.91 (m, 4H), 2.52 (s, 6H), 3.26-3.36 (m, 1H), 4.05 (s, 3H), 6.45 (d, J=1.9 Hz, 1H), 6.71 (s, 1H), 7.14 (s, 1H), 7.49 (d, J=1.9 Hz, 1H). LC/MS (m/z): calcd. for $C_{21}H_{24}ClN_5S$ (M+H)$^+$: 414.2; found: 414.2.

Example 107

Preparation of 3-(3-chloro-5-pyridin-4-yl-thiophen-2-yl)-8-(1-ethyl-propyl)-2,6-dimethyl-imidazo[1,2-b]pyridazine

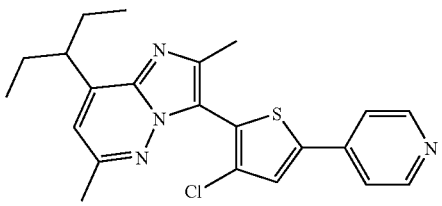

Using a procedure similar to Example 104, 3-(3-chloro-thiophen-2-yl-5-boronic acid)-8-(1-ethyl-propyl)-2,6-dimethyl-imidazo[1,2-b]pyridazine (0.25 g, 0.66 mmol), 4-bromo-pyridine hydrochloride (0.26 g, 1.32 mmol), 2 M $Na_2CO_3$ (1.00 mL, 1.99 mmol), i-PrOH (3 mL), $Pd(OAc)_2$ (7.4 mg, 0.033 mmol), and $PPh_3$ (0.026 g, 0.099 mmol) furnish the title compound (0.16 g, 0.59 mmol, 59%). $^1$H NMR ($CDCl_3$) δ 0.87 (d, J=7.5 Hz, 6H), 1.74-1.92 (m, 4H), 2.52 (s, 3H), 2.53 (s, 3H), 3.27-3.36 (m, 1H), 6.72 (s, 1H), 7.45-7.49 (m, 3H), 8.63 (d, J=1.3 Hz, 1H), 8.64 (d, J=1.3 Hz, 1H). LC/MS (m/z): calcd. for $C_{22}H_{23}ClN_4S$ (M+H)$^+$: 411.1; found: 411.1.

Example 108

Preparation of 3-[3-chloro-5-(3,5-dimethyl-isoxazol-4-yl)-thiophen-2-yl]-8-(1-ethyl-propyl)-2,6-dimethyl-imidazo[1,2-b]pyridazine

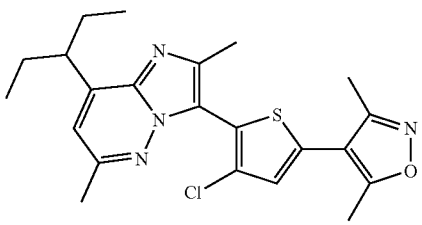

Using a procedure similar to Example 104, 3-(3-chloro-thiophen-2-yl-5-boronic acid)-8-(1-ethyl-propyl)-2,6-dimethyl-imidazo[1,2-b]pyridazine (0.25 g, 0.66 mmol), 4-iodo-3,5-dimethyl-isoxazole (0.30 g, 1.32 mmol), 2 M Na$_2$CO$_3$ (0.66 mL, 1.32 mmol) and i-PrOH (3 mL), Pd(OAc)$_2$ (7.4 mg, 0.033 mmol), and PPh$_3$ (0.026 g, 0.099 mmol) furnish the title compound (0.14 g, 0.50 mmol, 50%). $^1$H NMR (CDCl$_3$) δ 0.87 (d, J=7.5 Hz, 6H), 1.73-1.92 (m, 4H), 2.43 (s, 3H), 2.53 (s, 6H), 2.57 (s, 3H), 3.27-3.38 (m, 1H), 6.71 (s, 1H), 7.01 (s, 1H). LC/MS (m/z): calcd. for C$_{22}$H$_{25}$ClN$_4$OS (M+H)$^+$: 429.2; found: 429.2.

Example 109

Preparation of 3-(3-chloro-5-pyridin-2-yl-thiophen-2-yl)-8-(1-ethyl-propyl)-2,6-dimethyl-imidazo[1,2-b]pyridazine

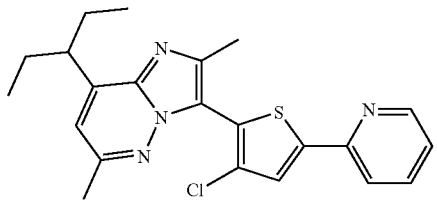

To a flask containing 3-(5-bromo-3-chloro-thiophen-2-yl)-8-(1-ethyl-propyl)-2,6-dimethyl-imidazo[1,2-b]pyridazine (0.25 g, 0.61 mmol) and PdCl$_2$(dppf) (0.022 g, 0.030 mmol) is added a 0.5 M solution of 2-pyridylzinc bromide (2.40 mL, 1.21 mmol) and the solution heated at 65° C. overnight, diluted with EtOAc (30 mL), washed with sat. NH$_4$Cl (2×30 mL), dried over MgSO$_4$, filtered and concentrated. The residue is purified by ISCO column chromatography (20%-40% EtOAc/hexane gradient) followed by recrystallization from CH$_3$CN furnish the title compound (0.15 g, 0.36 mmol, 60%). $^1$H NMR (CDCl$_3$) δ 0.88 (d, J=7.5 Hz, 6H), 1.73-1.93 (m, 4H), 2.52 (s, 3H), 2.53 (s, 3H), 3.29-3.38 (m, 1H), 6.70 (s, 1H), 7.17-7.23 (m, 1H), 7.56 (s, 1H), 7.66 (d, J=7.9 Hz, 1H), 7.70-7.76 (m, 1H), 8.59 (d, J=4.7 Hz, 1H). LC/MS (m/z): calcd. for C$_{22}$H$_{23}$ClN$_4$S (M+H)$^+$: 412.0; found: 412.4.

Example 110

Preparation of 3-(3-chloro-5-pyrimidin-5-yl-thiophen-2-yl)-8-(1-ethyl-propyl)-2,6-dimethyl-imidazo[1,2-b]pyridazine

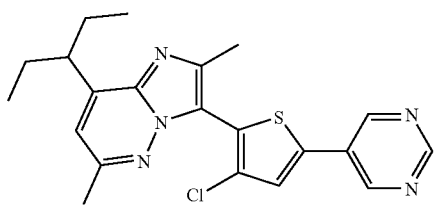

Using a procedure similar to Example 104, 3-(3-chloro-thiophen-2-yl-5-boronic acid)-8-(1-ethyl-propyl)-2,6-dimethyl-imidazo[1,2-b]pyridazine (0.25 g, 0.66 mmol), 4-bromo-pyrimidine (0.21 g, 1.32 mmol), 2 M Na$_2$CO$_3$ (0.66 mL, 1.32 mmol), i-PrOH (3 mL), Pd(OAc)$_2$ (7.4 mg, 0.033 mmol), and PPh$_3$ (0.026 g, 0.099 mmol) furnish the title compound (0.053 g, 0.13 mmol, 20%). $^1$H NMR (CDCl$_3$) δ 0.88 (d, J=7.5 Hz, 6H), 1.73-1.92 (m, 4H), 2.53 (s, 3H), 2.54 (s, 3H), 3.27-3.37 (m, 1H), 6.73 (s, 1H), 7.40 (s, 1H), 8.97 (s, 2H), 9.18 (s, 1H). LC/MS (m/z): calcd. for C$_{21}$H$_{22}$ClN$_5$S (M+H)$^+$: 412.1. found: 411.2.

Example 111

Preparation of 3-(3-chloro-5-pyrazin-2-yl-thiophen-2-yl)-8-(1-ethyl-propyl)-2,6-dimethyl-imidazo[1,2-b]pyridazine

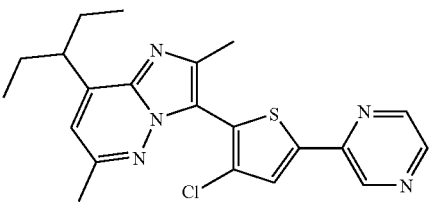

Using a procedure similar to Example 104, 3-(3-chloro-thiophen-2-yl-5-boronic acid)-8-(1-ethyl-propyl)-2,6-dimethyl-imidazo[1,2-b]pyridazine (0.40 g, 1.06 mmol), 2-iodo-pyrazine (0.16 g, 1.59 mmol), 2 M Na$_2$CO$_3$ (1.06 mL, 2.12 mmol) and i-PrOH (5 mL), Pd(OAc)$_2$ (0.012 g, 0.053 mmol), and PPh$_3$ (0.042 g, 0.16 mmol) furnish the title compound (0.15 g, 0.36 mmol, 34%). $^1$H NMR (CDCl$_3$) δ 0.87 (d, J=7.5 Hz, 6H), 1.73-1.92 (m, 4H), 2.51 (s, 3H), 2.52 (s, 3H), 3.25-3.37 (m, 1H), 6.71 (s, 1H), 7.66 (s, 1H), 8.45 (d, J=2.6 Hz, 1H), 8.51-8.53 (m, 1H), 8.96 (d, J=1.0 Hz, 1H). LC/MS (m/z): calcd. for C$_{21}$H$_{22}$ClN$_5$S (M+H)$^+$: 412.1; found: 412.3.

Example 112

Preparation of 3-(3-chloro-5-thiazol-4-yl-thiophen-2-yl)-8-(1-ethyl-propyl)-2,6-dimethyl-imidazo[1,2-b]pyridazine

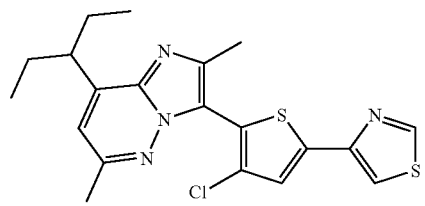

To a 0° C. solution of 3-(5-bromo-3-chloro-thiophen-2-yl)-8-(1-ethyl-propyl)-2,6-dimethyl-imidazo[1,2-b]pyridazine (0.60 g, 1.45 mmol) and THF (2 mL) is added 0.05 g/mL of Reike® Zn (3.80 mL, 2.91 mmol). The solution is heated at a reflux for 1 hour, and the excess Zn allowed to settle for 1 hour at ambient temperature. The solution is transferred to a flask of 4-bromo-thiazole (Kelly, T. et al. Tetrahedron, Lett. 1995, 51, 9293) (0.29 g, 1.74 mmol). PdCl$_2$(dppf) (0.027 g, 0.036 mmol) is added and the solution heated at 65° C. overnight, diluted with EtOAc (40 mL), washed with sat. NH$_4$Cl (30 mL), dried over MgSO$_4$, filtered and concentrated. The residue is purified by ISCO column chromatography (15%-20% EtOAc/hexane gradient) followed by ISCO column chromatography (100% Et$_2$O) to furnish the title compound (0.098 g, 0.24 mmol, 16%). $^1$H NMR (CDCl$_3$) δ 0.88 (d, J=7.5 Hz, 6H), 1.74-1.92 (m, 4H), 2.52 (s, 3H), 2.53

(s, 3H), 3.28-3.38 (m, 1H), 6.70 (s, 1H), 7.45 (s, 1H), 7.49 (d, J=2.0 Hz, 1H), 8.85 (d, J=2.0 Hz, 1H). LC/MS (m/z): calcd. for $C_{20}H_{21}ClN_4S_2$ $(M+H)^+$: 417.1; found: 417.3.

Example 113

Preparation of 8-(1-ethyl-1-fluoro-propyl)-2,6-dimethyl-3-[3-methyl-5-(6-methyl-pyridin-2-yl)-thiophen-2-yl]-imidazo[1,2-b]pyridazine

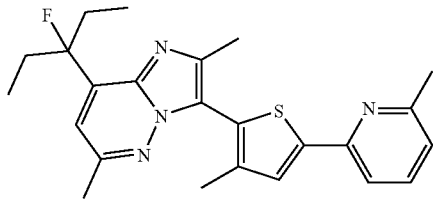

To a −78° C. solution of 3-{2,6-dimethyl-3-[3-methyl-5-(6-methyl-pyridin-2-yl)-thiophen-2-yl]-imidazo[1,2-b]pyridazin-8-yl}-pentan-3-ol (0.23 g, 0.55 mmol) and $CH_2Cl_2$ (3 mL) is added a solution of [bis(2-methoxyethyl)amino]sulfur triflouride (0.14 g, 0.60 mmol) and $CH_2Cl_2$ (2 mL). The solution is warmed to ambient temperature and stirred overnight. The solution is washed with sat. $NaHCO_3$ (5 mL) and concentrated. The reside is purified by ISCO column chromatography (15%-20% EtOAc/hexane gradient) furnish the title compound (0.13 g, 0.31 mmol, 57%). $^1H$ NMR ($CDCl_3$) δ 0.80 (t, J=7.5 Hz, 6H), 2.14 (s, 3H), 2.16-2.31 (m, 2H), 2.46 (s, 3H), 2.54 (s, 3H), 2.56 (s, 3H), 2.59-2.70 (m, 2H), 6.98 (s, 1H), 7.00 (d, J=7.6 Hz, 1H), 7.45 (d, J=7.8 Hz, 1H), 7.52 (s, 1H), 7.56 (dd, J=7.8, 7.6 Hz, 1H). LC/MS (m/z): calcd. for $C_{24}H_{27}FN_4S$ $(M+H)^+$: 423.2; found: 423.4.

Example 114

Preparation of 2-[8-(1-ethyl-propyl)-2,6-dimethyl-imidazo[1,2-b]pyridazin-3-yl]-thiophene-3-carbonitrile

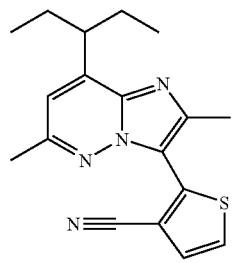

To a solution 0.05 g/mL of Reike® Zn (31 mL, 23.93 mmol) is added 2-bromo-thiophene-3-carbonitrile (Fournari, P. et al. Bull. Soc. Chim. Fr., 1967, 4115) (2.25 g, 11.96 mmol) and THF (5 mL). The solution is heated at a reflux for 2 hours, cooled to ambient temperature and the excess Zn allowed to settle. The solution is transferred via a cannula into a flask of 8-(1-ethyl-propyl)-3-iodo-2,6-dimethyl-imidazo[1,2-b]pyridazine (2.5 g, 7.98 mmol) and $PdCl_2$(dppf) (0.29 g, 0.040 mmol). The mixture is heated at 65° C. overnight, diluted with EtOAc (75 mL), washed with sat. $NH_4Cl$ (2×75 mL), dried over $MgSO_4$, filtered and concentrated. The residue is purified by ISCO column chromatography (10%-20% EtOAc/hexane gradient) furnish the title compound (1.10 g, 3.39 mmol, 42%). $^1H$ NMR ($CDCl_3$) δ 0.86 (t, J=7.5 Hz, 6H), 1.74-1.91 (m, 4H), 2.55 (s, 3H), 2.61 (s, 3H), 3.25-3.34 (m, 1H), 6.75 (s, 1H), 7.35 (d, J=5.2 Hz, 1H), 7.53 (d, J=5.2 Hz, 1H). LC/MS (m/z): calcd. for $C_{18}H_{20}N_4S$ $(M+H)^+$: 325.5; found: 325.2.

Example 115

Preparation of 5-bromo-2-[8-(1-ethyl-propyl)-2,6-dimethyl-imidazo[1,2-b]pyridazin-3-yl]-thiophene-3-carbonitrile

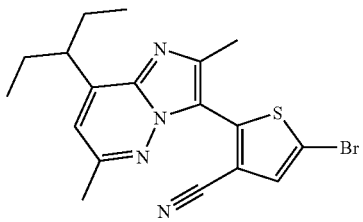

To a solution of 2-[8-(1-ethyl-propyl)-2,6-dimethyl-imidazo[1,2-b]pyridazin-3-yl]-thiophene-3-carbonitrile (0.83 g, 2.56 mmol) and $CH_2Cl_2$ (10 mL) is added NBS (0.48 g, 2.69 mmol). The solution is stirred for 1 hour, diluted with $Et_2O$ (100 mL), washed with water (3×100 mL), brine (100 mL), dried ($MgSO_4$) filtered and concentrated to furnish the title compound (1.03 g, 2.55 mmol, >99%). $^1H$ NMR ($CDCl_3$) δ 0.86 (t, J=7.5 Hz, 6H), 1.74-1.91 (m, 4H), 2.56 (s, 3H), 2.60 (s, 3H), 3.24-3.32 (m, 1H), 6.76 (s, 1H), 7.30 (s, 1H). LC/MS (m/z): calcd. for $C_{18}H_{19}BrN_4S$ $(M+H)^+$: 404.4; found: 404.1.

Example 116

Preparation of 2-[8-(1-ethyl-propyl)-2,6-dimethyl-imidazo[1,2-b]pyridazin-3-yl]-5-thiazol-2-yl-thiophene-3-carbonitrile

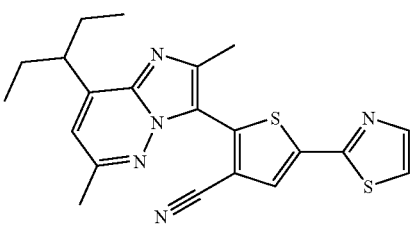

To a flask containing 5-bromo-2-[8-(1-ethyl-propyl)-2,6-dimethyl-imidazo[1,2-b]pyridazin-3-yl]-thiophene-3-carbonitrile (0.25 g, 0.62 mmol) and $PdCl_2$(dppf) (0.023 g, 0.031 mmol) is added a solution of 0.5 M 2-thiazolylzinc bromide (6.0 mL, 3.10 mmol). The solution is heated at 65° C. overnight, diluted with EtOAc (30 mL), washed with sat. $NH_4Cl$ (2×25 mL), dried over $MgSO_4$, filtered and concentrated. The residue is purified by ISCO column chromatography (15%-20% EtOAc/hexane gradient) furnish the title compound (0.16 g, 0.39 mmol, 64%). $^1H$ NMR ($CDCl_3$) δ 0.88 (t, J=7.5 Hz, 6H), 1.75-1.93 (m, 4H), 2.58 (s, 3H), 2.66 (s, 3H), 3.25-3.35 (m, 1H), 6.78 (s, 1H), 7.38 (d, J=3.5 Hz, 1H), 7.70 (s, 1H), 7.84 (d, J=3.5 Hz, 1H). LC/MS (m/z): calcd. for C$_{21}$H$_{21}$N$_5$S$_2$ (M+H)$^+$: 408.6; found: 408.1.

Example 117

Preparation of 2-[8-(1-ethyl-propyl)-2,6-dimethyl-imidazo[1,2-b]pyridazin-3-yl]-5-thiazol-2-yl-thiophene-3-carbonitrile

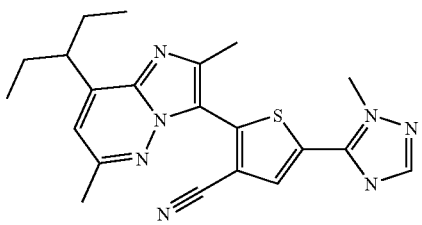

To a −78° C. solution of 1-methyl-1,2,4-triazole (0.14 mL, 1.86 mmol) and THF (5 mL) is added a 1.6 M solution of n-BuLi in hexanes (1.20 mL, 1.86 mmol) after 30 minutes a 0.5 M solution of ZnCl$_2$ in THF (4.70 mL, 2.33 mmol) is added and the solution warmed to ambient temperature and stirred for 30 minute. 5-Bromo-2-[8-(1-ethyl-propyl)-2,6-dimethyl-imidazo[1,2-b]pyridazin-3-yl]-thiophene-3-carbonitrile (example Rupp-122) (0.25 g, 0.62 mmol) and PdCl$_2$(dppf) (0.023 g, 0.031 mmol) is added and the solution heated at 65° C. overnight, diluted with EtOAc (25 mL), washed with sat. NH$_4$Cl (20 mL), dried over MgSO$_4$, filtered and concentrated. The residue is purified by ISCO column chromatography (15%-60% EtOAc/hexane gradient), and is chromatographed (50×250 C18 X-Terra RP column, 30-90% 10 mM NH$_4$HCO$_3$/water/5% ACN:ACN gradient). The residue is dissolved in Et$_2$O (25 mL), washed with sat. NaHCO$_3$ (25 mL), dried over MgSO4, filtered and concentrated to furnish the title compound (0.013 g, 0.032 mmol, 5%). $^1$H NMR (CDCl$_3$) δ 0.87 (t, J=7.5 Hz, 6H), 1.75-1.93 (m, 4H), 2.58 (s, 3H), 2.67 (s, 3H), 3.26-3.34 (m, 1H), 4.17 (s, 3H), 6.79 (s, 1H), 6.78 (s, 1H), 7.92 (s, 1H). LC/MS (m/z): calcd. for C$_{21}$H$_{23}$N$_7$S (M+H)$^+$: 406.5; found: 406.2.

Example 118

Preparation of 2-[8-(1-ethyl-propyl)-2,6-dimethyl-imidazo[1,2-b]pyridazin-3-yl]-5-(6-methyl-pyridin-2-yl)-thiophene-3-carbonitrile

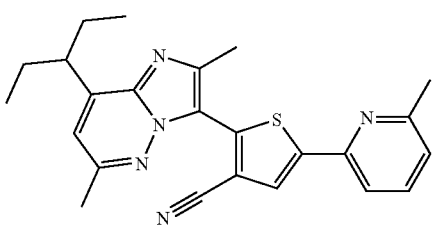

To a flask containing 5-bromo-2-[8-(1-ethyl-propyl)-2,6-dimethyl-imidazo[1,2-b]pyridazin-3-yl]-thiophene-3-carbonitrile (0.25 g, 0.62 mmol) and PdCl$_2$(dppf) (0.024 g, 0.033 mmol) is added a solution of 0.5 M 6-methyl-2-pyridylzinc bromide in THF (2.50 mL, 1.24 mmol). The solution is heated at 65° C. overnight, diluted with EtOAc (30 mL), washed with sat. NH$_4$Cl (2×30 mL), dried over MgSO$_4$, filtered and concentrated. The residue is purified by ISCO column chromatography (15%-25% EtOAc/hexane gradient), furnish the title compound (0.11 g, 0.26 mmol, 39%). $^1$H NMR (CDCl$_3$) δ 0.87 (t, J=7.5 Hz, 6H), 1.76-1.92 (m, 4H), 2.57 (s, 3H), 2.58 (s, 3H), 2.65 (s, 3H), 3.26-3.35 (m, 1H), 6.75 (s, 1H), 7.09 (d, J=7.5 Hz, 1H), 7.49 (d, J=7.9 Hz, 1H), 7.63 (dd, J=7.9, 7.5 Hz, 1H), 7.74 (s, 1H). LC/MS (m/z): calcd. for C$_{24}$H$_{25}$N$_5$S (M+H)$^+$: 416.6; found: 416.2.

Example 119

Preparation of 2-[8-(1-ethyl-propyl)-2,6-dimethyl-imidazo[1,2-b]pyridazin-3-yl]-5-pyridin-3-yl-thiophene-3-carbonitrile

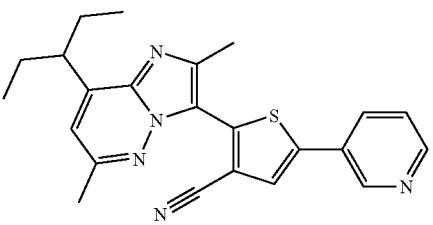

To a −78° C. solution of 3-iodo-pyridine (0.32 g, 1.56 mmol), 0.5 M ZnCl$_2$ in THF (3.20 mL, 1.59 mmol), and THF (2 mL) is added 1.7 M t-BuLi (1.85 mL, 3.15 mmol). The solution is warmed to ambient temperature and stirred for 30 minutes. 5-Bromo-2-[8-(1-ethyl-propyl)-2,6-dimethyl-imidazo[1,2-b]pyridazin-3-yl]-thiophene-3-carbonitrile (0.21 g, 0.52 mmol) and Pd(PPh$_3$)$_4$ (0.03 g, 0.026 mmol) are added and the solution heated at 55° C. for 1 hour, cooled to ambient temperature and stirred overnight, diluted with EtOAc (50 mL), washed with sat. NH$_4$Cl (2×40 mL), dried over MgSO$_4$, filtered and concentrated. The residue is purified by ISCO column chromatography (15%-40% EtOAc/hexane gradient), furnish the title compound (0.15 g, 0.37 mmol, 71%). $^1$H NMR (CDCl$_3$) δ 0.87 (t, J=7.5 Hz, 6H), 1.74-1.92 (m, 4H), 2.58 (s, 3H), 2.66 (s, 3H), 3.26-3.35 (m, 1H), 6.78 (s, 1H), 7.34-7.46 (m, 1H), 7.56 (s 1H), 7.91 (d, J=7.1 Hz, 1H), 8.62 (s, 1H), 8.91 (s, 1H). LC/MS (m/z): calcd. for C$_{23}$H$_{23}$N$_5$S (M+H)$^+$: 402.6; found: 402.4.

Example 120

Preparation of 3-(3,4-dimethyl-thiophen-2-yl)-8-(1-ethyl-propyl)-2,6-dimethyl-imidazo[1,2-b]pyridazine

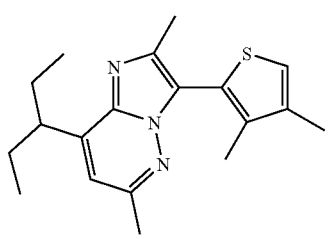

A. 2-Bromo-3,4-dimethyl-thiophene.

To a solution of 3,4-dimethyl-thiophene (2.0 g, 17.82 mmol) (Minato et. al., *Tetrahedron* 1982, 38, 3347) in CH$_2$Cl$_2$ (20 mL) is added NBS (3.3 g, 18.72 mmol). The solution is stirred for 1 hour, diluted with Et$_2$O (100 mL), washed with water (3×100 mL), brine (100 mL), dried (MgSO$_4$) filtered and concentrated. The residue is purified by ISCO column chromatography (100% hexane) furnish the title compound (3.0 g, 16.70 mmol). $^1$H NMR (CDCl$_3$) δ 2.10 (s, 3H), 2.17 (s, 3H), 6.85 (s, 1H).

B. 3-(3,4-Dimethyl-thiophen-2-yl)-8-(1-ethyl-propyl)-2,6-dimethyl-imidazo[1,2-b]pyridazine and 8-(1-ethyl-propyl)-2,6-dimethyl-3-(3,4,3',4'-tetramethyl-[2,2']bithiophenyl-5-yl)-imidazo[1,2-b]pyridazine, respectively.

To a solution of 8-(1-ethyl-propyl)-2,6-dimethyl-imidazo[1,2-b]pyridazine (2.30 g, 10.58 mmol), 2-bromo-3,4-dimethyl-thiophene (3.03 g, 15.88 mmol) and Cs$_2$CO$_3$ (7.24 g, 22.23 mmol) and DMF (50 mL) is de-gassed with N$_2$ for 20 minutes. Pd$_2$(dba)$_3$ (0.48 g, 0.053 mmol) and PPh$_3$ (0.56 g, 0.21 mmol) are added and the solution is heated at 120° C. overnight. The solution is diluted with EtOAc (200 mL), washed with water (3×200 mL), brine (200 mL), dried (MgSO$_4$), filtered and concentrated. The residue is purified by ISCO column chromatography (10%-15% EtOAc/hexane gradient) furnish 2.04 g of a brown oil which is chromatographed (50×250 C18 Symmetry column, 30-70% water: 0.1% TFA/ACN gradient) furnish the title compound (0.41 g, 1.25 mmol, 12%). $^1$H NMR (CDCl$_3$) δ 0.87 (t, J=7.5 Hz, 6H), 1.73-1.94 (m, 4H), 2.00 (s, 3H), 2.24 (d, J=1.0 Hz, 3H), 2.45 (s, 3H), 2.50 (s, 3H), 3.29-3.38 (m, 1H), 6.65 (s, 1H), 7.10 (s, 1H). LC/MS (m/z): calcd. for C$_{19}$H$_{25}$N$_3$S (M+H)$^+$: 328.5; found: 328.3.

Example 121

Preparation of 8-(1-ethyl-propyl)-2,6-dimethyl-3-[3-methyl-4-(6-methyl-pyridin-2-yl)-thiophen-2-yl]-imidazo[1,2-b]pyridazine

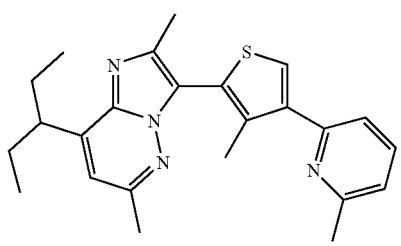

To a flask containing 3-(4-bromo-3-methyl-thiophen-2-yl)-8-(1-ethyl-propyl)-2,6-dimethyl-imidazo[1,2-b]pyridazine (below) (0.25 g, 0.64 mmol) and PdCl$_2$(dppf) (0.023 g, 0.032 mmol) is added a solution of 0.5 M 6-methyl-2-pyridylzinc bromide in THF (2.5 mL, 1.27 mmol). The solution is heated at 65° C. overnight, diluted with EtOAc (25 mL), washed with sat. NH$_4$Cl (20 mL), dried over MgSO$_4$, filtered and concentrated. The residue is purified by ISCO (15%-20% EtOAc gradient) and is chromatographed (50× 250 C18 Symmetry column, 10-70% water: 0.1% TFA/ACN: 0.1% TFA gradient). The residue is dissolved in Et$_2$O (20 mL), washed with sat. NaHCO$_3$ (15 mL) dried over MgSO$_4$, filtered and concentrated to furnish the title compound (0.066 g, 1.57 mmol, 31%). $^1$H NMR (CDCl$_3$) δ 0.87 (t, J=7.5 Hz, 6H), 1.73-1.91 (m, 4H), 2.20 (s, 3H), 2.47 (s, 3H), 2.49 (s, 3H), 2.61 (s, 3H), 3.29-3.38 (m, 1H), 6.66 (s, 1H), 7.09 (d, J=7.5 Hz, 1H), 7.43 (d, J=7.8 Hz, 1H), 7.54 (dd, J=7.5, 7.8 Hz, 1H), 7.72 (s, 1H). LC/MS (m/z): calcd. for C$_{24}$H$_{28}$N$_4$S (M+H)$^+$: 405.2; found: 405.3.

Example 122

Preparation of 3-(5-bromo-3,4-dimethyl-thiophen-2-yl)-8-(1-ethyl-propyl)-2,6-dimethyl-imidazo[1,2-b]pyridazine

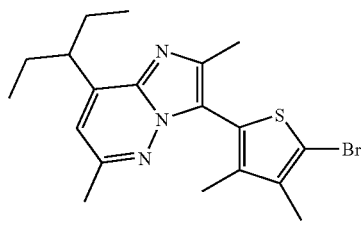

To a solution of 3-(3,4-dimethyl-thiophen-2-yl)-8-(1-ethyl-propyl)-2,6-dimethyl-imidazo[1,2-b]pyridazine (0.41 g, 1.25 mmol) and CH$_2$Cl$_2$ (30 mL) is added NBS (0.23 g, 1.32 mmol). The solution is stirred for 1 hour, diluted with Et$_2$O (100 mL), washed with water (3×100 mL), brine (100 mL), dried (MgSO$_4$) filtered and concentrated to furnish the title compound (0.41 g, 1.01 mmol, 80%). $^1$H NMR (CDCl$_3$) δ 0.86 (t, J=7.4 Hz, 6H), 1.72-1.94 (m, 4H), 2.02 (s, 3H), 2.18 (s, 3H), 2.43 (s, 3H), 2.49 (s, 3H), 3.27-3.36 (m, 1H), 6.67 (s, 1H). LC/MS (m/z): calcd. for C$_{19}$H$_{24}$BrN$_3$S (M+H)$^+$: 407.4; found: 407.3.

Example 123

Preparation of 3-[3,4-dimethyl-5-(2-methyl-2H-[1,2,4]triazol-3-yl)-thiophen-2-yl]-8-(1-ethyl-propyl)-2,6-dimethyl-imidazo[1,2-b]pyridazine

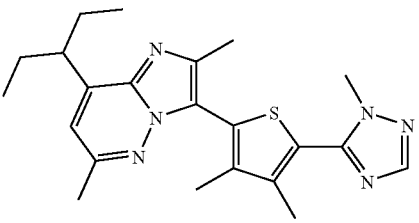

To a −78° C. solution of 1-methyl-1,2,4-triazole (0.056 mL, 0.74 mmol) and THF (2 mL) is added a 1.6 M solution of n-BuLi in hexanes (0.46 mL, 0.74 mmol). The solution is warmed to ambient temperature and stirred for 30 minutes. The solution is cooled to 0° C., a 0.5 M solution of ZnCl$_2$ in THF (4.70 mL, 2.33 mmol) is added and the solution warmed to ambient temperature and stirred for 30 minute. 3-(5-bromo-3,4-dimethyl-thiophen-2-yl)-8-(1-ethyl-propyl)-2,6-dimethyl-imidazo[1,2-b]pyridazine (0.10 g, 0.25 mmol) and PdCl$_2$(dppf) (0.009 g, 0.012 mmol) is added and the solution heated at 65° C. overnight, diluted with EtOAc (25 mL), washed with sat. NH$_4$Cl (20 mL), dried over MgSO$_4$, filtered and concentrated. The residue is purified by ISCO column chromatography (15%-60% EtOAc/hexane gradient), followed by a second purification by ISCO column chromatography (100% Et$_2$O) furnish the title compound (0.07 g, 0.17 mmol, 70%). $^1$H NMR (CDCl$_3$) δ 0.87 (t, J=7.5 Hz, 6H), 1.73-1.92 (m, 4H), 2.06 (s, 3H), 2.29 (s, 3H), 2.47 (s, 3H), 2.51 (s, 3H), 3.27-3.37 (m, 1H), 3.97 (s, 3H), 6.69 (s, 1H), 8.00 (s, 1H). LC/MS (m/z): calcd. for $C_{22}H_{28}N_6S$ (M+H)$^+$: 409.6; found: 409.2.

Example 124

Preparation of 3-(3,4-dimethyl-5-thiazol-2-yl-thiophen-2-yl)-8-(1-ethyl-propyl)-2,6-dimethyl-imidazo[1,2-b]pyridazine

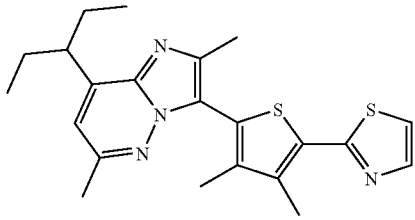

To a −78° C. solution of 3-(5-bromo-3,4-dimethyl-thiophen-2-yl)-8-(1-ethyl-propyl)-2,6-dimethyl-imidazo[1,2-b]pyridazine (0.10 g, 0.25 mmol) and THF (1 mL) is added 1.6 M n-BuLi (0.16 mL). The solution is stirred for 45 minutes and 0.5 M ZnCl$_2$ in THF (0.52 mL, 0.26 mmol) is added. The solution is warmed to ambient temperature and stirred for 30 minutes. 2-Bromo-thiazole (0.044 mL, 0.49 mmol), and PdCl$_2$(dppf) (0.009 g, 0.012 mmol) are added and the solution heated at 65° C. overnight, diluted with EtOAc (25 mL), washed with sat. NH$_4$Cl (20 mL), dried over MgSO$_4$, filtered and concentrated. The residue is purified by ISCO column chromatography (15%-20% EtOAc/hexane gradient), furnish the title compound (6.1 mg, 0.015 mmol, 6%). $^1$H NMR (CDCl$_3$), δ 0.87 (t, J=7.5 Hz, 6H), 1.74-1.92 (m, 4H), 2.07 (s, 3H), 2.49 (s, 3H), 2.51 (s, 3H), 2.53 (s, 3H), 3.29-3.39 (m, 1H), 6.68 (s, 1H), 7.35 (d, J=3.1 Hz, 1H), 7.86 (d, J=3.1 Hz, 1H). LC/MS (m/z): calcd. for $C_{22}H_{26}N_4S_2$ (M+H)$^+$: 411.6; found: 411.2.

Example 125

Preparation of 3-[3,4-dimethyl-5-(6-methyl-pyridin-2-yl)-thiophen-2-yl]-8-(1-ethyl-propyl)-2,6-dimethyl-imidazo[1,2-b]pyridazine

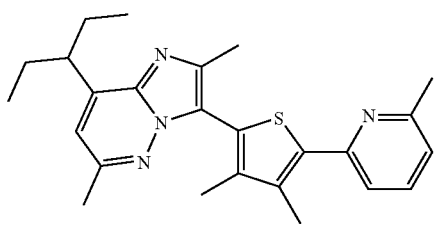

To a flask containing 3-(5-bromo-3,4-dimethyl-thiophen-2-yl)-8-(1-ethyl-propyl)-2,6-dimethyl-imidazo[1,2-b]pyridazine (0.10 g, 0.25 mmol) and PdCl$_2$(dppf) (9 mg, 0.012 mmol) is added a solution of 0.5 M 6-methyl-2-pyridylzinc bromide in THF (0.98 mL, 0.49 mmol). The solution is heated at 65° C. overnight, diluted with EtOAc (30 mL), washed with sat. NH$_4$Cl (30 mL), dried over MgSO$_4$, filtered and concentrated. The residue is purified by ISCO column chromatography (15%-30% EtOAc/hexane gradient) furnish the title compound (0.029 g, 0.069 mmol, 29%). $^1$H NMR (CDCl$_3$), δ 0.88 (t, J=7.5 Hz, 6H), 1.72-1.92 (m, 4H), 2.04 (s, 3H), 2.45 (s, 3H), 2.47 (s, 3H), 2.50 (s, 3H), 2.59 (s, 3H), 3.29-3.38 (m, 1H), 6.66 (s, 1H), 7.04 (d, J=8.0 Hz, 1H), 7.37 (d, J=7.8 Hz, 1H), 7.60 (d, J=8.0, 7.8 Hz, 1H). LC/MS (m/z): calcd. for $C_{25}H_{30}N_4S$ (M+H)$^+$: 419.6; found: 419.4.

Example 126

Preparation of 3-[3,4-dimethyl-5-(6-methyl-pyridin-2-yl)-thiophen-2-yl]-8-(1-ethyl-propyl)-2,6-dimethyl-imidazo[1,2-b]pyridazine

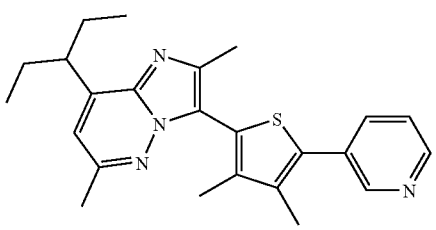

To a −78° C. solution of 3-iodo-pyridine (0.15 g, 0.74 mmol) and 0.5 M ZnCl$_2$ in THF (1.5 mL, 0.75 mmol) is added t-BuLi (0.88 mL, 1.49 mmol). The slurry is warmed to ambient temperature and stirred for 30 minutes. 3-(5-bromo-3,4-dimethyl-thiophen-2-yl)-8-(1-ethyl-propyl)-2,6-dimethyl-imidazo[1,2-b]pyridazine (0.10 g, 0.25 mmol) and Pd(PPh$_3$)$_4$ (0.014 g, 0.012 mmol) are added and the solution stirred at ambient temperature for 2 days, diluted with EtOAc (35 mL), washed with sat. NH$_4$Cl (30 mL), dried over MgSO$_4$, filtered and concentrated. The residue is purified by ISCO column chromatography (20%-30% EtOAc/hexane gradient) furnish the title compound (6.1 mg, 0.015 mmol, 6%). $^1$H NMR (CDCl$_3$), δ 0.88 (t, J=7.5 Hz, 6H), 1.74-1.92 (m, 4H), 2.07 (s, 3H), 2.29 (s, 3H), 2.49 (s, 3H), 2.53 (s, 3H), 3.30-3.39 (m, 1H), 6.68 (s, 1H), 7.36 (dd, J=8.0, 4.5 Hz, 1H), 7.79-7.83 (m 1H), 8.57 (d, J=4.5 Hz, 1H), 8.79 (d, J=0.9 Hz, 1H). LC/MS (m/z): calcd. for $C_{24}H_{28}N_4S$ (M+H)$^+$: 405.6; found: 405.2.

Example 127 & 128

Preparation of 8-(1-ethyl-propyl)-3-(3-methoxy-thiophen-2-yl)-2,6-dimethyl-imidazo[1,2-b]pyridazine and 8-(1-ethyl-propyl)-3-(4-methoxy-thiophen-2-yl)-2,6-dimethyl-imidazo[1,2-b]pyridazine

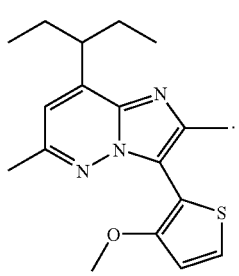

Ex. 127

-continued

Ex. 128

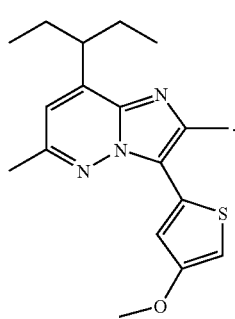

To a solution of 3-methoxy-thiophene (2.19 g, 19.14 mmol) in Et$_2$O (50 mL) is added 1.6 M n-BuLi (12.20 mL, 19.46 mmol). The solution is heated at a reflux for 30 minutes and cooled to ambient temperature. As solution of 0.5 M ZnCl$_2$ (38.9 mL, 19.5 mmol) and THF (50 mL) is added and the solution is stirred for 30 minutes. 8-(1-ethyl-propyl)-3-iodo-2,6-dimethyl-imidazo[1,2-b]pyridazine (2.0 g, 6.38 mmol) and PdCl$_2$(dppf) (0.23 g, 0.032 mmol) are added and the solution is heated at 65° C. for 4 hours, diluted with EtOAc (250 mL), washed with sat. NH$_4$Cl (250 mL), dried over MgSO$_4$, filtered and concentrated. The residue is purified by ISCO column chromatography (10%-25% EtOAc/hexane gradient) furnish the title compounds (1.50 g, 4.55 mmol, 71%) and (0.23 g, 0.70 mmol, 11%), respectively.

Example 127: $^1$H NMR (CDCl$_3$) δ 0.83 (t, J=7.5 Hz, 6H), 1.71-1.89 (m, 4H), 2.59 (s, 3H), 2.70 (s, 3H), 3.26-3.35 (m, 1H), 3.86 (s, 3H), 6.32 (d, J=1.6 Hz, 1H), 6.67 (s, 1H), 7.41 (d, J=1.6 Hz, 1H). LC/MS (m/z): calcd. for C$_{18}$H$_{23}$N$_3$OS (M+H)$^+$: 330.5; found: 330.3.

Example 128: $^1$H NMR (CDCl$_3$) δ 0.84 (t, J=7.5 Hz, 6H), 1.71-1.88 (m, 4H), 2.47 (s, 3H), 2.49 (s, 3H), 3.26-3.35 (m, 1H), 3.84 (s, 3H), 6.62 (s, 1H), 6.96 (d, J=5.5 Hz, 1H), 7.39 (d, J=5.5 Hz, 1H). LC/MS (m/z): calcd. for C$_{18}$H$_{23}$N$_3$OS (M+H)$^+$: 330.5; found: 330.3.

Example 129

Preparation of 3-(5-bromo-3-methoxy-thiophen-2-yl)-8-(1-ethyl-propyl)-2,6-dimethyl-imidazo[1,2-b]pyridazine

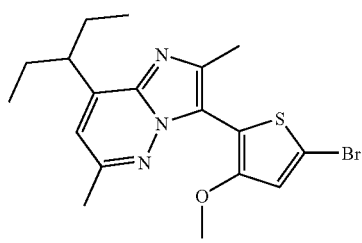

To a solution of 8-(1-ethyl-propyl)-3-(3-methoxy-thiophen-2-yl)-2,6-dimethyl-imidazo[1,2-b]pyridazine (0.78 g, 2.37 mmol) and CH$_2$Cl$_2$ (10 mL) is added NBS (0.44 g, 2.49 mmol). The solution is stirred for 1 hour, washed with water (3×10 mL), concentrated and purified by ISCO column chromatography (5%-15% EtOAc/hexane gradient) to furnish the title compound (0.87 g, 2.13 mmol, 90%). $^1$H NMR (CDCl$_3$) δ 0.85 (t, J=7.5 Hz, 6H), 1.71-1.89 (m, 4H), 2.46 (s, 3H), 2.52 (s, 3H), 3.25-3.35 (m, 1H), 3.82 (s, 3H), 6.65 (s, 1H), 6.97 (s, 1H). LC/MS (m/z): calcd. for C$_{18}$H$_{22}$BrN$_3$OS (M+H)$^+$: 408.1; found: 408.3.

Example 130

Preparation of 8-(1-ethyl-propyl)-3-[3-methoxy-5-(6-methyl-pyridin-2-yl)-thiophen-2-yl]-2,6-dimethyl-imidazo[1,2-b]pyridazine

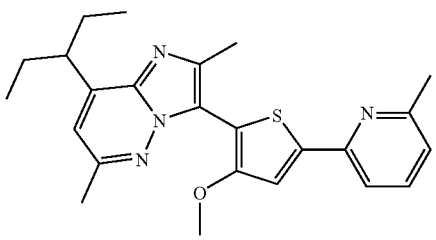

To a flask containing 3-(5-bromo-3-methoxy-thiophen-2-yl)-8-(1-ethyl-propyl)-2,6-dimethyl-imidazo[1,2-b]pyridazine (0.20 g, 0.49 mmol) and PdCl$_2$(dppf) (0.018 g, 0.024 mmol) is added a solution of 0.5 M 6-methyl-2-pyridylzinc bromide in THF (3.0 mL, 1.47 mmol). The solution is heated at 65° C. overnight, diluted with EtOAc (30 mL), washed with sat. NH$_4$Cl (2×30 mL), dried over MgSO$_4$, filtered and concentrated. The residue is purified by ISCO column chromatography (15%-20% EtOAc/hexane gradient) furnish the title compound (0.066 g, 1.57 mmol, 31%). $^1$H NMR (CDCl$_3$) δ 0.85 (t, J=7.5 Hz, 6H), 1.71-1.89 (m, 4H), 2.50 (s, 3H), 2.51 (s, 3H), 2.55 (s, 3H), 3.26-3.37 (m, 1H), 3.90 (s, 3H), 6.63 (s, 1H), 6.99 (d, J=7.4 Hz, 1H), 7.43 (d, J=7.7 Hz, 1H), 7.49 (s, 1H), 7.54 (dd, J=7.4, 7.7 Hz, 1H). LC/MS (m/z): calcd. for C$_{24}$H$_{28}$N$_4$OS (M+H)$^+$: 421.6; found: 422.4.

Example 131

Preparation of 8-(1-ethyl-propyl)-3-(3-methoxy-5-pyridin-3-yl-thiophen-2-yl)-2,6-dimethyl-imidazo[1,2-b]pyridazine

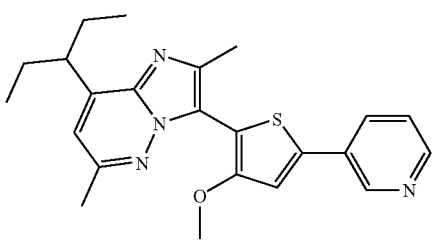

To a −78° C. solution of 3-iodo-pyridine (0.32 g, 1.56 mmol) and 0.5 M ZnCl$_2$ in THF (3.20 mL, 1.59 mmol) is added t-BuLi (2.27 mL, 3.85 mmol). The solution is warmed to ambient temperature and stirred for 30 minutes. 3-(5-bromo-3-methoxy-thiophen-2-yl)-8-(1-ethyl-propyl)-2,6-dimethyl-imidazo[1,2-b]pyridazine (0.26 g, 0.64 mmol) and Pd(PPh$_3$)$_4$ (0.037 g, 0.032 mmol) are added and the solution heated at 50° C. for 1 hour, cooled to ambient temperature and stirred overnight. The solution is diluted with EtOAc (30 mL), washed with sat. NH$_4$Cl (2×30 mL), dried over MgSO$_4$, filtered and concentrated. The residue is purified by ISCO column chromatography (20%-50% EtOAc/hexane gradient), furnish the title compound (0.16 g, 0.39 mmol, 61%). $^1$H NMR (CDCl$_3$) δ 0.87 (t, J=7.5 Hz, 6H), 1.74-1.91 (m, 4H), 2.52 (s, 3H), 2.55 (s, 3H), 3.28-3.38 (m, 1H), 3.93, (3H), 6.67 (s, 1H), 7.26 (d, J=3.5 Hz, 1H), 7.31-7.36 (m, 1H), 7.88-7.92

Example 132

Preparation of 8-(1-ethyl-propyl)-2,6-dimethyl-3-(4-methyl-2-pyridin-4-yl-thiazol-5-yl)-imidazo[1,2-b]pyridazine, hydrochloride salt

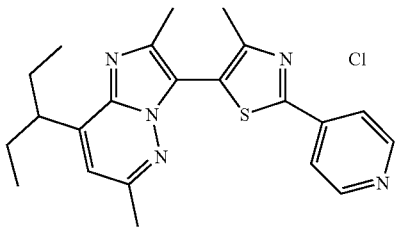

A mixture of 3-(2-bromo-4-methyl-thiazol-5-yl)-8-(1-ethyl-propyl)-2,6-dimethyl-imidazo[1,2-b]pyridazine (500 mg, 1.27 mmol), 4-pyridineboronic acid (500 mg, 4 mmol), Pd(PPh$_3$)$_4$ (100 mg, 0.08 mmol), toluene (2 mL), MeOH (1 mL), and K$_2$CO$_3$ (2 M aqueous solution, 3.5 mL) is heated at 100° C. for 18 hours. Ethyl acetate (20 mL) is added, and the organic layer is separated, dried over magnesium sulfate, filtered, and concentrated in vacuo. Purification is performed via silica gel chromatography using a 3:1 mixture of hexanes and ethyl acetate to obtain the free amine of the title compound (200 mg, 40%). The purified product is dissolved in ethyl acetate and a freshly prepared solution of hydrogen chloride (0.5 M in ethyl acetate, 2 mL) is added. The solvent is removed in vacuo to give the title compound $^1$H-NMR (CDCl$_3$), δ 8.2 (m, 2H); 7.05 (m, 2H); 6.55 (s, 1H); 3.24 (m, 1H); 2.43 (s, 3H); 2.40 (s, 3H); 2.33 (s, 3H); 1.76 (m, 4H); 0.80 (t, 6H) ppm. MS/ES$^+$=391 (100%, M+1).

Example 133

Preparation of 8-(1-ethyl-propyl)-3-[3-methoxy-5-(2-methyl-2H-[1,2,4]triazol-3-yl)-thiophen-2-yl]-2,6-dimethyl-imidazo[1,2-b]pyridazine

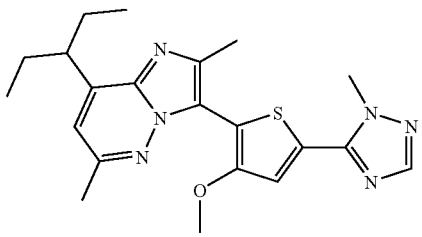

A. 5-Bromo-1-methyl-1H-[1,2,4]triazole.

To a −78° C. solution of 1-methyl-1H-[1,2,4]triazole (1.0 mL, 13.20 mmol) and THF (100 mL) is added 1.6 M n-BuLi (8.70 mL, 13.86 mmol). After 45 minutes 1,2-dibromo-1,1,2,2-tetrafluoro-ethane (1.76 mL, 14.52 mmol) is added, the solution warmed to ambient temperature and stirred for 2 hours. The solution is diluted with EtOAc (200 mL), washed with water (150 mL), brine (150 mL), dried over MgSO$_4$, filtered and concentrated to furnish the title compound (1.37 g, 8.46 mmol, 64%). $^1$H NMR (CDCl$_3$) δ 3.82 (s, 3H), 7.78 (s, 1H). LC/MS (m/z): calcd. for C$_3$H$_4$BrN$_3$ (M+H)$^+$: 162.0; found: 161.9.

B. 8-(1-Ethyl-propyl)-3-(5-iodo-3-methoxy-thiophen-2-yl)-2,6-dimethyl-imidazo[1,2-b]pyridazine.

To a solution of 8-(1-ethyl-propyl)-3-(3-methoxy-thiophen-2-yl)-2,6-dimethyl-imidazo[1,2-b]pyridazine (0.75 g, 2.28 mmol) and CH$_3$CN (10 mL) is added NIS (0.54 g, 2.39 mmol). The solution is stirred overnight, concentrated, diluted with EtOAc (30 mL), washed with water (30 mL), sat. NH$_4$Cl (30 mL), 20% (NaHSO$_3$) (30 mL), brine (30 mL), dried over MgSO$_4$, filtered and concentrated. The residue is purified by ISCO column chromatography (15%-20% EtOAc/hexane gradient) furnish the title compound (0.91 g, 2.00 mmol, 88%). $^1$H NMR (CDCl$_3$) δ 0.85 (t, J=7.5 Hz, 6H), 1.71-1.89 (m, 4H), 2.46 (s, 3H), 2.52 (s, 3H), 3.25-3.35 (m, 1H), 3.83 (s, 3H), 6.64 (s, 1H), 7.12 (s, 1H). LC/MS (m/z): calcd. for C$_{18}$H$_{22}$IN$_3$OS (M+H)$^+$: 456.4; found: 456.0.

C. 5-Bromo-1-methyl-1H-[1,2,4]triazole.

To a −78° C. solution of 1-methyl-1H-[1,2,4]triazole (1.0 mL, 13.20 mmol) and THF (100 mL) is added 1.6 M n-BuLi (8.70 mL, 13.86 mmol). After 45 minutes 1,2-dibromo-1,1,2,2-tetrafluoro-ethane (1.76 mL, 14.52 mmol) is added, the solution warmed to ambient temperature and stirred for 2 hours. The solution is diluted with EtOAc (200 mL), washed with water (150 mL), brine (150 mL), dried over MgSO$_4$, filtered and concentrated to furnish the title compound (1.37 g, 8.46 mmol, 64%). $^1$H NMR (CDCl$_3$) δ 3.82 (s, 3H), 7.78 (s, 1H). LC/MS (m/z): calcd. for C$_3$H$_4$BrN$_3$ (M+H)$^+$: 162.0; found: 161.9.

D. 8-(1-Ethyl-propyl)-3-[3-methoxy-5-(2-methyl-2H-[1,2,4]triazol-3-yl)-thiophen-2-yl]-2,6-dimethyl-imidazo[1,2-b]pyridazine.

To a slurry of 0.05 g/mL of Reike® Zn in THF (2.8 mL, 2.11 mmol) is added 5-bromo-1-methyl-1H-[1,2,4]triazole and THF (2 mL). The solution is heated at 65° C. for 1 hour, cooled to ambient temperature and the excess Zn allowed to settle for 1 hour. The solution is transferred to a flask containing 8-(1-ethyl-propyl)-3-(5-iodo-3-methoxy-thiophen-2-yl)-2,6-dimethyl-imidazo[1,2-b]pyridazine (0.32 g, 0.70 mmol) and Pd(PPh$_3$)$_4$ (0.041 g, 0.035 mmol). The solution is heated at 65° C. overnight, diluted with EtOAc (30 mL) washed with sat. NH$_4$Cl (30 mL). The aqueous phase is extracted with EtOAc (20 mL). The combined organic layers are dried over MgSO$_4$, filtered and concentrated. The reside is purified by ISCO column chromatography (20%-65% EtOAc/hexane gradient) followed by ISCO column chromatography (100% Et$_2$O) furnish the title compound (0.19 g, 0.46 mmol, 62%). $^1$H NMR (CDCl$_3$) δ 0.86 (t, J=7.5 Hz, 6H), 1.73-1.91 (m, 4H), 2.51 (s, 3H), 2.52 (s, 3H), 3.26-3.37 (m, 1H), 3.92 (s, 3H), 4.15 (s, 3H), 6.67 (s, 1H), 7.48 (s, 1H), 7.89 (s, 1H). LC/MS (m/z): calcd. for C$_{21}$H$_{26}$N$_6$OS (M+H)$^+$: 411.5. found: 411.3.

Example 134

Preparation of 8-(1-ethyl-propyl)-3-(3-methoxy-5-thiazol-2-yl-thiophen-2-yl)-2,6-dimethyl-imidazo[1,2-b]pyridazine

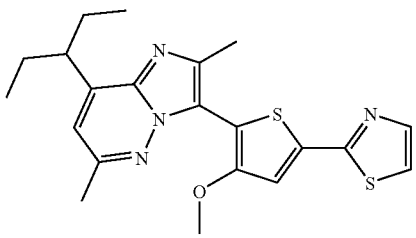

To a flask containing 8-(1-ethyl-propyl)-3-(5-iodo-3-methoxy-thiophen-2-yl)-2,6-dimethyl-imidazo[1,2-b]pyridazine (0.45 g, 0.99 mmol) and PdCl$_2$(dppf) (0.057 g, 0.078 mmol) is added a 0.5 M solution of 2-thiazolylzinc bromide (9.9 mL, 4.94 mmol). The solution is heated at 65° C. overnight, diluted with EtOAc (50 mL), washed with sat. NH$_4$Cl (50 mL), dried over MgSO$_4$, filtered and concentrated. The residue is purified by ISCO column chromatography (15%-20% EtOAc/hexane gradient) furnish the title compound (0.29 g, 0.70 mmol, 71%). $^1$H NMR (CDCl$_3$) δ0.86 (t, J=7.5 Hz, 6H), 1.72-1.90 (m, 4H), 2.51 (s, 3H), 2.53 (s, 3H), 3.28-

3.37 (m, 1H), 3.93 (s, 3H), 6.67 (s, 1H), 7.28 (d, J=3.3 Hz, 1H), 7.41 (s, 1H), 7.80 (d, J=3.3 Hz, 1H). LC/MS (m/z): calcd. for $C_{21}H_{24}N_4OS_2$ (M+H)$^+$: 413.6; found: 414.3.

Example 135

Preparation of 8-(1-ethyl-propyl)-2,6-dimethyl-3-(4-methyl-2-morpholin-4-yl-thiazol-5-yl)-imidazo[1,2-b]pyridazine

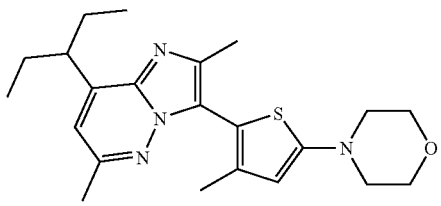

110 mg of 8-(1-ethyl-propyl)-3-[2-bromo-4-methyl-5-thiazolyl]-2,6-dimethyl-imidazo[1,2-b]pyridazine (0.28 mmol) and 122 mg of morpholine (1.4 mmol) are dissolved in 3.0 ml of THF and 182 mg of cesium carbonate (0.56 mmol) is added. The mixture is put in 4 ml vial with a Teflon® lined cap and heated at 110 C overnight. The reaction mixture is concentrated and applied to a silica-gel column chromatography column with hexane:EtOAc=3:1 eluent to give 98 mg of the title compound (88%). mass spectrum (m/e): 400 (M+1); $^1$H-NMR (CDCl3): δ 6.70 (s, 1H), 3.87 (t, 4H, J=4.8 Hz), 3.56 (t, 4H, J=4.8 Hz), 3.35 (m, 1H) 2.56 (s, 3H), 2.46 (s, 3H), 1.86 (m, 4H), 0.90 (t, 6H, J=7.6 Hz)

The following compounds are prepared essentially as described in Example 135. with 8-(1-ethyl-propyl)-3-[2-bromo-4-methyl-5-thiazolyl]-2,6-dimethyl-imidazo[1,2-b]pyridazine and the named amine:

| Ex | Name | Amine | $^1$H NMR (CDCl$_3$): δ | MS (found) (M + 1) |
|---|---|---|---|---|
| 136. | N-{5-[8-(1-Ethyl-propyl)-2,6-dimethyl-imidazo[1,2-b]pyridazin-3-yl]-4-methyl-thiazol-2-yl}-methylamine | 2M Methyl-amine/THF | 6.71 (s, 1H), 5.44 (s, NH), 3.35 (m, 1H), 3.06 (s, 3H), 2.57 (s, 3H), 2.47 (s, 3H), 2.19 (s, 3H), 1.86 (m, 4H), 0.90 (t, J = 7.6 Hz, 6H). | 344 |
| 137. | N-{5-[8-(1-Ethyl-propyl)-2,6-dimethyl-imidazo[1,2-b]pyridazin-3-yl]-4-methyl-thiazol-2-yl}-dimethylamine | 2M Dimethyl-amine/THF | 6.70 (s, 1H), 3.36 (m, 1H), 3.17 (s, 6H), 2.56 (s, 3H), 2.46 (s, 3H), 2.19 (s, 3H), 1.85 (m, 4H), 0.90 (t, J = 7.3 Hz, 6H). | 358 |
| 138. | N-Ethyl-N-{5-[8-(1-ethyl-propyl)-2,6-dimethyl-imidazo[1,2-b]pyridazin-3-yl]-4-methyl-thiazol-2-yl}-methylamine | N-Methyl-ethylamine | 6.70 (s, 1H), 3.59 (q, J = 7.6 Hz, 2H), 3.37 (m, 1H), 3.15 (s, 3H), 2.57 (s, 3H), 2.48 (s, 3H), 2.19 (s, 3H), 1.85 (m, 4H), 1.30 (t, J = 7.5 Hz, 2H), 0.90 (t, J = 7.1 Hz, 6H). | 372 |
| 139. | N-{5-[8-(1-ethyl-propyl)-2,6-dimethyl-imidazo[1,2-b]pyridazin-3-yl]-4-methyl-thiazol-2-yl}-diethylamine | Diethyl-amine | 6.71 (s, 1H), 3.56 (q, J = 7.1 Hz, 4H), 3.35 (m, 1H), 2.56 (s, 3H), 2.47 (s, 3H), 2.18 (s, 3H), 1.85 (m, 4H), 1.30 (t, J = 7.3 Hz, 6H), 0.90 (t, J = 7.3 Hz, 6H). | 386 |
| 140. | N-{5-[8-(1-Ethyl-propyl)-2,6-dimethyl-imidazo[1,2-b]pyridazin-3-yl]-4-methyl-thiazol-2-yl}-N-(furan-2-ylmethyl)-methylamine | N-Methyl-(furan-2-yl)-methyl-amine | 7.44 (s, 1H), 6.69 (s, 1H), 6.38 (s, 2H), 4.72 (s, 2H), 3.36 (m, 1H), 3.14 (s, 3H), 2.57 (s, 3H), 2.48 (s, 3H), 2.20 (s, 3H), 1.85 (m, 4H), 0.90 (t, J = 7.4 Hz, 6H). | 424 |
| 141. | N-{5-[8-(1-ethyl-propyl)-2,6-dimethyl-imidazo[1,2-b]pyridazin-3-yl]-4-methyl-thiazol-2-yl}thiomorpholine | Thio-morpholine | 6.71 (s, 1H), 3.92 (m, 4H), 3.37 (m, 1H), 2.80 (m, 4H), 2.57 (s, 3H), 2.48 (s, 3H), 2.18 (s, 3H), 1.85 (m, 4H), 0.90 (t, J = 7.2 Hz, 6H). | 416 |
| 142 | N-{5-[8-(1-Ethyl-propyl)-2,6-dimethyl-imidazo[1,2-b]pyridazin-3-yl]-4-methyl-thiazol-2-yl}-(2-methoxy-ethyl)-amine | 2-methoxy-ethylamine | 6.71 (s, 1H), 5.90 (s, NH), 3.66 (t, J = 5.4 Hz, 2H), 3.56 (t, J = 4.6 Hz, 2H), 3.44 (s, 3H), 3.35 (m, 1H), 2.57 (s, 3H), 2.47 (s, 3H), 2.18 (s, 3H), 1.85 (m, 4H), 0.90 (t, J = 7.2 Hz, 6H). | 388 |
| 143 | N-{5-[8-(1-Ethyl-propyl)-2,6-dimethyl-imidazo[1,2-b]pyridazin-3-yl]-4-methyl-thiazol-2-yl}-isopropyl-amine | i-propyl-amine | 6.69 (s, 1H), 5.15 (s, NH), 3.74 (m, 1H), 3.35 (m, 1H), 2.57 (s, 3H), 2.47 (s, 3H), 2.17 (s, 3H), 1.84 (m, 4H), 1.35 (d, J = 5.4 Hz, 6H), 0.90 (t, J = 7.4 Hz, 6H). | 372 |
| 144. | N-{5-[8-(1-ethyl-propyl)-2,6-dimethyl-imidazo[1,2-b]pyridazin-3-yl]-4-methyl-thiazol-2-yl}-pyrrolidine | Pyrrolidine | 6.68 (s, 1H), 3.55 (m, 4H), 3.36 (m, 1H), 2.56 (s, 3H), 2.46 (s, 3H), 2.19 (s, 3H), 2.09 (m, 4H), 1.86 (m, 4H), 0.91 (t, J = 7.6 Hz, 6H). | 384 |

-continued

| Ex | Name | Amine | $^1$H NMR (CDCl$_3$): δ | MS (found) (M + 1) |
|---|---|---|---|---|
| 145. | N-{5-[8-(1-Ethyl-propyl)-2,6-dimethyl-imidazo[1,2-b]pyridazin-3-yl]-4-methyl-thiazol-2-yl}-n-propylamine | n-propyl-amine | 6.70 (s, 1H), 5.21 (s, NH), 3.39 (t, J = 7.2 Hz, 2H), 3.29 (m, 1H), 2.57 (s, 3H), 2.47 (s, 3H), 2.16 (s, 3H), 1.85 (m, 4H), 1.74 (m, 2H), 1.05 (t, J = 7.3 Hz, 3H), 0.90 (t, J = 7.4 Hz, 6H). | 372 |
| 146 | N-{5-[8-(1-ethyl-propyl)-2,6-dimethyl-imidazo[1,2-b]pyridazin-3-yl]-4-methyl-thiazol-2-yl}-benzylamine | Benzyl-amine | 7.47-7.23 (m, 5H), 6.70 (s, 1H), 5.52 (s, NH), 6.70 (s, 2H), 3.34 (m, 1H), 2.56 (s, 3H), 2.46 (s, 3H), 2.19 (s, 3H), 1.85 (m, 4H), 0.91 (t, J = 7.2 Hz, 6H). | 420 |
| 147 | N-{5-[8-(1-ethyl-propyl)-2,6-dimethyl-imidazo[1,2-b]pyridazin-3-yl]-4-methyl-thiazol-2-yl}-N-(2-methoxy-ethyl)-ethylamine | N-(2-Methoxy-ethyl)-ethylamine | | 416 |
| 148 | N-{5-[8-(1-Ethyl-propyl)-2,6-dimethyl-imidazo[1,2-b]pyridazin-3-yl]-4-methyl-thiazol-2-yl}-(2-methoxy-ethyl)-n-propylamine | N-(2-methoxyethyl)-n-propyl-amine | 6.69 (s, 1H), 3.72 (m, 4H), 3.47 (t, J = 7.4 Hz, 2H), 3.42 (s, 3H), 3.36 (m, 1H), 2.57 (s, 3H), 2.47 (s, 3H), 2.16 (s, 3H), 1.87 (m, 6H), 0.99 (t, J = 7.2 Hz, 3H), 0.91 (t, J = 7.5 Hz, 6H). | 430 |
| 149 | N-{5-[8-(1-ethyl-propyl)-2,6-dimethyl-imidazo[1,2-b]pyridazin-3-yl]-4-methyl-thiazol-2-yl}-piperidine | piperidine | 6.68 (s, 1H), 3.53 (t, J = 4.7 Hz, 4H), 3.36 (m, 1H), 2.56 (s, 3H), 2.46 (s, 3H), 2.17 (s, 3H), 1.86 (m, 4H), 1.71 (m, 6H), 0.90 (t, J = 7.4 Hz, 6H). | 398 |
| 150 | N-{5-[8-(1-ethyl-propyl)-2,6-dimethyl-imidazo[1,2-b]pyridazin-3-yl]-4-methyl-thiazol-2-yl}-3-pentylamine | 3-amino-pentane | 6.70 (s, 1H), 5.24 (s, NH), 3.32 (m, 2H), 2.57 (s, 3H), 2.47 (s, 3H), 1.94 (s, 3H), 1.85 (m, 4H), 1.72 (m, 2H), 1.60 (m, 2H), 1.02 (t, J = 7.5 Hz, 6H), 0.90 (t, J = 7.3 Hz, 6H). | 400 |
| 151 | N-{5-[8-(1-ethyl-propyl)-2,6-dimethyl-imidazo[1,2-b]pyridazin-3-yl]-4-methyl-thiazol-2-yl}-cyclo-propylamine | Cyclo-propylamine | 6.70 (s, 1H), 6.51 (s, NH), 3.35 (m, 1H), 2.67 (m, 1H), 2.57 (s, 3H), 2.47 (s, 3H), 2.18 (s, 3H), 1.85 (m, 4H), 0.91 (t, J = 7.3 Hz, 6H), 0.82 (m, 2H), 0.77 (m, 2H). | 370 |
| 152 | N-{5-[8-(1-ethyl-propyl)-2,6-dimethyl-imidazo[1,2-b]pyridazin-3-yl]-4-methyl-thiazol-2-yl}-allylamine | Allylamine | 6.70 (s, 1H), 6.0 (m, 1H), 5.60 (s, NH), 5.38 (dd, J = 1.3, 17.4 Hz, 1H), 5.27 (dd, J = 1.2, 10.3 Hz, 1H), 4.0 (d, J = 5.2 Hz, 2H), 3.45 (m, 1H), 2.56 (s, 3H), 2.46 (s, 3H), 2.17 (s, 3H), 1.85 (m, 4H), 0.91 (t, J = 6.8 Hz, 6H). | 370 |
| 153 | N-{5-[8-(1-ethyl-propyl)-2,6-dimethyl-imidazo[1,2-b]pyridazin-3-yl]-4-methyl-thiazol-2-yl}-1,2,3,6-tetra-hydro-pyridine | 1,2,3,6-tetra-hydro-pyridine | 6.70 (s, 1H), 5.96 (m, 1H), 5.81 (m, 1H), 4.02 (t, J = 3.1 Hz, 2H), 3.72 (t, J = 5.5 Hz, 2H), 3.35 (m, 1H), 2.57 (s, 3H), 2.47 (s, 3H), 2.35 (m, 2H), 2.19 (s, 3H), 1.87 (m, 4H), 0.90 (t, J = 7.4 Hz, 6H). | 396 |
| 154 | N-Ethyl-N-{5-[8-(1-ethyl-propyl)-2,6-dimethyl-imidazo[1,2-b]pyridazin-3-yl]-4-methyl-thiazol-2-yl}-n-propylamine | N-ethyl-n-propyl-amine | 6.69 (s, 1H), 3.58 (q, J = 7.1 Hz, 2H), 3.43 (t, J = 7.5 Hz, 2H), 3.36 (m, 1H), 2.57 (s, 3H), 2.47 (s, 3H), 2.18 (s, 3H), 1.80 (m, 4H), 1.30 (t, J = 6.9 Hz, 3H), 1.04 (t, J = 6.9 Hz, 3H), 0.91 (t, J = 7.5 Hz, 6H). | 400 |
| 155 | N-Methyl-N-{5-[8-(1-Ethyl-propyl)-2,6-dimethyl-imidazo[1,2-b]pyridazin-3-yl]-4-methyl-thiazol-2-yl}-n-propylamine | N-methyl-n-propyl-amine | 6.68 (s, 1H), 3.46 (t, J = 8.3 Hz, 2H), 3.35 (m, 1H), 3.16 (s, 3H), 2.56 (s, 3H), 2.46 (s, 3H), 2.17 (s, 3H), 1.80 (m, | 386 |

-continued

| Ex | Name | Amine | $^1$H NMR (CDCl$_3$): δ | MS (found) (M + 1) |
|---|---|---|---|---|
|  | methyl-thiazol-2-yl}-n-propylamine |  | 2H), 1.00 (t, J = 7.7 Hz, 3H), 0.91 (t, J = 7.1 Hz, 6H). |  |
| 156 | N-Methyl-N-{5-[8-(1-Ethyl-propyl)-2,6-dimethyl-imidazo[1,2-b]pyridazin-3-yl]-4-methyl-thiazol-2-yl}-isopropyl-amine | N-Methyl-2-propyl-amine | 6.70 (s, 1H), 4.40 (m, 1H), 3.36 (m, 1H), 2.99 (s, 3H), 2.57 (s, 3H), 2.46 (s, 3H), 2.18 (s, 3H), 1.85 (m, 4H), 1.29 (d, J = 6.4 Hz, 6H), 0.90 (t, J = 7.1 Hz, 6H). | 386 |
| 157 | N-Methyl-N-{5-[8-(1-Ethyl-propyl)-2,6-dimethyl-imidazo[1,2-b]pyridazin-3-yl]-4-methyl-thiazol-2-yl}-2-propyn-1-amine | N-Methyl-2-Propyn-1-amine | 6.70 (s, 1H), 4.40 (d, J = 2.5 Hz, 2H), 3.35 (m, 1H), 3.17 (s, 3H), 2.56 (s, 3H), 2.45 (s, 3H), 2.34 (m, 1H), 2.19 (s, 3H), 1.85 (m, 4H), 0.90 (t, J = 7.1 Hz, 6H). | 382 |
| 158 | N-Methyl-N-{5-[8-(1-ethyl-propyl)-2,6-dimethyl-imidazo[1,2-b]pyridazin-3-yl]-4-methyl-thiazol-2-yl}-3-amino-propionitrile | N-Methyl-3-amino-propionitrile | 6.71 (s, 1H), 3.92 (t, J = 6.4 Hz, 2H), 3.37 (m, 1H), 3.25 (s, 3H), 2.9 (t, J = 6.4 Hz, 2H), 2.58 (s, 3H), 2.48 (s, 3H), 2.18 (s, 3H), 1.86 (m, 4H), 0.91 (t, J = 7.4 Hz, 6H). | 397 |
| 159 | N-{5-[8-(1-ethyl-propyl)-2,6-dimethyl-imidazo[1,2-b]pyridazin-3-yl]-4-methyl-thiazol-2-yl}-cyclopropyl-methylamine | Cyclo-propyl-methyl-amine | 6.68 (s, 1H), 5.35 (s, NH), 3.34 (m, 1H), 3.19 (t, J = 6.3 Hz, 2H), 2.56 (s, 3H), 2.45 (s, 3H), 2.16 (s, 3H), 1.86 (m, 4H), 1.19 (m, 1H), 0.91 (t, J = 7.1 Hz, 6H), 0.61 (m, 2H), 0.31 (m, 2H). | 384 |
| 160 | N-{5-[8-(1-Ethyl-propyl)-2,6-dimethyl-imidazo[1,2-b]pyridazin-3-yl]-4-methyl-thiazol-2-yl}-(2-methylsulfanyl)-ethylamine | 2-methyl-sulfanyl-ethylamine | 6.72 (s, 1H), 5.58 (s, NH), 3.58 (m, 2H), 3.35 (m, J = 7.3, 14.4, 1H), 2.85 (m, 2H), 2.57 (s, 3H), 2.46 (s, 3H), 2.17 (s, 6H), 1.85 (m, 4H), 0.90 (t, J = 6.7 Hz, 6H). | 404 |
| 161 | N-{5-[8-(1-Ethyl-propyl)-2,6-dimethyl-imidazo[1,2-b]pyridazin-3-yl]-4-methyl-thiazol-2-yl}-N-{[1,3]dioxolan-2-ylmethyl-methylamine | N-{[1,3]dioxolan-2-yl-methyl}-methyl-amine | 6.72 (s, 1H), 5.22 (m, 1H), 4.05 (m, 2H), 3.94 (m, 2H), 3.73 (d, J = 4.5 Hz, 2H), 3.35 (m, J = 6.6, 14.1 Hz, 1H), 3.23 (s, 3H), 2.56 (s, 3H), 2.46 (s, 3H), 2.17 (s, 3H), 1.84 (m, 4H), 0.91 (t, J = 7.1 Hz, 6H). | 430 |
| 162 | N-{5-[8-(1-ethyl-propyl)-2,6-dimethyl-imidazo[1,2-b]pyridazin-3-yl]-4-methyl-thiazol-2-yl}-N-Methyl-2-propen-1-yl-amine | N-Methyl-2-propen-1-yl-amine | 6.71 (s, 1H), 5.93 (m, 2H), 5.30 (m, 2H), 4.16 (d, J = 5.9 Hz, 2H), 3.39 (m, 1H), 3.12 (s, 3H), 2.58 (s, 3H), 2.48 (s, 3H), 2.20 (s, 3H), 1.86 (m, 4H), 0.91 (t, J = 7.5 Hz, 6H). | 384 |
| 163 | (R)—N-{5-[8-(1-Ethyl-propyl)-2,6-dimethyl-imidazo[1,2-b]pyridazin-3-yl]-4-methyl-thiazol-2-yl}-(tetrahydro-furan-2-ylmethyl)-amine | (R)-(tetrahydro-furan-2-ylmethyl)-amine | 6.70 (s, 1H), 5.44 (s, NH), 4.20 (m, 1H), 3.94 (m, 1H), 3.84 (m, 1H), 3.60 (m, 1H), 3.35 (m, 1H), 2.57 (s, 3H), 2.47 (s, 3H), 2.18 (s, 3H), 2.08 (m, 1H), 1.98 (m, 2H), 1.85 (m, 4H), 1.73 (m, 2H), 0.90 (t, J = 7.3 Hz, 6H). | 414 |
| 164 | (S)—N-{5-[8-(1-Ethyl-propyl)-2,6-dimethyl-imidazo[1,2-b]pyridazin-3-yl]-4-methyl-thiazol-2-yl}-(tetrahydro-furan-2-ylmethyl)-amine | (S)-(tetrahydro-furan-2-ylmethyl)-amine | 6.69 (s, 1H), 5.45 (s, NH), 4.20 (m, 1H), 3.94 (m, 1H), 3.84 (m, 1H), 3.59 (m, 1H), 3.34 (m, 2H), 2.57 (s, 3H), 2.47 (s, 3H), 2.17 (s, 3H), 2.08 (m, 1H), 1.98 (m, 2H), 1.85 (m, 4H), 1.73 (m, 1H), 0.90 (t, J = 7.2 Hz, 6H). | 414 |
| 165 | N-{5-[8-(1-Ethyl-propyl)-2,6-dimethyl-imidazo[1,2-b]pyridazin-3-yl]-4-methyl-thiazol-2-yl}-N-(2-methoxyethyl)-methylamine | N-Methyl-2-methoxy-ethyl-amine | 6.70 (s, 1H), 3.74 (t, J = 4.2 Hz, 2H), 3.71 (t, J = 4.1 Hz, 2H), 3.43 (s, 3H), 3.37 (m, 1H), 3.22 (s, 3H), 2.57 (s, 3H), 2.47 (s, 3H), 2.18 (s, 3H), 1.85 (m, 4H), 0.90 (t, J = 7.1 Hz, 6H). | 402 |
| 166 | N-{5-[8-(1-ethyl-propyl)-2,6-dimethyl- | N-Methyl-benzyl- | 7.43-7.32 (m, 5H), 6.69 (s, 1H), 4.76 (s, 2H), 3.35 (m, | 434 |

| Ex | Name | Amine | $^1$H NMR (CDCl$_3$): δ | MS (found) (M + 1) |
|---|---|---|---|---|
|  | imidazo[1,2-b]pyridazin-3-yl]-4-methyl-thiazol-2-yl}-N-methyl-benzylamine | amine | 1H), 3.10 (s, 3H), 2.57 (s, 3H), 2.48 (s, 3H), 2.21 (s, 3H), 1.85 (m, 4H), 0.91 (t, J = 7.3 Hz, 6H). |  |
| 167 | N-{5-[8-(1-ethyl-propyl)-2,6-dimethyl-imidazo[1,2-b]pyridazin-3-yl]-4-methyl-thiazol-2-yl}-N-ethyl-benzylamine | N-Ethyl-benzyl-amine | 7.41-7.31 (m, 5H), 6.68 (s, 1H), 4.76 (s, 2H), 3.54 (q, J = 7.3, 2H), 3.36 (m, 1H), 2.56 (s, 3H), 2.49 (s, 3H), 2.20 (s, 3H), 1.85 (m, 4H), 1.26 (t, J = 7.2 Hz, 3H), 0.91 (t, J = 7.1 Hz, 6H). | 448 |
| 168 | N-{5-[8-(1-Ethyl-propyl)-2,6-dimethyl-imidazo[1,2-b]pyridazin-3-yl]-4-methyl-thiazol-2-yl}-(1-methoxy-2-butyl)-amine | 1-Methoxy-2-amino-butane |  | 416 |
| 169 | N-{5-[8-(1-Ethyl-propyl)-2,6-dimethyl-imidazo[1,2-b]pyridazin-3-yl]-4-methyl-thiazol-2-yl}-N-methyl-isobutylamine | N,2-Di-methyl-n-propyl-amine |  | 400 |
| 170 | N-{5-[8-(1-Ethyl-propyl)-2,6-dimethyl-imidazo[1,2-b]pyridazin-3-yl]-4-methyl-thiazol-2-yl}-isobutyl-amine | 2-Methyl-n-propyl-amine |  | 386 |

Example 171

Preparation of 8-(1-ethyl-propyl)-2,6-dimethyl-3-(1-methyl-$^1$H-pyrrol-2-yl)-imidazo[1,2-b]pyridazine

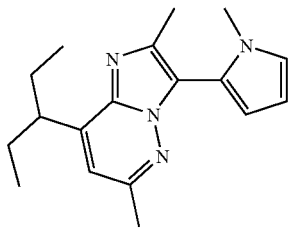

A THF solution (10 mL) of N-methylpyrrole (Aldrich, 800 µL, 9.0 mmol) is cooled to −78° C. under N$_2$ then treated with tert-BuLi (1.7 M in pentane, 5.3 mL, 9.0 mmol). The solution is warmed to room temperature for 30 minutes then cooled to −78° C. and treated with ZnCl$_2$ (Aldrich, 0.5 M in THF, 18 mL, 9.0 mmol). The resulting mixture is warmed to room temperature and treated with a THF slurry (5 mL) containing 8-(1-ethyl-propyl)-3-iodo-2,6-dimethyl-imidazo[1,2-b]pyridazine (1.02 gm, 3.0 mmol) and PdCl$_2$(dppf)-CH$_2$Cl$_2$ complex (Aldrich, 140 mg, 0.17 mmol). The mixture is heated to 60° C. overnight, then poured into sat'd aq NH$_4$Cl (50 mL) and extracted with diethyl ether (75 mL). The organic extract is ished with aq. brine, dried over Na$_2$SO$_4$, filtered, and concentrated. The crude product is purified by chromatography using hexane-ethyl acetate gradient (100% hexane to 20% ethyl acetate in hexane) to elute the title compound (407.5 mg, 46% yield) as an oil.

ES-MS (m/z): calc'd for C$_{18}$H$_{24}$N$_4$: 296.20; found 297.5 (M+H)$^+$ $^1$H NMR (400 mHz, CDCl$_3$): δ 6.86 (s, 1H), 6.65 (s, 1H), 6.32-6.28 (m, 2H), 3.50 (s, 3H), 3.35 (br s, 1H), 2.49 (s, 3H), 2.46 (s, 3H), 1.87-1.75 (m, 4H), 0.87 (t, J=7.0 Hz, 6H).

Example 172

Preparation of 8-(1-ethyl-propyl)-2,6-dimethyl-3-[1-methyl-5-(3-methyl-thiophen-2-yl)-$^1$H-pyrrol-2-yl]-imidazo[1,2-b]pyridazine

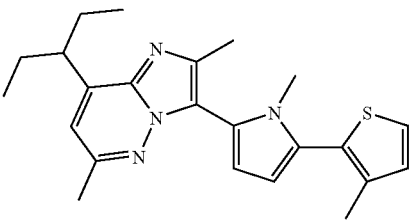

A. 3-(5-Bromo-1-methyl-$^1$H-pyrrol-2-yl)-8-(1-ethyl-propyl)-2,6-dimethyl-imidazo[1,2-b]pyridazine.

A THF solution (10 mL) of 8-(1-ethyl-propyl)-2,6-dimethyl-3-(1-methyl-1H-pyrrol-2-yl)-imidazo[1,2-b]pyridazine (414 mg, 1.40 mmol) is cooled to 0° C. and treated with a THF solution of NBS (250 mg, 1.40 mmol). Within 5 min, the reaction mixture is treated with sat Na$_2$SO$_3$ (1 mL) then concentrated. The resulting residue is diluted with ethyl acetate (50 mL) and ished with 50% aq sat'd Na$_2$SO$_3$ (2×50 mL). The organic extract is dried over Na$_2$SO$_4$, filtered, and concentrated. The crude product is purified by chromatography using hexane-ethyl acetate gradient (100% hexane to 20% ethyl acetate in hexane) to elute the title compound (374 mg, 71% yield) as a solid. ES-MS (m/z): calc'd for C$_{18}$H$_{23}$BrN$_4$: 374.11. found 375 (M+H)$^+$. $^1$H NMR (400 mHz, CDCl$_3$): δ 6.67 (s, 1H), 6.33 (d, J=4.0 Hz, 1H), 6.30 (d, J=4.0 Hz, 1H), 3.40 (s, 3H), 3.36 (br s, 1H), 2.50 (s, 3H), 2.44 (s, 3H), 1.88-1.75 (m, 4H), 0.87 (t, J=7.3 Hz, 6H).

B. 8-(1-Ethyl-propyl)-2,6-dimethyl-3-[1-methyl-5-(3-methyl-thiophen-2-yl)-$^1$H-pyrrol-2-yl]-imidazo[1,2-b]pyridazine.

A THF slurry (5 mL) of 3-(5-bromo-1-methyl-$^1$H-pyrrol-2-yl)-8-(1-ethyl-propyl)-2,6-dimethyl-imidazo[1,2-b]pyridazine (143 mg, 0.38 mmol) and PdCl$_2$(dppf)-CH$_2$Cl$_2$ complex (Aldrich, 19 mg, 0.023 mmol) is treated with 3-methyl-2-thienyl zinc bromide (Aldrich, 0.5 M in THF, 3.8 mL, 1.9 mmol) then heated to 60° C. for 1 hr. The resulting mixture is poured into sat'd NH$_4$Cl (25 mL) and extracted with diethyl ether (35 mL). The organic extract is washed with aq. NaCl, dried over Na$_2$SO$_4$, filtered, and concentrated. The crude product is purified by chromatography using hexane-ethyl acetate gradient (100% hexane to 15% ethyl acetate in hexane) to elute the product. The material is purified a second time by flash chromatography using hexane-ethyl acetate gradient (100% hexane to 12% ethyl acetate in hexane) to elute the product. Only the fractions containing pure desired product, as judged by MS analysis, are collected and give the title compound (82.6 mg, 55% yield) as an oil. ES-MS (m/z): calc'd for C$_{23}$H$_{28}$N$_4$S: 392.20. found 393.1 (M+H)$^+$. $^1$H NMR (400 mHz, CDCl$_3$): δ 7.28 (d, J=5.3 Hz, 1H), 6.96 (d, J=4.8 Hz, 1H), 6.67 (br s, 1H), 6.39 (d, J=3.5 Hz, 1H), 6.37 (d, J=4.0 Hz, 1H), 3.35 (br s, 1H), 3.33, (s, 3H), 2.52 (s, 3H), 2.51 (s, 3H), 2.26 (s, 3H), 1.89-1.76 (m, 4H), 0.87 (t, J=7.5 Hz, 6H).

Example 173

Preparation of 5-[8-(1-ethyl-propyl)-2,6-dimethyl-imidazo[1,2-b]pyridazin-3-yl]-4-methyl-thiazol-2-ylamine

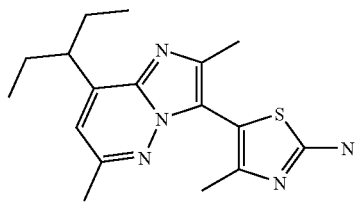

50 mg of 8-(1-ethyl-propyl)-3-[2-bromo-4-methyl-5-thiazolyl]-2,6-dimethyl-imidazo[1,2-b]pyridazine (0.13 mmol) and 10 mg of copper (I) oxide are added to 3 ml of 2 M NH3 in MeOH and vial is capped with a Teflon® lined cap, heated at 130° C. for overnight. The reaction mixture is concentrated under N2 gas and applied onto a silica-gel chromatography column (Hexane:AcOEt:2 M NH3 in MeOH=20:20:1) to give 22 mg of the title compound. Yield 54%: mass spectrum (m/e): 330 (M+1); $^1$H-NMR (CDCl3): 6.72 (s, 1H), 5.24 (br, 2H), 3.40 (m, 1H), 2.56 (s, 3H), 2.47 (s, 3H), 2.18 (s, 3H), 1.85 (m, 4H), 0.90 (t, 6H, J=7.4 Hz).

Example 174

Preparation of N-{5-[7-bromo-8-(1-ethyl-propyl)-2,6-dimethyl-imidazo[1,2-b]pyridazin-3-yl]-4-methyl-thiazol-2-yl}-morpholine

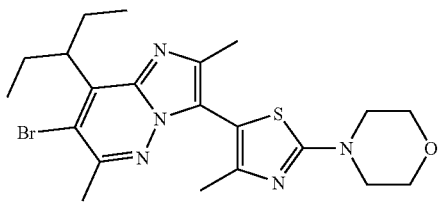

A. 7-Bromo-3-(2-bromo-4-methyl-thiazol-5-yl)-8-(1-ethyl-propyl)-2,6-dimethyl-imidazo[1,2-b]pyridazine.

547 mg of 8-(1-ethyl-propyl)-2,6-dimethyl-3-(4-methyl-thiazol-5-yl)-imidazo[1,2-b]pyridazine (1.74 mmol) and 341 mg of NBS (1.92 mmol) are dissolved in 20 ml of CHCl3 and stirred at room temperature overnight. The reaction mixture is washed with sat. Na$_2$S$_2$O$_3$, sat. NaCl, dried over Na$_2$SO$_4$ and evaporated. The crude materials are applied onto a silica-gel chromatography column (Hexane:AcOEt=8:1) to give 218 mg of the title compound. Yield 27%. mass spectrum (m/e): 473 (M+1); $^1$H-NMR (CDCl3): 3.44 (m, 1H), 2.70 (s, 3H), 2.45 (s, 3H), 2.37 (s, 3H), 2.03 (m, 4H), 0.90 (m, 6H).

B. N-{5-[7-bromo-8-(1-ethyl-propyl)-2,6-dimethyl-imidazo[1,2-b]pyridazin-3-yl]-4-methyl-thiazol-2-yl}-morpholine.

72 mg of 7-bromo-3-(2-bromo-4-methyl-thiazol-5-yl)-8-(1-ethyl-propyl)-2,6-dimethyl-imidazo[1,2-b]pyridazine (0.15 mmol) and 66 mg of morpholine (0.76 mmol) and 97 mg of cesium carbonate (0.3 mmol) are put in 4 ml vial with 3 ml of dry THF. The vial is capped with a Teflon® lined cap and heated at 100° C. overnight. The reaction mixture is concentrated and applied onto a silica-gel chromatography column (Hexane:AcOEt=3:1) to give 30 mg of the title compound. Yield 42%: mass spectrum (m/e): 479 (M+1); $^1$H-NMR (CDCl3): 3.87 (t, 4H, J=5.0 Hz), 3.55 (t, 4H, J=5.0 Hz), 3.45 (m, 1H), 2.70 (s, 3H), 2.44 (s, 3H), 2.40 (m, 2H), 2.18 (s, 3H), 2.01 (m, 2H), 0.88 (t, 6H, J=7.3 Hz).

Example 175

Preparation of 3-[3-chloro-4-(6-methyl-pyridin-2-yl)-thiophen-2-yl]-8-(1-ethyl-propyl)-2,6-dimethyl-imidazo[1,2-b]pyridazine, hydrochloride salt

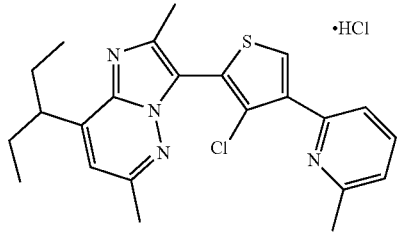

Reike® Zn (0.5 g/mL solution in THF (1.9 mL, 1.45 mmol) is added to a flask containing 3-(4-bromo-3-chloro-thiophen-2-yl)-8-(1-ethyl-propyl)-2,6-dimethyl-imidazo[1,2-b]pyridazine (0.30 g, 0.73 mmol). The slurry is heated at 65° C. for 1 hour, placed in a centrifuge for 5 minutes, and the resulting solution is transferred to a flask containing 2-bromo-6-methyl-pyridine (0.12 g, 0.73 mmol) and PdCl$_2$(dppf) (0.018 g, 0.024 mmol). The reaction is heated at 65° C. overnight, diluted with ethyl acetate (20 mL), and washed with a sat. solution of NH$_4$Cl (15 mL). The organic layer is dried over MgSO$_4$, filtered, and concentrated. The residue is purified by silica gel chromatography using a hexanes and ethyl acetate gradient. The resulting product is dissolved in dichloromethane (5 mL), treated with a 1 M solution of HCl in EtOH (0.35 mL, 0.35 mmol) and concentrated. The residue is recrystallized from ethyl acetate and hexanes furnish the title compound (0.033 g, 0.072 mmol, 11%). $^1$H-NMR (CDCl$_3$), δ 0.95 (t, J=7.3 Hz, 6H), 1.73-2.02 (m, 4H), 2.68 (s, 3H), 2.81 (s, 3H), 3.21 (s, 3H), 3.88-3.98 (m, 1H), 7.25 (s, 1H), 7.65 (d, J=7.5 Hz, 1H), 8.09 (d, J=7.5 Hz, 1H), 8.33 (dd, J=7.5, 7.1 Hz, 1H), 9.26 (s, 1H) ppm. LC/MS (m/z): calcd. for C$_{23}$H$_{26}$Cl$_2$N$_4$S (M+H)$^+$: 424.2; found: 424.2.

Example 176

Preparation of 3-(3-chloro-4-pyridin-3-yl-thiophen-2-yl)-8-(1-ethyl-propyl)-2,6-dimethyl-imidazo[1,2-b]pyridazine, hydrochloride salt

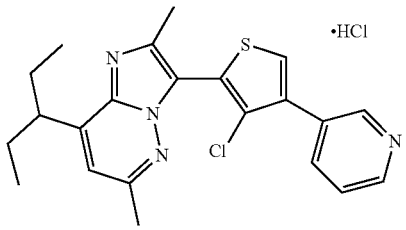

Using a procedure analogous to Example 175, 3-(4-bromo-3-chloro-thiophen-2-yl)-8-(1-ethyl-propyl)-2,6-dimethyl-imidazo[1,2-b]pyridazine (0.40 g, 0.97 mmol), Reike® Zn (0.5 g/mL solution in THF, 2.5 mL, 1.94 mmol), 3-iodo-pyridine (0.30 g, 1.45 mmol), PdCl$_2$(dppf) (0.035 g, 0.048 mmol), and a 1 M solution of HCl in EtOH (0.61 mL, 0.61 mmol) furnish the title compound (0.076 g, 0.17 mmol, 18%). $^1$H-NMR (CDCl$_3$), δ 0.95 (t, J=7.0 Hz, 6H), 1.71-1.88 (m, 2H), 1.88-2.01 (m, 2H), 2.68 (s, 3H), 2.81 (s, 3H), 3.85-3.96 (m, 1H), 5.28 (s, 1H), 7.27 (bs, 1H), 8.09 (bs, 1H), 8.23 (bs, 1H), 8.70 (bs, 1H), 8.89 (bs, 1H), 9.18 (bs, 1H). LC/MS (m/z): calcd. for C$_{22}$H$_{24}$Cl$_2$N$_4$S (M+H)$^+$: 411.1; found: 411.2.

Example 177

Preparation of 3-(3-chloro-4-thiazol-2-yl-thiophen-2-yl)-8-(1-ethyl-propyl)-2,6-dimethyl-imidazo[1,2-b]pyridazine

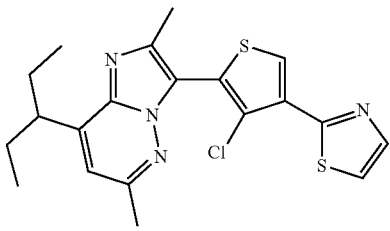

Using a procedure analogous to Example 175, 3-(4-bromo-3-chloro-thiophen-2-yl)-8-(1-ethyl-propyl)-2,6-dimethyl-imidazo[1,2-b]pyridazine (0.25 g, 0.61 mmol), Reike® Zn (0.5 g/mL solution in THF, 1.6 mL, 1.21 mmol), 2-bromo-thiazole (0.11 mL, 1.21 mmol), and PdCl$_2$(dppf) (0.022 g, 0.030 mmol) furnish the title compound (0.012 g, 0.29 mmol, 6.8%). $^1$H-NMR (CDCl$_3$), δ 0.89 (t, J=7.5 Hz, 6H), 1.75-1.94 (m, 4H), 2.52 (s, 6H), 3.27-3.43 (m, 1H), 6.73 (s, 1H), 7.43 (d, J=3.3 Hz, 1H), 7.94 (d, J=3.3 Hz, 1H), 8.30 (s, 1H) ppm. LC/MS (m/z): calcd. for C$_{20}$H$_{21}$ClN$_4$S$_2$ (M+H)$^+$: 417.1; found: 417.2.

Example 178

Preparation of N-{5-[8-(1-ethyl-propyl)-2,6-dimethyl-imidazo[1,2-b]pyridazin-3-yl]-4-methyl-thiazol-2-yl}-N-methyl-acetamide

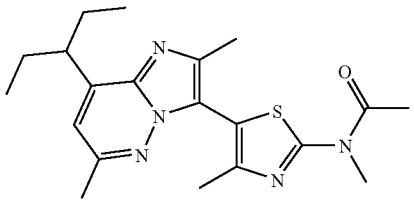

60 mg of N-{5-[8-(1-ethyl-propyl)-2,6-dimethyl-imidazo[1,2-b]pyridazin-3-yl]-4-methyl-thiazol-2-yl}-methylamine (0.17 mmol) and 86 mg of triethylamine (0.85 mmol) are dissolved in 3.0 ml of CH$_2$Cl$_2$ and 16 mg of acetylchloride (0.2 mmol) is added. The vial is capped with a Teflon® lined cap and shaken at room temperature for 2 h. The reaction mixture is concentrated and applied onto a silica-gel chromatography column (Hexane:AcOEt=3:1 and Hexane:AcOEt=2:1) to give 33.8 mg of the title compound. Yield 50%: mass spectrum (m/e): 386 (M+1); $^1$H-NMR (CDCl3): 7.03 (s, 1H), 3.79 (s, 3H), 3.47 (m, 1H), 2.54 (s, 3H), 2.47 (s, 3H), 2.46 (s, 3H), 2.31 (s, 3H), 1.86 (m, 4H), 0.91 (t, 6H, J=7.4 Hz).

Example 179

Preparation of N-{5-[8-(1-Ethyl-propyl)-2,6-dimethyl-imidazo[1,2-b]pyridazin-3-yl]-4-methyl-thiazol-2-yl}-N-methanesulfonyl-methylamine

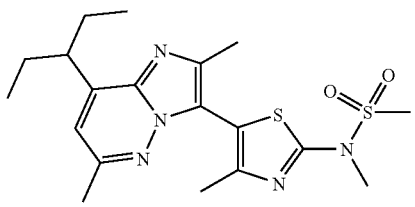

60 mg of N-{5-[8-(1-ethyl-propyl)-2,6-dimethyl-imidazo[1,2-b]pyridazin-3-yl]-4-methyl-thiazol-2-yl}-methylamine (0.17 mmol) and 86 mg of triethylamine (0.85 mmol) are dissolved in 3.0 ml of CH$_2$Cl$_2$ and 23 mg of methanesulfonyl chloride (0.2 mmol) is added. The vial is capped with a Teflon® lined cap and shaken at room temperature for 2 h. The reaction mixture is concentrated and applied to silica-gel chromatography (Hexane:AcOEt=2:1) to give 53.8 mg of the title compound. Yield 75%. mass spectrum (m/e): 422 (M+1); $^1$H-NMR (CDCl3): 6.96 (s, 1H), 3.60 (s, 3H), 3.34 (m, 1H), 3.19 (s, 3H), 2.56 (s, 3H), 2.48 (s, 3H), 2.29 (s, 3H), 1.86 (m, 4H), 0.90 (t, 6H, J=7.4 Hz).

Example 180

Preparation of N-{5-[8-(1-ethyl-propyl)-2,6-dimethyl-imidazo[1,2-b]pyridazin-3-yl]-4-methyl-thiazol-2-yl}-N-ethanesulfonyl-methylamine

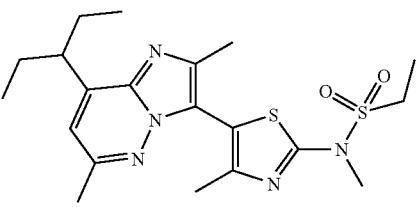

The title compound is prepared by a procedure analogous to Example 178. employing 50 mg of N-{5-[8-(1-ethyl-propyl)-2,6-dimethyl-imidazo[1,2-b]pyridazin-3-yl]-4-methyl-thiazol-2-yl}-methylamine (0.15 mmol), 51 mg of triethylamine (0.5 mmol) and 39 mg of ethanesulfonylchloride (0.3 mmol). 48.9 mg, Yield 75%: mass spectrum (m/e): 436 (M+1); $^1$H-NMR (CDCl3): 6.73 (s, 1H), 3.62 (s, 3H), 3.42 (q, 2H, J=7.4 Hz), 3.35 (m, 1H), 2.55 (s, 3H), 2.48 (s, 3H), 2.28 (s, 3H), 1.85 (m, 4H), 1.46 (t, 3H, J=7.4 Hz), 0.90 (t, 6H, J=7.5 Hz).

Example 181

Preparation of 3-[2-(1,1-dioxo-thiomorpholin-4-yl)-4-methyl-thiazol-5-yl]-8-(1-ethyl-propyl)-2,6-dimethyl-imidazo[1,2-b]pyridazine

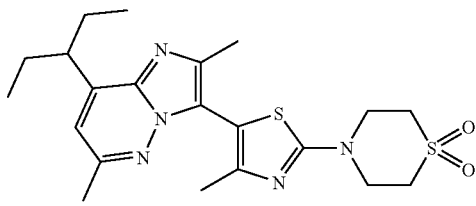

60 mg of N-{5-[8-(1-ethyl-propyl)-2,6-dimethyl-imidazo[1,2-b]pyridazin-3-yl]-4-methyl-thiazol-2-yl}thiomorpholine (0.14 mmol) is dissolved in 3 ml of CH$_2$Cl$_2$ and 62 mg of mCPBA (0.36 mmol) is added. The reaction mixture is stirred at room temperature for 30 min. The reaction mixture is diluted with CH$_2$Cl$_2$, washed with sat. NaHCO3 and sat. NaCl. The separated organic layer is dried over Na$_2$SO$_4$ and evaporated. The crude product is applied onto a silica-gel chromatography column (Hexane:AcOEt:2 M NH3 in MeOH=10:3:1) to give 20.3 mg of the title compound. Yield 33%: mass spectrum (m/e): 448 (M+1). $^1$H-NMR: 6.72 (s, 1H), 4.16 (t, J=4.7 Hz, 4H), 3.35 (m, 1H), 3.23 (t, J=5.2 Hz, 4H), 2.57 (s, 3H), 2.48 (s, 3H), 2.19 (s, 3H), 1.86 (m, 4H), 0.90 (t, J=7.1 Hz, 6H).

Example 182

Preparation of 3-[2-(3,5-Dimethyl-pyrazol-1-yl)-4-methyl-thiazol-5-yl]-8-(1-ethyl-propyl)-2,6-dimethyl-imidazo[1,2-b]pyridazine

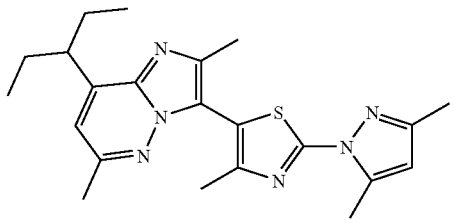

A. {5-[8-(1-Ethyl-propyl)-2,6-dimethyl-imidazo[1,2-b]pyridazin-3-yl]-4-methyl-thiazol-2-yl}-hydrazine.

The title compound is prepared essentially as described in Example 135 using hydrazine. MS found (M+1) 345.

B. 3-[2-(3,5-Dimethyl-pyrazol-1-yl)-4-methyl-thiazol-5-yl]-8-(1-ethyl-propyl)-2,6-dimethyl-imidazo[1,2-b]pyridazine.

28 mg of {5-[8-(1-ethyl-propyl)-2,6-dimethyl-imidazo[1,2-b]pyridazin-3-yl]-4-methyl-thiazol-2-yl}-hydrazine (0.08 mmol) and 80 mg of 2,4-pentanedione (0.8 mmol) are dissolved in 1.0 ml of AcOH and heated at 100° C. for 2 h. The reaction mixture is concentrated and applied onto a silica-gel chromatography column (Hexane:AcOEt=5:1) to give 23 mg of the title compound. Yield 70%: mass spectrum (m/e): 409 (M+1). 6.72 (s, 1H), 6.03 (s, 1H), 3.36 (m, J=7.1, 14.1 Hz, 1H), 2.75 (s, 3H), 2.55 (s, 3H), 2.50 (s, 3H), 2.32 (s, 3H), 2.31 (s, 3H), 1.87 (m, 4H), 0.91 (t, J=7.5 Hz, 6H).

Example 183

Preparation of 3-(3-chloro-4-pyridin-4-yl-thiophen-2-yl)-8-(1-ethyl-propyl)-2,6-dimethyl-imidazo[1,2-b]pyridazine, hydrochloride salt

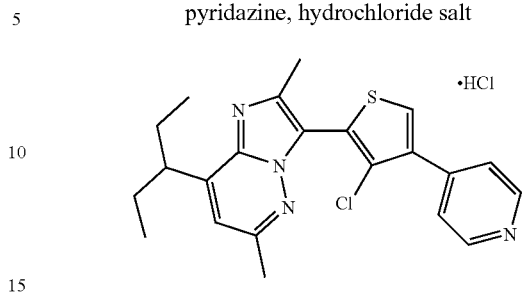

A solution of 3-(4-bromo-3-chloro-thiophen-2-yl)-8-(1-ethyl-propyl)-2,6-dimethyl-imidazo[1,2-b]pyridazine (0.25 g, 0.61 mmol), 4-pyridyl-boronic acid (0.82, 0.67 mmol), a 2 M solution of Na$_2$CO$_3$ (0.5 mL, 0.91 mmol), and n-PrOH (2.5 mL) are degassed with nitrogen for 10 minutes. Pd(OAc)$_2$ (0.0027 g, 0.012 mmol) and PPh$_3$ (0.0095 g, 0.036 mmol) are added, and the solution heated at a 90° C. overnight. The solution is diluted with ethyl acetate (40 mL) and washed with a 10% solution of Na$_2$CO$_3$ (30 mL). The organic layer is dried over MgSO$_4$, filtered, and concentrated. The residue is purified by ISCO flash chromatography (20%-30% EtOAc gradient). The resulting product is dissolved in dichloromethane (5 mL), treated with a 1 M solution of HCl in EtOH (0.35 mL, 0.35 mmol), and concentrated. The residue is recrystallized from acetonitrile and ethyl acetate furnish the title compound (0.15 g, 0.34 mmol, 56%). 1H-NMR (CDCl$_3$), δ 0.95 (t, J=7.5 Hz, 6H), 1.73-1.88 (m, 2H), 1.89-2.04 (m, 2H), 2.68 (s, 3H), 2.82 (s, 3H), 3.87-3.97 (m, 1H), 7.28 (s, 1H), 8.26-8.34 (m, 3H), 8.95 (d, J=5.3 Hz, 2H) ppm. LC/MS (m/z): calcd. for C$_{22}$H$_{24}$Cl$_2$N$_4$S (M+H)$^+$: 411.1; found: 411.2.

Example 184

Preparation of 3-[2-(3,6-dihydro-2H-pyran-4-yl)-4-methyl-thiazol-5-yl]-8-(1-ethyl-propyl)-2,6-dimethyl-imidazo[1,2-b]pyridazine

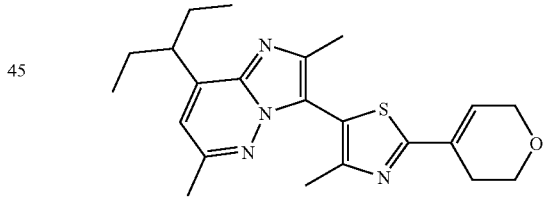

A. 4-{5-[8-(1-Ethyl-propyl)-2,6-dimethyl-imidazo[1,2-b]pyridazin-3-yl]-4-methyl-thiazol-2-yl}-tetrahydro-pyran-4-ol.

370 mg of 3-(2-Bromo-4-methyl-thiazol-5-yl)-8-(1-ethyl-propyl)-2,6-dimethyl-imidazo[1,2-b]pyridazine (0.93 mmol) is dissolved in 10 ml of dry THF and cooled to −78° C. 0.6 ml of n-BuLi 2.0 M in hexane (1.2 mmol) is added and stirred at −78° C. for 30 min. 141 mg of tetrahydro-4H-pyran-4-one (1.41 mmol) is added and stirred at −78° C. for 2 h. The reaction mixture is diluted with AcOEt, washed with sat. NH4Cl, dried over Na2SO4 and evaporated. The crude product is applied onto a silica-gel chromatography column (Hexane:AcOEt:2 M NH3 in MeOH=10:3:1) to give 152 mg of the title compound. Yield 40%: mass spectrum (m/e): 415 (M+1). $^1$H NMR (CDCl$_3$): δ 6.74 (s, 1H), 3.99 (t, J=2.2 Hz, 4H), 3.97 (t, J=2.2 Hz, 4H), 3.35 (m, 1H), 3.20 (s, OH), 2.56 (s, 3H), 2.48 (s, 3H), 2.36 (s, 3H), 1.88 (m, 4H), 0.91 (t, J=7.3 Hz, 6H).

B. 3-[2-(3,6-Dihydro-2H-pyran-4-yl)-4-methyl-thiazol-5-yl]-8-(1-ethyl-propyl)-2,6-dimethyl-imidazo[1,2-b]pyridazine.

150 mg of 4-{5-[8-(1-ethyl-propyl)-2,6-dimethyl-imidazo[1,2-b]pyridazin-3-yl]-4-methyl-thiazol-2-yl}-tetrahydro-pyran-4-ol (0.36 mmol) is dissolved in 5 ml of CH2Cl2 and 112 mg of triethylsilane (0.96 mmol) and 717 mg of trifluoroacetic acid (6.3 mmol) are added. The reaction mixture is stirred at room temperature for 1 h. The reaction mixture is stirred under reflux for 1 h and cooled down to room temperature. The solvent is removed in vacuo. The crude product is applied onto a silica-gel chromatography column (Hexane:AcOEt:2 M NH3 in MeOH=10:3:1) to give 64 mg of the title compound. Yield 45%. mass spectrum (m/e): 397 (M+1). 6.94 (s, 1H), 6.71 (s, 1H), 4.41 (d, J=2.6 Hz, 2H), 3.98 (t, J=5.3 Hz, 2H), 3.43 (m, 1H), 2.62 (s, 3H), 2.75 (m, 2H), 2.56 (s, 3H), 2.37 (s, 3H), 1.86 (m, 4H), 0.92 (t, J=8.2 Hz, 6H).

Example 185

Preparation of 8-(1-ethyl-propyl)-2,6-dimethyl-3-[4-methyl-2-(tetrahydro-pyran-4-yl)-thiazol-5-yl]-imidazo[1,2-b]pyridazine

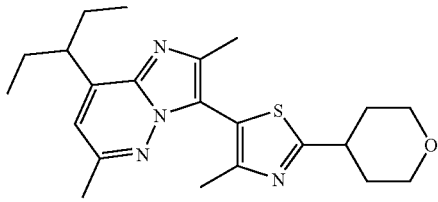

Add 3-[2-(3,6-dihydro-2H-pyran-4-yl)-4-methyl-thiazol-5-yl]-8-(1-ethyl-propyl)-2,6-dimethyl-imidazo[1,2-b]pyridazine (55 mg, 0.14 mmol), 5% palladium on carbon (55 mg) and absolute ethanol (50 ml) to a pressure vessel. Purge the reaction vessel with nitrogen, purge the reaction vessel with hydrogen, pressurize the reaction mixture with hydrogen (415 KPa), seal the vessel, agitate the reaction and heat to 40° C. Continue the reaction for 18 hours then turn off the heat and allow the reaction mixture to cool to ambient temperature. Vent the excess hydrogen from the vessel and purge the vessel with nitrogen. Filter the reaction mixture to remove the 5% palladium on carbon. The filtrate is concentrated and applied onto a silica-gel chromatography column (Hexane:AcOEt:2 M NH3 in MeOH=10:3:1) to give 12.8 mg of the title compound. Yield 23%. mass spectrum (m/e): 399 (M+1). $^1$H NMR (CDCl3): δ 6.73 (s, 1H), 4.14 (m, 2H), 3.60 (m, 2H), 3.34 (m, 2H), 2.56 (s, 3H), 2.48 (s, 3H), 2.36 (s, 3H), 2.16 (m, 2H), 2.02 (m, 2H), 1.87 (m, 4H), 0.91 (t, J=7.6 Hz, 6H).

Example 186

Preparation of 3-(4-chloro-2-morpholin-4-yl-thiazol-5-yl)-2,6-dimethyl-8-(1-propyl-butyl)-imidazo[1,2-b]pyridazine

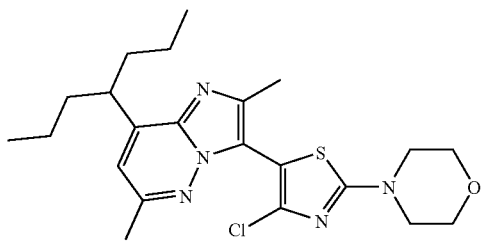

A. 6-Methyl-4-(1-propyl-butyl)-pyridazin-3-ylamine.

6-Methyl-4-(1-propyl-butyl)-pyridazin-3-ylamine can be made using chemistry described in J. Heterocylic Chem. 1991, 28, 583. A 250 mL three neck round bottom flask is charged with 3-amino-6-methylpyridazine (2.5 g, 0.229 moles, 1.0 equiv), water (70 mL), and acetonitrile (50 mL). Concentrated sulfuric acid (3.51 g, 1.91 mL, 0.0344 moles, 1.5 equiv), silver nitrate (3.87 g, 0.0229 moles, 1.0 equiv), and valproic acid (7.21 g, 7.95 mL, 0.050 moles, 2.2 equiv) are added to the reaction mixture. The reaction is heated to 75° C. As the reaction mixture is heating, a solution of (NH4)2S2O8 (7.85 g, 0.0344 moles, 1.5 equiv) in 40 mL of water is slowly added via an addition funnel over a period of 30 minutes. The reaction mixture is heated at 70-80° C. for two more hours. The reaction mixture is cooled and dichloromethane is added. The reaction is made basic with a 30% aqueous NaOH solution and filtered through a short Celite® plug. The organic layer is separated, and the aqueous layer is extracted two more times with dichloromethane. The combined organic extracts are dried over Na2SO4. The solvent is evaporated and the crude material is purified using silica gel chromatography with a 2.0 N solution of NH3 in MeOH and methylene chloride as eluent. Yield=0.61 g (13%). MS (APCI): 208 (M+1).

B. 2,6-Dimethyl-8-(1-propyl-butyl)-imidazo[1,2-b]pyridazine.

A 250 mL round bottom flask is charged with 6-methyl-4-(1-propyl-butyl)-pyridazin-3-ylamine (0.611 g, 0.00295 moles, 1 equiv), ethanol 2B (30 mL), and chloroacetone (0.382 g, 0.328 ml, 0.00412 moles, 1.4 equiv). The reaction mixture is heated at 75° C. overnight and then cooled to room temp. NaHCO3 (0.371 g, 0.00442 moles, 1.5 equiv) is slowly added to the reaction mixture that is then heated to 100° C. overnight. The reaction mixture is cooled and the solvent is evaporated. Dichloromethane is added and the reaction mixture is passed through filter paper. The solvent is evaporated to obtain a brown oil which is purified via silica gel chromatography. The material is eluted with a hexanes and ethyl acetate gradient to obtain 0.511 g of the final products. Two peaks are identified in the lc/ms. The mixture is used "as is" in the next reaction. MS (APCI): 246 (M+1).

C. 3-Iodo-2,6-dimethyl-8-(1-propyl-butyl)-imidazo[1,2-b]pyridazine.

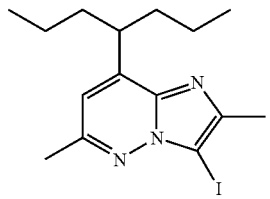

A 50 mL round bottom flask is charged with 2,6-dimethyl-8-(1-propyl-butyl)-imidazo[1,2-b]pyridazine (0.51 g, 0.0021 moles) and acetonitrile (3 mL). The reaction mixture is placed on an ice bath and NIS (0.468 g, 0.00208 moles) is added neat. The reaction is stirred overnight and the ice bath melts. The next day, the reaction mixture is partitioned between dichloromethane and a saturated aqueous solution of NaHCO3. The organic layer is collected and the aqueous layer is extracted two more times with dichloromethane. The organic extracts are combined, washed with brine, and dried over Na2SO4. The solvent is evaporated and the crude material is purified via silica gel chromatography eluting with hexanes and then a 25:75 mixture of ethyl acetate and hexanes. Yield=0.435 g (56%). MS (APCI): 372 (M+1).

D. 3-(4-Chloro-2-morpholin-4-yl-thiazol-5-yl)-2,6-dimethyl-8-(1-propyl-butyl)-imidazo[1,2-b]pyridazine.

A 15 mL round bottom flask is charged with 3-iodo-2,6-dimethyl-8-(1-propyl-butyl)-imidazo[1,2-b]pyridazine (0.200 g, 0.000539 moles), 4-(4-chloro-thiazol-2-yl)-morpholine (0.165 g, 0.000808 moles), Cs₂CO₃ (0.361 g, 0.00108 moles, 2.0 equiv), Pd(dba)₂ (0.0092 g, 0.0000161 moles, 0.03 equiv), PPh₃ (0.00847 gram, 0.000323 moles, 0.060 equiv) and DMF (2.0 mL). Nitrogen is bubbled through the reaction mixture for 15 minutes; then, the reaction mixture is heated at 130° C. overnight. The next day, the reaction mixture is partitioned between Et₂O and a saturated solution of NH₄Cl. The aqueous layer is extracted twice more with Et₂O. The organic extracts are combined, washed 2-3 times with H₂O, washed once with brine, and dried over Na₂SO₄. The solvents are evaporated in vacuo and the crude reaction mixture is purified via silica gel chromatography. Yield=0.1737 g (72%). ¹H-NMR (CDCl₃), δ 0.87 (t, J=7 Hz, 6H), 1.14-1.37 (m, 4H), 1.74 (q, J=8 Hz, 4H), 2.54 (s, 3H), 2.50 (s, 3H), 3.48 (m, 1H), 3.53 (t, J=5 Hz, 4H), 3.83 (t, J=5 Hz, 4H), 6.71 (br s, 1H) ppm. LC/MS (m/z): calcd. for $C_{22}H_{30}ClN_5OS$ (M+H)⁺: 448; found: 448.

Example 187

Preparation of 1-{5-[8-(1-ethyl-propyl)-2,6-dimethyl-imidazo[1,2-b]pyridazin-3-yl]-4-methyl-thiazol-2-yl}-piperidin-4-one

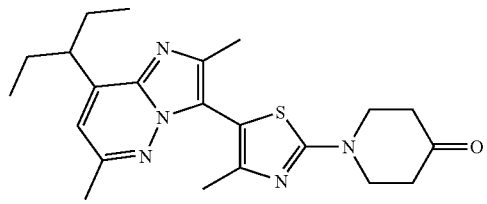

A. 8-{5-[8-(1-Ethyl-propyl)-2,6-dimethyl-imidazo[1,2-b]pyridazin-3-yl]-4-methyl-thiazol-2-yl}-1,4-dioxa-8-aza-spiro[4.5]decane.

100 mg of 3-(2-bromo-4-methyl-thiazol-5-yl)-8-(1-ethyl-propyl)-2,6-dimethyl-imidazo[1,2-b]pyridazine (0.25 mmol), 182 mg of 4-piperidineethylene ketal (1.27 mmol) and 244 mg of Cs2CO3 (0.75 mmol) are put into 4.0 ml vial with 2.0 ml of THF. The vial is capped with a Teflon® lined cap and heated at 110° C. for 3 days. The reaction mixture is concentrated and applied onto a silica-gel chromatography column (Hexane:AcOEt=3:1) to give 116 mg of the title compound. Yield 100%. mass spectrum (m/e): 456 (M+1). ¹H NMR (CDCl₃): δ 6.69 (s, 1H), 4.05 (s, 4H), 3.70 (t, J=6.2 Hz, 4H), 3.35 (m, 1H), 2.56 (s, 3H), 2.46 (s, 3H), 2.18 (s, 3H), 1.90-1.78 (m, 8H), 0.90 (t, J=7.2 Hz, 6H).

B. 1-{5-[8-(1-Ethyl-propyl)-2,6-dimethyl-imidazo[1,2-b]pyridazin-3-yl]-4-methyl-thiazol-2-yl}-piperidin-4-one.

70 mg of 8-{5-[8-(1-ethyl-propyl)-2,6-dimethyl-imidazo[1,2-b]pyridazin-3-yl]-4-methyl-thiazol-2-yl}-1,4-dioxa-8-aza-spiro[4.5]decane (0.15 mmol) is dissolved in 10. ml of conc. HCl and stirred at room temperature for 2 h. The reaction mixture is neutralized with sat. NaHCO3, extracted with CH2Cl2, dried over Na2SO4 and evaporated. The crude product is applied onto a silica-gel chromatography column (Hexane:AcOEt=2:1) to give 33.2 mg of the title compound. Yield 52%. mass spectrum (m/e): 412 (M+1) ¹H NMR (CDCl₃): δ 6.70 (s, 1H), 3.94 (t, J=6.2 Hz, 4H), 3.35 (m, 1H), 2.67 (t, J=6.5 Hz, 4H), 2.57 (s, 3H), 2.47 (s, 3H), 2.21 (s, 3H), 1.86 (m, 4H), 0.91 (t, J=7.1 Hz, 6H).

Example 188

Preparation of ({5-[8-(1-ethyl-propyl)-2,6-dimethyl-imidazo[1,2-b]pyridazin-3-yl]-4-methyl-thiazol-2-yl}-methyl-amino)-acetaldehyde

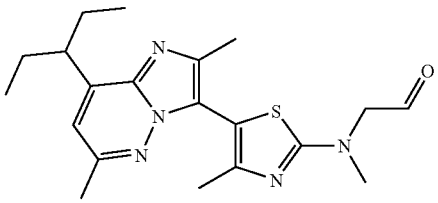

85 mg of N-{5-[8-(1-Ethyl-propyl)-2,6-dimethyl-imidazo[1,2-b]pyridazin-3-yl]-4-methyl-thiazol-2-yl}-N-{[1,3]dioxolan-2-ylmethyl-methylamine (0.2 mmol) is dissolved in 2 ml of conc. HCl and stirred at 50° C. for 30 min. The mixture is cooled to room temperature and neutralized with sat. NaHCO3. The mixture is extracted with CH2Cl2, dried over Na2SO4 and evaporated. The crude product is applied onto a silica-gel chromatography column (CH2Cl2:MeOH=20:1) to give 73.4 mg of the title compound. Yield 76%. mass spectrum (m/e): 386 (M+1). 9.79 (s, 1H), 6.72 (s, 1H), 4.39 (s, 2H), 3.36 (m, 1H), 3.22 (s, 3H), 2.57 (s, 3H), 2.47 (s, 3H), 2.20 (s, 3H), 1.85 (m, 4H), 0.90 (t, J=7.3 Hz, 6H).

Example 189

Preparation of 4-{3-[3-chloro-5-(2-methyl-2H-[1,2,4]triazol-3-yl)-thiophen-2-yl]-2,6-dimethyl-imidazo[1,2-b]pyridazin-8-yl}-heptan-4-ol

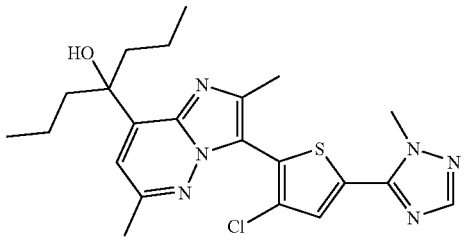

A. 3-[3-chloro-5-(2-methyl-2H-[1,2,4]triazol-3-yl)-thiophen-2-yl]-2,6-dimethyl-imidazo[1,2-b]pyridazine.

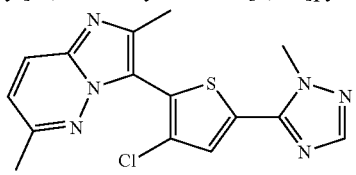

A solution of 2,6-dimethyl-imidazo[1,2-b]pyridazine (0.32 g, 2.17 mmol), 5-(5-bromo-4-chloro-thiophen-2-yl)-1-methyl-¹H-[1,2,4]triazole (0.72 g, 2.61 mmol), Cs₂CO₃ (1.49 g, 4.57 mmol) and DMF (6 mL) is de-gassed for 15 minutes with N₂. Pd(OAc)₂ (0.024 g, 0.11 mmol) and PPh₃ (0.057 g, 0.22 mmol) are added and the solution is heated at 135° C. for 4 hours. The solution is diluted with CH₂Cl₂ (50 mL), washed with sat. NH₄Cl (2×50 mL), water (50 mL), filtered and concentrated. The residue is purified by ISCO flash chromatography (30%-100% EtOAc gradient) furnish the title compound (0.29 g, 0.84 mmol, 39%). ¹H NMR (CDCl₃) δ 2.49 (s, 3H), 2.50 (s, 3H), 4.10 (s, 3H), 6.92 (d, J=9.2 Hz, 1H), 7.44 (s, 1H), 7.74 (d, J=7.5 Hz, 1H), 7.85 (s, 1H). LC/MS (m/z): calcd. for $C_{15}H_{13}ClN_6S$ (M+H)⁺: 345.1; found: 345.2.

B. 1-{3-[3-Chloro-5-(2-methyl-2H-[1,2,4]triazol-3-yl)-thiophen-2-yl]-2,6-dimethyl-imidazo[1,2-b]pyridazin-8-yl}-butan-1-one.

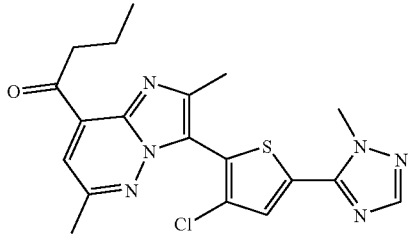

A solution of 3-[3-chloro-5-(2-methyl-2H-[1,2,4]triazol-3-yl)-thiophen-2-yl]-2,6-dimethyl-imidazo[1,2-b]pyridazine (0.20 g, 0.58 mmol), N-methoxy-N-methyl-butylamide (Wolberg, M. et. al. *Chem. Europ. J.* 2001, 7, 4562) (0.084 g, 0.64 mmol) in THF (3 mL) is cooled to a −78° C., and a 2.0 M solution of LDA in heptane/THF/ethyl benzene (0.58 mL, 1.16 mmol) is added. The solution is warmed to ambient temperature, diluted with dichloromethane (20 mL), and washed with a sat. NH$_4$Cl solution (15 mL). The organic layer is dried over MgSO$_4$, filtered and concentrated. The residue is purified by ISCO flash chromatography (20%-100% EtOAc gradient) to furnish the title compound (0.11 g, 0.27 mmol, 46%). $^1$H-NMR (CDCl$_3$), δ 1.04 (t, J=7.0 Hz, 3H), 1.76-1.86 (m, 2H), 2.56 (s, 3H), 2.59 (s, 3H), 3.51 (t, J=7.1 Hz, 2H), 4.15 (s, 3H), 7.36 (s, 1H), 7.49 (s, 1H), 7.90 (s, 1H) ppm. LC/MS (m/z): calcd. for C$_{19}$H$_{19}$ClN$_6$OS (M+H)$^+$: 415.1; found: 415.3.

C. 4-{3-[3-Chloro-5-(2-methyl-2H-[1,2,4]triazol-3-yl)-thiophen-2-yl]-2,6-dimethyl-imidazo[1,2-b]pyridazin-8-yl}-heptan-4-ol.

A solution of 1-{3-[3-chloro-5-(2-methyl-2H-[1,2,4]triazol-3-yl)-thiophen-2-yl]-2,6-dimethyl-imidazo[1,2-b]pyridazin-8-yl}-butan-1-one (0.15 g, 0.36 mmol) and THF (5 mL) is cooled to 0° C., and a 2.0 M propyl magnesium bromide solution in diethylether (0.22 mL, 0.43 mmol) is added. The reaction is warmed to ambient temperature, diluted with ethyl acetate (30 mL), and washed with a sat. NH$_4$Cl solution (30 mL). The organic layer is dried over MgSO$_4$, filtered, and concentrated. The residue is purified by ISCO flash chromatography (20%-40% EtOAc gradient) to furnish the title compound (0.016 g, 0.017 mmol, 47%). $^1$H-NMR (CDCl$_3$), δ 0.90 (t, J=7.4 Hz, 6H), 1.12-1.29 (m, 2H), 1.37-1.54 (m, 2H), 1.86-2.04 (m, 4H), 2.50 (s, 3H), 2.54 (s, 3H), 4.15 (s, 3H), 6.11 (bs, 1H), 6.73 (s, 1H), 7.48 (s, 1H), 7.90 (s, 1H) ppm. LC/MS (m/z): calcd. for C$_{22}$H$_{27}$ClN$_6$OS (M+H)$^+$: 459.2; found: 459.3.

Example 190, 191, and 192

Preparation of 7-bromo-3-(2,4-dibromo-thiazol-5-yl)-8-(1-ethyl-propyl)-2,6-dimethyl-imidazo[1,2-b]pyridazine; 3-(2,4-dibromo-thiazol-5-yl)-8-(1-ethyl-propyl)-2,6-dimethyl-imidazo[1,2-b]pyridazine; and 3-(4-bromo-thiazol-5-yl)-8-(1-ethyl-propyl)-2,6-dimethyl-imidazo[1,2-b]pyridazine

190

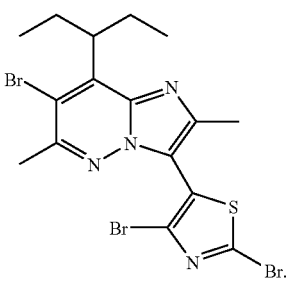

-continued

191

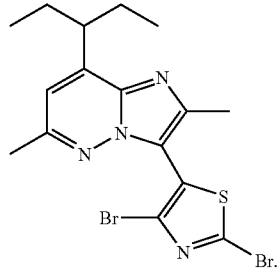

192

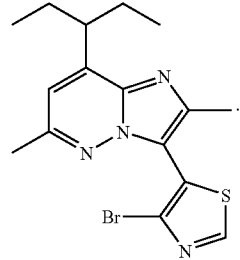

A. 8-(1-ethyl-propyl)-2,6-dimethyl-3-thiazol-5-yl-imidazo[1,2-b]pyridazine.

2.41 g (7 mmol) of 8-(1-ethyl-propyl)-3-iodo-2,6-dimethyl-imidazo[1,2-b]pyridazine, 3.00 g of thiazole (35.2 mmol), 378 mg of triphenylphosphine (1.44 mmol) and 4.71 g of Cs2CO3 (14.5 mmol) are combined with 25 ml of DMF and N2 gas is bubbled in for 30 min. 330 mg of Pd2 dba3 (0.36 mmol) is added and the tube is sealed. The reaction tube is heated at 130° C. overnight. To the reaction mixture is added water and CH2Cl2, and the CH2Cl2 layer is separated, washed with sat. NaCl and dried over Na2SO4. The solvents are removed in vacuo and crude product is applied onto a silica-gel chromatography column (Hexane:AcOEt=3:1) to give 1.48 g of the title compound. Yield 70%. mass spectrum (m/e): 301 (M+1); $^1$H-NMR (CDCl3): 8.93 (s, 1H), 8.52 (s, 1H), 6.78 (s, 1H), 3.35 (m, 1H), 2.76 (s, 3H), 2.66 (s, 3H), 1.86 (m, 4H), 0.89 (t, 6H, J=7.5 Hz).

B. 7-bromo-3-(2,4-dibromo-thiazol-5-yl)-8-(1-ethyl-propyl)-2,6-dimethyl-imidazo[1,2-b]pyridazine; 3-(2,4-dibromo-thiazol-5-yl)-8-(1-ethyl-propyl)-2,6-dimethyl-imidazo[1,2-b]pyridazine; and 3-(4-bromo-thiazol-5-yl)-8-(1-ethyl-propyl)-2,6-dimethyl-imidazo[1,2-b]pyridazine.

1.05 g (3.5 mmol) of 8-(1-Ethyl-propyl)-2,6-dimethyl-3-thiazol-5-yl-imidazo[1,2-b]pyridazine and 1.56 g of NBS (8.75 mmol) are dissolved in 50 ml of CH$_2$Cl$_2$ and stirred at room temperature for 3 days. The reaction mixture is diluted with CH$_2$Cl$_2$ and washed with sat. Na$_2$S$_2$O$_3$ and sat. NaCl. The separated organic layer is dried over Na$_2$SO$_4$ and evaporated. The reaction mixture is applied onto a silica-gel chromatography column (Hexane:AcOEt=20:1→8:1) to give three products:

149 mg of 7-bromo-3-(2,4-dibromo-thiazol-5-yl)-8-(1-ethyl-propyl)-2,6-dimethyl-imidazo[1,2-b]pyridazine (9%);

936 mg of 3-(2,4-dibromo-thiazol-5-yl)-8-(1-ethyl-propyl)-2,6-dimethyl-imidazo[1,2-b]pyridazine (58%); and 77 mg of 3-(4-bromo-thiazol-5-yl)-8-(1-ethyl-propyl)-2,6-dimethyl-imidazo[1,2-b]pyridazine (6%).

7-Bromo-3-(2,4-dibromo-thiazol-5-yl)-8-(1-ethyl-propyl)-2,6-dimethyl-imidazo[1,2-b]pyridazine mass spectrum (m/e): 538 (M+1); $^1$H-NMR (CDCl3): 3.45 (m, 1H), 2.71 (s, 3H), 2.52 (s, 3H), 2.38 (m, 2H), 2.02 (m, 2H), 0.88 (t, 6H, J=7.5 Hz);

3-(2,4-Dibromo-thiazol-5-yl)-8-(1-ethyl-propyl)-2,6-dimethyl-imidazo[1,2-b]pyridazine mass spectrum (m/e):

459 (M+1); ¹H-NMR (CDCl3): 6.79 (s, 1H), 5.33 (m, 1H), 2.57 (s, 3H), 2.55 (s, 3H), 1.87 (m, 4H), 0.90 (t, 6H, J=7.5 Hz); and 3-(4-Bromo-thiazol-5-yl)-8-(1-ethyl-propyl)-2,6-dimethyl-imidazo[1,2-b]pyridazine mass spectrum (m/e): 380 (M+1); ¹H-NMR (CDCl3): 9.01 (s, 1H), 6.77 (s, 1H), 3.35 (m, 1H), 2.55 (s, 3H), 2.54 (s, 3H), 1.87 (m, 4H), 0.91 (t, 6H, J=7.5 Hz).

Example 193

Preparation of 3-(4-Bromo-2-morpholin-4-yl-thiazol-5-yl)-8-(1-ethyl-propyl)-2,6-dimethyl-imidazo[1,2-b]pyridazine

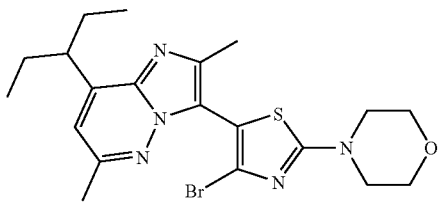

100 mg (0.22 mmol) of 3-(2,4-Dibromo-thiazol-5-yl)-8-(1-ethyl-propyl)-2,6-dimethyl-imidazo[1,2-b]pyridazine (0.22 mmol), 96 mg of morpholine (1.1 mmol) and 215 mg of Cs2CO3 (0.66 mmol) are put in a 4 ml vial with dry THF, and the vial is capped with a Teflon cap. The vial is heated at 120° C. for overnight. The reaction mixture is applied onto a silicagel chromatography column (Hexane:AcOEt:2 M NH3 in MeOH=9:3:1) to give 72.7 mg of the title compound. Yield 71%. mass spectrum (m/e): 465 (M+1); ¹H-NMR (CDCl3): 6.73 (s, 1H), 3.87 (t, 4H, J=5.1 Hz), 3.58 (t, 4H, J=5.1 Hz), 3.35 (m, 1H), 2.57 (s, 3H), 2.53 (s, 3H), 1.86 (m, 4H), 0.90 (t, 6H, J=7.5 Hz).

The following compounds are prepared essentially as described in Example 193. Examples 194-197 use 3-(2,4-dibromo-thiazol-5-yl)-8-(1-ethyl-propyl)-2,6-dimethyl-imidazo[1,2-b]pyridazine (0.22 mmol) and the named amine. Example 198. uses 7-bromo-3-(2,4-dibromo-thiazol-5-yl)-8-(1-ethyl-propyl)-2,6-dimethyl-imidazo[1,2-b]pyridazine and the named amine:

| Ex | Name | Amine | ¹H NMR (CDCl₃): δ | MS (found) (M + 1) |
|---|---|---|---|---|
| 194 | N-{4-Bromo-5-[8-(1-ethyl-propyl)-2,6-dimethyl-imidazo[1,2-b]pyridazin-3-yl]-thiazol-2-yl}-methyl-amine | Methyl-amine | 6.75 (s, 1H), 5.85 (s, NH), 3.37 (m, 1H), 3.07 (d, J = 5.3 Hz, 3H), 2.59 (s, 3H), 2.55 (s, 3H), 1.86 (m, 4H), 0.90 (t, J = 7.2 Hz, 6H). | 409 |
| 195 | N-{4-Bromo-5-[8-(1-ethyl-propyl)-2,6-dimethyl-imidazo[1,2-b]pyridazin-3-yl]-thiazol-2-yl}-dimethylamine | Dimethyl-amine | 6.72 (s, 1H), 3.36 (m, 1H), 3.19 (s, 6H), 2.57 (s, 3H), 2.52 (s, 3H), 1.85 (m, 4H), 0.90 (t, 6H, J = 7.3 Hz) | 423 |
| 196 | N-{4-Bromo-5-[8-(1-ethyl-propyl)-2,6-dimethyl-imidazo[1,2-b]pyridazin-3-yl]-thiazol-2-yl}-N-(2-methoxy-ethyl)-methylamine | N-2-methoxy-ethyl-methyl-amine | 6.71 (s, 1H), 3.76 (m, 2H), 3.71 (m, 2H), 3.42 (s, 3H), 3.35 (s, 1H), 3.21 (s, 3H), 2.57 (s, 3H), 2.53 (s, 3H), 1.85 (m, 4H), 0.90 (t, J = 7.3 Hz, 6H). | 467 |
| 197 | N-{4-Bromo-5-[8-(1-ethyl-propyl)-2,6-dimethyl-imidazo[1,2-b]pyridazin-3-yl]-thiazol-2-yl}-N-methyl-i-propyl-amine | N-methyl-i-propyl-amine | 6.72 (s, 1H), 4.43 (m, 1H), 3.36 (m, 1H), 3.0 (s, 3H), 2.57 (s, 3H), 2.54 (s, 3H), 1.86 (m, 4H), 1.31 (s, 3H), 1.29 (s, 3H), 0.90 (t, J = 7.4 Hz, 6H). | 451 |
| 198 | N-{5-[7-bromo-8-(1-ethyl-propyl)-2,6-dimethyl-imidazo[1,2-b]pyridazin-3-yl]-4-bromo-thiazol-2-yl}-morpholine | Morpholine | 3.87 (t, J = 4.5 Hz, 4H), 3.58 (t, J = 7.8 Hz, 4H), 3.43 (m, 1H), 2.71 (s, 3H), 2.50 (s, 3H), 2.38 (m, 2H), 2.01 (m, 2H), 0.88 (t, J = 7.5 Hz, 6H). | 544 |

Example 199 and 200

Preparation of N-{4-chloro-5-[8-(1-ethyl-propyl)-2,6-dimethyl-imidazo[1,2-b]pyridazin-3-yl]-thiazol-2-yl}-morpholine and N-{5-[8-(1-ethyl-propyl)-2,6-dimethyl-imidazo[1,2-b]pyridazin-3-yl]-thiazol-2-yl}-morpholine

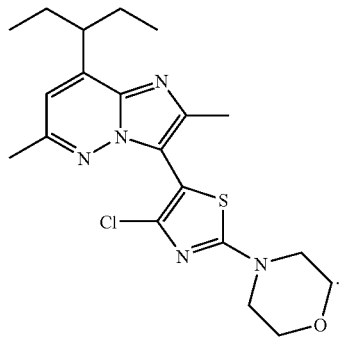

199

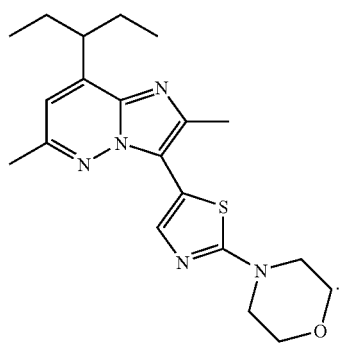

200

Method A 40 mg of 3-(4-Bromo-2-morpholin-4-yl-thiazol-5-yl)-8-(1-ethyl-propyl)-2,6-dimethyl-imidazo[1,2-b]pyridazine and 25 mg of CuCl (0.25 mmol) are put in a 4 ml vial with 2 ml of dry DMF and capped with a Teflon cap. The vial is heated at 120° C. overnight. The reaction mixture is filtered, washed with CH2Cl2 and the filtrate is concentrated. The crude product mixture is applied onto a silica-gel chromatography column (Hexane:AcOEt=2:1 and Hexane:AcOEt=8:1) to give two products:

4.2 mg of N-{4-chloro-5-[8-(1-ethyl-propyl)-2,6-dimethyl-imidazo[1,2-b]pyridazin-3-yl]-thiazol-2-yl}-morpholine (12%), and 7.2 mg of N-{5-[8-(1-ethyl-propyl)-2,6-dimethyl-imidazo[1,2-b]pyridazin-3-yl]-thiazol-2-yl}-morpholine (22%).

N-{4-Chloro-5-[8-(1-ethyl-propyl)-2,6-dimethyl-imidazo[1,2-b]pyridazin-3-yl]-thiazol-2-yl}-morpholine mass spectrum (m/e): 420 (M+1); $^1$H-NMR (CDCl3): 6.73 (s, 1H), 3.88 (t, 4H, J=5.0 Hz), 3.57 (t, 4H, J=5.0 Hz), 3.35 (m, 1H), 2.57 (s, 3H), 2.52 (s, 3H), 1.85 (m, 4H), 0.90 (t, 6H, J=7.5 Hz.

N-{5-[8-(1-Ethyl-propyl)-2,6-dimethyl-imidazo[1,2-b]pyridazin-3-yl]-thiazol-2-yl}-morpholine mass spectrum (m/e): 386 (M+1); $^1$H-NMR (CDCl3): 7.75 (s, 1H), 6.70 (s, 1H), 3.91 (t, 4H, J=5.0 Hz), 3.61 (t, 4H, J=5.0 Hz), 3.34 (m, 1H), 2.67 (s, 3H), 2.61 (s, 3H), 1.85 (m, 4H), 0.88 (t, 6H, J=7.5 Hz).

Method B N-{4-Chloro-5-[8-(1-ethyl-propyl)-2,6-dimethyl-imidazo[1,2-b]pyridazin-3-yl]-thiazol-2-yl}-morpholine.

A 20 L reactor flask under nitrogen is charged with 2900 ml of dry and degassed DMF then with 8-(1-ethyl-propyl)-3-iodo-2,6-dimethyl-imidazo[1,2-b]pyridazine (287 g, 0.836 mol), 2-morpholino-4-chlorothiazole (205.4 g, 1.01 mol, 1.2 equv.), Pd(OAc)$_2$ (3.74 g, 7.91 mmol, 0.01 equiv.), triphenylphosphine (8.77 g, 33.1 mmol, 0.04 equiv.), Copper iodide (8 g, 41.59 mmol, 0.05 equiv.) and cesium carbonate (544.9 g, 1.65 mol). The reaction mixture is heated at 120° C. After 16 h at 120° C., 1.87 g of Pd(OAc)$_2$ and 4.38 g of triphenylphosphine more is added. After 1 h, the mixture is cooled, quenched with NH$_4$Cl solution (4300 mL) and extracted with MTBE (2900 mL), the aqueous phase is extracted twice more with 2000 ml of MTBE. The organic phases are washed with sat NaCl aq (2000 mL), then treated with charcoal 72 g in flask bottle and filtered on Celite®. The filtrate is concentrated under vacuum to afford 373.8 g (79.3%) of the title compound which is 81.4%-area HPLC analysis the rest being solvent and with no detectable Example 200 by-product.

The following title compounds are prepared essentially as described in Examples 199 and 200 Method A:

| Example # | Name | Starting material | $^1$H NMR (CDCl$_3$): δ | MS (found) (M + 1) |
|---|---|---|---|---|
| 201 | N-{4-Chloro-5-[8-(1-ethyl-propyl)-2,6-dimethyl-imidazo[1,2-b]pyridazin-3-yl]-thiazol-2-yl}-dimethylamine | N-{4-Bromo-5-[8-(1-ethyl-propyl)-2,6-dimethyl-imidazo[1,2-b]pyridazin-3-yl]-thiazol-2-yl}-dimethylamine | 6.72 (s, 1H), 3.36 (m, 1H), 3.19 (s, 6H), 2.57 (s, 3H), 2.51 (s, 3H), 1.84 (m, 4H), 0.90 (t, J = 7.5 Hz, 6H). | 378 |
| 202 | N-{5-[8-(1-Ethyl-propyl)-2,6-dimethyl-imidazo[1,2-b]pyridazin-3-yl]-thiazol-2-yl}-dimethyl-amine | N-{4-Bromo-5-[8-(1-ethyl-propyl)-2,6-dimethyl-imidazo[1,2-b]pyridazin-3-yl]-thiazol-2-yl}-dimethylamine | 7.74 (s, 1H), 6.67 (s, 1H), 3.35 (m, 1H), 2.23 (s, 6H), 2.67 (s, 3H), 2.61 (s, 3H), 1.84 (m, 4H), 0.90 (t, J = 7.3 Hz, 6H). | 344 |
| 203 | N-{4-Chloro-5-[8-(1-ethyl-propyl)-2,6-dimethyl-imidazo[1,2-b]pyridazin-3-yl]-thiazol-2-yl}-N-(2-methoxy-ethyl)-methylamine | N-{4-Bromo-5-[8-(1-ethyl-propyl)-2,6-dimethyl-imidazo[1,2-b]pyridazin-3-yl]-thiazol-2-yl}-N-(2-methoxy-ethyl)-methylamine | 6.71 (s, 1H), 3.76 (t, J = 5.3 Hz, 2H), 3.71 (t, J = 5.1 Hz, 2H), 3.42 (s, 3H), 3.36 (m, 1H), 3.20 (s, 3H), 2.58 (s, 3H), 2.52 (s, 3H), 1.85 (m, 4H), 0.90 (t, J = 7.1 Hz, 6H). | 423 |

-continued

| Example # | Name | Starting material | ¹H NMR (CDCl₃): δ | MS (found) (M + 1) |
|---|---|---|---|---|
| 204 | N-{5-[8-(1-Ethyl-propyl)-2,6-dimethyl-imidazo[1,2-b]pyridazin-3-yl]-thiazol-2-yl}-N-(2-methoxy-ethyl)-methylamine | N-{4-Bromo-5-[8-(1-ethyl-propyl)-2,6-dimethyl-imidazo[1,2-b]pyridazin-3-yl]-thiazol-2-yl}-N-(2-methoxy-ethyl)-methylamine | 7.72 (s, 1H), 6.68 (s, 1H), 3.80 (t, J = 5.7 Hz, 2H), 3.72 (t, J = 5.7 Hz, 2H), 3.42 (s, 3H), 3.35 (m, 1H), 3.26 (s, 3H), 2.67 (s, 3H), 2.61 (s, 3H), 1.84 (m, 4H), 0.88 (t, J = 7.7 Hz, 6H). | 388 |
| 205 | N-{4-Chloro-5-[8-(1-ethyl-propyl)-2,6-dimethyl-imidazo[1,2-b]pyridazin-3-yl]-thiazol-2-yl}-N-methyl-i-propyl-amine | N-{4-Bromo-5-[8-(1-ethyl-propyl)-2,6-dimethyl imidazo[1,2-b]pyridazin-3-yl]-thiazol-2-yl}-N-methyl-i-propyl-amine | 6.71 (s, 1H), 4.48 (m, J = 7.4, 13.2 Hz, 1H), 3.34 (m, J = 7.6, 14.4 Hz, 1H), 3.04 (s, 3H), 2.76 (s, 3H), 2.61 (s, 3H), 1.85 (m, 4H), 1.31 (d, J = 7.1 Hz, 6H), 0.88 (t, J = 7.3 Hz, 6H). | 407 |
| 206 | N-{5-[8-(1-Ethyl-propyl)-2,6-dimethyl-imidazo[1,2-b]pyridazin-3-yl]-thiazol-2-yl}-N-methyl-isopropyl-amine | N-{4-Bromo-5-[8-(1-ethyl-propyl)-2,6-dimethyl-imidazo[1,2-b]pyridazin-3-yl]-thiazol-2-yl}-N-methyl-i-propyl-amine | 7.72 (s, 1H), 6.67 (s, 1H), 4.48 (m, 1H), 3.33 (m, 1H), 3.03 (s, 3H), 2.66 (s, 3H), 2.60 (s, 3H), 1.84 (m, 4H), 1.31 (d, J = 6.8, 6H), 0.88 (t, J = 7.2 Hz, 6H). | 371 |

Example 207

Preparation of N-{5-[7-chloro-8-(1-ethyl-propyl)-2,6-dimethyl-imidazo[1,2-b]pyridazin-3-yl]-4-methyl-thiazol-2-yl}-morpholine

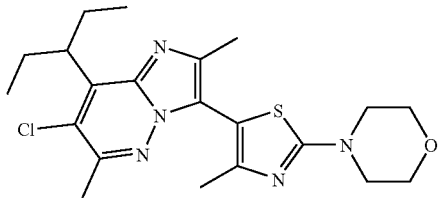

50 mg of N-{5-[7-Bromo-8-(1-ethyl-propyl)-2,6-dimethyl-imidazo[1,2-b]pyridazin-3-yl]-4-methyl-thiazol-2-yl}-morpholine (0.1 mmol) is dissolved in 2.0 ml of dry DMF and 31 mg of CuCl (0.3 mmol) is added. The vial is capped with a Teflon® lined cap and heated at 120° C. for overnight. The reaction mixture is applied onto a silica-gel chromatography column (Hexane:AcOEt=3:1) to give 39.2 mg of the title compound. Yield 87%. mass spectrum (m/e): 435 (M+1). 3.88 (t, J=4.8 Hz, 4H), 3.57 (t, J=5.1 Hz, 4H), 2.64 (s, 3H), 2.44 (s, 3H), 2.18 (s, 3H), 2.00 (m, 4H), 0.88 (t, J=7.4 Hz, 6H).

Example 208

Preparation of N-{5-[7-bromo-8-(1-ethyl-propyl)-2,6,7-trimethyl-imidazo[1,2-b]pyridazin-3-yl]-4-methyl-thiazol-2-yl}-morpholine

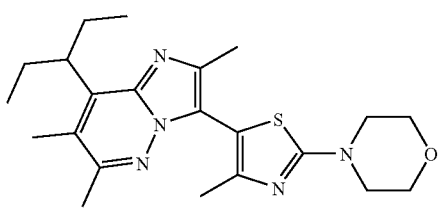

50 mg of N-{5-[7-Bromo-8-(1-ethyl-propyl)-2,6-dimethyl-imidazo[1,2-b]pyridazin-3-yl]-4-methyl-thiazol-2-yl}-morpholine (0.1 mmol) is dissolved in 4 ml of Et2O and cooled to −78° C. 0.09 ml of n-BuLi 1.6M in hexane (0.15 mmol) is added at −78° C. and stirred at −78° C. for 20 min. 43 mg of iodomethane (0.3 mmol) is added to the mixture and stirred at −78° C. and allowed to come to room temperature overnight. The reaction is quenched with sat. NH4Cl and extracted with Et2O. The separated organic layer is dried over Na2SO4 and evaporated. The crude product is applied onto a silica-gel chromatography column (Hexane:AcOEt=3:1) to give 29.6 mg of the title compound. Yield 69%. mass spectrum (m/e): 414 (M+1). ¹H NMR (CDCl₃): δ 3.87 (t, J=4.6 Hz, 4H), 3.56 (t, J=4.6 Hz, 4H), 3.35 (m, 1H), 2.54 (s, 3H), 2.43 (s, 3H), 2.35 (s, 3H), 2.20 (s, 3H), 2.01 (m, 4H), 0.88 (m, 6H).

Example 209

Preparation of N-{5-[8-(1-ethyl-propyl)-2,6-dimethyl-imidazo[1,2-b]pyridazin-3-yl]-4-trifluoromethyl-thiazol-2-yl}-morpholine

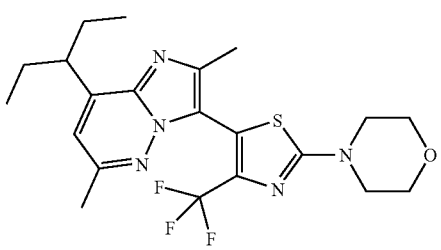

170 mg of 3-(4-Bromo-2-morpholin-4-yl-thiazol-5-yl)-8-(1-ethyl-propyl)-2,6-dimethyl-imidazo[1,2-b]pyridazine (0.37 mmol) and 100 mg of sodium trifluoroacetate (0.74 mmol) are dissolved in 3 ml of DMF/toluene=2/1. N2 gas is bubbled into the mixture for 20 min and 141 mg of CuI (0.74 mmol) is added. The vial is sealed and heated in the microwave at 210° C. for 30 min. The reaction mixture is applied onto a silica-gel chromatography column (Hexane: AcOEt=3:1 and CH3CN:CH2Cl2:Hexane=5:45:50) to give 64.3 mg of the title compound. Yield 38%. mass spectrum (m/e): 454 (M+1). ¹H NMR (CDCl₃): δ 6.72 (s, 1H), 3.88 (m, 4H), 3.60 (m, 4H), 3.32 (m, 1H), 2.54 (s, 3H), 2.47 (s, 3H), 1.85 (m, 4H), 0.89 (t, J=7.0 Hz, 6H).

Example 210

Preparation of N-{5-[8-(1-ethyl-propyl)-2,6-dimethyl-imidazo[1,2-b]pyridazin-3-yl]-4-phenyl-thiazol-2-yl}-morpholine

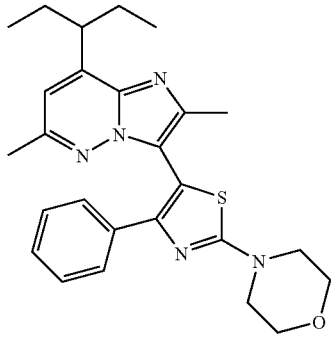

50 mg of 3-(4-Bromo-2-morpholin-4-yl-thiazol-5-yl)-8-(1-ethyl-propyl)-2,6-dimethyl-imidazo[1,2-b]pyridazine (0.11 mmol), 40 mg of phenylboronic acid (0.33 mmol) and 0.27 ml of 2 M Na2CO3aq. (0.55 mmol) are put in 2.5 ml of DME/water/EtOH=7/3/1. N2 gas is bubbled in the mixture for 20 min and 20 mg of Pd(PPh3)4 (0.017 mmol) is added. The vial is sealed and heated at 160° C. for 30 min in Microwave. The reaction mixture are added CH2Cl2 and water and the organic layer is separated, washed with brine, dried over Na2SO4 and evaporated. The crude product is applied onto a silica-gel chromatography column (Hexane:AcOEt=10:1) to give 27 mg of the title compound. Yield 54% mass spectrum (m/e): 462 (M+1). δ 8.29 (m, 1H), 7.60 (m, 2H), 7.44 (m, 1H), 7.22 (m, 1H), 6.70 (s, 1H), 3.90 (t, J=4.6 Hz, 4H), 3.64 (t, J=5.0 Hz, 4H), 3.36 (m, 1H), 2.52 (s, 3H), 2.09 (s, 3H), 1.86 (m, 4H), 0.90 (t, J=7.4 Hz, 6H).

Example 211

Preparation of N-{5-[8-(1-ethyl-propyl)-2,6-dimethyl-imidazo[1,2-b]pyridazin-3-yl]-4-methoxy-thiazol-2-yl}-morpholine

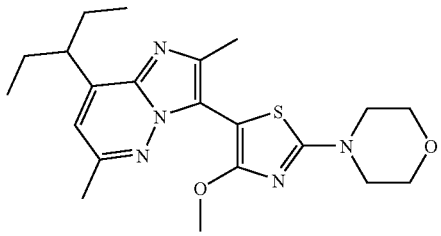

100 mg of 3-(4-Bromo-2-morpholin-4-yl-thiazol-5-yl)-8-(1-ethyl-propyl)-2,6-dimethyl-imidazo[1,2-b]pyridazine (0.22 mmol), 24 mg of sodium methoxide (0.44 mmol) and 21 mg of CuI (0.11 mmol) are put into 4 ml vial with MeOH 3 ml and capped with a Teflon® lined cap. The reaction vial is heated at 130° C. overnight. The reaction mixture is concentrated and applied onto a silica-gel chromatography column (Hexane: THF=10:1) to give 32.8 mg of the title compound.

Yield 36%. Mass spectrum (m/e): 416 (M+1). ¹H NMR (CDCl₃): δ 6.64 (s, 1H), 3.96 (s, 3H), 3.86 (t, J=4.7 Hz, 4H), 3.53 (m, 4H), 3.34 (m, 1H), 2.82 (s, 3H), 2.48 (s, 3H), 1.82 (m, 4H), 0.85 (t, J=7.4 Hz, 6H).

Example 212

Preparation of N-{5-[8-(1-ethyl-propyl)-2,6-dimethyl-imidazo[1,2-b]pyridazin-3-yl]-4-fluoro-thiazol-2-yl}-morpholine

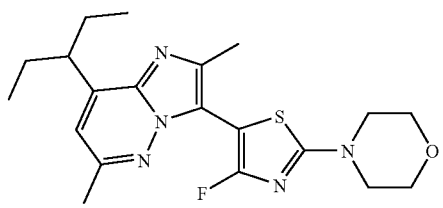

50 mg of 3-(4-Bromo-2-morpholin-4-yl-thiazol-5-yl)-8-(1-ethyl-propyl)-2,6-dimethyl-imidazo[1,2-b]pyridazine (0.11 mmol) is dissolved in 4 ml of diethylether and cooled to −78° C. and 0.1 ml of n-BuLi 1.6M in hexane (0.16 mmol) is added at −78° C. and stirred at −78° C. for 20 min. 104 mg of N-fluorobenzene sulfonimide (0.33 mmol) in 2 ml of toluene is added at −78° C. and stirred at room temperature for 1 h. sat. NH4Cl is added, and the mixture is extracted with Et2O, dried over Na2SO4 and evaporated. The crude product is applied onto a silica-gel chromatography column (Hexane:AcOEt=3:1) to give 4.1 mg of the title compound. Yield 10%. Mass spectrum (m/e): 404 (M+1). 6.71 (s, 1H), 3.87 (t, J=4.6 Hz, 4H), 3.55 (t, J=5.0 Hz, 4H), 3.34 (m, 1H), 2.58 (s, 3H), 2.54 (s, 3H), 1.84 (m, 4H), 0.88 (t, J=7.4 Hz, 6H).

Example 213

Preparation of N-{5-[8-(1-ethyl-propyl)-2,6-dimethyl-imidazo[1,2-b]pyridazin-3-yl]-4-iodo-thiazol-2-yl}-morpholine

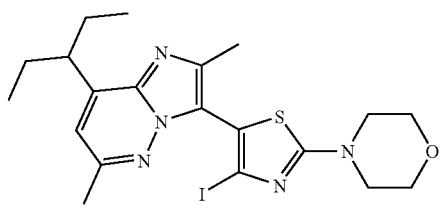

50 mg of 3-(4-Bromo-2-morpholin-4-yl-thiazol-5-yl)-8-(1-ethyl-propyl)-2,6-dimethyl-imidazo[1,2-b]pyridazine (0.11 mmol), 30 mg of CF3CO2Na (0.22 mmol) and 42 mg of CuI (0.22 mmol) are put into 4 ml vial with DMF/toluene=2:1. The vial is capped with a Teflon cap and heated at 150° C. overnight. The reaction mixture is applied onto a silica-gel chromatography column (Hexane:AcOEt=5:1) to give 54 mg of the title compound. 96%. Mass spectrum (m/e): 512 (M+1). ¹H NMR (CDCl₃): δ 6.71 (s, 1H), 3.87 (t, J=5.4 Hz, 4H), 3.58 (t, J=5.4 Hz, 4H), 3.36 (m, 1H), 2.57 (s, 3H), 2.53 (s, 3H), 1.85 (m, 4H), 0.91 (t, J=5.4 Hz, 6H).

Example 214

Preparation of 5-[8-(1-ethyl-propyl)-2,6-dimethyl-imidazo[1,2-b]pyridazin-3-yl]-2-morpholin-4-yl-thiazole-4-carbonitrile

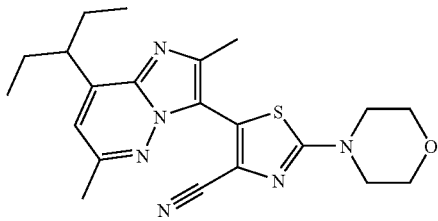

50 mg of 3-(4-Bromo-2-morpholin-4-yl-thiazol-5-yl)-8-(1-ethyl-propyl)-2,6-dimethyl-imidazo[1,2-b]pyridazine (0.11 mmol), and 30 mg of CuCN (0.33 mmol) are put into 4 ml vial with 2 ml of DMF and the vial is capped with a Teflon cap. The vial is heated at 150° C. overnight. The reaction mixture is applied onto a silica-gel chromatography column (Hexane:AcOEt=5:1) to give 12.3 mg of the title compound. Yield 28%. Mass spectrum (m/e): 411 (M+1). 6.77 (s, 1H), 3.89 (t, J=4.8 Hz, 4H), 3.61 (t, J=5.0 Hz, 4H), 3.32 (m, 1H), 2.62 (s, 3H), 2.59 (s, 3H), 1.86 (m, 4H), 0.90 (t, J=7.4 Hz, 6H).

Example 215

Preparation of N-{5-[8-(1-ethyl-propyl)-2,6-dimethyl-imidazo[1,2-b]pyridazin-3-yl]-4-iodo-thiazol-2-yl}-N-isopropyl-methylamine

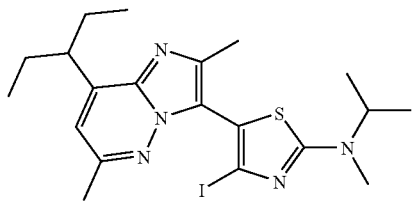

The title compound is prepared essentially as described in Example 213, employing N-{5-[8-(1-ethyl-propyl)-2,6-dimethyl-imidazo[1,2-b]pyridazin-3-yl]-4-bromo-thiazol-2-yl}-N-isopropyl-methylamine to give 17.9 mg. Yield 22%: mass spectrum (m/e): 498 (M+1). $^1$H NMR (CDCl$_3$): δ 6.71 (s, 1H), 4.41 (m, 1H), 3.35 (m, 1H), 2.97 (s, 3H), 2.57 (s, 3H), 2.53 (s, 3H), 1.84 (m, 4H), 1.29 (d, J=5.8 Hz, 6H), 0.90 (t, J=7.2 Hz, 6H).

Example 216

Preparation of N-{5-[8-(1-ethyl-propyl)-2,6-dimethyl-imidazo[1,2-b]pyridazin-3-yl]-4-methoxy-thiazol-2-yl}-N-isopropyl-methylamine

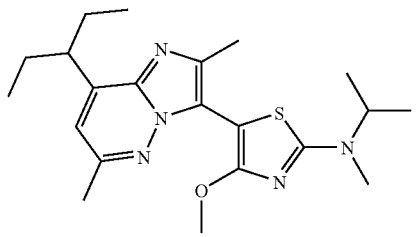

The title compound is prepared essentially as described in Example 211, employing N-{5-[8-(1-ethyl-propyl)-2,6-dimethyl-imidazo[1,2-b]pyridazin-3-yl]-4-bromo-thiazol-2-yl}-N-isopropyl-methylamine to give 52.7. Yield 36%: mass spectrum (m/e): 402 (M+1). $^1$H NMR (CDCl$_3$): δ 6.63 (s, 1H), 4.44 (m, 1H), 3.96 (s, 3H), 3.35 (m, 1H), 2.97 (s, 3H), 2.57 (s, 3H), 2.50 (s, 3H), 1.83 (m, 4H), 1.29 (d, J=6.7 Hz, 6H), 0.88 (t, J=8 Hz, 6H).

Example 217 and 218

Preparation of 5-[8-(1-ethyl-propyl)-2,6-dimethyl-imidazo[1,2-b]pyridazin-3-yl]-4-methyl-thiazole-2-carboxylic acid amide and 5-[8-(1-ethyl-propyl)-2,6-dimethyl-imidazo[1,2-b]pyridazin-3-yl]-4-methyl-thiazole-2-carboxylic acid N-methylamide

217

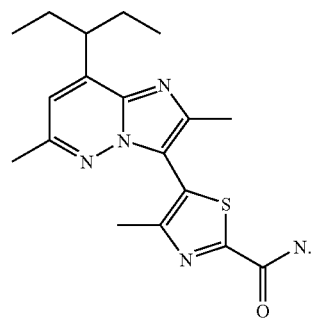

218

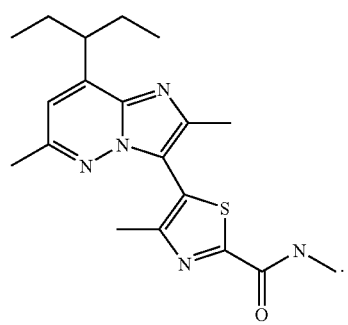

180 mg of 8-(1-Ethyl-propyl)-3-[2-bromo-4-methyl-5-thiazolyl]-2,6-dimethyl-imidazo[1,2-b]pyridazine (0.46 mmol) and 124 mg of copper(I) cyanide are put into 4 ml vial with 2 ml of dry DMF. The vial is closed with a Teflon can and heated at 130° C. overnight. The crude reaction mixture is applied onto a silica-gel chromatography column (Hexane:AcOEt=1:1→1:3) to give 52.1 mg of 5-[8-(1-ethyl-propyl)-2,6-dimethyl-imidazo[1,2-b]pyridazin-3-yl]-4-methyl-thiazole-2-carboxylic acid amide (32%) and 7.6 mg of 5-[8-(1-ethyl-propyl)-2,6-dimethyl-imidazo[1,2-b]pyridazin-3-yl]-4-methyl-thiazole-2-carboxylic acid methylamide.

5-[8-(1-ethyl-propyl)-2,6-dimethyl-imidazo[1,2-b]pyridazin-3-yl]-4-methyl-thiazole-2-carboxylic acid amide: mass spectrum (m/e): 358 (M+1) $^1$H NMR (CDCl$_3$): δ 7.21 (s, NH), 6.76 (s, 1H), 5.59 (s, NH), 3.34 (m, 1H), 2.55 (s, 3H), 2.50 (s, 3H), 2.42 (s, 3H), 1.87 (m, 4H), 0.91 (t, J=7.2 Hz, 6H). and 5-[8-(1-ethyl-propyl)-2,6-dimethyl-imidazo[1,2-b]pyridazin-3-yl]-4-methyl-thiazole-2-carboxylic acid methylamide: mass spectrum (m/e): 372 (M+1). $^1$H NMR (CDCl$_3$):

8.77 (s, NH), 6.75 (s, 1H), 4.06 (s, 3H), 3.35 (m, 1H), 2.55 (s, 3H), 2.49 (s, 3H), 2.43 (s, 3H), 1.87 (m, 4H), 0.91 (t, J=7.6 Hz, 6H).

Example 219

Preparation of 5-[8-(1-ethyl-propyl)-2,6-dimethyl-imidazo[1,2-b]pyridazin-3-yl]-4-methyl-thiazole-2-carboxylic acid dimethylamide

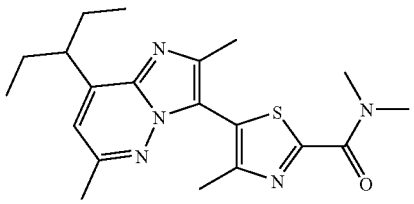

5-[8-(1-Ethyl-propyl)-2,6-dimethyl-imidazo[1,2-b]pyridazin-3-yl]-4-methyl-thiazole-2-carboxylic acid amide (46 mg, 0.13 mmol) and 28 mg of sodium tert-Butoxide (0.30 mmol) are put into 4 ml of dry DMSO and stirred at room temperature for 5 min. 141 mg of iodomethane (1.0 mmol) is added and stirred at room temperature for 1 h.

Water is added, and the mixture is extracted with $CH_2Cl_2$, dried over Na2SO4 and evaporated. The crude product is applied onto a silica-gel chromatography column (Hexane:AcOEt=3:1) to give 22.3 mg of the title compound. Yield 45%: mass spectrum (m/e): 386 (M+1). 6.75 (s, 1H), 3.70 (s, 3H), 3.35 (m, 1H), 3.21 (s, 3H), 2.55 (s, 3H), 2.50 (s, 3H), 2.41 (s, 3H), 1.86 (m, 4H), 0.91 (t, J=7.4 Hz, 6H).

Example 220

Preparation of 8-(1-ethyl-propyl)-2,6-dimethyl-3-(3-methyl-furan-2-yl)-imidazo[1,2-b]pyridazine

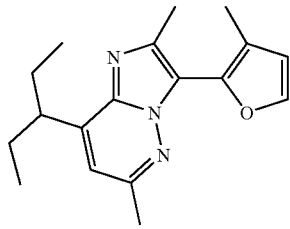

A THF solution (5 mL) of 3-methylfuran (Acros, 232 mg, 2.83 mmol) is cooled to −78° C. under $N_2$ then treated with nBuLi (1.6 M in hexane, 1.8 mL, 2.9 mmol). After addition of the nBuLi, the solution is warmed to 0° C. for 15 minutes, then to room temperature for an additional 5 minutes. The reaction mixture is then cooled to −78° C. and treated with $ZnCl_2$ (Aldrich, 0.5 M in THF, 5.8 mL, 2.9 mmol). The resulting mixture is warmed to room temperature and treated with 8-(1-ethyl-propyl)-3-iodo-2,6-dimethyl-imidazo[1,2-b]pyridazine (400 mg, 1.17 mmol) and $PdCl_2(dppf)\cdot CH_2Cl_2$ complex (Aldrich, 95 mg, 0.12 mmol). The mixture is heated to 60° C. for 4 hours, then poured into 1 N HCl (60 mL) and extracted with ethyl acetate (2×60 mL). The combined organic extracts are washed with aq. brine, dried over $Na_2SO_4$, filtered, and concentrated. The crude residue is purified by chromatography using hexane-ethyl acetate gradient (100% hexane to 20% ethyl acetate in hexane) to elute the title compound as an oil pyridazine (149 mg, 43% yield). ES-MS (m/z): calc'd for $C_{18}H_{23}N_3O$: 297.2; found: 298.5 (M+H); $^1$H NMR (400 mHz, $CDCl_3$): δ 7.59 (d, J=1.8 Hz, 1H), 6.71 (s, 1H), 6.47 (d, J=1.8 Hz, 1H), 3.36 (m, 1H), 2.55 (s, 3H), 2.50 (s, 3H), 2.10 (s, 3H), 1.92-1.79 (m, 4H), 0.90 (t, J=7.5 Hz, 6H).

Example 221

Preparation of 3-(5-bromo-3-methyl-furan-2-yl)-8-(1-ethyl-propyl)-2,6-dimethyl-imidazo[1,2-b]pyridazine

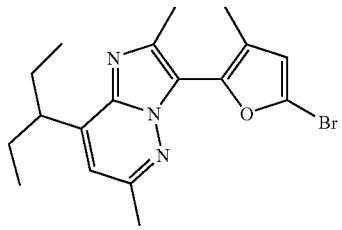

A $CH_2Cl_2$ solution (4 mL) of 8-(1-ethyl-propyl)-2,6-dimethyl-3-(3-methyl-furan-2-yl)-imidazo[1,2-b]pyridazine (32.4 mg, 0.11 mmol) is cooled to 0° C. under a $CaSO_4$ drying tube and treated with NBS (20.1 mg, 0.11 mmol). After 15 minutes at 0° C., the mixture is warmed to room temperature. After an additional 10 minutes, the reaction mixture is poured into $H_2O$ (25 mL) and extracted into $CH_2Cl_2$ (2×25 mL). The combined organic extracts are washed with aq. brine, dried over $Na_2SO_4$, filtered, and concentrated. The crude product is purified by chromatography using hexane-ethyl acetate gradient (100% hexane to 10% ethyl acetate in hexane) to elute the title compound (26.3 mg, 64% yield) as a solid. ES-MS (m/z): calc'd for $C_{18}H_{22}BrN_3O$: 375.1; found 376.2 (M+H); $^1$H NMR (400 mHz, $CDCl_3$): δ 6.72 (s, 1H), 6.40 (s, 1H), 3.34 (m, 1H), 2.56 (s, 3H), 2.49 (s, 3H), 2.07 (s, 3H), 1.93-1.77 (m, 4H), 0.89 (t, J=7.5 Hz, 6H).

Example 222

Preparation of 8-(1-ethyl-propyl)-2,6-dimethyl-3-(2-methyl-furan-3-yl)-imidazo[1,2-b]pyridazine

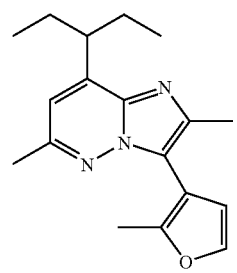

A. 3-Bromo-2-methyl furan.

A THF solution (10 mL) of 2,3-dibromofuran (Lancaster, 5.54 gm, 24.5 mmol) under $N_2$ is treated with $PdCl_2(PPh_3)_2$ (860 mg, 1.2 mmol) and stirred for 10 minutes at room temperature. The solution is then treated with $CH_3ZnCl$ (Aldrich, 2.0 M in THF, 15 mL, 30 mmol). The resulting mixture is stirred at room temperature overnight then poured into 1 N HCl and extracted into diethyl ether. The organic extract is washed with sat. NaCl, dried over $Na_2SO_4$, and filtered. The filtrate is then distilled and the product is collected at 120-125° C. to give the title compound as a colorless oil (1.71 gm, 43% yield). $^1$H NMR (400 mHz, $CDCl_3$): δ 7.25 (d, J=1.8 Hz, 1H), 6.34 (d, J=1.8 Hz, 1H), 2.28 (s, 3H).

B. 8-(1-Ethyl-propyl)-2,6-dimethyl-3-(2-methyl-furan-3-yl)-imidazo[1,2-b]pyridazine.

A THF solution (10 mL) of 3-bromo-2-methyl furan (prepared as described above) (1.06 gm, 6.58 mmol) is cooled to −78° C. under $N_2$ then treated with nBuLi (1.6 M in hexane, 4.1 mL, 6.6 mmol). After 10 minutes at −78° C., the mixture is treated with $ZnCl_2$ (Aldrich, 0.5 M in THF, 13.2 mL, 6.6 mmol). The resulting mixture is warmed to room temperature then treated with 8-(1-ethyl-propyl)-3-iodo-2,6-dimethyl-imidazo[1,2-b]pyridazine (1.13 gm, 3.29 mmol) and PdCl₂(dppf)-CH₂Cl₂ complex (Aldrich, 257 mg, 0.31 mmol). The mixture is heated to 60° C. for 4 hours, then poured into sat. NH₄Cl (50 mL) and extracted with diethyl ether (2×50 mL). The combined organic extracts are washed with sat. NaCl, dried over Na₂SO₄, filtered, and concentrated. The crude product is purified by chromatography using hexane-ethyl acetate gradient (100% hexane to 20% ethyl acetate in hexane) to elute the title product (685 mg, 70% yield) as an oil. ES-MS (m/z): calc'd for $C_{18}H_{23}N_3O$: 297.2. found 298.2 (M+H); ¹H NMR (400 mHz, CDCl₃): δ 7.45 (d, J=2.0 Hz, 1H), 6.63 (s, 1H), 6.60 (d, J=2.0 Hz, 1H), 3.35-3.31 (m, 1H), 2.51 (s, 3H), 2.44 (s, 3H), 2.30 (s, 3H), 1.88-1.75 (m, 4H), 0.86 (t, J=7.5 Hz, 6H).

Example 223

Preparation of 3-(5-bromo-2-methyl-furan-3-yl)-8-(1-ethyl-propyl)-2,6-dimethyl-imidazo[1,2-b]pyridazine

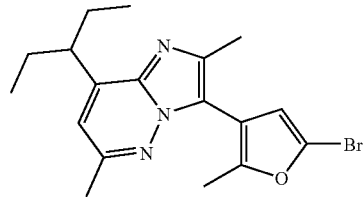

A CH₂Cl₂ solution (2 mL) of 8-(1-ethyl-propyl)-2,6-dimethyl-3-(2-methyl-furan-3-yl)-imidazo[1,2-b]pyridazine (42.3 mg, 0.14 mmol) under a CaSO₄ drying tube is treated with N-bromosuccinimide (27.6 mg, 0.16 mg). After 30 minutes the reaction mixture is poured into H₂O (25 mL) and extracted into CH₂Cl₂ (2×25 mL). The combined organic extracts are washed with sat. NaCl, dried over Na₂SO₄, filtered, and concentrated. The crude product is purified by chromatography using hexane-ethyl acetate gradient (100% hexane to 12% ethyl acetate in hexane) to elute the title product (36.9 mg, 70% yield) as a white solid. ES-MS (m/z): calc'd for $C_{18}H_{22}BrN_3O$: 375.1. found 376.3 (M+H). ¹H NMR (400 mHz, CDCl₃): δ 6.67 (s, 1H), 6.50 (s, 1H), 3.33 (m, 1H), 2.53 (s, 3H), 2.44 (s, 3H), 2.29 (s, 3H), 1.90-1.73 (m, 4H), 0.86 (t, J=7.3 Hz, 6H).

Example 224

Preparation of 3-(2,4-dimethyl-2H-pyrazol-3-yl)-8-(1-ethyl-propyl)-2,6-dimethyl-imidazo[1,2-b]pyridazine

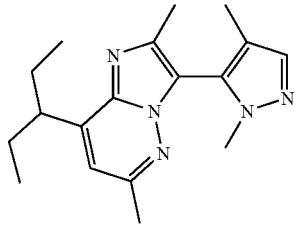

n-BuLi (1.3 ml, 2.09 mmol) is stirred in THF (4 ml), under N₂, and cooled to −72° C. 1,4-dimethyl-¹H-pyrazole (170 mg, 2.04 mmol, in THF, 1 ml) is added slowly, stirred for 5 min. then allowed to warm to ambient temp. and stirred for 45 min. The mixture is cooled to −72° C. and a zinc chloride solution (4.3 ml, 2.14 mmol, 0.5 M in toluene) added, warmed to ambient temp. and treated with 8-(1-ethyl-propyl)-3-iodo-2,6-dimethyl-imidazo[1,2-b]pyridazine and PdCl₂(dppf)-CH₂Cl₂ complex (Aldrich, 40 mg, 0.05 mmol). The mixture is heated to 65° C. overnight, cooled to ambient temp., added to water and extracted twice with EtOAc. The combined organic extracts were washed with brine, dried over Na₂SO₄, filtered and concentrated. The crude product is purified by chromatography using a hexane-ethyl acetate gradient (100% hexane to 50% ethyl acetate in hexane) to elute the product. The title compound is obtained (0.7% yield). ES-MS (m/z): calc'd for $C_{18}H_{25}N_5$: 311.4; found 312.2 (M+H)⁺. ¹H NMR (400 mHz, CDCl₃): δ 7.51 (s, 1H), 6.75 (s, 1H), 3.72 (s, 3H), 3.33 (m, 1H), 2.53 (s, 3H), 2.43 (s, 3H), 2.00 (s, 3H), 1.87 (m, 4H), 0.92 (m, 6H).

Example 225

Preparation of 3-(4,5-dibromo-2-methyl-2H-pyrazol-3-yl)-8-(1-ethyl-propyl)-2,6-dimethyl-imidazo[1,2-b]pyridazine

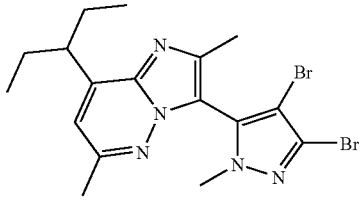

8-(1-Ethyl-propyl)-2,6-dimethyl-imidazo[1,2-b]pyridazine (300 mg, 1.4 mmol), 3,4,5-tribromo-1-methyl-1H-pyrazole (700 mg, 2.1 mmol) and cesium carbonate (900 mg, 2.8 mmol) are stirred in DMF (5 ml) and degassed by bubbling a stream of nitrogen through the mixture. PdCl₂(PPh₃)₂ (14 mg) is added and the mixture heated to 130° C. overnight. The mixture is added to water and extracted twice with EtOAc. The combined organic extracts are washed with brine, dried over Na₂SO₄, filtered and concentrated. The crude product is purified by chromatography using a hexane-ethyl acetate gradient (100% hexane to 20% ethyl acetate in hexane) to elute the title product (204 mg, 32% yield). ES-MS (m/z): calc'd for $C_{17}H_{21}Br_2N_5$: 455.2. found 455.9 (M+H)⁺. ¹H NMR (400 mHz, CDCl₃): δ 6.75 (s, 1H), 3.72 (s, 3H), 3.33 (m, 1H), 2.51 (s, 3H), 2.45 (s, 3H), 1.84 (m, 4H), 0.88 (t, 6H).

Example 226

Preparation of 8-(1-ethyl-propyl)-2,6-dimethyl-3-[3-methyl-5-(6-methyl-pyridin-2-yl)-thiophen-2-yl]-imidazo[1,2-b]pyridazine benzenesulfonic acid

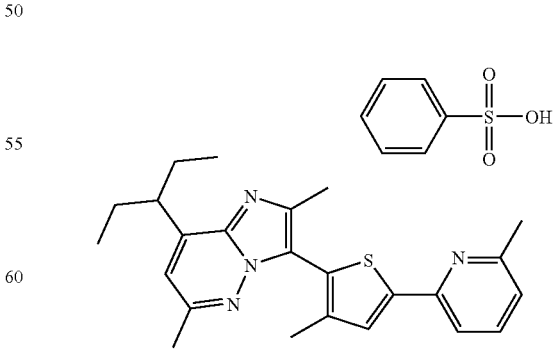

To a solution of 8-(1-ethyl-propyl)-2,6-dimethyl-3-[3-methyl-5-(6-methyl-pyridin-2-yl)-thiophen-2-yl]-imidazo[1,2-b]pyridazine (0.23 g, 0.57 mmol) and MeOH (1 mL) is added a solution of benzenesulfonic acid (0.096 g, 0.57 mmol) and MeOH (1 mL). The solution is concentrated to furnish the title compound (0.32 g, 0.57 mmol, >99%). $^1$H NMR (CDCl$_3$) δ 0.79 (t, J=7.0 Hz, 6H), 1.59-1.82 (m, 4H), 2.06 (s, 3H), 2.61 (s, 6H), 2.88 (s, 3H), 3.22-3.32 (m, 1H), 6.79 (bs, 2H), 7.25 (s, 1H), 7.33-7.42 (m, 3H), 7.49 (d, J=7.9 Hz, 1H), 7.80 (d, J=7.4 Hz, 2H), 7.92 (dd, J=7.4, 1.6 Hz, 1H) 8.23 (s, 1H). LC/MS (m/z): calcd. for C$_{24}$H$_{28}$N$_4$S (M+H)$^+$: 405.2; found: 405.4.

Example 227

Preparation of 8-(1-ethyl-propyl)-2,6-dimethyl-3-(3-methyl-4-morpholin-4-yl-thiophen-2-yl)-imidazo[1,2-b]pyridazine

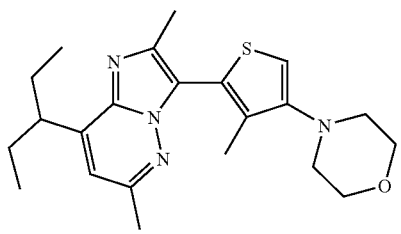

To a flask containing 3-(4-bromo-3-methyl-thiophen-2-yl)-8-(1-ethyl-propyl)-2,6-dimethyl-imidazo[1,2-b]pyridazine (0.30 g, 0.76 mmol), morpholine (0.10 mL, 1.15 mmol), Pd$_2$(dba)$_3$ (0.035 g, 0.038 mmol), and 2-dicyclohexylphosphino-biphenyl-2'-(N,N-dimethyl-amino)biphenyl (0.018 g, 0.046 mmol) is added 1 M LiHMDS (1.9 mL, 1.91 mmol). The solution is heated at 65° C. overnight, diluted with EtOAc (30 mL), washed with water (20 mL), brine (20 mL), dried over MgSO$_4$, filtered and concentrated. The residue is purified by ISCO (15%-30% EtOAc gradient), dissolved in Et$_2$O (20 mL) and extracted with 1 M HCl (2×30 mL). The aqueous layer is washed with Et$_2$O (20 mL), made basic with 5 M NaOH (15 mL), extracted with EtOAc (2×20 mL), the combined organic layers washed with brine (40 mL), dried over MgSO$_4$, filtered and concentrated to furnish the title compound (0.047 g, 0.12 mmol, 16%). $^1$H NMR (CDCl$_3$) δ 0.87 (t, J=7.5 Hz, 6H), 1.73-1.91 (m, 4H), 2.01 (s, 3H), 2.45 (s, 3H), 2.49 (s, 3H), 2.99-3.05 (m, 4H), 3.28-3.37 (m, 1H), 3.84-3.88 (m, 4H), 6.65 (s, 1H), 6.71 (s, 1H). LC/MS (m/z): calcd. for C$_{22}$H$_{30}$N$_4$OS (M+H)$^+$: 399.2; found: 399.2.

Example 228

Preparation of 8-(1-ethyl-propyl)-2,6-dimethyl-3-(2-methyl-5-thiazol-2-yl-furan-3-yl)-imidazo[1,2-b]pyridazine

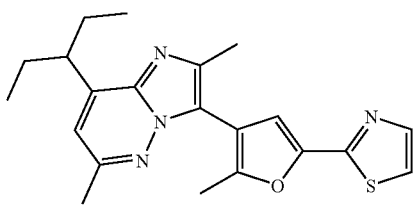

A THF solution (5 mL) of 2-bromothiazole (Aldrich, freshly distilled, 75.0 μL, 0.84 mmol) is cooled to −78° C. under N$_2$ then treated with nBuLi (1.6 M in hexane, 0.52 mL, 0.83 mmol). After 15 minutes at −78° C., the mixture is treated with ZnCl$_2$ (Aldrich, 0.5 M in THF, 1.8 mL, 0.90 mmol). The resulting mixture is warmed to room temperature then treated with a THF slurry (1 mL) containing 3-(5-bromo-2-methyl-furan-3-yl)-8-(1-ethyl-propyl)-2,6-dimethyl-imidazo[1,2-b]pyridazine (60.1 mg, 0.16 mmol) and PdCl$_2$(dppf)-CH$_2$Cl$_2$ complex (Aldrich, 22 mg, 0.027 mmol). The mixture is heated overnight at 60° C., then poured into sat'd NH$_4$Cl and extracted with diethyl ether. The organic extract is washed with aq. brine, dried over Na$_2$SO$_4$, filtered, and concentrated. The crude product is purified by chromatography using hexane-ethyl acetate gradient (100% hexane to 20% ethyl acetate in hexane) to elute the title compound (45.8 mg, 75% yield) as an oil. ES-MS (m/z): calc'd for C$_{21}$H$_{24}$N$_4$OS: 380.17. found 381.1 (M+H)$^+$. $^1$H NMR (400 mHz, CDCl$_3$): δ 7.83 (d, J=3.5 Hz, 1H), 7.29 (d, J=3.1 Hz, 1H), 7.20 (s, 1H), 6.68 (br s, 1H), 3.35 (br s, 1H), 2.53 (s, 3H), 2.49 (s, 3H), 2.40 (s, 3H), 1.90-1.76 (m, 4H), 0.88 (t, J=7.5 Hz, 6H).

Example 229

Preparation of 8-(1-ethyl-propyl)-2,6-dimethyl-3-[3-methyl-5-(6-methyl-pyridin-2-yl)-thiophen-2-yl]-imidazo[1,2-b]pyridazine; compound with methanesulfonic acid

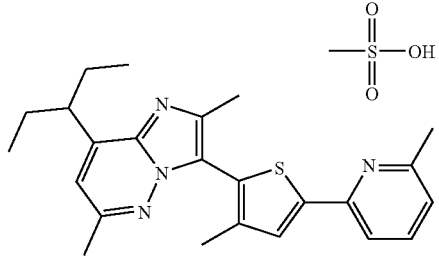

To a solution of 8-(1-ethyl-propyl)-2,6-dimethyl-3-(3-methyl-5-pyridin-2-yl-thiophen-2-yl)-imidazo[1,2-b]pyridazine (0.55 g, 1.36 mmol) and MeOH (6 mL) is added methane sulfonic acid (0.088 mL, 1.36 mmol). After one hour the solution is concentrated and the solution is treated with Darco-60® for 1 hour, filtered and concentrated to furnish the title compound (0.68 g, 1.36 mmol, >99%). $^1$H NMR (CDCl$_3$: CD$_3$OD 95:5) δ 0.85 (t, J=7.4 Hz, 6H), 1.67-1.91 (m, 4H), 1.96 (s, 3H), 1.97 (s, 3H), 2.20 (s, 3H), 2.61 (s, 3H), 2.90 (s, 3H), 3.17-3.29 (m, 1H), 7.33 (s, 1H), 7.64 (d, J=7.4 Hz, 1H), 7.89 (d, J=7.9 Hz, 1H), 8.18 (s, 1H), 8.34 (t, J=7.9 Hz, 1H), 9.95 (bs, 1H). LC/MS (m/z): calcd. for C$_{25}$H$_{32}$N$_4$O$_2$S$_2$ (M+H)$^+$: 405.6; found: 405.6.

Example 230

Preparation of {5-[8-(1-ethyl-propyl)-2,6-dimethyl-imidazo[1,2-b]pyridazin-3-yl]-4-methyl-thiophen-3-yl}-dimethyl-amine

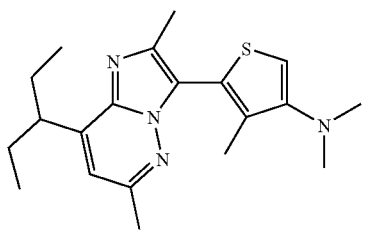

To a −78° C. solution of dimethyl-(4-methyl-thiophen-3-yl)-amine (0.43 g, 3.06 mmol) and THF (5 mL) is added 1.6

M n-BuLi (1.91 mL, 3.06 mmol). The solution is stirred for 1 hour, then 0.5 M ZnCl₂ (6.1 mL, 3.06 mmol) is added and the solution warmed to ambient temperature. After 30 minutes 8-(1-ethyl-propyl)-3-iodo-2,6-dimethyl-imidazo[1,2-b]pyridazine (0.70 g, 2.04 mmol) and PdCl₂(dppf) (0.075 g, 0.10 mmol) is added and the solution heated at 65° C. overnight. The solution is diluted with EtOAc (35 mL), washed with sat. NH₄Cl (30 mL), dried over MgSO₄, filtered and concentrated. The residue is purified by ISCO flash chromatography (15%-30% EtOAc gradient) furnish the title compound (0.13 g, 0.36 mmol, 18%). $^1$H NMR (CDCl₃) δ 0.86 (t, J=7.5 Hz, 6H), 1.72-1.90 (m, 4H), 2.03 (s, 3H), 2.45 (s, 3H), 2.50 (s, 3H), 2.77 (s, 6H), 3.28-3.37 (m, 1H), 6.63 (s, 1H), 6.65 (s, 1H). LC/MS (m/z): calcd. for C₂₀H₂₈N₄S (M+H)⁺: 357.2; found: 357.2

Example 231

Preparation of 3-[3-chloro-5-(2-methyl-2H-[1,2,4] triazol-3-yl)-thiophen-2-yl]-2,6-dimethyl-8-(1-propyl-butyl)-imidazo[1,2-b]pyridazine

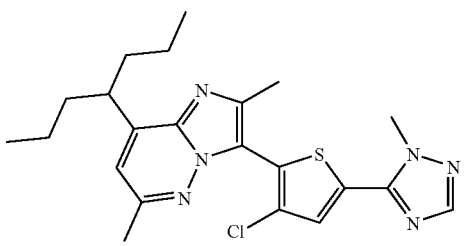

A slurry of 2,6-dimethyl-8-(1-propyl-butyl)-imidazo[1,2-b]pyridazine (below) (0.30 g, 1.22 mmol), 5-(5-bromo-4-chloro-thiophen-2-yl)-1-methyl-[1,2,4]triazole (below) (0.41 g, 1.47 mmol), KOAc (0.60 g, 6.11 mmol), TBABr (0.39 g, 1.22 mmol), and NMP (3 mL) is de-gassed with N₂ for 30 minutes. Pd(OAc)₂ (0.014 g, 0.061 mmol) and TDBPP (0.040 g, 0.061 mmol) are added and the solution heated at 125° C. for 2.5 hours. The solution is diluted with EtOAc (50 mL), washed with water (3×50 mL), brine (50 mL), dried over MgSO₄, filtered and concentrated. The residue is purified by ISCO flash chromatography (20%-40% EtOAc gradient) furnish the title compound (0.30 g, 0.68 mmol, 56%). $^1$H NMR (CDCl₃) δ 0.89 (t, J=7.4 Hz, 6H), 1.14-1.39 (m, 4H), 1.76 (q, J=16.3, 7.7 Hz, 4H), 2.51 (s, 3H), 2.52 (s, 3H), 3.41-3.50 (m, 1H), 4.15 (s, 3H), 6.73 (s, 1H), 7.48 (s, 1H), 7.90 (s, 1H). LC/MS (m/z): calcd. for C₂₂H₂₇ClN₆S (M+H)⁺: 443.2; found: 443.3.

Example 232

Preparation of (2-{4-chloro-5-[8-(1-ethyl-propyl)-2,6-dimethyl-imidazo[1,2-b]pyridazin-3-yl]-thiophen-2-yl}-pyrrol-1-yl)-dimethyl-amine

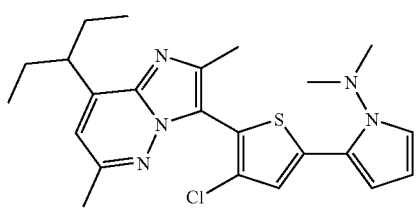

Using a procedure analogous to Example 27, 1-(dimethylamino)-pyrrole (0.20 mL, 1.65 mmol), THF (4 mL), 1.6 M n-BuLi (1.10 mL, 1.73 mmol), 0.5 M ZnCl₂ (3.46 mL, 1.73 mmol), 3-(5-bromo-3-chloro-thiophen-2-yl)-8-(1-ethyl-propyl)-2,6-dimethyl-imidazo[1,2-b]pyridazine (0.34 g, 0.82 mmol) and PdCl₂(dppf) (0.030 g, 0.041 mmol), furnish the title compound (0.17 g, 0.38 mmol, 46%). $^1$H NMR (CDCl₃) δ 0.87 (t, J=7.5 Hz, 6H), 1.74-1.92 (m, 4H), 2.52 (s, 6H), 2.84 (s, 6H), 3.28-3.39 (m, 1H), 6.21 (dd, J=4.1, 3.2 Hz, 1H), 6.38 (dd, J=4.1, 1.8 Hz, 1H), 6.68 (s, 1H), 7.02 (dd, J=3.2, 1.8 Hz, 1H), 7.29 (s, 1H). LC/MS (m/z): calcd. for C₂₃H₂₈ClN₅S (M+H)⁺: 442.2; found: 442.3.

Example 233

Preparation of 3-[3-chloro-5-(2-methyl-2H-[1,2,4] triazol-3-yl)-thiophen-2-yl]-8-iodo-2,6-dimethyl-imidazo[1,2-b]pyridazine

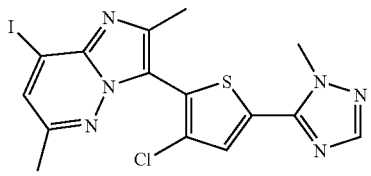

A. 4-Chloro-thiophene-2-carbonitrile.

A 22-L reaction flask is equipped with a cooling bath, air stirrer, gas addition tube, and thermometer probe. The flask is purged with nitrogen, then charged AlCl₃ (1025 g, 7.69 moles) and CHCl₃ (6.6 L, 16.5 vol.). After cooling the mixture to 0-5° C., it is charged with 2-thiophene carbonitrile (400 g, 3.66 moles) dropwise via an addition funnel over 10-15 minutes while maintaining the temperature at ≦10° C. The mixture is charged with Cl₂ gas (300 g, 4.23 moles, 1.16 EQ) subsurface at ≦10° C. over 1.25 hours. The progress of the reaction is monitored by GC, wherein the GC sampling method is quenching an aliquot of the reaction mixture into 6N HCl, extracting with EtOAc, drying over Na₂SO₄, filtering, and injecting the filtrate.

When the reaction is deemed complete by GC analysis [the reaction was deemed complete when the ratio of (sm:prod: dichloro) was approximately (1:5.8:1) by area % GC.], 6N HCl (8.0 L) is added dropwise via addition funnel over 1.5 hours, while maintaining the temperature at ≦20° C. [The HCl addition is extremely exothermic and evolves gas]. The reaction is transferred to a separatory funnel and the layers are separated. After extracting the aqueous layer with CHCl₃ (4.0 L), the chloroform layers are combined and washed with de-ionized H₂O (6.0 L). The organic layer is dried over Na₂SO₄, filtered and concentrated under vacuum to give a pale yellow semi solid 575 g, 109.3%). GC (60° C. to 280° C. temperature gradient) Area-% analysis shows ~68% product ($t_{ret}$=6.5 min) with major impurities being the unreacted starting material ($t_{ret}$=5.1 min) and the dichlorinated product ($t_{ret}$=7.4 min). GC Method: Column: DB1; $T_{inject}$=300° C.; $T_{initial}$=60° C., t=2.0 min; $T_{final}$=280° C., rate=18° C./min.

B. 4-Chloro-2-thiophene carboxamide.

A 12-L reaction flask equipped with a cooling bath, air stirrer, and thermometer probe is charged with KOH (288.6 g, 5.143 moles) and De-ionized H₂O (6.04 L) to form a solution that exotherms to ~31° C. After allowing the solution to cool to ~28.0° C., the mixture is charged with 4-chloro-2-thiophene carbonitrile (671.3 g, 4.675 moles)[1] followed by EtOH (675 mL). A gradual exotherm occurs upon the addition of EtOH and continues over 1-1.5 hours to ~38° C. The reaction is stirred at ambient temperature overnight.

[1] A small amount of solids were undissolved at this point.

The reaction mixture is filtered under vacuum, washed with de-ionized H$_2$O and dried to give crude product. The solids are dissolved in EtOAc (10.0 L) treated with Na$_2$SO$_4$ and Darco for 1-2 hours; then, filtered and washed with EtOAc. The filtrate is concentrated on the Büchi until solids began to precipitate out at 45° C. at which time the vacuum is released, and the temperature is increased to 60-65° C. to redissolve the solids. With stirring at 60° C., heptane (3.5 L) is added slowly to precipitate solids. After stirring for 15-20 minutes at 60° C., the mixture is cooled to 30-40° C. and filtered. The solids are washed with heptane (2×0.75 L), and dried to give the title compound (t$_{ret}$=9.9 min) as a white solid (235.4 g, 31.2% 96.4 area % by GC analysis). A second crop is obtained from the filtrate to give 67.8 g, 9.0%; 94.5% area-% by GC analysis). The Overall yield is 303.2 g, 40.1%.

C. 4-Chloro-N-dimethylaminomethylene-2-thiophene carboxamide.

A 5-L reaction flask equipped with a heating mantle, air stirrer, Dean-Stark apparatus, and thermometer probe is charged with 4-chloro-2-thiophene carboxamide. (300 g, 1.856 moles) and dimethylformamide dimethylacetal (872 mL) to form a slurry that endotherms 1-2° C. from 22-20° C. The mixture is heated gradually to 96° C. while collecting the distillate (mostly MeOH). The heating mantle is removed, and the mixture is cooled to ≦25° C. De-ionized H$_2$O (3.0 L) is added via an addition funnel and the temperature is maintained at ≦35° C. The reaction mixture is extracted with EtOAc (1×3.0 L, 1×1.5 L), then combined the organics are washed with de-ionized H$_2$O (1.5 L). The organic phase is dried over Na$_2$SO$_4$, filtered, and concentrated under vacuum to give crude product (400 g).

The crude product is dissolved in EtOAc (320 mL, 0.8 Vol) at 50-60° C.; then, heptane (1700 mL, 4.25 Vol) is added slowly while gradually increasing the temperature to 70° C. A seed crystal (Lot: PP6-H00086-075-1) is added to the cloudy solution to initiate precipitation. The resulting mixture is stirred to room temperature overnight, then filtered and washed with heptane. The solids are dried to give the title compound (t$_{ret}$=13.0 min) as a white solid (329.8 g, 82%; 98.2% area-% by GC analysis).

D. 5-(4-Chloro-thiophen-2-yl)-1-methyl-$^1$H-[1,2,4]triazole.

A 3-L reaction flask equipped with a cooling bath, air stirrer, and thermometer probe is charged with 4-chloro-N-dimethylaminomethylene-2-thiophene carboxamide. (155 g, 0.715 moles) and HOAc (1500 mL) to form a solution. Using an ice-water cooling bath to maintain the temperature at ≦30° C., methylhydrazine (33.2 g, 0.721 moles) is added dropwise via an addition funnel over 15-20 minutes to form a light yellow slurry. Gradually, the reaction is heated to 90° C. and held at 90° C. for 30 minutes. After analysis of the mixture by GC, the reaction is cooled to ~70° C.; then, concentrated to a thick oil/slurry. De-ionized H$_2$O (1.67 L) is slowly added to precipitate solids; then, the mixture is cooled to <30° C., filtered and washed with de-ionized H$_2$O (1.67 L). The wet solids (125.8 g) are re-dissolved in warm MTBE (1.64 L), dried over Na$_2$SO$_4$, filtered and concentrated to dryness giving the title compound as a pale yellow solid (85.8 g, 60.1% 91.9 area % by GC).

E. 5-(5-Bromo-4-chloro-thiophen-2-yl)-1-methyl-1H-[1,2,4]triazole.

A 3-L reaction flask equipped with a cooling bath, air stirrer, and thermometer probe is charged with 5-(4-Chloro-thiophen-2-yl)-1-methyl-$^1$H-[1,2,4]triazole (105.3 g, 0.527 moles), ACN (1053 mL) and HOAc (105 mL) to form a solution. NBS (103.2 g, 0.580 moles) is added portion-wise over 30-60 minutes while maintaining the temperature at ≦31° C. After stirring for 1 hour[2], GC analysis indicated reaction completion. The reaction mixture is poured into de-ionized H$_2$O (2.1 L, 20 vol), stirred for 30 minutes, filtered, and washed with de-ionized H$_2$O (2×1 L). The product is dried in a vacuum oven at 45° C. overnight to give the title compound as a pale yellow solid (123.0 g, 83.8%; 96.6% area-% by GC).

[2] The reaction temperature decreased after 1 hour to 26.7° C.

F. 2,6-Dimethyl-imidazo[1,2-b]pyridazine.

A 3 neck 1 L round bottom flask is charged with 6-methyl-pyridazin-3-ylamine (20 g, 0.18 moles), ethanol 2B (200 mL), and chloroacetone (23.7 g, 20.4 mL, 0.256 moles, 1.4 equiv). The reaction mixture is heated at 70° C. overnight. NaHCO3 (23.2 g, 0.276 moles, 1.5 equiv) is added portion wise. After most of bubbling subsides, the reaction is heated at 100° C. overnight. The solvents are removed in vacuo and the residue is taken up in dichloromethane and filtered through a filter paper. The solvent is again removed in vacuo. The residue is purified using silica gel chromatography with a hexanes:ethyl acetate gradient to obtain the title compound (15.5 g, 57%). $^1$H-NMR (DMSO-d6), δ 2.34 (s, 3H), 2.47 (s, 3H), 7.03, (d, J=10 Hz, 1H), 7.85 (d, J=10 Hz, 1H), 7.91 (s, 1H) ppm. MS (APCI): 148 (M+1).

G. 3-[3-chloro-5-(2-methyl-2H-[1,2,4]triazol-3-yl)-thiophen-2-yl]-2,6-dimethyl-imidazo[1,2-b]pyridazine.

A solution of 2,6-dimethyl-imidazo[1,2-b]pyridazine (0.32 g, 2.17 mmol), 5-(5-bromo-4-chloro-thiophen-2-yl)-1-methyl-$^1$H-[1,2,4]triazole (0.72 g, 2.61 mmol), Cs$_2$CO$_3$ (1.49 g, 4.57 mmol) and DMF (6 mL) is de-gassed for 15 minutes with N$_2$. Pd(OAc)$_2$ (0.024 g, 0.11 mmol) and PPh$_3$ (0.057 g, 0.22 mmol) are added and the solution is heated at 135° C. for 4 hours. The solution is diluted with CH$_2$Cl$_2$ (50 mL), washed with sat. NH$_4$Cl (2×50 mL), water (50 mL), filtered and concentrated. The residue is purified by ISCO flash chromatography (30%-100% EtOAc gradient) furnish the title compound (0.29 g, 0.84 mmol, 39%). $^1$H NMR (CDCl$_3$) δ 2.49 (s, 3H), 2.50 (s, 3H), 4.10 (s, 3H), 6.92 (d, J=9.2 Hz, 1H), 7.44 (s, 1H), 7.74 (d, J=7.5 Hz, 1H), 7.85 (s, 1H). LC/MS (m/z): calcd. for C$_{15}$H$_{13}$ClN$_6$S (M+H)$^+$: 345.1; found: 345.2.

H. 3-[3-Chloro-5-(2-methyl-2H-[1,2,4]triazol-3-yl)-thiophen-2-yl]-8-iodo-2,6-dimethyl-imidazo[1,2-b]pyridazine.

To a −78° C. solution of 3-[3-chloro-5-(2-methyl-2H-[1,2,4]triazol-3-yl)-thiophen-2-yl]-2,6-dimethyl-imidazo[1,2-b]pyridazine (1.50 g, 4.35 mmol) and THF (50 mL) is added 12 (1.21 g, 4.78 mmol). After 10 minutes 2 M LDA (5.44 mL, 10.87 mmol) is added. The solution is stirred for 30 minutes, quenched with water, diluted with EtOAc (100 mL), washed with water (100 mL), sat. Na$_2$S$_2$O$_3$ (100 mL), brine (100 mL), dried over MgSO$_4$, filtered and concentrated. The residue is purified by ISCO flash chromatography (100% EtOAc) furnish the title compound (0.61 g, 1.30 mmol, 30%). $^1$H NMR (CDCl$_3$) δ 2.50 (s, 3H), 2.55 (s, 3H), 4.14 (s, 3H), 7.47 (s, 1H), 7.51 (s, 1H), 7.89 (s, 1H), LC/MS (m/z): calcd. for C$_{15}$H$_{12}$ClIN$_6$S (M+H)$^+$: 471.0; found: 471.0.

Example 234

Preparation of 3-{3-chloro-5-[2-(2,2,2-trifluoro-ethyl)-2H-[1,2,4]triazol-3-yl]-thiophen-2-yl}-8-(1-ethyl-propyl)-2,6-dimethyl-imidazo[1,2-b]pyridazine

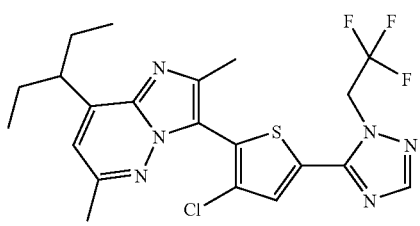

A. 5-(4-Chloro-thiophen-2-yl)-1-(2,2,2-trifluoro-ethyl)-1H-[1,2,4]triazole.

To a solution of 4-chloro-N-dimethylaminomethylene-2-thiophene carboxamide (1.00 g, 4.62 mmol) and AcOH (1. mL) is added 70% aqueous 2,2,2-trifluoroethyl-hydrazine (0.79 mL, 4.85 mmol). The solution is heated at 90° C. for 45 minutes, concentrated, dissolved in Et$_2$O (40 mL), washed with water (30 mL), sat. NaHCO$_3$ (30 mL), dried over MgSO$_4$, filtered and concentrated to furnish the title compound (1.24 g, 4.62 mmol, >99%). $^1$H NMR (CDCl$_3$) δ 4.88 (q, J=16.8, 7.8 Hz, 2H), 7.28 (d, J=0.9 Hz, 1H), 7.31-7.33 (m, 1H), 7.94 (s, 1H). LC/MS (m/z): calcd. for C$_8$H$_5$ClF$_3$N$_3$S (M+H)$^+$: 268.0; found: 268.0.

B. 5-(5-bromo-4-chloro-thiophen-2-yl)-1-(2,2,2-trifluoro-ethyl)-1H-[1,2,4]triazole.

To a solution of 5-(4-chloro-thiophen-2-yl)-1-(2,2,2-trifluoro-ethyl)-1H-[1,2,4]triazole (1.13 g, 4.22 mmol) and AcOH (10 mL) in a sealed tube, is added Br$_2$ (0.23 mL, 4.43 mmol). The solution is heated at 120° C. for 2 hours, and 140° C. for 5 hours. The solution is concentrated, diluted with Et$_2$O (150 mL), washed with sat NaHCO$_3$ (75 mL), sat. Na$_2$S$_2$O$_3$ (75 mL), brine (75 mL) dried over MgSO$_4$, filtered and concentrated. The residue is purified by ISCO flash chromatography (5%-15% EtOAc gradient) furnish the title compound (1.04 g, 3.00 mmol, 71%). $^1$H NMR (CDCl$_3$) δ 4.88 (q, J=16.0, 7.9 Hz, 2H), 7.22 (s, 1H), 7.99 (s, 1H). LC/MS (m/z): calcd. for C$_8$H$_4$BrClF$_3$N$_3$S (M+H)$^+$: 345.9; found: 346.0.

C. 3-{3-Chloro-5-[2-(2,2,2-trifluoro-ethyl)-2H-[1,2,4]triazol-3-yl]-thiophen-2-yl}-8-(1-ethyl-propyl)-2,6-dimethyl-imidazo[1,2-b]pyridazine.

Using a procedure analogous to Example 231, 8-(1-ethyl-propyl)-2,6-dimethyl-imidazo[1,2-b]pyridazine (0.25 g, 1.14 mmol), 5-(5-bromo-4-chloro-thiophen-2-yl)-1-(2,2,2-trifluoro-ethyl)-1H-[1,2,4]triazole (0.47 g, 1.37 mmol), KOAc (0.56 g, 5.60 mmol), TBABr (0.37 g, 1.14 mmol), and NMP (3 mL), Pd(OAc)$_2$ (0.013 g, 0.057 mmol) and TDBPP (0.037 g, 0.057 mmol) furnish the title compound (0.43 g, 0.89 mmol, 78%). $^1$H NMR (CDCl$_3$), δ 0.88 (t, J=7.5 Hz, 6H), 1.75-1.92 (m, 4H), 2.52 (s, 3H), 2.53 (s, 3H), 3.27-3.36 (m, 1H), 4.98 (q, J=15.7, 7.9 Hz, 2H), 6.74 (s, 1H), 7.45 (s, 1H), 8.03 (s, 1H). LC/MS (m/z): calcd. for C$_{21}$H$_{22}$ClF$_3$N$_6$S (M+H)$^+$: 483.1; found: 483.2.

Example 235

Preparation of 3-[5-(2-tert-butyl-2H-[1,2,4]triazol-3-yl)-3-chloro-thiophen-2-yl]-8-(1-ethyl-propyl)-2,6-dimethyl-imidazo[1,2-b]pyridazine

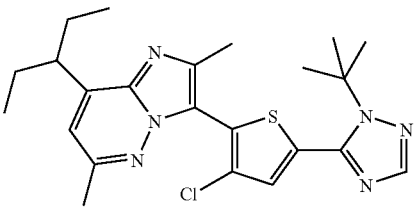

A. 1-tert-Butyl-5-(4-chloro-thiophen-2-yl)-1H-[1,2,4]triazole.

Using a procedure analogous to Example 234A, 4-chloro-N-dimethylaminomethylene-2-thiophene carboxamide (5.00 g, 23.07 mmol) and AcOH (50. mL), tert-butylhydrazine hydrochloride (3.16 g, 25.38 mmol) furnish the title compound (0.20 g, 0.83 mmol, 3.6%). $^1$H NMR (CDCl$_3$) δ 1.63 (s, 9H), 7.07 (d, J=1.3 Hz, 1H), 7.51 (d, J=1.3 Hz, 1H), 8.08 (s, 1H).

B. 5-(5-Bromo-4-chloro-thiophen-2-yl)-1-(2,2,2-trifluoro-ethyl)-1H-[1,2,4]triazole.

Using a procedure analogous to Example 249B, 1-tert-butyl-5-(4-chloro-thiophen-2-yl)-1H-[1,2,4]triazole (0.20 g, 0.83 mmol), AcOH (3 mL) and Br$_2$ (0.051 mL, 0.99 mmol) furnish the title compound (0.27 g, 0.83 mmol, >99%). $^1$H NMR (CDCl$_3$) δ 1.62 (s, 9H), 7.42 (s, 1H), 8.08 (s, 1H). LC/MS (m/z): calcd. for C$_{10}$H$_{11}$BrClN$_3$S (M+H)$^+$: 320.0; found: 320.0.

C. 3-[5-(2-tert-Butyl-2H-[1,2,4]triazol-3-yl)-3-chloro-thiophen-2-yl]-8-(1-ethyl-propyl)-2,6-dimethyl-imidazo[1,2-b]pyridazine.

Using a procedure analogous to Example 231, 8-(1-ethyl-propyl)-2,6-dimethyl-imidazo[1,2-b]pyridazine (0.15 g, 0.68 mmol), 5-(5-bromo-4-chloro-thiophen-2-yl)-1-(2,2,2-trifluoro-ethyl)-1H-[1,2,4]triazole (0.20 g, 0.82 mmol), KOAc (0.34 g, 3.42 mmol), TBABr (0.22 g, 0.68 mmol), and NMP (3 mL), Pd(OAc)$_2$ (0.0077 g, 0.034 mmol) and TDBPP (0.022 g, 0.034 mmol) furnish the title compound (0.039 g, 0.085 mmol, 13%). $^1$H NMR (CDCl$_3$), δ 0.87 (t, J=7.5 Hz, 6H), 1.65 (s, 9H), 1.73-1.91 (m, 4H), 2.51 (s, 6H), 3.26-3.37 (m, 1H), 6.69 (s, 1H), 7.65 (s, 1H), 8.11 (s, 1H). LC/MS (m/z): calcd. for C$_{23}$H$_{29}$ClN$_6$S (M+H)$^+$: 457.2; found: 457.3.

Example 236

Preparation of 3-(3-chloro-5-[1,2,4]triazol-1-yl-thiophen-2-yl)-8-(1-ethyl-propyl)-2,6-dimethyl-imidazo[1,2-b]pyridazine

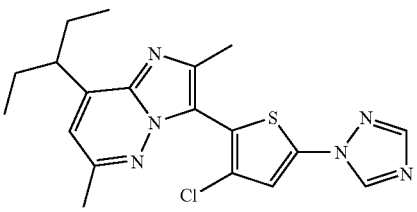

A. 3-(3-Chloro-5-iodo-thiophen-2-yl)-8-(1-ethyl-propyl)-2,6-dimethyl-imidazo[1,2-b]pyridazine.

To a solution of 3-(3-chloro-thiophen-2-yl)-8-(1-ethyl-propyl)-2,6-dimethyl-imidazo[1,2-b]pyridazine (2 g, 6 mmol) in 10 mL of anhydrous CH$_3$CN under nitrogen was added portionwise NIS (1.6 g, 7.2 mmol). The reaction mixture is stirred at reflux for 14 hours. After cooling, the solvent is concentrated under vacuum, the residue is dissolved in EtOAc and washed with H₂O, 5% solution of sodium bisulfite, H₂O and brine. The organic layer is dried over magnesium sulfate, filtered and concentrated under vacuum. The crude residue is purified by silica gel chromatography using hex/EtOAc 8:2 as eluent mixture, to obtain 2.4 g (90%) of the title compound; mass spectrum 460 (M+1); 1H-NMR (CDCl₃, 300 MHz) δ 7.24 (s, 1H), 6.71 (s, 1H), 3.32 (q, 1H, J=7.2 Hz), 2.52 (s, 3H), 2.49 (s, 3H), 1.84 (q, 4H, J=7.2 Hz); 0.88 (t, 6H, J=7.2 Hz) ppm.

B. 3-(3-Chloro-5-[1,2,4]triazol-1-yl-thiophen-2-yl)-8-(1-ethyl-propyl)-2,6-dimethyl-imidazo[1,2-b]pyridazine.

To a solution of 3-(3-chloro-5-iodo-thiophen-2-yl)-8-(1-ethyl-propyl)-2,6-dimethyl-imidazo[1,2-b]pyridazine (0.30 g, 0.65 mmol), 1H-triazole (0.047 g, 0.69 mmol), CuI (0.0062, 0.033 mmol), Cs₂CO₃ (0.45 g, 1.37 mmol) and DMF (3 mL) is added (1S,2S)-(+)-N,N'-dimethylcyclohexane-1,2-diamine (0.014 mL, 0.098 mmol). The solution is heated at 112° C. overnight, diluted with CH₂Cl₂ (10 mL) and filtered thru Celite® and concentrated. The residue is purified by ISCO flash chromatography (30%-40% EtOAc gradient furnish the title compound (0.028 g, 0.070 mmol, 11%). ¹H NMR (CDCl₃) δ 0.87 (t, J=7.5 Hz, 6H), 1.75-1.92 (m, 4H), 2.51 (s, 3H), 2.52 (s, 3H), 3.26-3.35 (m, 1H), 6.72 (s, 1H), 7.22 (s, 1H), 8.10 (s, 1H), 8.50 (s, 1H). LC/MS (m/z): calcd. for C₁₉H₂₁ClN₆S (M+H)⁺: 401.1; found: 401.2.

Example 237

Preparation of 3-[3-chloro-5-(2,5-dimethyl-2H-[1,2,4]triazol-3-yl)-thiophen-2-yl]-8-(1-ethyl-propyl)-2,6-dimethyl-imidazo[1,2-b]pyridazine

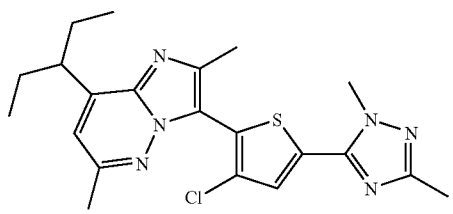

To a −78° C. solution of 3-[3-chloro-5-(2-methyl-2H-[1,2,4]triazol-3-yl)-thiophen-2-yl]-8-(1-ethyl-propyl)-2,6-dimethyl-imidazo[1,2-b]pyridazine (0.30 g, 0.72 mmol) and THF (5 mL) is added 1.7 M tert-BuLi (0.47 mL, 0.80 mmol). After 15 minutes MeI (0.052 mL, 0.83 mmol) is added and the solution warmed to ambient temperature. The solution is diluted with EtOAc (40 mL), washed with brine (40 mL), dried over MgSO₄, filtered and concentrated. The solution is recrystallized from acetone:hexane furnish the title compound (0.13 g, 0.30 mmol, 42%). ¹H NMR (CDCl₃) δ0.88 (t, J=7.5 Hz, 6H), 1.74-1.92 (m, 4H), 2.36 (s, 3H), 2.51 (s, 6H), 3.27-3.39 (m, 1H), 3.40 (s, 3H), 6.72 (s, 1H), 8.02 (s, 1H). LC/MS (m/z): calcd. for C₂₁H₂₅ClN₆S (M+H)⁺: 429.2; found: 429.2.

Example 238

Preparation of 3-[3-Chloro-5-(2-methyl-2H-[1,2,4]triazol-3-yl)-thiophen-2-yl]-8-(1-ethyl-propyl)-2,6-dimethyl-imidazo[1,2-b]pyridazine

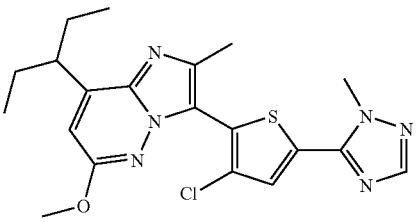

A. N-(6-Methoxy-pyridazin-3-yl)-2,2-dimethyl-propionamide.

3-Chloro-6-methoxy-pyridazine (10.0 g, 69.18 mmol) is mixed with 2,2-dimethyl-propionamide (8.40 g, 83.01 mmol), BINAP (2.15 g, 3.46 mmol), Cs₂CO₃ (33.8 g, 103.77 mmol) in 1,4-dioxane (150 mL). It is degassed by passing N₂ through for 10 min at rt. Pd₂(dba)₃ (3.16 g, 3.46 mmol) is added and the resulting mixture is refluxed overnight. The mixture is cooled to rt, diluted with EtoAc (150 mL); filtered through silica gel; washed with EtOAc (2×150 mL). The filtrate is washed with H2O (2×300 mL); dried with MgSO₄; filtered and concentrated. Purification of the crude material by silica gel chromatography gives the title compound (6.59 g, 31.53 mmol, 46%). ¹H NMR (CDCl3): δ. 1.35 (s, 9H), 4.08 (s, 3H), 7.01 (d, J=9.7 Hz, 1H), 8.41 (d, J=9.7 Hz, 1H), 8.44 (bs, 1H). ES-MS (m/z): calcd for C₁₀H₁₅N₃O₂ (M+H)⁺: 210.3; found: 210.1.

B. N-[4-(1-Ethyl-propyl)-6-methoxy-pyridazin-3-yl]-2,2-dimethyl-propionamide.

Using a procedure analogous to Example 6a, from N-(6-methoxy-pyridazin-3-yl)-2,2-dimethyl-propionamide (6.09 g, 29.14 mmol) and a Grignard reagent prepared from 3-pentyl bromide (18.1 mL, 160.3 mmol) and Mg (3.84 g, 160.26 mmol) gives the title compound (5.32 g, 19.08 mmol, 65%). ¹H NMR (CDCl₃): δ. 0.84 (t, J=7.5 Hz, 6H), 1.36 (s, 9H), 1.50-1.72 (m, 4H), 3.50-3.70 (m, 1H), 4.07 (s, 3H), 6.96 (s, 1H). ES-MS (m/z): calcd for C₁₅H₂₅N₃O₂ (M+H)⁺: 280.4; found: 280.2.

C. 4-(1-Ethyl-propyl)-2-methoxy-6-methyl-pyrrolo[1,2-b]pyridazine.

A solution of N-[4-(1-ethyl-propyl)-6-methoxy-pyridazin-3-yl]-2,2-dimethyl-propionamide (5.32 g, 19.08 mmol) in EtOH (250 mL) is treated with ZnCl₂ (26.0 g, 190.8 mmol) and refluxed for 48 h. The reaction is cooled to rt and concentrated. The residue is taken up with EtOAc (250 mL), and H₂O (100 mL). It is washed with H₂O (2×100 mL); dried with Na₂SO₄; filtered and concentrated. The residue is then dissolved in EtOAc (80 mL), reacted with chloroacetone (1.6 mL, 20.03 mmol.) at reflux overnight. While it is hot, NaHCO₃ (8.10 g) is added and the reaction is refluxed for 1 h. It is cooled to rt and filtered through silica gel washed with EtOAc and concentrated. Purification of the crude material by chromatography gives the title compound (0.48 g, 2.07 mmol, 11%). ¹H NMR (CDCl₃): δ. 0.84 (t, J=7.5 Hz, 6H), 1.69-1.869 (m, 4H), 2.45 (s, 3H), 3.19-3.30 (m, 1H), 3.94 (s, 3H), 6.39 (s, 1H), 7.49 (s, 1H). ES-MS (m/z): calcd for C₁₄H₂₀N₂O (M+H)⁺: 233.3; found: 234.1.

D. 3-[3-Chloro-5-(2-methyl-2H-[1,2,4]triazol-3-yl)-thiophen-2-yl]-8-(1-ethyl-propyl)-2,6-dimethyl-imidazo[1,2-b]pyridazine.

A solution of 4-(1-ethyl-propyl)-2-methoxy-6-methyl-pyrrolo[1,2-b]pyridazine (74.8 mg, 0.32 mmol), 5-(5-bromo- 4-chloro-thiophen-2-yl)-1-methyl-¹H-[1,2,4]triazole (107.5 mg, 0.38 mmol), TDBPP (10.4 mg, 0.016 mmol), tetrabutylammonium bromide (103.0 mg, 0.32 mmol), KOAc (158 mg, 1.61 mmol) in NMP (15 mL) is purged with N2 for 5 min. Pd(OAc)$_2$ (3.6 mg, 0.016 mmol) is added and the resulting mixture is stirred at 125° C. for 6 h. The reaction is cooled to rt, and diluted with EtOAc (10 mL); filtered through silica gel; washed with EtOAc (3×30 mL). The filtrate is washed with H2O (3×30 m); dried with Na2SO4, filtered and concentrated. Purification of the crude material by silica gel chromatography gives the title compound (0.1062 g, 0.2469 mmol, 77%). 1H NMR (CDCl$_3$): δ. 0.89 (t, J=7.6 Hz, 6H), 1.75-1.90 (m, 4H), 2.52 (s, 3H), 3.22-3.38 (m, 1H), 3.93 (s, 3H), 4.15 (s, 3H), 6.52 (s, 1H), 7.48 (s, 1H), 7.91 (s, 1H). ES-MS (m/z): calcd for $C_{20}H_{23}ClN_6OS$ (M+H)$^+$: 431.9; found: 431.3.

Example 239

Preparation of 3-[3-chloro-5-(5-fluoro-2-methyl-2H-[1,2,4]triazol-3-yl)-thiophen-2-yl]-8-(1-ethyl-propyl)-2,6-dimethyl-imidazo[1,2-b]pyridazine

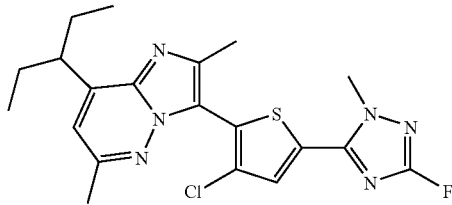

To a −78° C. solution of 3-[3-chloro-5-(2-methyl-2H-[1,2,4]triazol-3-yl)-thiophen-2-yl]-8-(1-ethyl-propyl)-2,6-dimethyl-imidazo[1,2-b]pyridazine (0.40 g, 0.72 mmol) and THF (8 mL) is added 1.7 M tert-BuLi (0.47 mL, 0.80 mmol). After 30 minutes the solution is transferred via a cannula into a solution of N-fluorobenzenesulfonamide (0.40 g, 1.25 mmol) and THF. After 30 minutes the solution warmed to ambient temperature. The solution is diluted with EtOAc (40 mL), washed with water (30 mL), brine (30 mL), dried over MgSO$_4$, filtered and concentrated. The solution is purified by ISCO (20%-30% EtOAc gradient) furnish the title compound (0.068 g, 0.16 mmol, 16%). ¹H NMR (CDCl$_3$) δ 0.87 (t, J=7.5 Hz, 6H), 1.71-1.93 (m, 4H), 2.53 (s, 3H), 2.54 (s, 3H), 3.26-3.36 (m, 1H), 4.08 (d J=2.7 Hz, 3H), 6.75 (s, 1H), 7.97 (s, 1H). LC/MS (m/z): calcd. for $C_{20}H_{22}ClFN_6S$ (M+H)$^+$: 433.2; found: 433.2.

Example 240

Preparation of Preparation of 3-(4,5-dibromo-3-chloro-thiophen-2-yl)-8-(1-ethyl-propyl)-2,6-dimethyl-imidazo[1,2-b]pyridazine

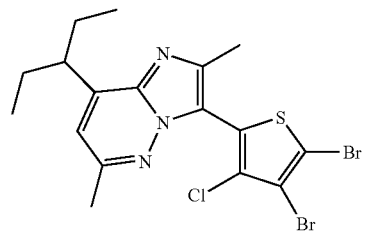

To a solution of 3-(5-bromo-3-chloro-thiophen-2-yl)-8-(1-ethyl-propyl)-2,6-dimethyl-imidazo[1,2-b]pyridazine (5.92 g, 14.34 mmol) and trifluoroacetic acid (40 mL) and 98% H$_2$SO$_4$ (10 ml) is added NBS (3.83 g, 21.15 mmol). After 10 minutes the solution is poured into ice, and made basic with 5M NaOH. The slurry is extracted with EtOAc (3×100 mL), the combined organic layers washed with water (2×400 mL), brine (400 mL), dried over MgSO$_4$, filtered and concentrated to furnish the title compound (6.61 g, 13.44 mmol, 94%). ¹H NMR (CDCl$_3$) δ 0.87 (t, J=7.5 Hz, 6H), 1.72-1.92 (m, 4H), 2.47 (s, 3H), 2.52 (s, 3H), 3.25-3.34 (m, 1H), 6.72 (s, 1H). LC/MS (m/z): calcd. for $C_{17}H_{18}Br_2ClN_3S$ (M+H)$^+$: 489.9; found: 490.0.

Example 241

Preparation of 3-(4-bromo-3-chloro-thiophen-2-yl)-8-(1-ethyl-propyl)-2,6-dimethyl-imidazo[1,2-b]pyridazine

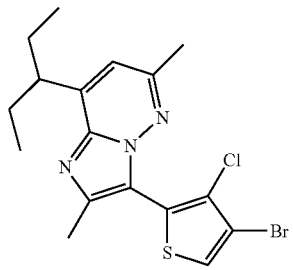

Using a procedure similar to Example 76, 3-(4,5-dibromo-3-chloro-thiophen-2-yl)-8-(1-ethyl-propyl)-2,6-dimethyl-imidazo[1,2-b]pyridazine (1.83 g, 3.72 mmol), 1.6 M n-BuLi (2.56 mL, 4.09 mmol), and THF (30 mL) furnish the title compound (1.05 g, 2.54 mmol, 68%). ¹H NMR (CDCl$_3$) δ 0.87 (t, J=7.5 Hz, 6H), 1.73-1.92 (m, 4H), 2.48 (s, 3H), 2.51 (s, 3H), 3.27-3.36 (m, 1H), 6.71 (s, 1H), 7.55 (s, 1H). LC/MS (m/z): calcd. for $C_{17}H_{19}BrClN_3S$ (M+H)$^+$: 412.0; found: 412.1.

Example 242

Preparation of 3-(1-methyl-3-phenyl-1H-pyrazol-4-yl)-8-(1-ethyl-propyl)-2,6-dimethyl-imidazo[1,2-b]pyridazine

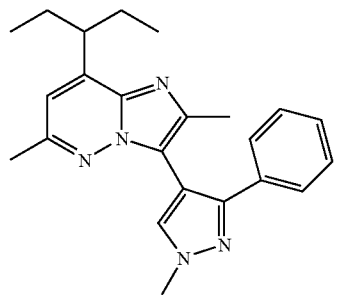

A. 1-methyl-3-phenyl-1H-pyrazole and 1-methyl-5-phenyl-¹H-pyrazole.

Sodium hydride (60% dispersion in mineral oil, 0.83 g, 20.8 mmol) is suspended in THF (45 ml) and stirred under a nitrogen atmosphere. 3-Phenyl pyrazole (2.5 g, 17.3 mmol dissolved in THF, 15 ml) is added slowly, stirred for 30 minutes then iodomethane (1.3 ml, 20.8 mmol) added and stirred for 3 hrs. The reaction is added to water and extracted twice with ethyl acetate. The combined organic extracts are ished with brine, dried over $Na_2SO_4$, filtered and concentrated. The crude product is purified by chromatography using a hexane-ethyl acetate gradient (100% hexane to 40% ethyl acetate in hexane) to elute the title compound. Obtained is a mixture of 1-methyl-3-phenyl-1H-pyrazole and 1-methyl-5-phenyl-$^1$H-pyrazole (2.6 g, 95% yield).

B. 4-Bromo-1-methyl-3-phenyl-$^1$H-pyrazole and 4-bromo-1-methyl-5-phenyl-$^1$H-pyrazole.

The mixture of isomers, 1-methyl-3-phenyl-1H-pyrazole and 1-methyl-5-phenyl-$^1$H-pyrazole (1.0 g, 6.3 mmol) and NBS (1.1 g, 6.3 mmol) are combined in acetonitrile (25 ml), stirred and heated to 70° C. for 1 hr. The solution is concentrated and the crude product is purified by chromatography using a hexane-ethyl acetate gradient (100% hexane to 25% ethyl acetate in hexane) to elute 4-bromo-1-methyl-3-phenyl-$^1$H-pyrazole (504 mg, 34% yield) and 4-bromo-1-methyl-5-phenyl-1H-pyrazole (295 mg, 20% yield), respectively:

$^1$H NMR: (400 mHz, DMSO): δ 8.01 (s, 1H), 7.95 (d, 2H), 7.41 (t, 2H), 7.38 (d, 1H), 3.85 (s, 3H).

$^1$H NMR: (400 mHz, DMSO): δ 7.63 (s, 1H), 7.50 (m, 5H) 3.77 (s, 3H).

C. 3-(1-Methyl-3-phenyl-1H-pyrazol-4-yl)-8-(1-ethyl-propyl)-2,6-dimethyl-imidazo[1,2-b]pyridazine.

8-(1-Ethyl-propyl)-2,6-dimethyl-imidazo[1,2-b]pyridazine (160 mg, 0.73 mmol), 4-bromo-1-methyl-3-phenyl-$^1$H-pyrazole (250 mg, 1.1 mmol) and cesium carbonate (490 mg, 1.50 mmol) are stirred in DMF (5 ml) and degassed by bubbling a stream of nitrogen through the mixture. $PdCl_2(PPh_3)_2$ (15 mg) is added and the mixture is heated to 130° C. overnight. The mixture is added to water and extracted twice with ethyl acetate. The combined organic extracts are dried over $Na_2SO_4$, filtered and concentrated. The crude product is purified by chromatography using a hexane-ethyl acetate gradient (100% hexane to 50% ethyl acetate in hexane) to elute the title compound (17.5 mg, 4% yield). ES-MS (m/z): calc'd for $C_{23}H_{27}N_5$: 373.5; found 374.2 (M+H)$^+$. $^1$H NMR (400 mHz, $CDCl_3$): δ 7.68 (s, 1H), 7.37 (m, 2H), 7.20 (m, 3H), 6.59 (s, 1H), 4.04 (s, 3H), 3.36 (m, 1H), 2.38 (s, 3H), 2.15 (s, 3H), 1.82 (m, 4H), 0.86 (t, 6H).

Example 243

Preparation of 3-(1-methyl-5-phenyl-1H-pyrazol-4-yl)-8-(1-ethyl-propyl)-2,6-dimethyl-imidazo[1,2-b]pyridazine

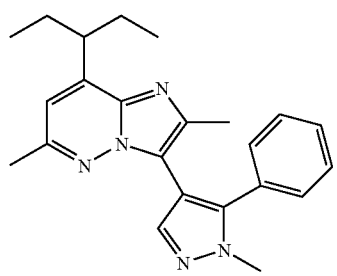

Using the procedure analogous to Example 242, from 8-(1-ethyl-propyl)-2,6-dimethyl-imidazo[1,2-b]pyridazine (160 mg, 0.73 mmol), 4-bromo-1-methyl-5-phenyl-$^1$H-pyrazole (250 mg, 1.1 mmol), cesium carbonate (490 mg, 1.50 mmol) and $PdCl_2(PPh_3)_2$ (15 mg) in DMF (5 ml) gives the title compound (18 mg, 4% yield). ES-MS (m/z): calc'd for $C_{23}H_{27}N_5$: 373.5; found 374.2 (M+H)$^+$. $^1$H NMR (400 mHz, $CDCl_3$): δ 7.85 (s, 1H), 7.32 (m, 3H), 7.23 (m, 2H), 6.55 (s, 1H), 3.94 (s, 3H), 3.27 (m, 1H), 2.38 (s, 3H), 2.03 (s, 3H), 1.76 (m, 4H), 0.83 (t, 6H).

Example 244

Preparation of 3-(3,5-dimethyl isoxazol-4-yl)-8-(1-ethyl-propyl)-2,6-dimethyl-imidazo[1,2-b]pyridazine

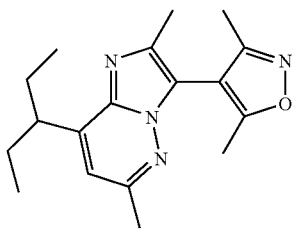

Using the procedure analogous to Example 242, from 8-(1-ethyl-propyl)-2,6-dimethyl-imidazo[1,2-b]pyridazine (200 mg, 0.90 mmol), 4-bromo-3,5-dimethyl isoxazole (Alfa, 320 mg, 1.8 mmol), cesium carbonate (880 mg, 2.70 mmol) and $PdCl_2(PPh_3)_2$ (25 mg) in DMF (5 ml), heated at 130 for 4 hrs, then overnight at ambient temperature gives the title compound (65 mg, 23% yield). ES-MS (m/z): calc'd for $C_{18}H_{24}N_4O$: 312.4; found 313.2 (M+H)$^+$. $^1$H NMR (400 mHz, $CDCl_3$): δ 6.68 (s, 1H), 3.32 (m, 1H), 2.50 (s, 3H), 2.39 (s, 3H), 2.33 (s, 3H), 2.19 (s, 3H), 1.82 (m, 4H), 0.87 (m, 6H).

Example 245

Preparation of 3-(3-methyl-5-phenyl-isoxazol-4-yl)-8-(1-ethyl-propyl)-2,6-dimethyl-imidazo[1,2-b]pyridazine

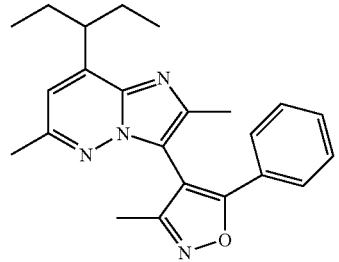

A. 4-Bromo-3-methyl-5-phenyl isoxazole.

3-Methyl-5-phenyl isoxazole (Synthesis, 1997, 439-442) (1.0 g, 6.3 mmol) and N-bromosuccinimide (1.2 g, 6.9 mmol) are combined together in acetic acid (30 ml) and heated to reflux with stirring for 2 hrs. The solution is added to water and extracted twice with ethyl acetate. The combined organic extracts are washed with sodium bicarbonate (sat'd) and sat. NaCl then dried over $Na_2SO_4$, filtered and concentrated. The crude product is purified by chromatography using a hexane-ethyl acetate gradient (100% hexane to 10% ethyl acetate in hexane) to elute the title compound (1.5 g, 100% yield). $^1$H NMR (400 mHz, $CDCl_3$): δ 8.02 (m, 2H), 7.49 (m, 3H), 6.34, 2.35 (s, 3H).

B. 3-(3-Methyl-5-phenyl-isoxazol-4-yl)-8-(1-ethyl-propyl)-2,6-dimethyl-imidazo[1,2-b]pyridazine.

Using the procedure analogous to Example 257, 8-(1-ethyl-propyl)-2,6-dimethyl-imidazo[1,2-b]pyridazine (200 mg, 0.90 mmol), 4-bromo-3-methyl-5-phenyl isoxazole (430 mg, 1.8 mmol), cesium carbonate (880 mg, 2.70 mmol) and $PdCl_2(PPh_3)_2$ (25 mg) in DMF (5 ml) are combined and heated at 130° C. for 5 hrs to give the title compound (65 mg, 23% yield). ES-MS (m/z): calc'd for $C_{23}H_{26}N_4O$: 374.5.

found 375.1 (M+H)+. 1H NMR (400 mHz, CDCl3): δ 7.50 (d, 2H), 7.31 (m, 3H), 6.69 (s, 1H), 3.39 (m, 1H), 2.48 (s, 3H), 2.20 (s, 6H), 2.33 (s, 3H), 1.84 (m, 4H), 0.88 (m, 6H).

Example 246

{5-[8-(1-Ethyl-propyl)-2,6-dimethyl-imidazo[1,2-b]pyridazin-3-yl]-4-methyl-thiazol-2-yl}-dipropyl-amine

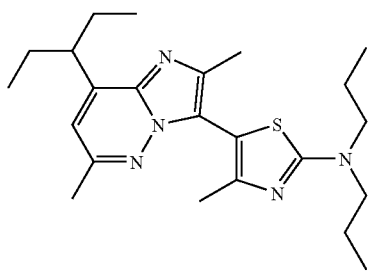

35 mg of 3-(2-Bromo-4-methyl-thiazol-5-yl)-8-(1-ethyl-propyl)-2,6-dimethyl-imidazo[1,2-b]pyridazine (0.09 mmol) and 45 mg of di-n-propylamine (0.44 mmol) and 57 mg of cesium carbonate (0.18 mmol) are place into 4 ml reaction vial with 3 ml of dry THF and the vial is capped with a Teflon cap. The reaction vial is heated at 100° C. for 4 h. The reaction mixture is transferred into microwave reaction vessel and sealed. The reaction mixture is heated at 160° C. for 30 min by microwave. The mixture is concentrated and applied onto silica-gel chromatography column (Hexane:AcOEt=3:1) to give the title compound. 5.3 mg (14%); mass spectrum (m/e): 414; 1H-NMR (CDCl3): 5.59 (s, 1H), 3.45 (m, 4H), 3.36 (m, 1H), 2.57 (s, 3H), 2.47 (s, 3H), 2.17 (s, 3H), 1.80 (m, 8H), 0.99 (t, 6H, J=7.5 Hz), 0.89 (t, 6H, J=9.4 Hz).

Example 247

N-{5-[8-(1-Ethyl-propyl)-2,6-dimethyl-imidazo[1,2-b]pyridazin-3-yl]-4-chloro-thiazol-2-yl}-dimethylamine, mesylate salt

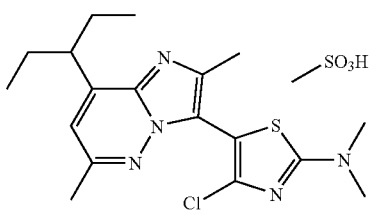

89 mg of N-{5-[8-(1-Ethyl-propyl)-2,6-dimethyl-imidazo[1,2-b]pyridazin-3-yl]-4-chloro-thiazol-2-yl}-dimethylamine (0.236 mmol) is dissolved in 2.0 ml of ethylacetate and 0.236 ml of 1M methanesulfonic acid in ethylacetate (0.236 mmol) is added. The solvents are removed under N2 gas and precipitated crystals are collected, washed with Et2O and dried. 92 mg (83%); mass spectrum (m/e): 378 (M+1); 1H-NMR (CDCl3): 7.30 (s, 1H), 3.67 (m, 1H), 3.22 (s, 6H), 2.93 (s, 3H), 2.78 (s, 3H), 2.78 (s, 3H), 2.71 (s, 3H), 1.95 (m, 2H), 1.82 (m, 2H), 0.96 (t, 6H, J=7.3 Hz).

Example 248

Preparation of {5-Bromo-4-[8-(1-ethyl-propyl)-2,6-dimethyl-imidazo[1,2-b]pyridazin-3-yl]-oxazol-2-yl}-dimethyl-amine

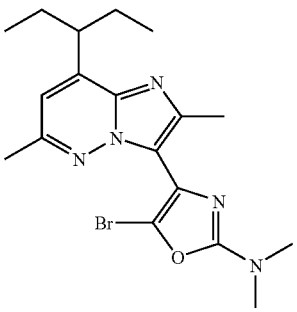

A. 8-(1-Ethyl-propyl)-2,6-dimethyl-3-oxazol-4-yl-imidazo[1,2-b]pyridazine.

500 mg of 8-(1-ethyl-propyl)-3-iodo-2,6-dimethyl-imidazo[1,2-b]pyridazine (1.46 mmol), 622 mg of oxazole (9.0 mmol), 79 mg of triphenylphosphine (0.3 mmol) and 989 mg of cesium carbonate (3.03 mmol) are placed into reaction vial with 7 ml of dry DMF. N2 gas is bubbled into the mixture for 30 min and 67 mg of Pd2 dba3 (0.07 mmol) is added. The reaction vial is capped with a Teflon cap and stirred at 130° C. for 3 days. The reaction mixture is diluted with dichloromethane, washed with sat NaCl, dried over Na2SO4 and evaporated. The crude product is applied onto a silica-gel chromatography column (Hexane:EtOAc=3:1) to give the title compound 172 mg (42%); mass spectrum (m/e): 285; 1H-NMR (CDCl3): 8.04 (s, 1H), 7.97 (s, 1H), 6.78 (s, 1H), 3.35 (m, 1H), 2.80 (s, 3H), 2.65 (s, 3H), 1.86 (m, 4H), 0.88 (t, 6H).

B. 3-(2,5-Dibromo-oxazol-4-yl)-8-(1-ethyl-propyl)-2,6-dimethyl-imidazo[1,2-b]pyridazine.

172 mg of 8-(1-ethyl-propyl)-2,6-dimethyl-3-oxazol-4-yl-imidazo[1,2-b]pyridazine (0.60 mmol) and 270 mg of NBS (1.51 mmol) are dissolved in 8.0 ml of dichloromethane and stirred at room temperature overnight. The reaction mixture is concentrated and applied onto a silica-gel chromatography column (Hexane:EtOAc=3:1) to give 70 mg of the title compound (26%); mass spectrum (m/e): 442; 1H-NMR (CDCl3): 6.82 (s, 1H), 3.32 (m, 1H), 2.59 (s, 3H), 2.54 (s, 3H), 1.86 (m, 4H), 0.89 (t, 6H, J=7.4 Hz).

C. {5-Bromo-4-[8-(1-ethyl-propyl)-2,6-dimethyl-imidazo[1,2-b]pyridazin-3-yl]-oxazol-2-yl}-dimethyl-amine.

67 mg of 3-(2,5-Dibromo-oxazol-4-yl)-8-(1-ethyl-propyl)-2,6-dimethyl-imidazo[1,2-b]pyridazine (0.15 mmol), 146 mg of cesium carbonate (0.45 mmol) and 3.0 ml of dimethylamine 2.0M in THF (6 mmol) are placed into a 4 ml of reaction vial and the vial is capped with a Teflon cap. The reaction vial is heated at 130° C. overnight. The reaction mixture is concentrated and applied onto a silica-gel chromatography column (Hexane:AcOE t=3:1) to give 53 mg of the title compound (87%); mass spectrum (m/e): 406; 1H-NMR (CDCl3): 6.72 (s, 1H), 3.37 (m, 1H), 3.15 (s, 6H), 2.58 (s, 3H), 2.53 (s, 3H), 1.85 (m, 4H), 0.90 (t, 6H, J=7.2 Hz).

Example 249

Preparation of 3-[3-chloro-4-(2-methyl-2H-[1,2,4]triazol-3-yl)-thiophen-2-yl]-8-(1-ethyl-propyl)-2,6-dimethyl-imidazo[1,2-b]pyridazine

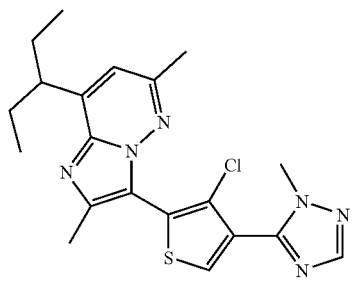

To a flask of 3-(4-bromo-3-chloro-thiophen-2-yl)-8-(1-ethyl-propyl)-2,6-dimethyl-imidazo[1,2-b]pyridazine (0.20 g, 0.49 mmol) is added 0.5 g/mL Reike® Zn (1.3 mL, 0.97 mmol). The slurry is heated at 65° C. for 1 hour, placed in a centrifuge for 5 minutes, and the solution transferred to a flask containing 5-bromo-1-methyl-$^1$H-[1,2,4]triazole (0.12 g, 0.73 mmol) and PdCl2(dppf) (0.018 g, 0.024 mmol). The solution is heated at 65° C. overnight, diluted with EtOAc (20 mL), washed with sat. NH$_4$Cl (15 mL), dried over MgSO$_4$, filtered and concentrated. The residue is purified by ISCO flash chromatography (20%-50% EtOAc gradient) furnish the title compound (0.018 g, 0.043 mmol, 9%). $^1$H NMR (CDCl$_3$) δ 0.87 (t, J=7.5 Hz, 6H), 1.74-1.92 (m, 4H), 2.51 (s, 3H), 2.52 (s, 3H), 3.26-3.37 (m, 1H), 3.95 (s, 3H), 6.72 (s, 1H), 7.82 (s, 1H), 8.01 (s, 1H). LC/MS (m/z): calcd. for C$_{20}$H$_{23}$ClN$_6$S (M+H)$^+$: 415.2; found: 415.3.

Example 250

Preparation of {5-[8-(1-ethyl-propyl)-2,6-dimethyl-imidazo[1,2-b]pyridazin-3-yl]-4-trifluoromethyl-thiazol-2-yl}-dimethyl-amine

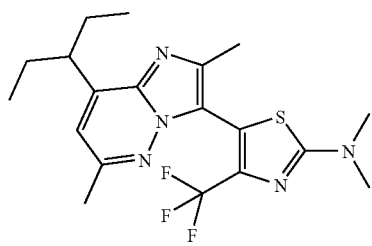

A. 8-(1-Ethyl-propyl)-2,6-dimethyl-3-thiazol-5-yl-imidazo[1,2-b]pyridazine.

Iodoimidazopiridazine (6.75 g, 19.7 mmol), triphenylphosphine (1.03 g, 3.94 mmol), Cs$_2$CO$_3$ (12.84 g, 39.4 mmol) and Pd$_2$(dba)$_3$ (900 mg, 0.98 mmol) are put into a sealed tube with 65 mL of dry DMF and N$_2$ gas is bubbled into the mixture for 5 minutes. Thiazole (8.36 g, 6.7 mL, 98.4 mmol) is added, and the mixture is heated at 130° C. overnight. The mixture is cooled to r.t. and quenched by addition of NH$_4$Cl saturated solution (200 mL). The mixture is extracted with Et$_2$O (3×100 mL) and the organic layers washed with water (2×100 mL) and sat. NaCl (100 mL), dried over MgSO$_4$ and concentrated. The crude product is purified by flash chromatography on silica gel (eluent; hexane:EtOAc=4:1) to give 3.80 g of the title compound (Yield: 64%). ESIMS: m/z 301 [M+H]$^+$.

B. 3-(2,4-Dibromo-thiazol-5-yl)-8-(1-ethyl-propyl)-2,6-dimethyl-imidazo[1,2-b]pyridazine.

To a solution of 8-(1-ethyl-propyl)-2,6-dimethyl-3-thiazol-5-yl-imidazo[1,2-b]pyridazine. (3.80 g, 12.6 mmol) in CH$_3$CN (55 mL) at room temperature is added NBS (5.18 g, 29.1 mmol), and the mixture is stirred at room temperature for 3 hours. A white precipitate is formed that is filtered in vacuo, to give 4.86 g of the title compound (Yield: 84%). ESIMS: m/z 459, 461 [M+H]$^+$.

C. 3-(4-Bromo-thiazol-5-yl)-8-(1-ethyl-propyl)-2,6-dimethyl-imidazo[1,2-b]pyridazine.

To a solution of 3-(2,4-dibromo-thiazol-5-yl)-8-(1-ethyl-propyl)-2,6-dimethyl-imidazo[1,2-b]pyridazine (4.86 g, 10.6 mmol) in THF (150 mL) under N$_2$ atmosphere at −78° C., BuLi (6.63 mL 1.6 M in hexane, 10.6 mmol) is added dropwise for a period of 10 minutes. The mixture is stirred at −78° C. for 30 minutes. Water is added, and the mixture is extracted with Et$_2$O (3×100 mL), dried over MgSO$_4$ and concentrated in vacuo. Crude product is purified by flash chromatography on silica gel (eluent hexane:EtOAc 5:1) to give 3.28 g of the title compound (Yield: 82%). ESIMS: m/z 379, 381 [M+H]$^+$.

D. 8-(1-Ethyl-propyl)-2,6-dimethyl-3-(4-trifluoromethyl-thiazol-5-yl)-imidazo[1,2-b]pyridazine.

To a solution of 3-(4-bromo-thiazol-5-yl)-8-(1-ethyl-propyl)-2,6-dimethyl-imidazo[1,2-b]pyridazine (2.45 g, 6.5 mmol) in NMP (35 mL) in a sealed tube is added FSO$_2$CF$_2$CO$_2$Me (2.5 g, 1.65 mL, 13 mmol) and CuI (2.48 g, 13 mmol). N$_2$ gas is bubbled into the mixture for 5 minutes, and the mixture is heated at 120° C. for 9 hours. After cooling to room temperature, water (100 mL) and NaCl saturated solution (100 mL) are added to the mixture. The mixture is extracted with Et$_2$O (5×80 mL); washed with water (2×100 mL), and dried over MgSO$_4$ and concentrated. The crude product is purified by flash chromatography on silica gel (eluent hexane:EtOAc 5:1) to obtain 960 mg of the title compound (Yield: 40%). ESIMS: m/z 369 [M+H]$^+$.

E. 3-(2-bromo-4-trifluoromethyl-thiazol-5-yl)-8-(1-ethyl-propyl)-2,6-dimethyl-imidazo[1,2-b]pyridazine.

To a solution of 8-(1-ethyl-propyl)-2,6-dimethyl-3-(4-trifluoromethyl-thiazol-5-yl)-imidazo[1,2-b]pyridazine (915 mg, 2.48 mmol) in 40 mL of THF under N$_2$ atmosphere al −78° C., BuLi (1.86 mL 1.6 M in hexane, 2.98 mmol) is slowly added. The mixture is stirred at −78° C. for 30 minutes. Then, a solution of CBr$_4$ (989 mg, 2.98 mmol) in 3 mL of THF is added, and the mixture is stirred at −78° C. for 45 minutes. The reaction is quenched by addition of NH$_4$Cl saturated solution (50 mL), extracted with Et$_2$O (2×50 mL), dried over MgSO$_4$, and concentrated in vacuo. Crude product is purified by flash chromatography on silica gel (eluent CH$_2$Cl$_2$) to obtain 685 mg of the title compound (Yield: 62%). $^1$H NMR (CDCl$_3$): δ0.86 (t, J=7.5 Hz, 6H), 1.82 (m, 4H), 2.45 (s, 3H), 2.51 (s, 3H), 3.27 (m, 1H), 6.74 (s, 1H). ESIMS: m/z 447, 449 [M+H]$^+$.

F. {5-[8-(1-Ethyl-propyl)-2,6-dimethyl-imidazo[1,2-b]pyridazin-3-yl]-4-trifluoromethyl-thiazol-2-yl}-dimethylamine.

100 mg of 3-(2-Bromo-4-trifluoromethyl-thiazol-5-yl)-8-(1-ethyl-propyl)-2,6-dimethyl-imidazo[1,2-b]pyridazine (0.22 mmol) and 218 mg of cesium carbonate (0.66 mmol) are placed in 4 ml reaction vial and 3 ml of dimethylamine 2 M in THF is added. The reaction vial is capped with a Teflon cap and heated at 120° C. overnight. The reaction mixture is filtered and concentrated and applied onto a silica-gel chro-

Example 251

Preparation of 8-(1-Ethyl-propyl)-2,6-dimethyl-3-[2-(2-methyl-2H-[1,2,4]triazol-3-yl)-4-trifluoromethyl-thiazol-5-yl]-imidazo[1,2-b]pyridazine

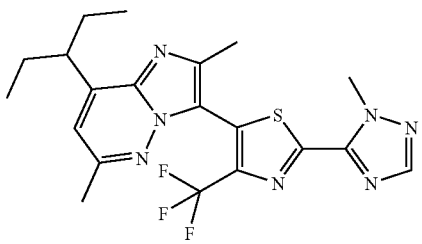

164 mg of 1-Methyl-1,2,4-triazole (1.96 mmol) is dissolved in 2 ml of THF and cooled to −78° C. 0.8 ml of 2.5M n-butyllithium in hexane (1.96 mmol) is added slowly and stirred at −78° C., warmed up to room temperature and stirred at r.t. for 15 min and cooled to −78° C. 3.96 ml of 0.5 M $ZnCl_2$ in THF (1.98 mmol) is added and stirred at room temperature for 15 min. 180 mg of 3-(2-bromo-4-trifluoromethyl-thiazol-5-yl)-8-(1-ethyl-propyl)-2,6-dimethyl-imidazo[1,2-b]pyridazine and 54 mg of PdCl2(pddf) (0.06 mmol) are added. The vial is capped with a Teflon cap and heated at 80° C. overnight. $NH_4Cl$ aq. is added to quench the reaction and the mixture is extracted by $CH_2Cl_2$, dried over Na2SO4 and evaporated. The crude product is applied onto silica-gel chromatography column (Hexane:AcOEt=3:1) to give 119 mg of the title compound. Yield 58%. mass spectrum (m/e): 449 (M+1).

Example 252

Preparation of 8-(1-Ethyl-propyl)-6-methyl-3-(3-methyl-thiophen-2-yl)-2-trifluoromethyl-imidazo[1,2-b]pyridazine

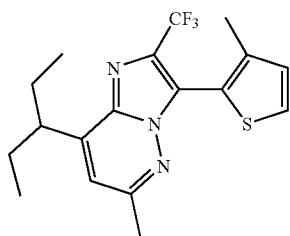

A. 8-(1-Ethyl-propyl)-6-methyl-2-trifluoromethyl-imidazo[1,2-b]pyridazine.

α-Bromotrifluoroacetone (402 mg, 2.93 mmol) is added to a dry 10 mL microwave reaction tube containing 4-(1-ethyl-propyl)-6-methyl-pyridazin-3-ylamine (500 mg, 2.79 mmol) in EtOH (2.0 mL). The resulting mixture is heated at 110° C. in the microwave for 1 hour. $NaHCO_3$ (246.5 mg, 2.93 mmol) is added, and the reaction is mixed well for 5 minutes. Then, the reaction is heated at 110° C. in the microwave for 1 hour. The solvent is removed via reduced pressure, and the reaction is diluted with ethyl acetate (30 mL). The organic layer is washed with $H_2O$ (3×10 mL), and the combined aqueous layers are extracted with ethyl acetate (2×20 mL). The combined organic extracts are dried over $Na_2SO_4$, filtered, and purified by silica gel chromatography to give the title compound (29.5 mg, 0.068 mmol, 9.8%). $^1$H-NMR (CDCl$_3$), δ 0.87 (t, J=7.6 Hz, 6H), 1.86 (m, 4H), 2.60 (s, 3H), 3.30 (m, 1H), 6.80 (s, 1H), 8.14 (s, 1H) ppm. ES-MS (m/z): calcd for $C_{13}H_{16}F_3N_3$ (M+H)$^+$: 271.29; found: 272.2

B. 8-(1-Ethyl-propyl)-6-methyl-3-(3-methyl-thiophen-2-yl)-2-trifluoromethyl-imidazo[1,2-b]pyridazine.

To a dry 10 ml round bottom flask with reflux condenser containing 8-(1-ethyl-propyl)-6-methyl-2-trifluoromethyl-imidazo[1,2-b]pyridazine (300 mg, 1.11 mmol), 2-bromo-3-methyl-thiophene (216 mg, 1.22 mmol), and $Cs_2CO_3$ (760 mg, 2.33 mmol) is added NMP (1.7 ml). The mixture is degassed with bubbling $N_2$ for 15 min and $Pd_2(dba)_3$ (50.8 mg, 0.055 mmol) and $PPh_3$ (58.2 mg, 0.222 mmol) are added. The reaction mixture is stirred at 130° C. overnight. The mixture is cooled to rt, diluted with $H_2O$; and extracted with EtOAc (3×20 ml). The organic layers are dried ($Na_2SO_4$), filtered and purified by HPLC to give title compound (32 mg, 0.087 mmol, 8%). 1H-NMR (CDCl$_3$), δ 0.93 (t, J=7.2 Hz, 6H), 1.91 (m, 4H), 2.15 (s, 3H), 2.58 (s, 3H), 3.36 (m, 1H), 6.91 (s, 1H), 7.08 (d, J=5.3 Hz, 1H), 7.55 (d, J=5.5 Hz, 1H) ppm. ES-MS (m/z): calcd for $C_{19}H_{20}F_3N_3S$ (M+H)$^+$: 367.44; found: 368.1.

Example 253

Preparation of 3-[3-Chloro-5-(2-methyl-2H-[1,2,4]triazol-3-yl)-thiophen-2-yl]-8-(1-ethyl-propyl)-6-methyl-2-trifluoromethyl-imidazo[1,2-b]pyridazine

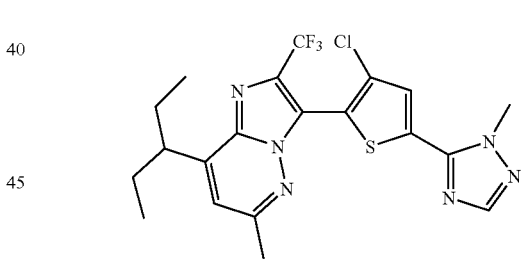

In a dry 25 mL round bottom flask, 8-(1-ethyl-propyl)-6-methyl-2-trifluoromethyl-imidazo[1,2-b]pyridazine (182 mg, 0.671 mmol), 5-(5-bromo-4-chloro-thiophen-2-yl)-1-methyl-$^1$H-[1,2,4]triazole (225 mg, 0.805 mmol), KOAc (330.2 mg, 3.36 mmol), and TBAB (217 mg, 0.671 mmol) are dissolved in NMP (3 mL). The mixture is degassed with bubbling nitrogen for 20 minutes. Then, Pd(OAc)$_2$ (8 mg, 0.034 mmol) and TDBPP (20.4 g, 0.34 moles) are added. The reaction mixture is heated to 125° C. for 3 hours to give the title compound (125 mg, 0.267 mmol, 40%). $^1$H-NMR (CDCl$_3$), δ 0.88 (t, J=7.2 Hz, 6H), 1.87 (m, 4H), 2.537 (s, 3H), 3.32 (m, 1H), 4.16 (s, 3H), 6.86 (s, 1H), 7.51 (s, 1H), 7.91 (s, 1H) ppm. ES-MS (m/z): calcd for $C_{20}H_{20}ClF_3N_6S$ (M+H)$^+$: 468.93; found: 469.2.

Example 254

Preparation of 3-(4-Chloro-2-morpholin-4-yl-thiazol-5-yl)-8-(1-ethyl-propyl)-6-methyl-2-trifluoromethyl-imidazo[1,2-b]pyridazine

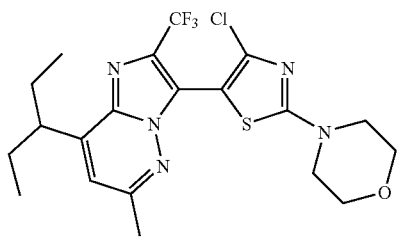

A. 8-(1-Ethyl-propyl)-3-iodo-6-methyl-2-trifluoromethyl-imidazo[1,2-b]pyridazine.

In a dry 25 mL round bottom flask, 8-(1-ethyl-propyl)-6-methyl-2-trifluoromethyl-imidazo[1,2-b]pyridazine (460 mg, 1.70 mmol) are dissolved in dry THF (3.5 mL) and cooled to −78° C. A solution of 2.5 M n-butyllithium in hexanes (748 µL, 1.87 mmol) is added dropwise. The reaction mixture is stirred for 20 minutes at −78° C., then warmed to 0° C. for 15 minutes. A solution of 12 (453 mg, 1.79 moles) in THF (2.0 mL) is added dropwise. The reaction is stirred for 15 minutes at 0° C., and then warmed to room temp. The reaction is stirred overnight, and the solvent is removed via reduced pressure. The reaction mixture is redissolved in ethyl acetate (50 mL) and washed with a 1 N solution of $Na_2S_2O_3$ (2×20 mL). The aqueous layer is extracted with ethyl acetate (2×40 mL). The combined organic extracts are dried with $Na_2SO_4$, filtered, and purified via silica gel chromatography to give the title compound (595 mg, 1.50 mmol, 88%). 1H-NMR (CDCl$_3$), δ 0.82 (t, J=8.0 Hz, 6H), 1.83 (m, 4H), 2.64 (s, 3H), 3.27 (m, 1H), 6.82 (s, 1H) ppm. ES-MS (m/z): calcd for $C_{13}H_{15}F_{31}N_3$ (M+H)$^+$: 397.18; found: 398.3.

B. 2,4-Dichloro-thiazole.

In a 250 mL round bottom flask, 2,4-thiazolidine dione (12.5 g, 107 mmol) is dissolved in phosphorousoxychloride (70 mL) and pyridine (8.5 mL). The mixture is stirred under reflux for 3 hours and cooled to room temp. The reaction mixture is poured into ice water slowly and extracted with dichloromethane. The combined organic extracts are dried with $Na_2SO_4$, filtered, and concentrated. The residue is purified via silica gel chromatography to give title compound (9.18 g, 59.6 mmol, 56%). 1H-NMR (CDCl$_3$), δ 7.01 (s, 1H) ppm.

C. 4-(4-Chloro-thiazol-2-yl)-morpholine.

In a 75 mL dry pressure vessel, 2,4-dichloro-thiazole (500 mg, 3.2 mmol) and morpholine (560 µL, 6.4 mmol) are dissolved in dry THF (2.0 mL). $Cs_2CO_3$ (1.56 g, 4.8 mmol) is added, and the reaction vessel is sealed. The reaction mixture is heated to 110° C. overnight. Solvent is removed via reduced pressure, and the crude reaction mixture is purified via silica gel chromatography to give the title compound (597 mg, 2.92 mmol, 91%). 1H-NMR (CDCl$_3$), δ 3.45 (m, 4H), 3.79 (m, 4H), 6.31 (s, 1H) ppm. ES-MS (m/z): calcd for $C_7H_9ClN_2OS$ (M+H)$^+$: 204.68; found: 205.2.

D. 3-(4-Chloro-2-morpholin-4-yl-thiazol-5-yl)-8-(1-ethyl-propyl)-6-methyl-2-trifluoromethyl-imidazo[1,2-b]pyridazine.

In a dry 25 mL round bottom flask, 8-(1-ethyl-propyl)-3-iodo-6-methyl-2-trifluoromethyl-imidazo[1,2-b]pyridazine (250 mg, 0.630 mmol), 4-(4-chloro-thiazol-2-yl)-morpholine (194 mg, 0.945 mmol), and $Cs_2CO_3$ (410 mg, 1.26 mmol) are dissolved in DMF. The mixture is degassed with bubbling nitrogen for 15 minutes. Then, $Pd_2(dba)_3$ (18 mg, 0.032 mmol) and $PPh_3$ (33 mg, 0.126 mmol) are added. The reaction mixture is heated to 130° C. overnight. The reaction is cooled to room temp., quenched with a solution of $NH_4Cl$ sat? (20 mL), and extracted with $Et_2O$ (3×50 mL). The combined organic extracts are washed with brine (30 mL), dried with $Na_2SO_4$, filtered and concentrated. The residue is purified via reverse phase HPLC with a 30-80% gradient of $CH_3CN$ in 10 mM $NH_4HCO_3/H_2O$/5% $CH_3CN$ (pH 10.0) to give the title compound (11 mg, 0.023 mmol, 4%). 1H-NMR (CDCl$_3$), δ 0.86 (t, J=7.3 Hz, 6H), 1.84 (m, 4H), 2.55 (s, 3H), 3.31 (m, 1H), 3.54 (dd, J=5.2, 4H), 3.84 (dd, J=5.2 Hz, 4H), 6.82 (s, 1H) ppm. ES-MS (m/z): calcd for $C_{20}H_{23}ClF_3N_5OS$ (M+H)$^+$: 473.95; found: 474.2.

Example 255

Preparation of {4-Chloro-5-[8-(1-ethyl-propyl)-6-methyl-2-trifluoromethyl-imidazo[1,2-b]pyridazin-3-yl]-thiazol-2-yl}-dimethyl-amine

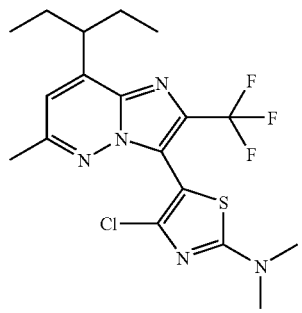

A. (4-Chloro-thiazol-2-yl)-dimethyl-amine.

Using a procedure analogous to Example 254C, 2,4-dichloro-thiazole (500 mg, 3.2 mmol) and dimethylamine (a 2.0 M solution in THF, 3 mL, 6.4 mmol) are reacted to give the title compound (60 mg, 0.152 mmol, 15%). 1H-NMR (CDCl$_3$), δ 3.09 (s, 6H), 6.22 (s, 1H) ppm. ES-MS (m/z): calcd for $C_5H_7ClN_2S$ (M+H)$^+$: 162.64; found: 163.2.

B. {4-Chloro-5-[8-(1-ethyl-propyl)-6-methyl-2-trifluoromethyl-imidazo[1,2-b]pyridazin-3-yl]-thiazol-2-yl}-dimethyl-amine.

Using a procedure analogous to Example 254D, 8-(1-ethyl-propyl)-3-iodo-6-methyl-2-trifluoromethyl-imidazo[1,2-b]pyridazine (250 mg, 0.630 mmol) is coupled with (4-chloro-thiazol-2-yl)-dimethyl-amine (154 mg, 0.945 mmol) to provide desired product. 1H-NMR (CDCl$_3$), δ 0.85 (t, J=7.4 Hz, 6H), 1.83 (m, 4H), 2.55 (s, 3H), 3.16 (s, 6H), 3.31 (m, 1H), 6.81 (s, 1H) ppm. ES-MS (m/z): calcd for $C_{18}H_{21}ClF_3N_5S$ (M+H)$^+$: 431.91; found: 432.2.

Example A

In Vivo Potency Assessment Using Ex Vivo Binding

To assess in vivo potency, a compound of the present invention is evaluated using ex vivo binding. Using the procedures as provided in D. R. Gehlert et al., *EJP* 509: 145-153 (2005), a compound is administered to a rat via the oral route. The binding of $^{125}$I-sauvagine to the cerebellum is then assessed ex vivo as described in Gehlert et al. For example, Example 199 provides an $ED_{50}$ result of 1.3 mg/kg.

Example B

CRF1 Filter Binding Assay

The limitations of plasmid-based human CRF1 expression, in terms of generating a recombinant cell line with sufficient receptor density to develop a binding assay, are overcome by using a Phoenix retroviral expression system licensed from Stanford. The stable HEK-hCRF1 cell line is used to prepare membranes and binding reactions (200 µl) are set up as follows: 50 µl of $^{125}$I-sauvagine (0.2 nM final), 50 µl compound and 100 µl CRF1 membrane (25 µg/reaction). The reactions are incubated at room temperature for 2 hours and then terminated by filtration through pre-treated FB Millipore glass fiber filter plates (96 well). The plates are wash twice with ice-cold assay buffer (50 mM tris, 12.5 mM NaCl, 1 mM EDTA, 10 mM $MgCl_2$, 0.05% BSA, pH 7.2), air dried over night and counted with 100 µl Microscint 40 in a MicroBeta counter. Non-specific binding (NSB) is determined in the presence of 0.5 µM non-labeled sauvagine. Triplicate determinations are typically run and the median data points plotted by Graph Pad Prism.

Using this assay, the claimed exemplified compounds of the present invention inhibit the binding of $^{125}$I-Sauvagine (4 nM) in roller/adherent cells with a Ki (inhibition constant) below 1 µM. For example, Examples 102 and 199 exhibit a Ki of 4.92±0.57 nM and 9.98±0.72 nM, respectively.

Example C

CRF2 Filter Binding Assay

The limitations of plasmid-based human CRF2 expression, in terms of generating a recombinant cell line with sufficient receptor density to develop a binding assay, are overcome by using a Phoenix retroviral expression system licensed from Stanford. The stable HEK-hCRF2 cell line is used to prepare membranes and binding reactions (200 µl) are set up as follows: 50 ul of $^{125}$I-sauvagine (0.2 nM final concentration), 50 µl compound and 100 µl CRF2 membrane (25 µg/reaction). The reactions are incubated at room temperature for 2 hours and then terminated by filtration through pre-treated FB Millipore glass fiber filter plates (96 well). The plates are washed twice with ice-cold assay buffer (50 mM tris, 12.5 mM NaCl, 1 mM EDTA, 10 mM $MgCl_2$, 0.05% BSA, pH 7.2), air dried over night and counted with 100 µl Microscint 40 in a Micro-Beta counter. Non-specific binding (NSB) is determined in the presence of 0.5 µM non-labeled sauvagine. Alternatively, compounds are evaluated using a Scintillation Proximity assay. This assay is set up as follows: 50 ul of $^{125}$I-Sauvagine (0.2 nM final concentration), 50 µl compound or non-labelled sauvagine (NSB) and 100 µl containing 250 µg wheat germ agglutinin (WGA) SPA beads and CRF2 membrane (1.5 µg/reaction). Plates are incubated for 4-5 hours at room temperature and then centrifuged at 200×g for 10 minutes. Bound radioactivity is assessed using a Wallac Trilux scintillation counter. Binding is assessed typically using triplicate determinations and the median data points plotted by Graph Pad Prism. Compounds are initially screened at a fixed concentration and, if sufficient activity is noted, subsequent concentration-response curves are generated.

Compounds of the present invention are tested in the CRF2 binding assay and exhibit weak affinity for the CRF2 receptor. For example, Examples 102 and 199 exhibit a percent inhibition at 50 µM of 9.0±2.6 and 16.9±1.9, respectively. These results suggest that the compounds of the present invention are highly selective for the CRF1 receptor.

Example D

Bioavailability and Pharmacokinetic Properties

The compounds of Formula I are antagonists of CRF1, and possess surprisingly useful properties related to their pharmacokinetics and bioavailability.

The volume of distribution (Vdist) relates the amount of the drug in the body to the concentration of the drug in the blood or plasma. The volume of distribution refers to the fluid volume that would be required to contain the total amount of the drug in the body at the same concentration as in the blood or plasma: Vdist=amount of drug in the body/concentration of drug in blood or plasma (Goodman and Gillman's). For a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, Vdist can be used to determine a loading dose achieve a steady state concentration.

To test for volume of distribution, Male Sprague Dawley rats (N=3) are administered a single 3 mg/kg intravenous dose of compound. Multiple plasma samples are collected at time points from 0.08 to 24 hours post-dose. The plasma samples are analyzed by LC/MS/MS to determine the plasma concentrations. Plasma pharmacokinetic calculations are performed to determine the pharmacokinetic parameters including Vdist and plasma clearance (Clp).

An overwhelming majority of commercial CNS and cardiovascular drugs exhibit a human Vdist of <10 L/Kg. In comparison with CRF antagonists CP154526 (Schulz et al., *Proc. Natl. Acad. Sci.* (*USA*), 93:10477 (1996)) and NBI30775 (Chen et al., *Drug Development Research*, 65:216 (2005)) which exhibit a rat Vdist of 114 L/Kg and 76 L/Kg, respectively, following a single intravenous dose, thiazole Examples 48 and 199 of the present invention exhibits a rat Vdist of only 9 and 2 L/Kg, respectively. Furthermore, thiophene Examples 88 and 39 of the present invention exhibit a rat Vdist of only 44 and 17 L/kg, respectively.

We claim:
1. A compound of Formula I

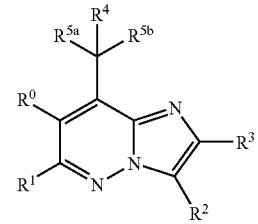

Formula I wherein:
$R^0$ is hydrogen, halo, methyl or ethyl;
$R^1$ and $R^3$ are independently methyl, methoxy, or trifluoromethyl;
$R^2$ is selected from the group consisting of:

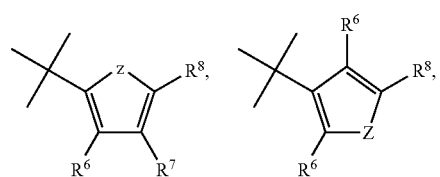

R⁴ is hydrogen, halo, or hydroxy;

R⁵ᵃ and R⁵ᵇ are independently ethyl or n-propyl;

R⁶ at each occurrence is independently hydrogen, halo, cyano, (C₁-C₄)alkyl, trifluoromethyl, methoxy, or phenyl;

R⁷ is hydrogen, halo, methyl, methoxy, dimethylamino,

R⁸ is selected from the group consisting of hydrogen, halo, cyano, (C₁-C₄)alkyl, RᵃRᵇN—, carbamyl, (C₁-C₂)alkoxy(C₁-C₂)alkyl, R¹¹—C(O)—, R¹¹ is methoxy, methylamino, dimethylamino, or phenyl;

R¹² is hydrogen, halo, methyl, ethyl, trifluoromethyl, methoxy, trifluoromethoxy dimethylamino, acetyl, or methylsulfonyl;

R¹³ is hydrogen, methyl or halo;

R¹⁴ is hydrogen or hydroxy;

R¹⁵ is methylthio, cyclopropyl, phenyl,

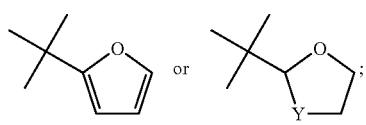

$R^a$ is hydrogen, $(C_1-C_5)$alkyl, $(C_3-C_5)$cycloalkyl, methoxy $(C_2-C_4)$alkyl, acetyl, $(C_1-C_2)$alkylsulfonyl, $(C_3)$alkenyl, $R^{15}$—$(CH_2)n$-, or $(C_1-C_2)$alkyl substituted with cyano, formyl, vinyl, or ethynyl;

$R^b$ is hydrogen or $(C_1-C_3)$alkyl;

X is —$CH_2$—, —CO—, —O—, —S— or —$SO_2$—;

Y is —$CH_2$— or —O—;

z is S or O;

n is 1 or 2;

Q is hydrogen or methyl;

T is hydrogen or methyl;

J is methyl, trifluoroethyl, or tert-butyl; and

M is methyl or halo;

or a pharmaceutically acceptable salt thereof.

2. The compound according to claim 1 wherein $R^0$ and $R^4$ are hydrogen, $R^1$ and $R^3$ are methyl, and $R^{5a}$ and $R^{5b}$ are ethyl.

3. The compound according to claim 2, wherein $R^2$ is

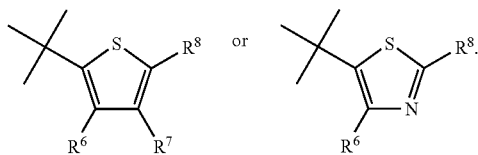

4. The compound according to claim 3, wherein $R^8$ is

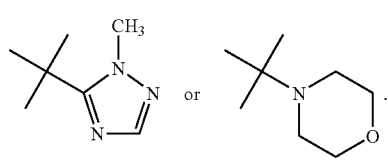

5. The compound according to claim 4 which is N-{4-chloro-5-[8-(1-ethyl-propyl)-2,6-dimethyl-imidazo[1,2-b]pyridazin-3-yl]-thiazol-2-yl}-morpholine or a pharmaceutically acceptable salt thereof.

6. The compound according to claim 4 which is N-{4-chloro-5-[8-(1-ethyl-propyl)-2,6-dimethyl-imidazo[1,2-b]pyridazin-3-yl]-thiazol-2-yl}-morpholine, hydrochloride salt.

7. The compound according to claim 4 which is 3-[4-bromo-2-(2-methyl-2H-[1,2,4]triazol-3-yl)-thiazol-5-yl]-8-(1-ethyl-propyl)-2,6-dimethyl -imidazo[1,2-b]pyridazine or a pharmaceutically acceptable salt thereof.

8. The compound according to claim 4 which is 3-[4-chloro-2-(2-methyl-2H-[1,2,4]triazol-3-yl)-thiazol-5-yl]-8-(1-ethyl-propyl)-2,6-dimethyl-imidazo[1,2-b]pyridazine or a pharmaceutically acceptable salt thereof.

9. The compound according to claim 4 which is 3-[3-chloro-5-(2-methyl-2H-[1,2,4]triazol-3-yl)-thiophen-2-yl]-8-(1-ethyl-propyl)-2,6-dimethyl -imidazo[1,2-b]pyridazine or a pharmaceutically acceptable salt thereof.

10. A pharmaceutical composition comprising the compound according to claim 1, or a pharmaceutically acceptable salt thereof, and a pharmaceutically acceptable carrier, diluent or excipient.

* * * * *